(12) United States Patent
Duffy et al.

(10) Patent No.: US 9,212,227 B2
(45) Date of Patent: Dec. 15, 2015

(54) ST2L ANTIBODY ANTAGONISTS FOR THE TREATMENT OF ST2L-MEDIATED INFLAMMATORY PULMONARY CONDITIONS

(71) Applicant: Janssen Biotech, Inc., Horsham, PA (US)

(72) Inventors: Karen Duffy, Spring House, PA (US); Natalie Fursov, Spring House, PA (US); LeRoy Hall, Raritan, NJ (US); Catherine Healy, Spring House, PA (US); Roberta Lamb, Spring House, PA (US); Jinquan Luo, Spring House, PA (US); Ravi Malaviya, Spring House, PA (US); Michael Naso, Spring House, PA (US); Michael Pratta, Mulica Hill, NJ (US); Mark Tornetta, Spring House, PA (US); John Wheeler, Spring House, PA (US); Sheng-Jiun Wu, Spring House, PA (US)

(73) Assignee: Janssen Biotech, Inc., Horsham, PA (US)

(*) Notice: Subject to any disclaimer, the term of this patent is extended or adjusted under 35 U.S.C. 154(b) by 0 days.

(21) Appl. No.: 13/798,226

(22) Filed: Mar. 13, 2013

(65) Prior Publication Data
US 2013/0287777 A1 Oct. 31, 2013

Related U.S. Application Data

(60) Provisional application No. 61/640,407, filed on Apr. 30, 2012, provisional application No. 61/640,238, filed on Apr. 30, 2012.

(51) Int. Cl.
*A61K 39/395* (2006.01)
*C07K 16/28* (2006.01)
*A61K 38/01* (2006.01)
*C07K 16/44* (2006.01)
*C07K 16/18* (2006.01)
*A61K 39/00* (2006.01)

(52) U.S. Cl.
CPC ............ *C07K 16/2866* (2013.01); *A61K 38/012* (2013.01); *C07K 16/44* (2013.01); *A61K 2039/505* (2013.01); *C07K 2317/21* (2013.01); *C07K 2317/33* (2013.01); *C07K 2317/34* (2013.01); *C07K 2317/55* (2013.01); *C07K 2317/565* (2013.01); *C07K 2317/567* (2013.01); *C07K 2317/76* (2013.01); *C07K 2317/92* (2013.01)

(58) Field of Classification Search
None
See application file for complete search history.

(56) References Cited

U.S. PATENT DOCUMENTS

| | | | |
|---|---|---|---|
| 6,323,334 B1 * | 11/2001 | Kingsbury et al. | ......... 536/23.5 |
| 7,087,396 B2 | 8/2006 | Tominaga et al. | |
| 8,187,596 B1 | 5/2012 | Chackerian et al. | |
| 2003/0190311 A1 | 10/2003 | Dell'Acqua et al. | |
| 2009/0118127 A1 | 5/2009 | Raghunathan | |
| 2010/0021477 A1 | 1/2010 | Tsui et al. | |
| 2010/0260770 A1 | 10/2010 | Coyle | |

FOREIGN PATENT DOCUMENTS

| | | |
|---|---|---|
| WO | WO 99/34217 A1 | 7/1999 |
| WO | WO 00/69914 A2 | 11/2000 |
| WO | WO 01/21641 A1 | 3/2001 |
| WO | WO 2005/079844 A2 | 9/2005 |
| WO | WO 2006/055347 A2 | 5/2006 |
| WO | WO 2008/022295 A2 | 2/2008 |
| WO | WO 2009/085462 A1 | 7/2009 |
| WO | WO 2010/080833 A1 | 7/2010 |
| WO | WO 2011/127412 A2 | 10/2011 |
| WO | WO 2012/113813 A1 | 8/2012 |
| WO | WO 2013/173761 A2 | 11/2013 |

OTHER PUBLICATIONS

Stolarski et al, The Journal of Immunology, 2010, vol. 185, pp. 3472-3480.*
PCT International Search Report dated Feb. 13, 2014.
Alcorn, et al., "$T_H17$ Cells in Asthma and COPD," Annual Review of Physiology, 72: 495-516 (2010).
Kawa Amin, "The role of mast cells in allergic inflammation," Respiratory Medicine, 106: 9-14 (2012).
Brüsselbach, et al., "Enzyme recruitment and tumor cell killing in vitro by a secreted bispecific single-chain diabody," Tumor Targeting, 4: 115-123 (1999).
Corren, et al., "Lebrikizumab Treatment in Adults with Asthma," The New England Journal of Medicine, 365(12): 1088-1098(2011).
Drube, et al., "The receptor tyrosine kinase c-Kit controls IL-33 receptor signaling in mast cells," Blood, 115(19): 3899-3906 (2010).
Fahy, et al., "'Reactive Airways Disease' A Lazy Term of Uncertain Meaning that Should be Abandoned," American Journal of Respiratory and Critical Care Medicine, 163: 822-823 (2001).
Fransson, et al., "Human Framework Adaptation of a Mouse Anti-Human IL-13 Antibody," Journal of Molecular Biology, 398: 214-231 (2010).
Freese, et al., "Chronic allograft nephropathy-biopsy findings and outcome," Nephrology Dialysis Transplantation, 16: 2401-2406 (2001).
Fursov, et al., "Generation and Characterization of Rat Anti-mouse ST2L Monoclonal Antibodies," Hybridoma, 30(2): 153-162 (2011).
Hammad, et al., "House dust mite allergen induces asthma via Toll-like receptor 4 triggering of airway structural cells," Nature Medicine, 15(4): 410-416 (2009).
Henderson, et al., "The Importance of Leukotrienes in Airway Inflammation in a Mouse Model of Asthma," Journal of Experimental Medicine, 184: 1483-1494 (1996).

(Continued)

*Primary Examiner* — Joanne Hama
*Assistant Examiner* — Fozia Hamud
(74) *Attorney, Agent, or Firm* — Kirk Baumeister

(57) ABSTRACT

The present invention relates to ST2L antagonists, polynucleotides encoding the antagonists or fragments thereof, and methods of making and using the foregoing.

15 Claims, 42 Drawing Sheets

(56) References Cited

OTHER PUBLICATIONS

Kamekura, et al., "The role of IL-33 and its receptor St2 in human nasal epithelium with allergic rhinitis," Clinical & Experimental Allergy, 42: 218-228 (2012).

Koyasu, et al., "Type 2 innate immune responses and the natural helper cell," Immunology, 132: 475-481 (2011).

Linden, et al., "Airway neutrophils and interleukin-17," European Respiratory Journal, 15: 973-977 (2000).

Lingel, et al., "Structure of IL-33 and Its Interaction with the ST2 and IL-1RAcP Receptors—Insight into Heterotrimeric IL-1 Signaling Complexes," Structure, 17: 1398-1410 (2009).

Youhua Liu, "Renal fibrosis: New insights into the pathogenesis and therapeutics," Kidney International, 69: 213-217 (2006).

Clare M. Lloyd, "IL-33 family members and asthma—bridging innate and adaptive immune responses," Current Opinion in Immunology, 22: 800-806 (2010).

Manetti, et al., "The IL1-like cytokine IL33 and its receptor ST2 are abnormally expressed in the affected skin and visceral organs of patients with systemic sclerosis," Annals of the Rheumatic Disease, 69: 598-605 (2010).

Meng, et al., "Mast Cells Are Not Potent Regulators of Endothelial Cell Adhesion Molecule ICAM-1 and VCAM-1 Expression," Journal of Cellular Physiology, 165: 40-53 (1995).

Nair, et al., "Mepolizumab for Prednisone-Dependent Asthma with Sputum Eosinophilia," The New England Journal of Medicine, 360: 985-993 (2009).

Okayama, et al., "Role of mast cells in airway remodeling," Current Opinion in Immunology, 19: 687-693 (2007).

Palmer, et al., "Interleukin-33 biology with potential insights into human diseases," Nature Reviews Rheumatology, 7: 321-329 (2011).

Aled Phillips, "The Role of Proximal Tubular Cells in Interstitial Fibrosis: Understanding TGF-β," Chang Gung Medical Journal, 30(1): 2-6 (2007).

Phillips, et al., "Diabetic nephropathy: The central role of renal proximal tubulointerstitial injury," Histology and Histopathology, 17: 247-252 (2002).

Rahman, et al., "IL-17R activation of human airway smooth muscle cells induces CXCL-8 production via a transcriptional-dependent mechanism," Clinical Immunology: 268-276 (2005).

Ritz, et al., "Nephropathy of type II diabetes mellitus," Nephrology Dialysis Transplantation, 11 (Suppl. 9): 38-44 (1996).

Shimizu, et al., "Functional SNPs in the distal promoter of the ST2 gene are associated with atopic dermatitis," Human and Molecular Genetics, 14(19): 2919-2927 (2005).

Shi, et al., "De Novo Selection of High-Affinity Antibodies from Synthetic Fab Libraries Displayed on Phage as pIX Fusion Proteins," Journal of Molecular Biology, 397: 385-396 (2010).

MS Simonson, "Phenotypic transitions and fibrosis in diabetic nephropathy," Kidney International, 71: 846-854 (2007).

Spits, et al., "Innate lymphoid cells—a proposal for uniform nomenclature," Nature Reviews Immunology, 13: 145-149 (2013).

Thomas, et al., "Structure of the activating IL-1 receptor signaling complex," Nature Structural & Molecular Biology, 19(4): 455-457 (2012).

Wang, et al., "Structural insights into the assembly and activation of IL-1β with its receptors," Nature Immunology, 11(10): 905-912 (2010).

Martha V. White, "The role of histamine in allergic diseases," Journal of Allergy and Clinical Immunology, 86: 599-605 (1990).

Xu, et al., "IL-33 exacerbates antigen-induced arthritis by activating mast cells," Proceedings of the National Academy of Science, 105(31): 10913-10918 (2008).

Zhao, et al., "The enigmatic processing and secretion of interleukin-33," Cellular & Molecular Immunology, 7: 260-262 (2010).

Ramaprakash, et al., "Targeting ST2L Potentiates CpG-Mediated Therapeutic Effects in a Chronic Fungal Asthma Model," The American Journal of Pathology, 179(1): 104-115 (2011).

Brorson, et al., "Mutational Analysis of Avidity and Fine Specificity of Anti-Levan Antibodies," Journal of Immunology, 163: 6694-6701 (1999).

Brummell, et al., "Probing the combining Site of an Anti-Carbohydrate Antibody by Saturation-Mutagenesis: Role of the Heavy-Chain CDR3 Residues," Biochemistry, 32: 1180-1187 (1993).

P.M. Colman, "Effects of amino acid sequence changes on antibody-antigen interactions," Research in Immunology, 145: 33-36 (1994).

Kobayashi, et al., "Tryptophan H33 plays an important role in pyrimidine (6-4) pyrimidine photoproduct binding by a high-affinity antibody," Protein Engineering, 12(10): 879-884 (1999).

* cited by examiner

Figure 9.

Stimulation with 1ng/ml IL-33 in StemPro-34 medium + 100ng/ml SCF

| ST2L Domain* | Mab | Average % Inhibition by 50µg/ml Mab | | | | | | Averave % Inhibition by 2µg/ml Mab | | | | | |
|---|---|---|---|---|---|---|---|---|---|---|---|---|---|
| | | GM-CSF | IL-5 | IL-8 | IL-10 | IL-13 | | GM-CSF | IL-5 | IL-8 | IL-10 | IL-13 | |
| D1 | C2244 | 95.3 | 99.4 | 91.6 | 86.3 | 100.0 | | 62.1 | 68.3 | 57.1 | 50.6 | 62.5 | |
| D1 | C2494 | 95.3 | 99.4 | 93.5 | 87.3 | 100.0 | | 84.1 | 96.2 | 83.0 | 76.1 | 95.8 | |
| D3 | C2519 | -179.9 | -481.5 | -95.5 | -120.6 | -180.0 | | -205.3 | -516.3 | -103.3 | -144.5 | -195.6 | |
| D3 | C2521 | -12.2 | -39.4 | 25.5 | 38.8 | 36.0 | | -295.3 | -594.4 | -190.0 | -130.6 | -207.8 | |

Stimulation with 3ng/ml IL-33 in RPMI/10% FCS + 100ng/ml SCF

| ST2L Domain* | Mab | Average % Inhibition by 50µg/ml Mab | | | | | | Averave % Inhibition by 2µg/ml Mab | | | | | |
|---|---|---|---|---|---|---|---|---|---|---|---|---|---|
| | | GM-CSF | IL-5 | IL-8 | IL-10 | IL-13 | | GM-CSF | IL-5 | IL-8 | IL-10 | IL-13 | |
| D1 | C2494 | 95.0 | 99.4 | 67.0 | 87.8 | 99.3 | | 92.9 | 99.6 | 62.2 | 84.7 | 98.8 | |
| D3 | ST2M48 | 23.2 | 20.7 | 28.7 | 8.3 | 11.0 | | -61.6 | -46.1 | -5.8 | -79.1 | -80.8 | |
| D3 | ST2M49 | -7.0 | -20.9 | -5.7 | -12.4 | 9.3 | | -65.4 | -33.1 | -30.0 | -36.8 | -35.7 | |
| D3 | ST2M50 | -5.7 | 25.7 | 13.2 | 2.0 | 31.9 | | -26.0 | 1.6 | -4.4 | -18.7 | 14.9 | |
| D3 | ST2M51 | 1.9 | 27.3 | 15.0 | 1.3 | 28.6 | | -35.3 | 1.2 | 11.8 | -3.6 | 3.0 | |

*ST2L domain antibody binds to

Figure 10.

| mAb/Fab name | VH name | HCDR1 Sequence | HCDR1 SEQ ID NO: | HCDR2 Sequence | HCDR2 SEQ ID NO: | HCDR3 Sequence | HCDR3 SEQ ID NO: |
|---|---|---|---|---|---|---|---|
| ST2F6 | ST2H41 | SYAMS | 78 | AISGSGGSTYYADSVKG | 81 | DPWSTEGSFFVLDY | 84 |
| ST2F14 | ST2H41 | SYAMS | 78 | AISGSGGSTYYADSVKG | 81 | DPWSTEGSFFVLDY | 84 |
| ST2F17 | ST2H41 | SYAMS | 78 | AISGSGGSTYYADSVKG | 81 | DPWSTEGSFFVLDY | 84 |
| ST2F31 | ST2H41 | SYAMS | 78 | AISGSGGSTYYADSVKG | 81 | DPWSTEGSFFVLDY | 84 |
| ST2F41 | ST2H41 | SYAMS | 78 | AISGSGGSTYYADSVKG | 81 | DPWSTEGSFFVLDY | 84 |
| STLM103 | ST2H112 | FYDMF | 95 | SIRGEGGRTDYADSVKG | 109 | DPWSTEGSFFVLDY | 84 |
| STLM107 | ST2H52 | DYAMF | 96 | AIEGEGGETNYADSVKG | 110 | DPWSTEGSFFVLDY | 84 |
| STLM108 | ST2H50 | IYDMI | 97 | TIKGEGGGTYYADSVKG | 111 | DPWSTEGSFFVLDY | 84 |
| STLM123 | ST2H52 | DYAMF | 96 | AIEGEGGETNYADSVKG | 110 | DPWSTEGSFFVLDY | 84 |
| STLM124 | ST2H50 | IYDMI | 97 | TIKGEGGGTYYADSVKG | 111 | DPWSTEGSFFVLDY | 84 |
| STLM206 | ST2H232 | IYDMI | 97 | TIRGEGGSTYYADSVKG | 112 | DPWSTEGSFFVLDY | 84 |
| STLM207 | ST2H228 | SYDMI | 98 | TIRGEGGTTAYADSVKG | 113 | DPWSTEGSFFVLDY | 84 |
| STLM208 | ST2H257 | IYDMI | 97 | SIRGEGGGTYYADSVKG | 114 | DPWSTEGSFFVLDY | 84 |
| STLM209 | ST2H231 | IYDMI | 97 | TIRGEGGGTSYADSVKG | 115 | DPWSTEGSFFVLDY | 84 |
| STLM210 | ST2H318 | DDAMI | 99 | YIGGNGGTTYYADSVKG | 116 | DPWSTEGSFFVLDY | 84 |
| STLM211 | ST2H316 | GYAMI | 100 | YIEGEGGETYYADSVKG | 117 | DPWSTEGSFFVLDY | 84 |
| STLM212 | ST2H314 | VYDMI | 101 | TIRGEGGGTYYADSVKG | 118 | DPWSTEGSFFVLDY | 84 |
| STLM213 | ST2H202 | FYDMI | 102 | TIRGEGGDTNYADSVKG | 120 | DPWSTEGSFFVLDY | 84 |
| STLM214 | ST2H179 | SYDMF | 103 | DIKGEGGRTAYADSVKG | 121 | DPWSTEGSFFVLDY | 84 |
| STLM215 | ST2H172 | SYDMF | 103 | AIAGEGGRTYYADSVKG | 122 | DPWSTEGSFFVLDY | 84 |
| STLM216 | ST2H173 | SYDMF | 103 | DIKGEGGATNYADSVKG | 123 | DPWSTEGSFFVLDY | 84 |
| STLM217 | ST2H163 | VYDMF | 104 | DIKGEGGETSYADSVKG | 124 | DPWSTEGSFFVLDY | 84 |
| STLM218 | ST2H162 | VDSMF | 105 | SIEGNGGATYYADSVKG | 125 | DPWSTEGSFFVLDY | 84 |
| STLM219 | ST2H139 | GYDMF | 106 | DIGGEGGSTNYADSVKG | 126 | DPWSTEGSFFVLDY | 84 |
| STLM220 | ST2H137 | FYDMF | 95 | DIRGEGGTAYADSVKG | 127 | DPWSTEGSFFVLDY | 84 |
| STLM221 | ST2H136 | IYDMF | 107 | YIRGEGGDTNYADSVKG | 128 | DPWSTEGSFFVLDY | 84 |
| STLM222 | ST2H129 | IYSMF | 108 | DIGGEGGGTSYADSVKG | 129 | DPWSTEGSFFVLDY | 84 |

Figure 11.

| mAb/Fab name | VL name | LCDR1 | | LCDR2 | | LCDR3 | |
|---|---|---|---|---|---|---|---|
| | | Sequence | SEQ ID NO: | Sequence | SEQ ID NO: | Sequence | SEQ ID NO: |
| ST2F6 | ST2L24 | RASQSVDDALA | 87 | DASNRAT | 90 | QQFYNWPLT | 92 |
| ST2F14 | ST2L32 | RASQSVDDDLA | 130 | DASNRAT | 90 | QQYIGAPIT | 131 |
| ST2F17 | ST2L35 | RASQSVDDDLA | 130 | DASNRAT | 90 | QQYIDAPLT | 132 |
| ST2F31 | ST2L49 | RASQSVDDDLA | 130 | DASNRAT | 90 | QQYNDAIT | 133 |
| ST2F41 | ST2L59 | RASQSVDDDLA | 130 | DASNRAT | 90 | QQYITAPLT | 134 |
| STLM103 | ST2L32 | RASQSVDDDLA | 130 | DASNRAT | 90 | QQYIGAPIT | 131 |
| STLM107 | ST2L32 | RASQSVDDDLA | 130 | DASNRAT | 90 | QQYIGAPIT | 131 |
| STLM108 | ST2L32 | RASQSVDDDLA | 130 | DASNRAT | 90 | QQYIGAPIT | 131 |
| STLM123 | ST2L59 | RASQSVDDDLA | 130 | DASNRAT | 90 | QQYITAPLT | 134 |
| STLM124 | ST2L59 | RASQSVDDDLA | 130 | DASNRAT | 90 | QQYITAPLT | 134 |
| STLM206 | ST2L59 | RASQSVDDDLA | 130 | DASNRAT | 90 | QQYITAPLT | 134 |
| STLM207 | ST2L59 | RASQSVDDDLA | 130 | DASNRAT | 90 | QQYITAPLT | 134 |
| STLM208 | ST2L59 | RASQSVDDDLA | 130 | DASNRAT | 90 | QQYITAPLT | 134 |
| STLM209 | ST2L59 | RASQSVDDDLA | 130 | DASNRAT | 90 | QQYITAPLT | 134 |
| STLM210 | ST2L49 | RASQSVDDDLA | 130 | DASNRAT | 90 | QQYNDAIT | 133 |
| STLM211 | ST2L49 | RASQSVDDDLA | 130 | DASNRAT | 90 | QQYNDAIT | 133 |
| STLM212 | ST2L49 | RASQSVDDDLA | 130 | DASNRAT | 90 | QQYNDAIT | 133 |
| STLM213 | ST2L35 | RASQSVDDDLA | 130 | DASNRAT | 90 | QQYIDAPLT | 132 |
| STLM214 | ST2L35 | RASQSVDDDLA | 130 | DASNRAT | 90 | QQYIDAPLT | 132 |
| STLM215 | ST2L32 | RASQSVDDDLA | 130 | DASNRAT | 90 | QQYIGAPIT | 131 |
| STLM216 | ST2L32 | RASQSVDDDLA | 130 | DASNRAT | 90 | QQYIGAPIT | 131 |
| STLM217 | ST2L32 | RASQSVDDDLA | 130 | DASNRAT | 90 | QQYIGAPIT | 131 |
| STLM218 | ST2L32 | RASQSVDDDLA | 130 | DASNRAT | 90 | QQYIGAPIT | 131 |
| STLM219 | ST2L32 | RASQSVDDDLA | 130 | DASNRAT | 90 | QQYIGAPIT | 131 |
| STLM220 | ST2L32 | RASQSVDDDLA | 130 | DASNRAT | 90 | QQYIGAPIT | 131 |
| STLM221 | ST2L32 | RASQSVDDDLA | 130 | DASNRAT | 90 | QQYIGAPIT | 131 |
| STLM222 | ST2L32 | RASQSVDDDLA | 130 | DASNRAT | 90 | QQYIGAPIT | 131 |

Figure 12.

| mAb name | VH name | VL name | H-CDR1 | | H-CDR2 | | H-CDR3 | |
|---|---|---|---|---|---|---|---|---|
| | | | Sequence | SEQ ID NO: | Sequence | SEQ ID NO: | Sequence | SEQ ID NO: |
| STLM208 | ST2H257 | ST2L59 | IYDMI | 97 | SIRGEGGGTYYADSVKG | 114 | DPWSTEGSFFVLDY | 84 |
| STLM352 | STLH255 | ST2L59 | IYDMI | 97 | SIRGEGGGTYYADSVKG | 114 | APWSTEGSFFVLDY | 165 |
| STLM351 | STLH256 | ST2L59 | IYDMI | 97 | SIRGEGGGTYYADSVKG | 114 | RPWSTEGSFFVLDY | 166 |
| STLM350 | STLH257 | ST2L59 | IYDMI | 97 | SIRGEGGGTYYADSVKG | 114 | NPWSTEGSFFVLDY | 167 |
| STLM349 | STLH258 | ST2L59 | IYDMI | 97 | SIRGEGGGTYYADSVKG | 114 | QPWSTEGSFFVLDY | 168 |
| STLM348 | STLH259 | ST2L59 | IYDMI | 97 | SIRGEGGGTYYADSVKG | 114 | EPWSTEGSFFVLDY | 169 |
| STLM347 | STLH260 | ST2L59 | IYDMI | 97 | SIRGEGGGTYYADSVKG | 114 | IPWSTEGSFFVLDY | 170 |
| STLM346 | STLH261 | ST2L59 | IYDMI | 97 | SIRGEGGGTYYADSVKG | 114 | HPWSTEGSFFVLDY | 171 |
| STLM345 | STLH262 | ST2L59 | IYDMI | 97 | SIRGEGGGTYYADSVKG | 114 | SPWSTEGSFFVLDY | 172 |
| STLM344 | STLH263 | ST2L59 | IYDMI | 97 | SIRGEGGGTYYADSVKG | 114 | TPWSTEGSFFVLDY | 173 |
| STLM343 | STLH264 | ST2L59 | IYDMI | 97 | SIRGEGGGTYYADSVKG | 114 | YPWSTEGSFFVLDY | 174 |
| STLM342 | STLH265 | ST2L59 | IYDMI | 97 | SIRGEGGGTYYADSVKG | 114 | DAWSTEGSFFVLDY | 175 |
| STLM341 | STLH266 | ST2L59 | IYDMI | 97 | SIRGEGGGTYYADSVKG | 114 | DHWSTEGSFFVLDY | 176 |
| STLM340 | STLH267 | ST2L59 | IYDMI | 97 | SIRGEGGGTYYADSVKG | 114 | DYWSTEGSFFVLDY | 177 |
| STLM339 | STLH268 | ST2L59 | IYDMI | 97 | SIRGEGGGTYYADSVKG | 114 | DEWSTEGSFFVLDY | 178 |
| STLM338 | STLH269 | ST2L59 | IYDMI | 97 | SIRGEGGGTYYADSVKG | 114 | DQWSTEGSFFVLDY | 179 |
| STLM337 | STLH270 | ST2L59 | IYDMI | 97 | SIRGEGGGTYYADSVKG | 114 | DIWSTEGSFFVLDY | 180 |
| STLM336 | STLH271 | ST2L59 | IYDMI | 97 | SIRGEGGGTYYADSVKG | 114 | DSWSTEGSFFVLDY | 181 |
| STLM335 | STLH272 | ST2L59 | IYDMI | 97 | SIRGEGGGTYYADSVKG | 114 | DNWSTEGSFFVLDY | 182 |
| STLM334 | STLH273 | ST2L59 | IYDMI | 97 | SIRGEGGGTYYADSVKG | 114 | DTWSTEGSFFVLDY | 183 |
| STLM333 | STLH274 | ST2L59 | IYDMI | 97 | SIRGEGGGTYYADSVKG | 114 | DVWSTEGSFFVLDY | 184 |
| STLM332 | STLH275 | ST2L59 | IYDMI | 97 | SIRGEGGGTYYADSVKG | 114 | DIWSTEGSFFVLDY | 185 |

Figure 13A.

| mAb | VH ID | Sequence | SEQ ID NO: |
|---|---|---|---|
| STLM103 | ST2H112 | EVQLLESGGGLVQPGGSLRLSCAASGFTFSFYDMFWVRQAPGKGLEWVSSIRGEGGRTDYADSVKGRFTISRDNSKNTLYLQMNSLRAEDTAVYYCARDPWSTEGSFFVLDYWGQGTLVTVSS | 205 |
| STLM107 | ST2H52 | EVQLLESGGGLVQPGGSLRLSCAASGFTFSDYAMFWVRQAPGKGLEWVSAIEGEGGETNYADSVKGRFTISRDNSKNTLYLQMNSLRAEDTAVYYCARDPWSTEGSFFVLDYWGQGTLVTVSS | 186 |
| STLM108 | ST2H50 | EVQLLESGGGLVQPGGSLRLSCAASGFTFSIYDMIWVRQAPGKGLEWVSTIKGEGGGTYYADSVKGRFTISRDNSKNTLYLQMNSLRAEDTAVYYCARDPWSTEGSFFVLDYWGQGTLVTVSS | 187 |
| STLM123 | ST2H52 | EVQLLESGGGLVQPGGSLRLSCAASGFTFSDYAMFWVRQAPGKGLEWVSAIEGEGGETNYADSVKGRFTISRDNSKNTLYLQMNSLRAEDTAVYYCARDPWSTEGSFFVLDYWGQGTLVTVSS | 186 |
| STLM124 | ST2H50 | EVQLLESGGGLVQPGGSLRLSCAASGFTFSIYDMIWVRQAPGKGLEWVSTIKGEGGGTYYADSVKGRFTISRDNSKNTLYLQMNSLRAEDTAVYYCARDPWSTEGSFFVLDYWGQGTLVTVSS | 187 |
| STLM206 | ST2H232 | EVQLLESGGGLVQPGGSLRLSCAASGFTFSIYDMIWVRQAPGKGLEWVSIIRGEGGSTYYADSVKGRFTISRDNSKNTLYLQMNSLRAEDTAVYYCARDPWSTEGSFFVLDYWGQGTLVTVSS | 192 |
| STLM207 | ST2H228 | EVQLLESGGGLVQPGGSLRLSCAASGFTFSSYDMIWVRQAPGKGLEWVSIIRGEGGTTAYADSVKGRFTISRDNSKNTLYLQMNSLRAEDTAVYYCARDPWSTEGSFFVLDYWGQGTLVTVSS | 194 |
| STLM208 | ST2H257 | EVQLLESGGGLVQPGGSLRLSCAASGFTFSIYDMIWVRQAPGKGLEWVSSIRGEGGGTYYADSVKGRFTISRDNSKNTLYLQMNSLRAEDTAVYYCARDPWSTEGSFFVLDYWGQGTLVTVSS | 191 |
| STLM209 | ST2H231 | EVQLLESGGGLVQPGGSLRLSCAASGFTFSIYDMIWVRQAPGKGLEWVSIIRGEGGGTSYADSVKGRFTISRDNSKNTLYLQMNSLRAEDTAVYYCARDPWSTEGSFFVLDYWGQGTLVTVSS | 193 |
| STLM210 | ST2H318 | EVQLLESGGGLVQPGGSLRLSCAASGFTFSDDAMIWVRQAPGKGLEWVSYIGGNGGTTYYADSVKGRFTISRDNSKNTLYLQMNSLRAEDTAVYYCARDPWSTEGSFFVLDYWGQGTLVTVSS | 188 |
| STLM211 | ST2H316 | EVQLLESGGGLVQPGGSLRLSCAASGFTFSGYAMIWVRQAPGKGLEWVSYIEGEGGETYYADSVKGRFTISRDNSKNTLYLQMNSLRAEDTAVYYCARDPWSTEGSFFVLDYWGQGTLVTVSS | 189 |
| STLM212 | ST2H314 | EVQLLESGGGLVQPGGSLRLSCAASGFTFSVYDMIWVRQAPGKGLEWVSTIRGEGGGTYYADSVKGRFTISRDNSKNTLYLQMNSLRAEDTAVYYCARDPWSTEGSFFVLDYWGQGTLVTVSS | 190 |
| STLM213 | ST2H202 | EVQLLESGGGLVQPGGSLRLSCAASGFTFSFYDMIWVRQAPGKGLEWVSTIRGEGGDTNYADSVKGRFTISRDNSKNTLYLQMNSLRAEDTAVYYCARDPWSTEGSFFVLDYWGQGTLVTVSS | 195 |
| STLM214 | ST2H179 | EVQLLESGGGLVQPGGSLRLSCAASGFTFSSYDMFWVRQAPGKGLEWVSDIKGEGGRTAYADSVKGRFTISRDNSKNTLYLQMNSLRAEDTAVYYCARDPWSTEGSFFVLDYWGQGTLVTVSS | 196 |
| STLM215 | ST2H172 | EVQLLESGGGLVQPGGSLRLSCAASGFTFSSYDMFWVRQAPGKGLEWVSAIAGEGGRTYYADSVKGRFTISRDNSKNTLYLQMNSLRAEDTAVYYCARDPWSTEGSFFVLDYWGQGTLVTVSS | 198 |
| STLM216 | ST2H173 | EVQLLESGGGLVQPGGSLRLSCAASGFTFSSYDMFWVRQAPGKGLEWVSDIKGEGGATNYADSVKGRFTISRDNSKNTLYLQMNSLRAEDTAVYYCARDPWSTEGSFFVLDYWGQGTLVTVSS | 197 |
| STLM217 | ST2H163 | EVQLLESGGGLVQPGGSLRLSCAASGFTFSVYDMFWVRQAPGKGLEWVSDIKGEGGETSYADSVKGRFTISRDNSKNTLYLQMNSLRAEDTAVYYCARDPWSTEGSFFVLDYWGQGTLVTVSS | 199 |
| STLM218 | ST2H162 | EVQLLESGGGLVQPGGSLRLSCAASGFTFSVDMFWVRQAPGKGLEWVSSIEGNGGATYYADSVKGRFTISRDNSKNTLYLQMNSLRAEDTAVYYCARDPWSTEGSFFVLDYWGQGTLVTVSS | 200 |
| STLM219 | ST2H139 | EVQLLESGGGLVQPGGSLRLSCAASGFTFSGYDMFWVRQAPGKGLEWVSDIGGEGGSTNYADSVKGRFTISRDNSKNTLYLQMNSLRAEDTAVYYCARDPWSTEGSFFVLDYWGQGTLVTVSS | 201 |
| STLM220 | ST2H137 | EVQLLESGGGLVQPGGSLRLSCAASGFTFSFYDMFWVRQAPGKGLEWVSDIRGEGGTAYADSVKGRFTISRDNSKNTLYLQMNSLRAEDTAVYYCARDPWSTEGSFFVLDYWGQGTLVTVSS | 202 |
| STLM221 | ST2H136 | EVQLLESGGGLVQPGGSLRLSCAASGFTFSIYDMFWVRQAPGKGLEWVSYIRGEGGDTNYADSVKGRFTISRDNSKNTLYLQMNSLRAEDTAVYYCARDPWSTEGSFFVLDYWGQGTLVTVSS | 203 |
| STLM222 | ST2H129 | EVQLLESGGGLVQPGGSLRLSCAASGFTFSIYSMFWVRQAPGKGLEWVSDIGGEGGGTSYADSVKGRFTISRDNSKNTLYLQMNSLRAEDTAVYYCARDPWSTEGSFFVLDYWGQGTLVTVSS | 204 |

Figure 13B.

| mAb | VH ID | Sequence | SEQ ID NO: |
|---|---|---|---|
| STLM103 | ST2L32 | EIVLTQSPATLSLSPGERATLSCRASQSVDDDLAWYQQKPGQAPRLLIYDASNRATGIPARFSGSGSGTDFTLTISSLEPEDFAVYYCQQYIGAPITFGQGTKVEIK | 206 |
| STLM107 | ST2L32 | EIVLTQSPATLSLSPGERATLSCRASQSVDDDLAWYQQKPGQAPRLLIYDASNRATGIPARFSGSGSGTDFTLTISSLEPEDFAVYYCQQYIGAPITFGQGTKVEIK | 206 |
| STLM108 | ST2L32 | EIVLTQSPATLSLSPGERATLSCRASQSVDDDLAWYQQKPGQAPRLLIYDASNRATGIPARFSGSGSGTDFTLTISSLEPEDFAVYYCQQYIGAPITFGQGTKVEIK | 206 |
| STLM123 | ST2L59 | EIVLTQSPATLSLSPGERATLSCRASQSVDDDLAWYQQKPGQAPRLLIYDASNRATGIPARFSGSGSGTDFTLTISSLEPEDFAVYYCQQYITAPLTFGQGTKVEIK | 209 |
| STLM124 | ST2L59 | EIVLTQSPATLSLSPGERATLSCRASQSVDDDLAWYQQKPGQAPRLLIYDASNRATGIPARFSGSGSGTDFTLTISSLEPEDFAVYYCQQYITAPLTFGQGTKVEIK | 209 |
| STLM206 | ST2L59 | EIVLTQSPATLSLSPGERATLSCRASQSVDDDLAWYQQKPGQAPRLLIYDASNRATGIPARFSGSGSGTDFTLTISSLEPEDFAVYYCQQYITAPLTFGQGTKVEIK | 209 |
| STLM207 | ST2L59 | EIVLTQSPATLSLSPGERATLSCRASQSVDDDLAWYQQKPGQAPRLLIYDASNRATGIPARFSGSGSGTDFTLTISSLEPEDFAVYYCQQYITAPLTFGQGTKVEIK | 209 |
| STLM208 | ST2L59 | EIVLTQSPATLSLSPGERATLSCRASQSVDDDLAWYQQKPGQAPRLLIYDASNRATGIPARFSGSGSGTDFTLTISSLEPEDFAVYYCQQYITAPLTFGQGTKVEIK | 209 |
| STLM209 | ST2L59 | EIVLTQSPATLSLSPGERATLSCRASQSVDDDLAWYQQKPGQAPRLLIYDASNRATGIPARFSGSGSGTDFTLTISSLEPEDFAVYYCQQYITAPLTFGQGTKVEIK | 209 |
| STLM210 | ST2L49 | EIVLTQSPATLSLSPGERATLSCRASQSVDDDLAWYQQKPGQAPRLLIYDASNRATGIPARFSGSGSGTDFTLTISSLEPEDFAVYYCQQYNDAITFGQGTKVEIK | 208 |
| STLM211 | ST2L49 | EIVLTQSPATLSLSPGERATLSCRASQSVDDDLAWYQQKPGQAPRLLIYDASNRATGIPARFSGSGSGTDFTLTISSLEPEDFAVYYCQQYNDAITFGQGTKVEIK | 208 |
| STLM212 | ST2L49 | EIVLTQSPATLSLSPGERATLSCRASQSVDDDLAWYQQKPGQAPRLLIYDASNRATGIPARFSGSGSGTDFTLTISSLEPEDFAVYYCQQYNDAITFGQGTKVEIK | 208 |
| STLM213 | ST2L35 | EIVLTQSPATLSLSPGERATLSCRASQSVDDDLAWYQQKPGQAPRLLIYDASNRATGIPARFSGSGSGTDFTLTISSLEPEDFAVYYCQQYIDAPLTFGQGTKVEIK | 207 |
| STLM214 | ST2L35 | EIVLTQSPATLSLSPGERATLSCRASQSVDDDLAWYQQKPGQAPRLLIYDASNRATGIPARFSGSGSGTDFTLTISSLEPEDFAVYYCQQYIDAPLTFGQGTKVEIK | 207 |
| STLM215 | ST2L32 | EIVLTQSPATLSLSPGERATLSCRASQSVDDDLAWYQQKPGQAPRLLIYDASNRATGIPARFSGSGSGTDFTLTISSLEPEDFAVYYCQQYIGAPITFGQGTKVEIK | 206 |
| STLM216 | ST2L32 | EIVLTQSPATLSLSPGERATLSCRASQSVDDDLAWYQQKPGQAPRLLIYDASNRATGIPARFSGSGSGTDFTLTISSLEPEDFAVYYCQQYIGAPITFGQGTKVEIK | 206 |
| STLM217 | ST2L32 | EIVLTQSPATLSLSPGERATLSCRASQSVDDDLAWYQQKPGQAPRLLIYDASNRATGIPARFSGSGSGTDFTLTISSLEPEDFAVYYCQQYIGAPITFGQGTKVEIK | 206 |
| STLM218 | ST2L32 | EIVLTQSPATLSLSPGERATLSCRASQSVDDDLAWYQQKPGQAPRLLIYDASNRATGIPARFSGSGSGTDFTLTISSLEPEDFAVYYCQQYIGAPITFGQGTKVEIK | 206 |
| STLM219 | ST2L32 | EIVLTQSPATLSLSPGERATLSCRASQSVDDDLAWYQQKPGQAPRLLIYDASNRATGIPARFSGSGSGTDFTLTISSLEPEDFAVYYCQQYIGAPITFGQGTKVEIK | 206 |
| STLM220 | ST2L32 | EIVLTQSPATLSLSPGERATLSCRASQSVDDDLAWYQQKPGQAPRLLIYDASNRATGIPARFSGSGSGTDFTLTISSLEPEDFAVYYCQQYIGAPITFGQGTKVEIK | 206 |
| STLM221 | ST2L32 | EIVLTQSPATLSLSPGERATLSCRASQSVDDDLAWYQQKPGQAPRLLIYDASNRATGIPARFSGSGSGTDFTLTISSLEPEDFAVYYCQQYIGAPITFGQGTKVEIK | 206 |
| STLM222 | ST2L32 | EIVLTQSPATLSLSPGERATLSCRASQSVDDDLAWYQQKPGQAPRLLIYDASNRATGIPARFSGSGSGTDFTLTISSLEPEDFAVYYCQQYIGAPITFGQGTKVEIK | 206 |

```
              1         2         3         4         5         6
     1234567890123456789012345678901234567890123456789012345678901234567890
>VL2494  ETTVTQSPASLSVATGEKVTIRCITNTDIDDVIHWYQQKPGEPPKLLISEGNTLRPGVPS
Chothia                                 ---                 --------
HFA                                     ---

6         7         8         9        10
     123456789012345678901234567890123456789012345 6
>VL2494  RFSSSGYGTDFVFTIENTLSEDVADYYCLQSDNMLTFGAGTKLELK
Chothia                           ---------
HFA                               ======
```

$V_H$:

```
              1         2         3         4         5         6
     123456789012345678901234567890123456789012345678901234567890a12345
>VH2494  EVQLQQSVAELVRPGASVKLRPGASVKLSCTASAFNIKDDYMHWVKQRPEQGLEWIGRIDPAIGNTEYAPKFQD
Chothia                             -----          ---------------
HFA                                 =====          ==============

6         7         8         9        10        11
     67890123456789012abc3456789012345678901234567890ab123456789012
>VH2494  KATMTADTSSNTAYLQLSSLTSEDTAVYYCALGDFYAMDYWGQGTSVTVSS
Chothia                      --------
HFA                          ========
```

Figure 15.

| mAb | VL ID | VH ID | VL SEQ ID NO: | VH SEQ ID NO: | H-CDR1 | | H-CDR2 | | H-CDR3 | |
|---|---|---|---|---|---|---|---|---|---|---|
| | | | | | Sequence | SEQ ID NO: | Sequence | SEQ ID NO: | Sequence | SEQ ID NO: |
| STLM226 | STLL280 | STLH201 | 142 | 145 | DDYMH | 24 | RIDPAIGNTEYAEKFQG | 28 | GDFYAMAY | 146 |
| STLM227 | STLL277 | STLH201 | 140 | 145 | DDYMH | 24 | RIDPAIGNTEYAEKFQG | 28 | GDFYAMAY | 146 |
| STLM228 | STLL276 | STLH201 | 139 | 145 | DDYMH | 24 | RIDPAIGNTEYAEKFQG | 28 | GDFYAMAY | 146 |
| STLM229 | STLL275 | STLH201 | 138 | 145 | DDYMH | 24 | RIDPAIGNTEYAEKFQG | 28 | GDFYAMAY | 146 |
| STLM230 | STLL274 | STLH201 | 137 | 145 | DDYMH | 24 | RIDPAIGNTEYAEKFQG | 28 | GDFYAMAY | 146 |
| STLM231 | STLL273 | STLH201 | 136 | 145 | DDYMH | 24 | RIDPAIGNTEYAEKFQG | 28 | GDFYAMAY | 146 |
| STLM232 | STLL272 | STLH201 | 135 | 145 | DDYMH | 24 | RIDPAIGNTEYAEKFQG | 28 | GDFYAMAY | 146 |

| mAb | VL ID | VH ID | VL SEQ ID NO: | VH SEQ ID NO: | L-CDR1 | | L-CDR2 | | L-CDR3 | |
|---|---|---|---|---|---|---|---|---|---|---|
| | | | | | Sequence | SEQ ID NO: | Sequence | SEQ ID NO: | Sequence | SEQ ID NO: |
| STLM226 | STLL280 | STLH201 | 142 | 145 | ITNTDIDDVIH | 36 | EGNTLRP | 40 | LQSDNLLT | 147 |
| STLM227 | STLL277 | STLH201 | 140 | 145 | ITNTDIDDVIH | 36 | EGNTLRP | 40 | LQSDNMLT | 44 |
| STLM228 | STLL276 | STLH201 | 139 | 145 | ITNTDIDDVIH | 36 | EGNTLRP | 40 | LQSDNMLT | 44 |
| STLM229 | STLL275 | STLH201 | 138 | 145 | ITNTDIDDVIH | 36 | EGNTLRP | 40 | LQSDNMLT | 44 |
| STLM230 | STLL274 | STLH201 | 137 | 145 | ITNTDIDDVIH | 36 | EGNTLRP | 40 | LQSDNMLT | 44 |
| STLM231 | STLL273 | STLH201 | 136 | 145 | ITNTDIDDVIH | 36 | EGNTLRP | 40 | LQSDNMLT | 44 |
| STLM232 | STLL272 | STLH201 | 135 | 145 | ITNTDIDDVIH | 36 | EGNTLRP | 40 | LQSDNMLT | 44 | mAb Significance is compared to isotype control at same concentration

Figure 19.

| ST2L variant | Antibody |||||||
| | STLB206 (STLM208) ||| STLB252 |||
| | ka | kd | $K_D$ | ka | kd | $K_D$ |
| | 1/Ms | 1/s | pM | 1/Ms | 1/s | pM |
| Wild type | 1.14E+07 | 1.22E-04 | 10.8 | 8.85E+06 | 1.22E-04 | 13.8 |
| $_{18}AKF_{20}$-->TEG | 1.30E+07 | 2.29E-04 | 19.3 | 8.34E+06 | 1.93E-04 | 23.2 |
| $K_{55}E$ | 1.26E+07 | 1.29E-04 | 10 | 1.07E+07 | 1.26E-04 | 11.8 |
| $E_{61}K$ | 1.55E+07 | 1.26E-04 | 8.1 | 1.56E+07 | 1.21E-04 | 7.8 |
| $_{69}GQL_{71}$-->RDR | 1.02E+07 | 9.27E-05 | 9.6 | 8.06E+06 | 9.36E-05 | 11.6 |
| $A_{78}R$ | 1.24E+07 | 1.30E-04 | 10.4 | 1.08E+07 | 1.23E-04 | 11.4 |
| $A_{80}E$ | 1.15E+07 | 1.27E-04 | 11 | 1.13E+07 | 1.39E-04 | 12.4 |
| $_{93}TF_{94}$-->NL | 1.27E+07 | 6.25E-04 | 49.5 | 1.07E+07 | 5.22E-04 | 48.9 |
| $_{108}QSD_{110}$-->PPS | 1.28E+07 | 1.19E-04 | 10 | 8.99E+06 | 1.17E-04 | 13 |

SEQUENCE LISTING

<160> NUMBER OF SEQ ID NOS: 215

<210> SEQ ID NO 1
<211> LENGTH: 556
<212> TYPE: PRT
<213> ORGANISM: Homo sapiens

```
<400> SEQUENCE: 1

Met Gly Phe Trp Ile Leu Ala Ile Leu Thr Ile Leu Met Tyr Ser Thr
1               5                   10                  15

Ala Ala Lys Phe Ser Lys Gln Ser Trp Gly Leu Glu Asn Glu Ala Leu
            20                  25                  30

Ile Val Arg Cys Pro Arg Gln Gly Lys Pro Ser Tyr Thr Val Asp Trp
                35                  40                  45

Tyr Tyr Ser Gln Thr Asn Lys Ser Ile Pro Thr Gln Glu Arg Asn Arg
    50                  55                  60

Val Phe Ala Ser Gly Gln Leu Leu Lys Phe Leu Pro Ala Ala Val Ala
65                  70                  75                  80

Asp Ser Gly Ile Tyr Thr Cys Ile Val Arg Ser Pro Thr Phe Asn Arg
                85                  90                  95

Thr Gly Tyr Ala Asn Val Thr Ile Tyr Lys Lys Gln Ser Asp Cys Asn
                100                 105                 110

Val Pro Asp Tyr Leu Met Tyr Ser Thr Val Ser Gly Ser Glu Lys Asn
            115                 120                 125

Ser Lys Ile Tyr Cys Pro Thr Ile Asp Leu Tyr Asn Trp Thr Ala Pro
    130                 135                 140

Leu Glu Trp Phe Lys Asn Cys Gln Ala Leu Gln Gly Ser Arg Tyr Arg
145                 150                 155                 160

Ala His Lys Ser Phe Leu Val Ile Asp Asn Val Met Thr Glu Asp Ala
                165                 170                 175

Gly Asp Tyr Thr Cys Lys Phe Ile His Asn Glu Asn Gly Ala Asn Tyr
                180                 185                 190

Ser Val Thr Ala Thr Arg Ser Phe Thr Val Lys Asp Glu Gln Gly Phe
            195                 200                 205

Ser Leu Phe Pro Val Ile Gly Ala Pro Ala Gln Asn Glu Ile Lys Glu
    210                 215                 220

Val Glu Ile Gly Lys Asn Ala Asn Leu Thr Cys Ser Ala Cys Phe Gly
225                 230                 235                 240

Lys Gly Thr Gln Phe Leu Ala Ala Val Leu Trp Gln Leu Asn Gly Thr
                245                 250                 255

Lys Ile Thr Asp Phe Gly Glu Pro Arg Ile Gln Gln Glu Glu Gly Gln
                260                 265                 270

Asn Gln Ser Phe Ser Asn Gly Leu Ala Cys Leu Asp Met Val Leu Arg
            275                 280                 285

Ile Ala Asp Val Lys Glu Glu Asp Leu Leu Leu Gln Tyr Asp Cys Leu
    290                 295                 300

Ala Leu Asn Leu His Gly Leu Arg Arg His Thr Val Arg Leu Ser Arg
305                 310                 315                 320

Lys Asn Pro Ile Asp His His Ser Ile Tyr Cys Ile Ala Val Cys
                325                 330                 335

Ser Val Phe Leu Met Leu Ile Asn Val Leu Val Ile Ile Leu Lys Met
            340                 345                 350

Phe Trp Ile Glu Ala Thr Leu Leu Trp Arg Asp Ile Ala Lys Pro Tyr
    355                 360                 365

Lys Thr Arg Asn Asp Gly Lys Leu Tyr Asp Ala Tyr Val Val Tyr Pro
370                 375                 380

Arg Asn Tyr Lys Ser Ser Thr Asp Gly Ala Ser Arg Val Glu His Phe
385                 390                 395                 400

Val His Gln Ile Leu Pro Asp Val Leu Glu Asn Lys Cys Gly Tyr Thr
                405                 410                 415
```

Leu Cys Ile Tyr Gly Arg Asp Met Leu Pro Gly Glu Asp Val Val Thr
            420                 425                 430

Ala Val Glu Thr Asn Ile Arg Lys Ser Arg Arg His Ile Phe Ile Leu
435                 440                 445

Thr Pro Gln Ile Thr His Asn Lys Glu Phe Ala Tyr Glu Gln Glu Val
    450                 455                 460

Ala Leu His Cys Ala Leu Ile Gln Asn Asp Ala Lys Val Ile Leu Ile
465                 470                 475                 480

Glu Met Glu Ala Leu Ser Glu Leu Asp Met Leu Gln Ala Glu Ala Leu
                485                 490                 495

Gln Asp Ser Leu Gln His Leu Met Lys Val Gln Gly Thr Ile Lys Trp
            500                 505                 510

Arg Glu Asp His Ile Ala Asn Lys Arg Ser Leu Asn Ser Lys Phe Trp
        515                 520                 525

Lys His Val Arg Tyr Gln Met Pro Val Pro Ser Lys Ile Pro Arg Lys
    530                 535                 540

Ala Ser Ser Leu Thr Pro Leu Ala Ala Gln Lys Gln
545                 550                 555

<210> SEQ ID NO 2
<211> LENGTH: 556
<212> TYPE: PRT
<213> ORGANISM: Macaca fascicularis

<400> SEQUENCE: 2

Met Gly Leu Trp Ile Leu Ala Ile Leu Thr Ile Leu Val Tyr Ser Thr
1               5                   10                  15

Ala Ala Lys Phe Ser Lys Gln Ser Trp Gly Leu Glu Asn Glu Ala Leu
            20                  25                  30

Ile Val Arg Cys Pro Arg Gln Gly Lys Ser Ser Tyr Ile Val Asp Trp
        35                  40                  45

Tyr Tyr Ser Gln Thr Asn Lys Ser Ile Pro Thr Gln Glu Arg Asn Arg
    50                  55                  60

Val Phe Ala Ser Gly Gln Leu Leu Lys Phe Leu Pro Ala Glu Val Ala
65                  70                  75                  80

Asp Ser Gly Ile Tyr Thr Cys Ile Val Arg Ser Pro Thr Phe Asn Arg
                85                  90                  95

Thr Gly Tyr Ala Asn Val Thr Ile Tyr Lys Lys Gln Pro Asp Cys Asn
            100                 105                 110

Val Pro Asp Tyr Leu Met Tyr Ser Thr Val Ser Gly Ser Glu Lys Asn
        115                 120                 125

Ser Lys Ile Tyr Cys Pro Thr Ile Asp Leu Tyr Asn Trp Thr Ala Pro
    130                 135                 140

Leu Glu Trp Phe Lys Asn Cys Gln Ala Leu Gln Gly Ser Arg Tyr Lys
145                 150                 155                 160

Ala His Lys Ser Phe Leu Val Ile Asp Asn Val Met Thr Asp Asp Ala
                165                 170                 175

Gly Asp Tyr Thr Cys Lys Phe Ile His Asn Glu Asn Gly Ala Asn Tyr
            180                 185                 190

Ser Val Thr Ala Thr Arg Ser Phe Thr Val Lys Asp Glu Gln Gly Phe
        195                 200                 205

Ser Leu Phe Pro Val Ile Arg Ala Pro Ala His Asn Glu Thr Lys Glu
    210                 215                 220

Val Glu Ile Gly Glu Asn Thr Asn Leu Thr Cys Ser Ala Cys Phe Gly

```
                     225                 230                 235                 240

Lys Gly Ala Gln Phe Leu Ala Thr Val Gln Trp Gln Leu Asn Gly Asn
                         245                 250                 255

Lys Ile Thr Asp Phe Ser Glu Pro Arg Ile Gln Gln Glu Glu Gly Gln
                         260                 265                 270

Asn Gln Ser Phe Ser Asn Gly Leu Ala Cys Val Asn Thr Val Leu Arg
                         275                 280                 285

Ile Ala Asp Val Lys Glu Glu Asp Leu Leu Arg Tyr Asp Cys Leu
                290                 295                 300

Ala Leu Asn Leu His Gly Leu Arg Arg His Thr Ile Arg Leu Ser Arg
        305                 310                 315                 320

Lys Asn Pro Ile Asp His Gln Ser Thr Tyr Cys Ile Ala Val Cys
                            325                 330                 335

Ser Val Leu Leu Met Leu Ile Asn Val Leu Val Ile Ile Leu Lys Thr
                        340                 345                 350

Phe Trp Ile Glu Ala Thr Leu Leu Trp Arg Asp Ile Ala Lys Pro Tyr
                        355                 360                 365

Lys Thr Arg Asn Asp Gly Lys Leu Tyr Asp Ala Tyr Val Ile Tyr Pro
                370                 375                 380

Arg Asn Tyr Thr Ser Ser Thr Asp Gly Ala Ser Arg Val Glu Tyr Phe
        385                 390                 395                 400

Val His Gln Ile Leu Pro Asp Val Leu Glu Asn Lys Cys Gly Tyr Thr
                        405                 410                 415

Leu Cys Ile Tyr Gly Arg Asp Met Leu Pro Gly Glu Asp Val Val Thr
                        420                 425                 430

Ala Val Glu Thr Asn Ile Arg Lys Ser Arg Arg His Ile Phe Ile Leu
                        435                 440                 445

Thr Pro Gln Ile Thr His Asn Glu Glu Phe Ala Tyr Glu Gln Glu Val
                    450                 455                 460

Ala Leu His Ser Ala Leu Ile Gln Asn Asp Ser Lys Val Ile Leu Ile
        465                 470                 475                 480

Glu Met Glu Ala Leu Ser Glu Leu Asp Met Leu Gln Ala Glu Ala Leu
                        485                 490                 495

Gln Asp Ser Leu Arg His Leu Met Glu Val Gln Gly Thr Ile Lys Trp
                        500                 505                 510

Arg Glu Asp His Val Ala Asn Lys Arg Ser Leu Asn Ser Lys Phe Trp
                        515                 520                 525

Lys His Val Arg Tyr Gln Met Pro Val Pro Ser Lys Met Pro Arg Lys
                    530                 535                 540

Ala Ser Ser Leu Thr Ser Leu Ala Ala Gln Lys Gln
        545                 550                 555

<210> SEQ ID NO 3
<211> LENGTH: 270
<212> TYPE: PRT
<213> ORGANISM: Homo sapiens

<400> SEQUENCE: 3

Met Lys Pro Lys Met Lys Tyr Ser Thr Asn Lys Ile Ser Thr Ala Lys
        1               5                   10                  15

Trp Lys Asn Thr Ala Ser Lys Ala Leu Cys Phe Lys Leu Gly Lys Ser
                        20                  25                  30

Gln Gln Lys Ala Lys Glu Val Cys Pro Met Tyr Phe Met Lys Leu Arg
                    35                  40                  45
```

```
Ser Gly Leu Met Ile Lys Lys Glu Ala Cys Tyr Phe Arg Arg Glu Thr
    50                  55                  60
Thr Lys Arg Pro Ser Leu Lys Thr Gly Arg Lys His Lys Arg His Leu
65                  70                  75                  80
Val Leu Ala Ala Cys Gln Gln Gln Ser Thr Val Glu Cys Phe Ala Phe
                85                  90                  95
Gly Ile Ser Gly Val Gln Lys Tyr Thr Arg Ala Leu His Asp Ser Ser
                100                 105                 110
Ile Thr Gly Ile Ser Pro Ile Thr Glu Tyr Leu Ala Ser Leu Ser Thr
                115                 120                 125
Tyr Asn Asp Gln Ser Ile Thr Phe Ala Leu Glu Asp Glu Ser Tyr Glu
    130                 135                 140
Ile Tyr Val Glu Asp Leu Lys Lys Asp Glu Lys Lys Asp Lys Val Leu
145                 150                 155                 160
Leu Ser Tyr Tyr Glu Ser Gln His Pro Ser Asn Glu Ser Gly Asp Gly
                165                 170                 175
Val Asp Gly Lys Met Leu Met Val Thr Leu Ser Pro Thr Lys Asp Phe
                180                 185                 190
Trp Leu His Ala Asn Asn Lys Glu His Ser Val Glu Leu His Lys Cys
                195                 200                 205
Glu Lys Pro Leu Pro Asp Gln Ala Phe Phe Val Leu His Asn Met His
    210                 215                 220
Ser Asn Cys Val Ser Phe Glu Cys Lys Thr Asp Pro Gly Val Phe Ile
225                 230                 235                 240
Gly Val Lys Asp Asn His Leu Ala Leu Ile Lys Val Asp Ser Ser Glu
                245                 250                 255
Asn Leu Cys Thr Glu Asn Ile Leu Phe Lys Leu Ser Glu Thr
                260                 265                 270

<210> SEQ ID NO 4
<211> LENGTH: 269
<212> TYPE: PRT
<213> ORGANISM: Macaca fascicularis

<400> SEQUENCE: 4

Met Lys Pro Lys Met Lys Tyr Ser Thr Asn Lys Ile Ser Thr Ala Lys
1               5                   10                  15
Arg Lys Asn Thr Ala Ser Lys Ala Leu Cys Phe Lys Leu Gly Lys Ser
                20                  25                  30
Gln Gln Lys Ala Lys Glu Val Cys His Val Tyr Phe Met Lys Leu Arg
                35                  40                  45
Ser Gly Leu Met Ile Lys Lys Glu Ala Cys Tyr Phe Arg Arg Glu Thr
    50                  55                  60
Thr Lys Arg Pro Ser Leu Lys Thr Gly Gly Lys His Lys Gly His Leu
65                  70                  75                  80
Val Leu Ala Ala Cys Gln Gln Gln Ser Thr Val Glu Cys Phe Ala Phe
                85                  90                  95
Gly Ile Ser Gly Val Pro Lys Tyr Thr Arg Ala Leu His Asp Ser Ser
                100                 105                 110
Ile Thr Gly Ile Ser Pro Ile Thr Glu Ser Leu Ala Ser Leu Ser Thr
                115                 120                 125
Tyr Asn Asp Gln Ser Ile Thr Phe Ala Leu Glu Asp Glu Ser Tyr Glu
    130                 135                 140
Ile Tyr Val Glu Asp Leu Lys Lys Asp Lys Lys Lys Asp Lys Val Leu
145                 150                 155                 160
```

```
Leu Ser Tyr Tyr Glu Ser Gln His Pro Ser Glu Ser Gly Asp Gly
            165                 170                 175

Val Asp Gly Lys Met Leu Met Val Thr Leu Ser Pro Thr Lys Asp Phe
        180                 185                 190

Trp Leu Gln Ala Asn Asn Lys Glu His Ser Val Glu Leu His Lys Cys
        195                 200                 205

Glu Lys Pro Leu Pro Asp Gln Ala Phe Phe Val Leu His Asn Arg Ser
    210                 215                 220

Phe Asn Cys Val Ser Phe Glu Cys Lys Thr Asp Pro Gly Val Phe Ile
225                 230                 235                 240

Gly Val Lys Asp Asn His Leu Ala Leu Ile Lys Val Asp Tyr Ser Glu
                245                 250                 255

Asn Leu Gly Ser Glu Asn Ile Leu Phe Lys Leu Ser Glu
            260                 265

<210> SEQ ID NO 5
<211> LENGTH: 567
<212> TYPE: PRT
<213> ORGANISM: Mus musculus

<400> SEQUENCE: 5

Met Ile Asp Arg Gln Arg Met Gly Leu Trp Ala Leu Ala Ile Leu Thr
1               5                   10                  15

Leu Pro Met Tyr Leu Thr Val Thr Glu Gly Ser Lys Ser Ser Trp Gly
            20                  25                  30

Leu Glu Asn Glu Ala Leu Ile Val Arg Cys Pro Gln Arg Gly Arg Ser
        35                  40                  45

Thr Tyr Pro Val Glu Trp Tyr Tyr Ser Asp Thr Asn Glu Ser Ile Pro
    50                  55                  60

Thr Gln Lys Arg Asn Arg Ile Phe Val Ser Arg Asp Arg Leu Lys Phe
65                  70                  75                  80

Leu Pro Ala Arg Val Glu Asp Ser Gly Ile Tyr Ala Cys Val Ile Arg
                85                  90                  95

Ser Pro Asn Leu Asn Lys Thr Gly Tyr Leu Asn Val Thr Ile His Lys
            100                 105                 110

Lys Pro Pro Ser Cys Asn Ile Pro Asp Tyr Leu Met Tyr Ser Thr Val
        115                 120                 125

Arg Gly Ser Asp Lys Asn Phe Lys Ile Thr Cys Pro Thr Ile Asp Leu
    130                 135                 140

Tyr Asn Trp Thr Ala Pro Val Gln Trp Phe Lys Asn Cys Lys Ala Leu
145                 150                 155                 160

Gln Glu Pro Arg Phe Arg Ala His Arg Ser Tyr Leu Phe Ile Asp Asn
                165                 170                 175

Val Thr His Asp Asp Glu Gly Asp Tyr Thr Cys Gln Phe Thr His Ala
            180                 185                 190

Glu Asn Gly Thr Asn Tyr Ile Val Thr Ala Thr Arg Ser Phe Thr Val
        195                 200                 205

Glu Glu Lys Gly Phe Ser Met Phe Pro Val Ile Thr Asn Pro Pro Tyr
    210                 215                 220

Asn His Thr Met Glu Val Glu Ile Gly Lys Pro Ala Ser Ile Ala Cys
225                 230                 235                 240

Ser Ala Cys Phe Gly Lys Gly Ser His Phe Leu Ala Asp Val Leu Trp
                245                 250                 255

Gln Ile Asn Lys Thr Val Val Gly Asn Phe Gly Glu Ala Arg Ile Gln
```

```
                260                 265                 270
Glu Glu Glu Gly Arg Asn Glu Ser Ser Asn Asp Met Asp Cys Leu
            275                 280                 285

Thr Ser Val Leu Arg Ile Thr Gly Val Thr Glu Lys Asp Leu Ser Leu
        290                 295                 300

Glu Tyr Asp Cys Leu Ala Leu Asn Leu His Gly Met Ile Arg His Thr
305                 310                 315                 320

Ile Arg Leu Arg Arg Lys Gln Pro Ile Asp His Arg Ser Ile Tyr Tyr
                325                 330                 335

Ile Val Ala Gly Cys Ser Leu Leu Met Phe Ile Asn Val Leu Val
            340                 345                 350

Ile Val Leu Lys Val Phe Trp Ile Glu Val Ala Leu Phe Trp Arg Asp
        355                 360                 365

Ile Val Thr Pro Tyr Lys Thr Arg Asn Asp Gly Lys Leu Tyr Asp Ala
370                 375                 380

Tyr Ile Ile Tyr Pro Arg Val Phe Arg Gly Ser Ala Ala Gly Thr His
385                 390                 395                 400

Ser Val Glu Tyr Phe Val His His Thr Leu Pro Asp Val Leu Glu Asn
                405                 410                 415

Lys Cys Gly Tyr Lys Leu Cys Ile Tyr Gly Arg Asp Leu Leu Pro Gly
            420                 425                 430

Gln Asp Ala Ala Thr Val Val Glu Ser Ser Ile Gln Asn Ser Arg Arg
        435                 440                 445

Gln Val Phe Val Leu Ala Pro His Met Met His Ser Lys Glu Phe Ala
    450                 455                 460

Tyr Glu Gln Glu Ile Ala Leu His Ser Ala Leu Ile Gln Asn Asn Ser
465                 470                 475                 480

Lys Val Ile Leu Ile Glu Met Glu Pro Leu Gly Glu Ala Ser Arg Leu
                485                 490                 495

Gln Val Gly Asp Leu Gln Asp Ser Leu Gln His Leu Val Lys Ile Gln
            500                 505                 510

Gly Thr Ile Lys Trp Arg Glu Asp His Val Ala Asp Lys Gln Ser Leu
        515                 520                 525

Ser Ser Lys Phe Trp Lys His Val Arg Tyr Gln Met Pro Val Pro Glu
    530                 535                 540

Arg Ala Ser Lys Thr Ala Ser Val Ala Ala Pro Leu Ser Gly Lys Ala
545                 550                 555                 560

Cys Leu Asp Leu Lys His Phe
                565

<210> SEQ ID NO 6
<211> LENGTH: 300
<212> TYPE: PRT
<213> ORGANISM: Artificial sequence
<220> FEATURE:
<223> OTHER INFORMATION: ST2L human mouse chimera HHM

<400> SEQUENCE: 6

Lys Phe Ser Lys Gln Ser Trp Gly Leu Glu Asn Glu Ala Leu Ile Val
1               5                   10                  15

Arg Cys Pro Arg Gln Gly Lys Pro Ser Tyr Thr Val Asp Trp Tyr Tyr
                20                  25                  30

Ser Gln Thr Asn Lys Ser Ile Pro Thr Gln Glu Arg Asn Arg Val Phe
            35                  40                  45

Ala Ser Gly Gln Leu Leu Lys Phe Leu Pro Ala Ala Val Ala Asp Ser
```

```
            50                  55                  60
Gly Ile Tyr Thr Cys Ile Val Arg Ser Pro Thr Phe Asn Arg Thr Gly
 65                  70                  75                  80

Tyr Ala Asn Val Thr Ile Tyr Lys Lys Gln Ser Asp Cys Asn Val Pro
                 85                  90                  95

Asp Tyr Leu Met Tyr Ser Thr Val Ser Gly Ser Glu Lys Asn Ser Lys
                100                 105                 110

Ile Tyr Cys Pro Thr Ile Asp Leu Tyr Asn Trp Thr Ala Pro Leu Glu
            115                 120                 125

Trp Phe Lys Asn Cys Gln Ala Leu Gln Gly Ser Arg Tyr Arg Ala His
        130                 135                 140

Lys Ser Phe Leu Val Ile Asp Asn Val Met Thr Glu Asp Ala Gly Asp
145                 150                 155                 160

Tyr Thr Cys Lys Phe Ile His Asn Glu Asn Gly Ala Asn Tyr Ser Val
                165                 170                 175

Thr Ala Thr Arg Ser Phe Thr Val Glu Glu Lys Gly Phe Ser Met Phe
                180                 185                 190

Pro Val Ile Thr Asn Pro Pro Tyr Asn His Thr Met Glu Val Glu Ile
            195                 200                 205

Gly Lys Pro Ala Ser Ile Ala Cys Ser Ala Cys Phe Gly Lys Gly Ser
        210                 215                 220

His Phe Leu Ala Asp Val Leu Trp Gln Ile Asn Lys Thr Val Val Gly
225                 230                 235                 240

Asn Phe Gly Glu Ala Arg Ile Gln Glu Glu Gly Arg Asn Glu Ser
                245                 250                 255

Ser Ser Asn Asp Met Asp Cys Leu Thr Ser Val Leu Arg Ile Thr Gly
            260                 265                 270

Val Thr Glu Lys Asp Leu Ser Leu Glu Tyr Asp Cys Leu Ala Leu Asn
                275                 280                 285

Leu His Gly Met Ile Arg His Thr Ile Arg Leu Arg
        290                 295                 300

<210> SEQ ID NO 7
<211> LENGTH: 297
<212> TYPE: PRT
<213> ORGANISM: Artificial sequence
<220> FEATURE:
<223> OTHER INFORMATION: ST2L human-mouse chimera MHM

<400> SEQUENCE: 7

Lys Ser Ser Trp Gly Leu Glu Asn Glu Ala Leu Ile Val Arg Cys Pro
 1               5                  10                  15

Gln Arg Gly Arg Ser Thr Tyr Pro Val Glu Trp Tyr Tyr Ser Asp Thr
                20                  25                  30

Asn Glu Ser Ile Pro Thr Gln Lys Arg Asn Arg Ile Phe Val Ser Arg
            35                  40                  45

Asp Arg Leu Lys Phe Leu Pro Ala Arg Val Glu Asp Ser Gly Ile Tyr
        50                  55                  60

Ala Cys Val Ile Arg Ser Pro Asn Leu Asn Lys Thr Gly Tyr Leu Asn
 65                  70                  75                  80

Val Thr Ile His Lys Lys Pro Pro Ser Cys Asn Ile Pro Asp Tyr Leu
                85                  90                  95

Met Tyr Ser Thr Val Ser Gly Ser Glu Lys Asn Ser Lys Ile Tyr Cys
                100                 105                 110

Pro Thr Ile Asp Leu Tyr Asn Trp Thr Ala Pro Leu Glu Trp Phe Lys
```

```
            115                 120                 125
Asn Cys Gln Ala Leu Gln Gly Ser Arg Tyr Arg Ala His Lys Ser Phe
            130                 135                 140

Leu Val Ile Asp Asn Val Met Thr Glu Asp Ala Gly Asp Tyr Thr Cys
145                 150                 155                 160

Lys Phe Ile His Asn Glu Asn Gly Ala Asn Tyr Ser Val Thr Ala Thr
                165                 170                 175

Arg Ser Phe Thr Val Glu Glu Lys Gly Phe Ser Met Phe Pro Val Ile
                180                 185                 190

Thr Asn Pro Pro Tyr Asn His Thr Met Glu Val Glu Ile Gly Lys Pro
            195                 200                 205

Ala Ser Ile Ala Cys Ser Ala Cys Phe Gly Lys Gly Ser His Phe Leu
        210                 215                 220

Ala Asp Val Leu Trp Gln Ile Asn Lys Thr Val Val Gly Asn Phe Gly
225                 230                 235                 240

Glu Ala Arg Ile Gln Glu Glu Gly Arg Asn Glu Ser Ser Ser Asn
                245                 250                 255

Asp Met Asp Cys Leu Thr Ser Val Leu Arg Ile Thr Gly Val Thr Glu
                260                 265                 270

Lys Asp Leu Ser Leu Glu Tyr Asp Cys Leu Ala Leu Asn Leu His Gly
            275                 280                 285

Met Ile Arg His Thr Ile Arg Leu Arg
            290                 295

<210> SEQ ID NO 8
<211> LENGTH: 303
<212> TYPE: PRT
<213> ORGANISM: Artificial sequence
<220> FEATURE:
<223> OTHER INFORMATION: ST2L human-mouse chimera HMH

<400> SEQUENCE: 8

Lys Phe Ser Lys Gln Ser Trp Gly Leu Glu Asn Glu Ala Leu Ile Val
1               5                   10                  15

Arg Cys Pro Arg Gln Gly Lys Pro Ser Tyr Thr Val Asp Trp Tyr Tyr
            20                  25                  30

Ser Gln Thr Asn Lys Ser Ile Pro Thr Gln Glu Arg Asn Arg Val Phe
        35                  40                  45

Ala Ser Gly Gln Leu Leu Lys Phe Leu Pro Ala Ala Val Ala Asp Ser
    50                  55                  60

Gly Ile Tyr Thr Cys Ile Val Arg Ser Pro Thr Phe Asn Arg Thr Gly
65                  70                  75                  80

Tyr Ala Asn Val Thr Ile Tyr Lys Lys Gln Ser Asp Cys Asn Val Pro
                85                  90                  95

Asp Tyr Leu Met Tyr Ser Thr Val Arg Gly Ser Asp Lys Asn Phe Lys
            100                 105                 110

Ile Thr Cys Pro Thr Ile Asp Leu Tyr Asn Trp Thr Ala Pro Val Gln
        115                 120                 125

Trp Phe Lys Asn Cys Lys Ala Leu Gln Glu Pro Arg Phe Arg Ala His
    130                 135                 140

Arg Ser Tyr Leu Phe Ile Asp Asn Val Thr His Asp Asp Glu Gly Asp
145                 150                 155                 160

Tyr Thr Cys Gln Phe Thr His Ala Glu Asn Gly Thr Asn Tyr Ile Val
                165                 170                 175

Thr Ala Thr Arg Ser Phe Thr Val Lys Asp Glu Gln Gly Phe Ser Leu
```

```
                180                 185                 190
        Phe Pro Val Ile Gly Ala Pro Ala Gln Asn Glu Ile Lys Glu Val Glu
                    195                 200                 205

Ile Gly Lys Asn Ala Asn Leu Thr Cys Ser Ala Cys Phe Gly Lys Gly
            210                 215                 220

Thr Gln Phe Leu Ala Ala Val Leu Trp Gln Leu Asn Gly Thr Lys Ile
        225                 230                 235                 240

Thr Asp Phe Gly Glu Pro Arg Ile Gln Gln Glu Glu Gly Gln Asn Gln
                        245                 250                 255

Ser Phe Ser Asn Gly Leu Ala Cys Leu Asp Met Val Leu Arg Ile Ala
                    260                 265                 270

Asp Val Lys Glu Glu Asp Leu Leu Leu Gln Tyr Asp Cys Leu Ala Leu
                275                 280                 285

Asn Leu His Gly Leu Arg Arg His Thr Val Arg Leu Ser Arg Lys
            290                 295                 300

<210> SEQ ID NO 9
<211> LENGTH: 104
<212> TYPE: PRT
<213> ORGANISM: Homo sapiens

<400> SEQUENCE: 9

Lys Phe Ser Lys Gln Ser Trp Gly Leu Glu Asn Glu Ala Leu Ile Val
1               5                   10                  15

Arg Cys Pro Arg Gln Gly Lys Pro Ser Tyr Thr Val Asp Trp Tyr Tyr
                20                  25                  30

Ser Gln Thr Asn Lys Ser Ile Pro Thr Gln Glu Arg Asn Arg Val Phe
            35                  40                  45

Ala Ser Gly Gln Leu Leu Lys Phe Leu Pro Ala Ala Val Ala Asp Ser
        50                  55                  60

Gly Ile Tyr Thr Cys Ile Val Arg Ser Pro Thr Phe Asn Arg Thr Gly
65                  70                  75                  80

Tyr Ala Asn Val Thr Ile Tyr Lys Lys Gln Ser Asp Cys Asn Val Pro
                85                  90                  95

Asp Tyr Leu Met Tyr Ser Thr Val
            100

<210> SEQ ID NO 10
<211> LENGTH: 80
<212> TYPE: PRT
<213> ORGANISM: Homo sapiens

<400> SEQUENCE: 10

Ser Gly Ser Glu Lys Asn Ser Lys Ile Tyr Cys Pro Thr Ile Asp Leu
1               5                   10                  15

Tyr Asn Trp Thr Ala Pro Leu Glu Trp Phe Lys Asn Cys Gln Ala Leu
                20                  25                  30

Gln Gly Ser Arg Tyr Arg Ala His Lys Ser Phe Leu Val Ile Asp Asn
            35                  40                  45

Val Met Thr Glu Asp Ala Gly Asp Tyr Thr Cys Lys Phe Ile His Asn
        50                  55                  60

Glu Asn Gly Ala Asn Tyr Ser Val Thr Ala Thr Arg Ser Phe Thr Val
65                  70                  75                  80

<210> SEQ ID NO 11
<211> LENGTH: 116
<212> TYPE: PRT
```

<213> ORGANISM: Homo sapiens

<400> SEQUENCE: 11

Ser Leu Phe Pro Val Ile Gly Ala Pro Ala Gln Asn Glu Ile Lys Glu
1               5                   10                  15

Val Glu Ile Gly Lys Asn Ala Asn Leu Thr Cys Ser Ala Cys Phe Gly
            20                  25                  30

Lys Gly Thr Gln Phe Leu Ala Ala Val Leu Trp Gln Leu Asn Gly Thr
        35                  40                  45

Lys Ile Thr Asp Phe Gly Glu Pro Arg Ile Gln Gln Glu Glu Gly Gln
    50                  55                  60

Asn Gln Ser Phe Ser Asn Gly Leu Ala Cys Leu Asp Met Val Leu Arg
65                  70                  75                  80

Ile Ala Asp Val Lys Glu Glu Asp Leu Leu Leu Gln Tyr Asp Cys Leu
                85                  90                  95

Ala Leu Asn Leu His Gly Leu Arg Arg His Thr Val Arg Leu Ser Arg
            100                 105                 110

Lys Asn Pro Ile
        115

<210> SEQ ID NO 12
<211> LENGTH: 101
<212> TYPE: PRT
<213> ORGANISM: Homo sapiens

<400> SEQUENCE: 12

Lys Ser Ser Trp Gly Leu Glu Asn Glu Ala Leu Ile Val Arg Cys Pro
1               5                   10                  15

Gln Arg Gly Arg Ser Thr Tyr Pro Val Glu Trp Tyr Tyr Ser Asp Thr
            20                  25                  30

Asn Glu Ser Ile Pro Thr Gln Lys Arg Asn Arg Ile Phe Val Ser Arg
        35                  40                  45

Asp Arg Leu Lys Phe Leu Pro Ala Arg Val Glu Asp Ser Gly Ile Tyr
    50                  55                  60

Ala Cys Val Ile Arg Ser Pro Asn Leu Asn Lys Thr Gly Tyr Leu Asn
65                  70                  75                  80

Val Thr Ile His Lys Lys Pro Pro Ser Cys Asn Ile Pro Asp Tyr Leu
                85                  90                  95

Met Tyr Ser Thr Val
            100

<210> SEQ ID NO 13
<211> LENGTH: 5
<212> TYPE: PRT
<213> ORGANISM: Mus musculus

<400> SEQUENCE: 13

His Tyr Gly Met Ala
1               5

<210> SEQ ID NO 14
<211> LENGTH: 17
<212> TYPE: PRT
<213> ORGANISM: Mus musculus

<400> SEQUENCE: 14

Ser Ile Ile Thr Asp Gly Thr Ser Thr Tyr Tyr Arg Asp Ser Val Lys
1               5                   10                  15

Gly

<210> SEQ ID NO 15
<211> LENGTH: 8
<212> TYPE: PRT
<213> ORGANISM: Mus musculus

<400> SEQUENCE: 15

Gln Ser Asp Asp Tyr Phe Asp Tyr
1               5

<210> SEQ ID NO 16
<211> LENGTH: 16
<212> TYPE: PRT
<213> ORGANISM: Mus musculus

<400> SEQUENCE: 16

Lys Ser Ser Gln Ser Leu Glu Tyr Ser Asp Gly Asp Ser Tyr Leu Glu
1               5                   10                  15

<210> SEQ ID NO 17
<211> LENGTH: 7
<212> TYPE: PRT
<213> ORGANISM: Mus musculus

<400> SEQUENCE: 17

Gly Val Ser Asn Arg Phe Ser
1               5

<210> SEQ ID NO 18
<211> LENGTH: 9
<212> TYPE: PRT
<213> ORGANISM: Mus musculus

<400> SEQUENCE: 18

Phe Gln Ala Thr His Asp Pro Phe Thr
1               5

<210> SEQ ID NO 19
<211> LENGTH: 117
<212> TYPE: PRT
<213> ORGANISM: Mus musculus

<400> SEQUENCE: 19

Glu Val Gln Leu Val Glu Ser Gly Gly Gly Leu Leu Gln Pro Gly Arg
1               5                   10                  15

Ser Leu Lys Leu Ser Cys Thr Ala Ser Gly Phe Ile Phe Ser His Tyr
            20                  25                  30

Gly Met Ala Trp Val Arg Gln Ala Pro Thr Lys Gly Leu Glu Trp Val
        35                  40                  45

Ser Ser Ile Ile Thr Asp Gly Thr Ser Thr Tyr Tyr Arg Asp Ser Val
    50                  55                  60

Lys Gly Arg Phe Thr Ile Ser Arg Asp Asn Ala Lys Asn Thr Gln Tyr
65                  70                  75                  80

Leu Gln Met Asp Ser Leu Arg Ser Glu Asp Thr Ala Thr Tyr Tyr Cys
                85                  90                  95

Ala Arg Gln Ser Asp Asp Tyr Phe Asp Tyr Trp Gly Gln Gly Val Met
            100                 105                 110

Val Thr Val Ser Ser
        115

```
<210> SEQ ID NO 20
<211> LENGTH: 112
<212> TYPE: PRT
<213> ORGANISM: Mus musculus

<400> SEQUENCE: 20

Asp Val Val Leu Thr Gln Thr Pro Val Ser Leu Ser Val Thr Leu Gly
1               5                  10                  15

Asp Gln Ala Ser Ile Ser Cys Lys Ser Ser Gln Ser Leu Glu Tyr Ser
            20                  25                  30

Asp Gly Asp Ser Tyr Leu Glu Trp Tyr Leu Gln Lys Pro Gly Gln Ser
        35                  40                  45

Pro Gln Leu Leu Ile Tyr Gly Val Ser Asn Arg Phe Ser Gly Val Pro
    50                  55                  60

Asp Arg Phe Ile Gly Ser Gly Ser Gly Thr Asp Phe Thr Leu Lys Ile
65                  70                  75                  80

Ser Arg Val Glu Pro Glu Asp Leu Gly Val Tyr Tyr Cys Phe Gln Ala
                85                  90                  95

Thr His Asp Pro Phe Thr Phe Gly Ser Gly Thr Lys Leu Glu Ile Lys
            100                 105                 110

<210> SEQ ID NO 21
<211> LENGTH: 5
<212> TYPE: PRT
<213> ORGANISM: Mus musculus

<400> SEQUENCE: 21

Asp Tyr Asn Met Asn
1               5

<210> SEQ ID NO 22
<211> LENGTH: 5
<212> TYPE: PRT
<213> ORGANISM: Mus musculus

<400> SEQUENCE: 22

Thr Tyr Trp Met Asn
1               5

<210> SEQ ID NO 23
<211> LENGTH: 6
<212> TYPE: PRT
<213> ORGANISM: Mus musculus

<400> SEQUENCE: 23

Ser Asp Tyr Ala Trp Asn
1               5

<210> SEQ ID NO 24
<211> LENGTH: 5
<212> TYPE: PRT
<213> ORGANISM: Mus musculus

<400> SEQUENCE: 24

Asp Asp Tyr Met His
1               5

<210> SEQ ID NO 25
<211> LENGTH: 17
<212> TYPE: PRT
<213> ORGANISM: Mus musculus

<400> SEQUENCE: 25
```

```
Asn Ile Asn Pro Tyr Tyr Gly Ser Thr Thr Tyr Asn Gln Lys Phe Lys
1               5                   10                  15
Gly

<210> SEQ ID NO 26
<211> LENGTH: 17
<212> TYPE: PRT
<213> ORGANISM: Mus musculus

<400> SEQUENCE: 26

Gln Ile Phe Pro Ala Ser Gly Ser Thr Tyr Tyr Asn Glu Met Phe Lys
1               5                   10                  15
Asp

<210> SEQ ID NO 27
<211> LENGTH: 16
<212> TYPE: PRT
<213> ORGANISM: Mus musculus

<400> SEQUENCE: 27

Phe Ile Ser Tyr Ser Gly Asp Thr Ser Phe Asn Pro Ser Leu Lys Ser
1               5                   10                  15

<210> SEQ ID NO 28
<211> LENGTH: 17
<212> TYPE: PRT
<213> ORGANISM: Mus musculus

<400> SEQUENCE: 28

Arg Ile Asp Pro Ala Ile Gly Asn Thr Glu Tyr Ala Pro Lys Phe Gln
1               5                   10                  15
Asp

<210> SEQ ID NO 29
<211> LENGTH: 11
<212> TYPE: PRT
<213> ORGANISM: Mus musculus

<400> SEQUENCE: 29

Glu Gly Asp Thr Tyr Leu Ala Trp Phe Ala Tyr
1               5                   10

<210> SEQ ID NO 30
<211> LENGTH: 15
<212> TYPE: PRT
<213> ORGANISM: Mus musculus

<400> SEQUENCE: 30

Ser Glu Asn Ile Tyr Tyr Ile Asn Phe Gln Tyr Tyr Phe Ala Tyr
1               5                   10                  15

<210> SEQ ID NO 31
<211> LENGTH: 8
<212> TYPE: PRT
<213> ORGANISM: Mus musculus

<400> SEQUENCE: 31

Tyr Asp Gly Tyr Ser Phe Asp Tyr
1               5

<210> SEQ ID NO 32
<211> LENGTH: 8
```

<212> TYPE: PRT
<213> ORGANISM: Mus musculus

<400> SEQUENCE: 32

Gly Asp Phe Tyr Ala Met Asp Tyr
1               5

<210> SEQ ID NO 33
<211> LENGTH: 16
<212> TYPE: PRT
<213> ORGANISM: Mus musculus

<400> SEQUENCE: 33

Arg Ser Ser Gln Ser Ile Val Tyr Ser Asn Gly Asn Thr Tyr Leu Glu
1               5                   10                  15

<210> SEQ ID NO 34
<211> LENGTH: 11
<212> TYPE: PRT
<213> ORGANISM: Mus musculus

<400> SEQUENCE: 34

Arg Ala Ser Gln Asn Ile Gly Thr Arg Met His
1               5                   10

<210> SEQ ID NO 35
<211> LENGTH: 15
<212> TYPE: PRT
<213> ORGANISM: Mus musculus

<400> SEQUENCE: 35

Arg Ala Ser Lys Ser Val Ser Thr Ser Gly Ser Ser Tyr Met Phe
1               5                   10                  15

<210> SEQ ID NO 36
<211> LENGTH: 11
<212> TYPE: PRT
<213> ORGANISM: Mus musculus

<400> SEQUENCE: 36

Ile Thr Asn Thr Asp Ile Asp Asp Val Ile His
1               5                   10

<210> SEQ ID NO 37
<211> LENGTH: 7
<212> TYPE: PRT
<213> ORGANISM: Mus musculus

<400> SEQUENCE: 37

Lys Val Ser Asn Arg Phe Ser
1               5

<210> SEQ ID NO 38
<211> LENGTH: 7
<212> TYPE: PRT
<213> ORGANISM: Mus musculus

<400> SEQUENCE: 38

Tyr Ala Ser Glu Ser Ile Ser
1               5

<210> SEQ ID NO 39
<211> LENGTH: 7
<212> TYPE: PRT
<213> ORGANISM: Mus musculus

<400> SEQUENCE: 39

Leu Ala Ser Asn Leu Glu Ser
1               5

<210> SEQ ID NO 40
<211> LENGTH: 7
<212> TYPE: PRT
<213> ORGANISM: Mus musculus

<400> SEQUENCE: 40

Glu Gly Asn Thr Leu Arg Pro
1               5

<210> SEQ ID NO 41
<211> LENGTH: 9
<212> TYPE: PRT
<213> ORGANISM: Mus musculus

<400> SEQUENCE: 41

Phe Gln Gly Ser His Val Pro Pro Thr
1               5

<210> SEQ ID NO 42
<211> LENGTH: 9
<212> TYPE: PRT
<213> ORGANISM: Mus musculus

<400> SEQUENCE: 42

Gln Gln Ser Asn Thr Trp Pro Phe Thr
1               5

<210> SEQ ID NO 43
<211> LENGTH: 9
<212> TYPE: PRT
<213> ORGANISM: Mus musculus

<400> SEQUENCE: 43

Gln His Ser Arg Glu Ile Pro Tyr Thr
1               5

<210> SEQ ID NO 44
<211> LENGTH: 8
<212> TYPE: PRT
<213> ORGANISM: Mus musculus

<400> SEQUENCE: 44

Leu Gln Ser Asp Asn Met Leu Thr
1               5

<210> SEQ ID NO 45
<211> LENGTH: 120
<212> TYPE: PRT
<213> ORGANISM: Artificial sequence
<220> FEATURE:
<223> OTHER INFORMATION: C2519A VH

<400> SEQUENCE: 45

Glu Phe Gln Leu Gln Gln Ser Gly Pro Glu Leu Val Lys Pro Gly Ala
1               5                   10                  15

Ser Val Lys Ile Ser Cys Lys Ala Ser Gly Tyr Ser Phe Thr Asp Tyr
            20                  25                  30

Asn Met Asn Trp Val Lys Gln Ser His Gly Lys Ser Leu Glu Trp Ile
        35                  40                  45

```
Gly Asn Ile Asn Pro Tyr Tyr Gly Ser Thr Thr Tyr Asn Gln Lys Phe
        50                  55                  60

Lys Gly Lys Ala Thr Leu Thr Val Asp Lys Ser Asn Thr Ala Tyr
65                  70                  75                  80

Met His Leu Asn Ser Leu Thr Ser Glu Asp Ser Ala Val Tyr Tyr Cys
                85                  90                  95

Ala Arg Glu Gly Asp Thr Tyr Leu Ala Trp Phe Ala Tyr Trp Gly Gln
                100                 105                 110

Gly Thr Leu Val Thr Val Ser Ala
            115                 120
```

<210> SEQ ID NO 46
<211> LENGTH: 124
<212> TYPE: PRT
<213> ORGANISM: Artificial sequence
<220> FEATURE:
<223> OTHER INFORMATION: C2521A VH

<400> SEQUENCE: 46

```
Gln Ile Gln Leu Gln Gln Ser Gly Pro Glu Leu Val Arg Pro Gly Thr
1               5                   10                  15

Ser Val Lys Ile Ser Cys Lys Ala Ser Gly Tyr Thr Phe Leu Thr Tyr
                20                  25                  30

Trp Met Asn Trp Val Lys Gln Arg Pro Gly Gln Gly Leu Glu Trp Ile
            35                  40                  45

Gly Gln Ile Phe Pro Ala Ser Gly Ser Thr Tyr Tyr Asn Glu Met Phe
        50                  55                  60

Lys Asp Lys Ala Thr Leu Thr Val Asp Thr Ser Ser Ser Thr Ala Tyr
65                  70                  75                  80

Met Gln Leu Ser Ser Leu Thr Ser Glu Asp Thr Ala Val Tyr Phe Cys
                85                  90                  95

Ala Arg Ser Glu Asn Ile Tyr Tyr Ile Asn Phe Gln Tyr Tyr Phe Ala
                100                 105                 110

Tyr Trp Gly Gln Gly Thr Thr Leu Thr Val Ser Ser
            115                 120
```

<210> SEQ ID NO 47
<211> LENGTH: 117
<212> TYPE: PRT
<213> ORGANISM: Artificial sequence
<220> FEATURE:
<223> OTHER INFORMATION: C2244/ STLM15 VH

<400> SEQUENCE: 47

```
Glu Val Gln Leu Gln Glu Ser Gly Pro Gly Leu Val Lys Pro Ser Gln
1               5                   10                  15

Ser Leu Ser Leu Thr Cys Thr Val Thr Gly Phe Ser Ile Thr Ser Asp
                20                  25                  30

Tyr Ala Trp Asn Trp Ile Arg Gln Phe Pro Gly Ser Lys Leu Glu Trp
            35                  40                  45

Met Gly Phe Ile Ser Tyr Ser Gly Asp Thr Ser Phe Asn Pro Ser Leu
        50                  55                  60

Lys Ser Arg Ile Ser Val Thr Arg Asp Thr Ser Lys Asn Gln Phe Phe
65                  70                  75                  80

Leu Gln Leu Asn Ser Val Thr Thr Glu Asp Thr Ala Thr Tyr Tyr Cys
                85                  90                  95

Ala Ser Tyr Asp Gly Tyr Ser Phe Asp Tyr Trp Gly Gln Gly Thr Thr
```

```
              100                 105                 110

Leu Thr Val Ser Ser
        115

<210> SEQ ID NO 48
<211> LENGTH: 117
<212> TYPE: PRT
<213> ORGANISM: Artificial sequence
<220> FEATURE:
<223> OTHER INFORMATION: C2494A/ STLM62 VH

<400> SEQUENCE: 48

Glu Val Gln Leu Gln Gln Ser Val Ala Glu Leu Val Arg Pro Gly Ala
1               5                   10                  15

Ser Val Lys Leu Ser Cys Thr Ala Ser Ala Phe Asn Ile Lys Asp Asp
                20                  25                  30

Tyr Met His Trp Val Lys Gln Arg Pro Glu Gln Gly Leu Glu Trp Ile
            35                  40                  45

Gly Arg Ile Asp Pro Ala Ile Gly Asn Thr Glu Tyr Ala Pro Lys Phe
    50                  55                  60

Gln Asp Lys Ala Thr Met Thr Ala Asp Thr Ser Ser Asn Thr Ala Tyr
65                  70                  75                  80

Leu Gln Leu Ser Ser Leu Thr Ser Glu Asp Thr Ala Val Tyr Tyr Cys
                85                  90                  95

Ala Leu Gly Asp Phe Tyr Ala Met Asp Tyr Trp Gly Gln Gly Thr Ser
            100                 105                 110

Val Thr Val Ser Ser
        115

<210> SEQ ID NO 49
<211> LENGTH: 112
<212> TYPE: PRT
<213> ORGANISM: Artificial sequence
<220> FEATURE:
<223> OTHER INFORMATION: C2519A VL

<400> SEQUENCE: 49

Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Ser Ile Val Tyr Ser
                20                  25                  30

Asn Gly Asn Thr Tyr Leu Glu Trp Tyr Leu Gln Lys Pro Gly Gln Ser
            35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Val Pro Pro Thr Phe Gly Gly Gly Thr Lys Leu Glu Ile Lys
            100                 105                 110

<210> SEQ ID NO 50
<211> LENGTH: 106
<212> TYPE: PRT
<213> ORGANISM: Artificial sequence
<220> FEATURE:
<223> OTHER INFORMATION: C2521A VL

<400> SEQUENCE: 50
```

```
Ile Leu Leu Thr Gln Ser Pro Ala Ile Leu Ser Val Ser Pro Gly Glu
1               5                   10                  15

Arg Val Ser Phe Ser Cys Arg Ala Ser Gln Asn Ile Gly Thr Arg Met
            20                  25                  30

His Trp Tyr Gln Gln Arg Thr Asn Gly Ser Pro Arg Leu Leu Ile Lys
        35                  40                  45

Tyr Ala Ser Glu Ser Ile Ser Gly Ile Pro Ser Arg Phe Ser Gly Ser
    50                  55                  60

Gly Ser Gly Thr Asp Phe Thr Leu Thr Ile Ser Ser Val Glu Ser Glu
65                  70                  75                  80

Asp Ile Ala Asp Tyr Tyr Cys Gln Gln Ser Asn Thr Trp Pro Phe Thr
                85                  90                  95

Phe Gly Ser Gly Thr Lys Leu Glu Ile Lys
                100                 105
```

<210> SEQ ID NO 51
<211> LENGTH: 111
<212> TYPE: PRT
<213> ORGANISM: Artificial sequence
<220> FEATURE:
<223> OTHER INFORMATION: C2244/ STLM15 VL

<400> SEQUENCE: 51

```
Asp Ile Val Leu Thr Gln Ser Pro Ala Ser Leu Ala Ile Ser Leu Gly
1               5                   10                  15

Gln Arg Ala Thr Ile Ser Cys Arg Ala Ser Lys Ser Val Ser Thr Ser
            20                  25                  30

Gly Ser Ser Tyr Met Phe Trp Tyr Gln Gln Lys Pro Gly Gln Pro Pro
        35                  40                  45

Lys Leu Leu Ile Tyr Leu Ala Ser Asn Leu Glu Ser Gly Val Pro Ala
    50                  55                  60

Arg Phe Ser Gly Ser Gly Ser Gly Thr Asp Phe Thr Leu Asn Ile His
65                  70                  75                  80

Pro Val Glu Glu Glu Asp Ala Ala Ala Tyr Tyr Cys Gln His Ser Arg
                85                  90                  95

Glu Ile Pro Tyr Thr Phe Gly Gly Gly Thr Lys Leu Glu Ile Lys
                100                 105                 110
```

<210> SEQ ID NO 52
<211> LENGTH: 106
<212> TYPE: PRT
<213> ORGANISM: Artificial sequence
<220> FEATURE:
<223> OTHER INFORMATION: C2494A/ STLM62 VL

<400> SEQUENCE: 52

```
Glu Thr Thr Val Thr Gln Ser Pro Ala Ser Leu Ser Val Ala Thr Gly
1               5                   10                  15

Glu Lys Val Thr Ile Arg Cys Ile Thr Asn Thr Asp Ile Asp Asp Val
            20                  25                  30

Ile His Trp Tyr Gln Gln Lys Pro Gly Glu Pro Pro Lys Leu Leu Ile
        35                  40                  45

Ser Glu Gly Asn Thr Leu Arg Pro Gly Val Pro Ser Arg Phe Ser Ser
    50                  55                  60

Ser Gly Tyr Gly Thr Asp Phe Val Phe Thr Ile Glu Asn Thr Leu Ser
65                  70                  75                  80

Glu Asp Val Ala Asp Tyr Tyr Cys Leu Gln Ser Asp Asn Met Leu Thr
```

```
                    85                  90                  95
Phe Gly Ala Gly Thr Lys Leu Glu Leu Lys
                100                 105
```

<210> SEQ ID NO 53
<211> LENGTH: 6
<212> TYPE: PRT
<213> ORGANISM: Artificial sequence
<220> FEATURE:
<223> OTHER INFORMATION: STLM48, STLM49, STLM50  HCDR1

<400> SEQUENCE: 53

```
Thr Ser Tyr Trp Ile Gly
1               5
```

<210> SEQ ID NO 54
<211> LENGTH: 6
<212> TYPE: PRT
<213> ORGANISM: Artificial sequence
<220> FEATURE:
<223> OTHER INFORMATION: STLM51 HCDR1

<400> SEQUENCE: 54

```
Ser Ser Tyr Ala Ile Ser
1               5
```

<210> SEQ ID NO 55
<211> LENGTH: 18
<212> TYPE: PRT
<213> ORGANISM: Artificial sequence
<220> FEATURE:
<223> OTHER INFORMATION: STLM48, STLM49, STLM50  HCDR2

<400> SEQUENCE: 55

```
Gly Ile Ile Tyr Pro Gly Asp Ser Tyr Thr Arg Tyr Ser Pro Ser Phe
1               5                   10                  15

Gln Gly
```

<210> SEQ ID NO 56
<211> LENGTH: 17
<212> TYPE: PRT
<213> ORGANISM: Artificial sequence
<220> FEATURE:
<223> OTHER INFORMATION: STLM51 HCDR2

<400> SEQUENCE: 56

```
Gly Ile Ile Pro Ile Phe Gly Thr Ala Asn Tyr Ala Gln Lys Phe Gln
1               5                   10                  15

Gly
```

<210> SEQ ID NO 57
<211> LENGTH: 7
<212> TYPE: PRT
<213> ORGANISM: Artificial sequence
<220> FEATURE:
<223> OTHER INFORMATION: STLM48, STLM50  HCDR3

<400> SEQUENCE: 57

```
Leu Ser Gly Arg Phe Asp Tyr
1               5
```

<210> SEQ ID NO 58
<211> LENGTH: 7
<212> TYPE: PRT
<213> ORGANISM: Artificial sequence

```
<220> FEATURE:
<223> OTHER INFORMATION: STLM49 HCDR3

<400> SEQUENCE: 58

Ile Gly Gly Met Phe Asp Tyr
1               5

<210> SEQ ID NO 59
<211> LENGTH: 7
<212> TYPE: PRT
<213> ORGANISM: Artificial sequence
<220> FEATURE:
<223> OTHER INFORMATION: STLM51 HCDR3

<400> SEQUENCE: 59

Asp Thr Pro Gln Leu Asp Tyr
1               5

<210> SEQ ID NO 60
<211> LENGTH: 11
<212> TYPE: PRT
<213> ORGANISM: Artificial sequence
<220> FEATURE:
<223> OTHER INFORMATION: STLM48 LCDR1

<400> SEQUENCE: 60

Arg Ala Ser Gln Ser Val Arg Asp Ala Leu Ala
1               5                   10

<210> SEQ ID NO 61
<211> LENGTH: 11
<212> TYPE: PRT
<213> ORGANISM: Artificial sequence
<220> FEATURE:
<223> OTHER INFORMATION: STLM49 LCDR1

<400> SEQUENCE: 61

Arg Ala Ser Gln Ser Val Ala Asn Ala Leu Ala
1               5                   10

<210> SEQ ID NO 62
<211> LENGTH: 11
<212> TYPE: PRT
<213> ORGANISM: Artificial sequence
<220> FEATURE:
<223> OTHER INFORMATION: STLM50 LCDR1

<400> SEQUENCE: 62

Arg Ala Ser Gln Ser Val Ser Asn Ala Leu Ala
1               5                   10

<210> SEQ ID NO 63
<211> LENGTH: 11
<212> TYPE: PRT
<213> ORGANISM: Artificial sequence
<220> FEATURE:
<223> OTHER INFORMATION: STLM51 LCDR1

<400> SEQUENCE: 63

Arg Ala Ser Gln Ser Ile Ser Ser Tyr Leu Asn
1               5                   10

<210> SEQ ID NO 64
<211> LENGTH: 7
<212> TYPE: PRT
<213> ORGANISM: Artificial sequence
<220> FEATURE:
```

<223> OTHER INFORMATION: STLM48, STLM50 LCDR2

<400> SEQUENCE: 64

Phe Ala Ser Asn Arg Ala Thr
1               5

<210> SEQ ID NO 65
<211> LENGTH: 7
<212> TYPE: PRT
<213> ORGANISM: Artificial sequence
<220> FEATURE:
<223> OTHER INFORMATION: STLM49 LCDR2

<400> SEQUENCE: 65

Lys Ala Ser Asn Arg Ala Thr
1               5

<210> SEQ ID NO 66
<211> LENGTH: 7
<212> TYPE: PRT
<213> ORGANISM: Artificial sequence
<220> FEATURE:
<223> OTHER INFORMATION: STLM51 LCDR2

<400> SEQUENCE: 66

Tyr Ala Ser Ser Leu Gln Ser
1               5

<210> SEQ ID NO 67
<211> LENGTH: 9
<212> TYPE: PRT
<213> ORGANISM: Artificial sequence
<220> FEATURE:
<223> OTHER INFORMATION: STLM48 LCDR3

<400> SEQUENCE: 67

Gln Gln Phe Asn Thr Trp Pro Ile Thr
1               5

<210> SEQ ID NO 68
<211> LENGTH: 9
<212> TYPE: PRT
<213> ORGANISM: Artificial sequence
<220> FEATURE:
<223> OTHER INFORMATION: STLM49 LCDR3

<400> SEQUENCE: 68

Gln Gln Tyr Tyr Gly Trp Pro Ile Thr
1               5

<210> SEQ ID NO 69
<211> LENGTH: 9
<212> TYPE: PRT
<213> ORGANISM: Artificial sequence
<220> FEATURE:
<223> OTHER INFORMATION: STLM50 LCDR3

<400> SEQUENCE: 69

Gln Gln Phe Phe Asn Trp Pro Ile Thr
1               5

<210> SEQ ID NO 70
<211> LENGTH: 9
<212> TYPE: PRT
<213> ORGANISM: Artificial sequence
<220> FEATURE:
<223> OTHER INFORMATION: STLM51 LCDR3

-continued

<400> SEQUENCE: 70

Gln Gln Ser Tyr Ser Thr Pro Leu Thr
1               5

<210> SEQ ID NO 71
<211> LENGTH: 116
<212> TYPE: PRT
<213> ORGANISM: Artificial sequence
<220> FEATURE:
<223> OTHER INFORMATION: STLM48, STLM50 VH

<400> SEQUENCE: 71

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
            20                  25                  30

Trp Ile Gly Trp Val Arg Gln Met Pro Gly Lys Gly Leu Glu Trp Met
        35                  40                  45

Gly Ile Ile Tyr Pro Gly Asp Ser Tyr Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Leu Ser Gly Arg Phe Asp Tyr Trp Gly Gln Gly Thr Leu Val
            100                 105                 110

Thr Val Ser Ser
        115

<210> SEQ ID NO 72
<211> LENGTH: 116
<212> TYPE: PRT
<213> ORGANISM: Artificial sequence
<220> FEATURE:
<223> OTHER INFORMATION: STLM49 VH

<400> SEQUENCE: 72

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
            20                  25                  30

Trp Ile Gly Trp Val Arg Gln Met Pro Gly Lys Gly Leu Glu Trp Met
        35                  40                  45

Gly Ile Ile Tyr Pro Gly Asp Ser Tyr Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Ile Gly Gly Met Phe Asp Tyr Trp Gly Gln Gly Thr Leu Val
            100                 105                 110

Thr Val Ser Ser
        115

<210> SEQ ID NO 73
<211> LENGTH: 116
<212> TYPE: PRT
<213> ORGANISM: Artificial sequence

```
<220> FEATURE:
<223> OTHER INFORMATION: STLM51 VH

<400> SEQUENCE: 73
```

| | | | | | | | | | | | | | | |
|---|---|---|---|---|---|---|---|---|---|---|---|---|---|---|
| Gln | Val | Gln | Leu | Val | Gln | Ser | Gly | Ala | Glu | Lys | Lys | Pro | Gly | Ser |
| 1 | | | | 5 | | | | | 10 | | | | | 15 |
| Ser | Val | Lys | Val | Ser | Cys | Lys | Ala | Ser | Gly | Gly | Thr | Phe | Ser | Ser | Tyr |
| | | | 20 | | | | | 25 | | | | | 30 |
| Ala | Ile | Ser | Trp | Val | Arg | Gln | Ala | Pro | Gly | Gln | Gly | Leu | Glu | Trp | Met |
| | | 35 | | | | | 40 | | | | | 45 |
| Gly | Gly | Ile | Ile | Pro | Ile | Phe | Gly | Thr | Ala | Asn | Tyr | Ala | Gln | Lys | Phe |
| 50 | | | | | 55 | | | | | 60 |
| Gln | Gly | Arg | Val | Thr | Ile | Thr | Ala | Asp | Glu | Ser | Thr | Ser | Thr | Ala | Tyr |
| 65 | | | | 70 | | | | | 75 | | | | | 80 |
| Met | Glu | Leu | Ser | Ser | Leu | Arg | Ser | Glu | Asp | Thr | Ala | Val | Tyr | Tyr | Cys |
| | | | | 85 | | | | | 90 | | | | | 95 |
| Ala | Arg | Asp | Thr | Pro | Gln | Leu | Asp | Tyr | Trp | Gly | Gln | Gly | Thr | Leu | Val |
| | | | 100 | | | | | 105 | | | | | 110 |
| Thr | Val | Ser | Ser |
| | | | 115 |

```
<210> SEQ ID NO 74
<211> LENGTH: 107
<212> TYPE: PRT
<213> ORGANISM: Artificial sequence
<220> FEATURE:
<223> OTHER INFORMATION: STLM48 VL

<400> SEQUENCE: 74
```

| | | | | | | | | | | | | | | |
|---|---|---|---|---|---|---|---|---|---|---|---|---|---|---|
| Glu | Ile | Val | Leu | Thr | Gln | Ser | Pro | Ala | Thr | Leu | Ser | Leu | Ser | Pro | Gly |
| 1 | | | | 5 | | | | | 10 | | | | | 15 |
| Glu | Arg | Ala | Thr | Leu | Ser | Cys | Arg | Ala | Ser | Gln | Ser | Val | Arg | Asp | Ala |
| | | | 20 | | | | | 25 | | | | | 30 |
| Leu | Ala | Trp | Tyr | Gln | Gln | Lys | Pro | Gly | Gln | Ala | Pro | Arg | Leu | Leu | Ile |
| | | | 35 | | | | | 40 | | | | | 45 |
| Tyr | Phe | Ala | Ser | Asn | Arg | Ala | Thr | Gly | Ile | Pro | Ala | Arg | Phe | Ser | Gly |
| 50 | | | | | 55 | | | | | 60 |
| Ser | Gly | Ser | Gly | Thr | Asp | Phe | Thr | Leu | Thr | Ile | Ser | Ser | Leu | Glu | Pro |
| 65 | | | | 70 | | | | | 75 | | | | | 80 |
| Glu | Asp | Phe | Ala | Val | Tyr | Tyr | Cys | Gln | Gln | Phe | Asn | Thr | Trp | Pro | Ile |
| | | | | 85 | | | | | 90 | | | | | 95 |
| Thr | Phe | Gly | Gln | Gly | Thr | Lys | Val | Glu | Ile | Lys |
| | | | 100 | | | | | 105 |

```
<210> SEQ ID NO 75
<211> LENGTH: 107
<212> TYPE: PRT
<213> ORGANISM: Artificial sequence
<220> FEATURE:
<223> OTHER INFORMATION: STLM49 VL

<400> SEQUENCE: 75
```

| | | | | | | | | | | | | | | |
|---|---|---|---|---|---|---|---|---|---|---|---|---|---|---|
| Glu | Ile | Val | Leu | Thr | Gln | Ser | Pro | Ala | Thr | Leu | Ser | Leu | Ser | Pro | Gly |
| 1 | | | | 5 | | | | | 10 | | | | | 15 |
| Glu | Arg | Ala | Thr | Leu | Ser | Cys | Arg | Ala | Ser | Gln | Ser | Val | Ala | Asn | Ala |
| | | | 20 | | | | | 25 | | | | | 30 |
| Leu | Ala | Trp | Tyr | Gln | Gln | Lys | Pro | Gly | Gln | Ala | Pro | Arg | Leu | Leu | Ile |
| | | | 35 | | | | | 40 | | | | | 45 |

```
Tyr Lys Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Tyr Tyr Gly Trp Pro Ile
                85                  90                  95

Thr Phe Gly Gln Gly Thr Lys Val Glu Ile Lys
                100                 105
```

<210> SEQ ID NO 76
<211> LENGTH: 107
<212> TYPE: PRT
<213> ORGANISM: Artificial sequence
<220> FEATURE:
<223> OTHER INFORMATION: STLM50 VL

<400> SEQUENCE: 76

```
Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Asp Asp Trp
                20                  25                  30

Leu Ala Trp Tyr Gln Gln Lys Pro Gly Gln Ala Pro Arg Leu Leu Ile
            35                  40                  45

Tyr Lys Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Tyr Asn Arg Ala Pro Trp
                85                  90                  95

Thr Phe Gly Gln Gly Thr Lys Val Glu Ile Lys
                100                 105
```

<210> SEQ ID NO 77
<211> LENGTH: 107
<212> TYPE: PRT
<213> ORGANISM: Artificial sequence
<220> FEATURE:
<223> OTHER INFORMATION: STLM51 VL

<400> SEQUENCE: 77

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
                20                  25                  30

Leu Asn Trp Tyr Gln Gln Lys Pro Gly Lys Ala Pro Lys Leu Leu Ile
            35                  40                  45

Tyr Tyr Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Leu
                85                  90                  95

Thr Phe Gly Gln Gly Thr Lys Val Glu Ile Lys
                100                 105
```

<210> SEQ ID NO 78
<211> LENGTH: 5
<212> TYPE: PRT
<213> ORGANISM: Artificial sequence

```
<220> FEATURE:
<223> OTHER INFORMATION: ST2F6 HCDR1

<400> SEQUENCE: 78

Ser Tyr Ala Met Ser
1               5

<210> SEQ ID NO 79
<211> LENGTH: 5
<212> TYPE: PRT
<213> ORGANISM: Artificial sequence
<220> FEATURE:
<223> OTHER INFORMATION: ST2F4 HCDR1

<400> SEQUENCE: 79

Ser Tyr Trp Met His
1               5

<210> SEQ ID NO 80
<211> LENGTH: 5
<212> TYPE: PRT
<213> ORGANISM: Artificial sequence
<220> FEATURE:
<223> OTHER INFORMATION: ST2F1 HCDR1

<400> SEQUENCE: 80

Ser Tyr Trp Ile Gly
1               5

<210> SEQ ID NO 81
<211> LENGTH: 17
<212> TYPE: PRT
<213> ORGANISM: Artificial sequence
<220> FEATURE:
<223> OTHER INFORMATION: ST2F6 HCDR2

<400> SEQUENCE: 81

Ala Ile Ser Gly Ser Gly Gly Ser Thr Tyr Tyr Ala Asp Ser Val Lys
1               5                   10                  15

Gly

<210> SEQ ID NO 82
<211> LENGTH: 17
<212> TYPE: PRT
<213> ORGANISM: Artificial sequence
<220> FEATURE:
<223> OTHER INFORMATION: ST2F4 HCDR2

<400> SEQUENCE: 82

Gly Ile Ser Ser Gly Gly Gly Ser Thr Tyr Tyr Ala Asp Ser Val Lys
1               5                   10                  15

Gly

<210> SEQ ID NO 83
<211> LENGTH: 17
<212> TYPE: PRT
<213> ORGANISM: Artificial sequence
<220> FEATURE:
<223> OTHER INFORMATION: ST2F1 HCDR2

<400> SEQUENCE: 83

Ile Ile Tyr Pro Gly Asp Ser Asp Thr Arg Tyr Ser Pro Ser Phe Gln
1               5                   10                  15

Gly
```

```
<210> SEQ ID NO 84
<211> LENGTH: 14
<212> TYPE: PRT
<213> ORGANISM: Artificial sequence
<220> FEATURE:
<223> OTHER INFORMATION: ST2F6 HCDR3

<400> SEQUENCE: 84

Asp Pro Trp Ser Thr Glu Gly Ser Phe Phe Val Leu Asp Tyr
1               5                   10

<210> SEQ ID NO 85
<211> LENGTH: 12
<212> TYPE: PRT
<213> ORGANISM: Artificial sequence
<220> FEATURE:
<223> OTHER INFORMATION: ST2F4 HCDR3

<400> SEQUENCE: 85

Asp Gly Trp Gly Thr Val Tyr Phe Pro Phe Asp Tyr
1               5                   10

<210> SEQ ID NO 86
<211> LENGTH: 12
<212> TYPE: PRT
<213> ORGANISM: Artificial sequence
<220> FEATURE:
<223> OTHER INFORMATION: ST2F1 HCDR3

<400> SEQUENCE: 86

Asp Thr Ala Asp Phe Arg Arg Trp Asp Phe Asp Tyr
1               5                   10

<210> SEQ ID NO 87
<211> LENGTH: 11
<212> TYPE: PRT
<213> ORGANISM: Artificial sequence
<220> FEATURE:
<223> OTHER INFORMATION: ST2F6 LCDR1

<400> SEQUENCE: 87

Arg Ala Ser Gln Ser Val Asp Asp Ala Leu Ala
1               5                   10

<210> SEQ ID NO 88
<211> LENGTH: 11
<212> TYPE: PRT
<213> ORGANISM: Artificial sequence
<220> FEATURE:
<223> OTHER INFORMATION: ST2F4 LCDR1

<400> SEQUENCE: 88

Arg Ala Ser Gln Ser Val Arg Asp Asp Leu Ala
1               5                   10

<210> SEQ ID NO 89
<211> LENGTH: 17
<212> TYPE: PRT
<213> ORGANISM: Artificial sequence
<220> FEATURE:
<223> OTHER INFORMATION: ST2F1 LCDR1

<400> SEQUENCE: 89

Lys Ser Ser Gln Ser Val Leu Tyr Ser Ser Asn Asn Lys Asn Tyr Leu
1               5                   10                  15

Ala
```

```
<210> SEQ ID NO 90
<211> LENGTH: 7
<212> TYPE: PRT
<213> ORGANISM: Artificial sequence
<220> FEATURE:
<223> OTHER INFORMATION: ST2F6, ST2F4  LCDR2

<400> SEQUENCE: 90

Asp Ala Ser Asn Arg Ala Thr
1               5

<210> SEQ ID NO 91
<211> LENGTH: 7
<212> TYPE: PRT
<213> ORGANISM: Artificial sequence
<220> FEATURE:
<223> OTHER INFORMATION: ST2F1 LCDR2

<400> SEQUENCE: 91

Trp Ala Ser Thr Arg Glu Ser
1               5

<210> SEQ ID NO 92
<211> LENGTH: 9
<212> TYPE: PRT
<213> ORGANISM: Artificial sequence
<220> FEATURE:
<223> OTHER INFORMATION: ST2F6 LCDR3

<400> SEQUENCE: 92

Gln Gln Phe Tyr Asn Trp Pro Leu Thr
1               5

<210> SEQ ID NO 93
<211> LENGTH: 9
<212> TYPE: PRT
<213> ORGANISM: Artificial sequence
<220> FEATURE:
<223> OTHER INFORMATION: ST2F4 LCDR3

<400> SEQUENCE: 93

Gln Gln Tyr Ile His Ala Pro Leu Thr
1               5

<210> SEQ ID NO 94
<211> LENGTH: 9
<212> TYPE: PRT
<213> ORGANISM: Artificial sequence
<220> FEATURE:
<223> OTHER INFORMATION: ST2F1 LCDR3

<400> SEQUENCE: 94

Gln Gln Ser Asn Thr Tyr Pro Phe Thr
1               5

<210> SEQ ID NO 95
<211> LENGTH: 5
<212> TYPE: PRT
<213> ORGANISM: Artificial sequence
<220> FEATURE:
<223> OTHER INFORMATION: ST2H112, ST2H137 HCDR1

<400> SEQUENCE: 95

Phe Tyr Asp Met Phe
1               5
```

```
<210> SEQ ID NO 96
<211> LENGTH: 5
<212> TYPE: PRT
<213> ORGANISM: Artificial sequence
<220> FEATURE:
<223> OTHER INFORMATION: ST2H52 HCDR1

<400> SEQUENCE: 96

Asp Tyr Ala Met Phe
1               5

<210> SEQ ID NO 97
<211> LENGTH: 5
<212> TYPE: PRT
<213> ORGANISM: Artificial sequence
<220> FEATURE:
<223> OTHER INFORMATION: ST2H50, ST2H232, ST2H257, ST2H231 HCDR1

<400> SEQUENCE: 97

Ile Tyr Asp Met Ile
1               5

<210> SEQ ID NO 98
<211> LENGTH: 5
<212> TYPE: PRT
<213> ORGANISM: Artificial sequence
<220> FEATURE:
<223> OTHER INFORMATION: ST2H228 HCDR1

<400> SEQUENCE: 98

Ser Tyr Asp Met Ile
1               5

<210> SEQ ID NO 99
<211> LENGTH: 5
<212> TYPE: PRT
<213> ORGANISM: Artificial sequence
<220> FEATURE:
<223> OTHER INFORMATION: ST2H318 HCDR1

<400> SEQUENCE: 99

Asp Asp Ala Met Ile
1               5

<210> SEQ ID NO 100
<211> LENGTH: 5
<212> TYPE: PRT
<213> ORGANISM: Artificial sequence
<220> FEATURE:
<223> OTHER INFORMATION: ST2H316 HCDR1

<400> SEQUENCE: 100

Gly Tyr Ala Met Ile
1               5

<210> SEQ ID NO 101
<211> LENGTH: 5
<212> TYPE: PRT
<213> ORGANISM: Artificial sequence
<220> FEATURE:
<223> OTHER INFORMATION: ST2H314 HCDR1

<400> SEQUENCE: 101

Val Tyr Asp Met Ile
1               5
```

```
<210> SEQ ID NO 102
<211> LENGTH: 5
<212> TYPE: PRT
<213> ORGANISM: Artificial sequence
<220> FEATURE:
<223> OTHER INFORMATION: ST2H202 HCDR1

<400> SEQUENCE: 102

Phe Tyr Asp Met Ile
1               5

<210> SEQ ID NO 103
<211> LENGTH: 5
<212> TYPE: PRT
<213> ORGANISM: Artificial sequence
<220> FEATURE:
<223> OTHER INFORMATION: ST2H179, ST2H172, ST2H173 HCDR1

<400> SEQUENCE: 103

Ser Tyr Asp Met Phe
1               5

<210> SEQ ID NO 104
<211> LENGTH: 5
<212> TYPE: PRT
<213> ORGANISM: Artificial sequence
<220> FEATURE:
<223> OTHER INFORMATION: ST2H163 HCDR1

<400> SEQUENCE: 104

Val Tyr Asp Met Phe
1               5

<210> SEQ ID NO 105
<211> LENGTH: 5
<212> TYPE: PRT
<213> ORGANISM: Artificial sequence
<220> FEATURE:
<223> OTHER INFORMATION: ST2H162 HCDR1

<400> SEQUENCE: 105

Val Asp Ser Met Phe
1               5

<210> SEQ ID NO 106
<211> LENGTH: 5
<212> TYPE: PRT
<213> ORGANISM: Artificial sequence
<220> FEATURE:
<223> OTHER INFORMATION: ST2H139 HCDR1

<400> SEQUENCE: 106

Gly Tyr Asp Met Phe
1               5

<210> SEQ ID NO 107
<211> LENGTH: 5
<212> TYPE: PRT
<213> ORGANISM: Artificial sequence
<220> FEATURE:
<223> OTHER INFORMATION: ST2H136 HCDR1

<400> SEQUENCE: 107

Ile Tyr Asp Met Phe
1               5

<210> SEQ ID NO 108
```

```
<211> LENGTH: 5
<212> TYPE: PRT
<213> ORGANISM: Artificial sequence
<220> FEATURE:
<223> OTHER INFORMATION: ST2H129 HCDR1

<400> SEQUENCE: 108

Ile Tyr Ser Met Phe
1               5

<210> SEQ ID NO 109
<211> LENGTH: 17
<212> TYPE: PRT
<213> ORGANISM: Artificial sequence
<220> FEATURE:
<223> OTHER INFORMATION: ST2H112 HCDR3

<400> SEQUENCE: 109

Ser Ile Arg Gly Glu Gly Gly Arg Thr Asp Tyr Ala Asp Ser Val Lys
1               5                   10                  15

Gly

<210> SEQ ID NO 110
<211> LENGTH: 17
<212> TYPE: PRT
<213> ORGANISM: Artificial sequence
<220> FEATURE:
<223> OTHER INFORMATION: ST2H52 HCDR3

<400> SEQUENCE: 110

Ala Ile Glu Gly Glu Gly Gly Glu Thr Asn Tyr Ala Asp Ser Val Lys
1               5                   10                  15

Gly

<210> SEQ ID NO 111
<211> LENGTH: 17
<212> TYPE: PRT
<213> ORGANISM: Artificial sequence
<220> FEATURE:
<223> OTHER INFORMATION: ST2H50 HCDR3

<400> SEQUENCE: 111

Thr Ile Lys Gly Glu Gly Gly Gly Thr Tyr Tyr Ala Asp Ser Val Lys
1               5                   10                  15

Gly

<210> SEQ ID NO 112
<211> LENGTH: 17
<212> TYPE: PRT
<213> ORGANISM: Artificial sequence
<220> FEATURE:
<223> OTHER INFORMATION: ST2H232 HCDR3

<400> SEQUENCE: 112

Thr Ile Arg Gly Glu Gly Gly Ser Thr Tyr Tyr Ala Asp Ser Val Lys
1               5                   10                  15

Gly

<210> SEQ ID NO 113
<211> LENGTH: 17
<212> TYPE: PRT
<213> ORGANISM: Artificial sequence
<220> FEATURE:
<223> OTHER INFORMATION: ST2H228 HCDR3
```

```
<400> SEQUENCE: 113

Thr Ile Arg Gly Glu Gly Gly Thr Thr Ala Tyr Ala Asp Ser Val Lys
1               5                   10                  15
Gly

<210> SEQ ID NO 114
<211> LENGTH: 17
<212> TYPE: PRT
<213> ORGANISM: Artificial sequence
<220> FEATURE:
<223> OTHER INFORMATION: ST2H257 HCDR3

<400> SEQUENCE: 114

Ser Ile Arg Gly Glu Gly Gly Thr Tyr Tyr Ala Asp Ser Val Lys
1               5                   10                  15
Gly

<210> SEQ ID NO 115
<211> LENGTH: 17
<212> TYPE: PRT
<213> ORGANISM: Artificial sequence
<220> FEATURE:
<223> OTHER INFORMATION: ST2H231 HCDR3

<400> SEQUENCE: 115

Thr Ile Arg Gly Glu Gly Gly Gly Thr Ser Tyr Ala Asp Ser Val Lys
1               5                   10                  15
Gly

<210> SEQ ID NO 116
<211> LENGTH: 17
<212> TYPE: PRT
<213> ORGANISM: Artificial sequence
<220> FEATURE:
<223> OTHER INFORMATION: ST2H318 HCDR3

<400> SEQUENCE: 116

Tyr Ile Gly Gly Asn Gly Gly Thr Thr Tyr Tyr Ala Asp Ser Val Lys
1               5                   10                  15
Gly

<210> SEQ ID NO 117
<211> LENGTH: 17
<212> TYPE: PRT
<213> ORGANISM: Artificial sequence
<220> FEATURE:
<223> OTHER INFORMATION: ST2H316 HCDR3

<400> SEQUENCE: 117

Tyr Ile Glu Gly Glu Gly Gly Glu Thr Tyr Tyr Ala Asp Ser Val Lys
1               5                   10                  15
Gly

<210> SEQ ID NO 118
<211> LENGTH: 17
<212> TYPE: PRT
<213> ORGANISM: Artificial sequence
<220> FEATURE:
<223> OTHER INFORMATION: ST2H314 HCDR3

<400> SEQUENCE: 118

Thr Ile Arg Gly Glu Gly Gly Gly Thr Tyr Tyr Ala Asp Ser Val Lys
1               5                   10                  15
```

Gly

<210> SEQ ID NO 119
<211> LENGTH: 311
<212> TYPE: PRT
<213> ORGANISM: Homo sapiens

<400> SEQUENCE: 119

Ala Lys Phe Ser Lys Gln Ser Trp Gly Leu Glu Asn Glu Ala Leu Ile
1               5                   10                  15

Val Arg Cys Pro Arg Gln Gly Lys Pro Ser Tyr Thr Val Asp Trp Tyr
                20                  25                  30

Tyr Ser Gln Thr Asn Lys Ser Ile Pro Thr Gln Glu Arg Asn Arg Val
            35                  40                  45

Phe Ala Ser Gly Gln Leu Leu Lys Phe Leu Pro Ala Glu Val Ala Asp
        50                  55                  60

Ser Gly Ile Tyr Thr Cys Ile Val Arg Ser Pro Thr Phe Asn Arg Thr
65                  70                  75                  80

Gly Tyr Ala Asn Val Thr Ile Tyr Lys Lys Gln Ser Asp Cys Asn Val
                85                  90                  95

Pro Asp Tyr Leu Met Tyr Ser Thr Val Ser Gly Ser Glu Lys Asn Ser
                100                 105                 110

Lys Ile Tyr Cys Pro Thr Ile Asp Leu Tyr Asn Trp Thr Ala Pro Leu
            115                 120                 125

Glu Trp Phe Lys Asn Cys Gln Ala Leu Gln Gly Ser Arg Tyr Arg Ala
        130                 135                 140

His Lys Ser Phe Leu Val Ile Asp Asn Val Met Thr Glu Asp Ala Gly
145                 150                 155                 160

Asp Tyr Thr Cys Lys Phe Ile His Asn Glu Asn Gly Ala Asn Tyr Ser
                165                 170                 175

Val Thr Ala Thr Arg Ser Phe Thr Val Lys Asp Glu Gln Gly Phe Ser
                180                 185                 190

Leu Phe Pro Val Ile Gly Ala Pro Ala Gln Asn Glu Ile Lys Glu Val
            195                 200                 205

Glu Ile Gly Lys Asn Ala Asn Leu Thr Cys Ser Ala Cys Phe Gly Lys
        210                 215                 220

Gly Thr Gln Phe Leu Ala Ala Val Leu Trp Gln Leu Asn Gly Thr Lys
225                 230                 235                 240

Ile Thr Asp Phe Gly Glu Pro Arg Ile Gln Gln Glu Glu Gly Gln Asn
                245                 250                 255

Gln Ser Phe Ser Asn Gly Leu Ala Cys Leu Asp Met Val Leu Arg Ile
                260                 265                 270

Ala Asp Val Lys Glu Glu Asp Leu Leu Leu Gln Tyr Asp Cys Leu Ala
            275                 280                 285

Leu Asn Leu His Gly Leu Arg Arg His Thr Val Arg Leu Ser Arg Lys
        290                 295                 300

Asn Pro Ser Lys Glu Cys Phe
305                 310

<210> SEQ ID NO 120
<211> LENGTH: 17
<212> TYPE: PRT
<213> ORGANISM: Artificial sequence
<220> FEATURE:
<223> OTHER INFORMATION: ST2H202 HCDR3

```
<400> SEQUENCE: 120

Thr Ile Arg Gly Glu Gly Gly Asp Thr Asn Tyr Ala Asp Ser Val Lys
1               5                  10                  15

Gly

<210> SEQ ID NO 121
<211> LENGTH: 17
<212> TYPE: PRT
<213> ORGANISM: Artificial sequence
<220> FEATURE:
<223> OTHER INFORMATION: ST2H179 HCDR3

<400> SEQUENCE: 121

Asp Ile Lys Gly Glu Gly Gly Arg Thr Ala Tyr Ala Asp Ser Val Lys
1               5                  10                  15

Gly

<210> SEQ ID NO 122
<211> LENGTH: 17
<212> TYPE: PRT
<213> ORGANISM: Artificial sequence
<220> FEATURE:
<223> OTHER INFORMATION: ST2H172 HCDR3

<400> SEQUENCE: 122

Ala Ile Ala Gly Glu Gly Gly Arg Thr Tyr Tyr Ala Asp Ser Val Lys
1               5                  10                  15

Gly

<210> SEQ ID NO 123
<211> LENGTH: 17
<212> TYPE: PRT
<213> ORGANISM: Artificial sequence
<220> FEATURE:
<223> OTHER INFORMATION: ST2H173 HCDR3

<400> SEQUENCE: 123

Asp Ile Lys Gly Glu Gly Gly Ala Thr Asn Tyr Ala Asp Ser Val Lys
1               5                  10                  15

Gly

<210> SEQ ID NO 124
<211> LENGTH: 17
<212> TYPE: PRT
<213> ORGANISM: Artificial sequence
<220> FEATURE:
<223> OTHER INFORMATION: ST2H163 HCDR3

<400> SEQUENCE: 124

Asp Ile Lys Gly Glu Gly Gly Glu Thr Ser Tyr Ala Asp Ser Val Lys
1               5                  10                  15

Gly

<210> SEQ ID NO 125
<211> LENGTH: 17
<212> TYPE: PRT
<213> ORGANISM: Artificial sequence
<220> FEATURE:
<223> OTHER INFORMATION: ST2H162 HCDR3

<400> SEQUENCE: 125

Ser Ile Glu Gly Asn Gly Gly Ala Thr Tyr Tyr Ala Asp Ser Val Lys
1               5                  10                  15
```

Gly

```
<210> SEQ ID NO 126
<211> LENGTH: 17
<212> TYPE: PRT
<213> ORGANISM: Artificial sequence
<220> FEATURE:
<223> OTHER INFORMATION: ST2H139 HCDR3

<400> SEQUENCE: 126

Asp Ile Gly Gly Glu Gly Gly Ser Thr Asn Tyr Ala Asp Ser Val Lys
1               5                   10                  15

Gly

<210> SEQ ID NO 127
<211> LENGTH: 17
<212> TYPE: PRT
<213> ORGANISM: Artificial sequence
<220> FEATURE:
<223> OTHER INFORMATION: ST2H137 HCDR3

<400> SEQUENCE: 127

Asp Ile Arg Gly Glu Gly Gly Gly Thr Ala Tyr Ala Asp Ser Val Lys
1               5                   10                  15

Gly

<210> SEQ ID NO 128
<211> LENGTH: 17
<212> TYPE: PRT
<213> ORGANISM: Artificial sequence
<220> FEATURE:
<223> OTHER INFORMATION: ST2H136 HCDR3

<400> SEQUENCE: 128

Tyr Ile Arg Gly Glu Gly Gly Asp Thr Asn Tyr Ala Asp Ser Val Lys
1               5                   10                  15

Gly

<210> SEQ ID NO 129
<211> LENGTH: 17
<212> TYPE: PRT
<213> ORGANISM: Artificial sequence
<220> FEATURE:
<223> OTHER INFORMATION: ST2H129 HCDR3

<400> SEQUENCE: 129

Asp Ile Gly Gly Glu Gly Gly Gly Thr Ser Tyr Ala Asp Ser Val Lys
1               5                   10                  15

Gly

<210> SEQ ID NO 130
<211> LENGTH: 11
<212> TYPE: PRT
<213> ORGANISM: Artificial sequence
<220> FEATURE:
<223> OTHER INFORMATION: ST2L32 LCDR1

<400> SEQUENCE: 130

Arg Ala Ser Gln Ser Val Asp Asp Asp Leu Ala
1               5                   10

<210> SEQ ID NO 131
<211> LENGTH: 9
```

```
<212> TYPE: PRT
<213> ORGANISM: Artificial sequence
<220> FEATURE:
<223> OTHER INFORMATION: ST2L32 LCDR3

<400> SEQUENCE: 131

Gln Gln Tyr Ile Gly Ala Pro Ile Thr
1               5

<210> SEQ ID NO 132
<211> LENGTH: 9
<212> TYPE: PRT
<213> ORGANISM: Artificial sequence
<220> FEATURE:
<223> OTHER INFORMATION: ST2L35 LCDR3

<400> SEQUENCE: 132

Gln Gln Tyr Ile Asp Ala Pro Leu Thr
1               5

<210> SEQ ID NO 133
<211> LENGTH: 8
<212> TYPE: PRT
<213> ORGANISM: Artificial sequence
<220> FEATURE:
<223> OTHER INFORMATION: ST2L49 LCDR3

<400> SEQUENCE: 133

Gln Gln Tyr Asn Asp Ala Ile Thr
1               5

<210> SEQ ID NO 134
<211> LENGTH: 9
<212> TYPE: PRT
<213> ORGANISM: Artificial sequence
<220> FEATURE:
<223> OTHER INFORMATION: ST2L59 LCDR3

<400> SEQUENCE: 134

Gln Gln Tyr Ile Thr Ala Pro Leu Thr
1               5

<210> SEQ ID NO 135
<211> LENGTH: 106
<212> TYPE: PRT
<213> ORGANISM: Artificial sequence
<220> FEATURE:
<223> OTHER INFORMATION: VL2494-IGKV1-33*01 O18

<400> SEQUENCE: 135

Asp Ile Gln Met Thr Gln Ser Pro Ser Ser Leu Ser Ala Ser Val Gly
1               5                   10                  15

Asp Arg Val Thr Ile Thr Cys Ile Thr Asn Thr Asp Ile Asp Asp Val
            20                  25                  30

Ile His Trp Tyr Gln Gln Lys Pro Gly Lys Ala Pro Lys Leu Leu Ile
        35                  40                  45

Tyr Glu Gly Asn Thr Leu Arg Pro Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Leu Gln Ser Asp Asn Met Leu Thr
                85                  90                  95

Phe Gly Gln Gly Thr Lys Leu Glu Ile Lys
            100                 105
```

<210> SEQ ID NO 136
<211> LENGTH: 106
<212> TYPE: PRT
<213> ORGANISM: Artificial sequence
<220> FEATURE:
<223> OTHER INFORMATION: VL2494-IGKV1-27*01 A20

<400> SEQUENCE: 136

```
Asp Ile Gln Met Thr Gln Ser Pro Ser Ser Leu Ser Ala Ser Val Gly
1               5                   10                  15

Asp Arg Val Thr Ile Thr Cys Ile Thr Asn Thr Asp Ile Asp Asp Val
            20                  25                  30

Ile His Trp Tyr Gln Gln Lys Pro Gly Lys Val Pro Lys Leu Leu Ile
        35                  40                  45

Tyr Glu Gly Asn Thr Leu Arg Pro Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Leu Gln Ser Asp Asn Met Leu Thr
                85                  90                  95

Phe Gly Gln Gly Thr Lys Leu Glu Ile Lys
            100                 105
```

<210> SEQ ID NO 137
<211> LENGTH: 106
<212> TYPE: PRT
<213> ORGANISM: Artificial sequence
<220> FEATURE:
<223> OTHER INFORMATION: VL2494-IGKV1-39*01O12

<400> SEQUENCE: 137

```
Asp Ile Gln Met Thr Gln Ser Pro Ser Ser Leu Ser Ala Ser Val Gly
1               5                   10                  15

Asp Arg Val Thr Ile Thr Cys Ile Thr Asn Thr Asp Ile Asp Asp Val
            20                  25                  30

Ile His Trp Tyr Gln Gln Lys Pro Gly Lys Ala Pro Lys Leu Leu Ile
        35                  40                  45

Tyr Glu Gly Asn Thr Leu Arg Pro Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Ser Asp Asn Met Leu Thr
                85                  90                  95

Phe Gly Gln Gly Thr Lys Leu Glu Ile Lys
            100                 105
```

<210> SEQ ID NO 138
<211> LENGTH: 106
<212> TYPE: PRT
<213> ORGANISM: Artificial sequence
<220> FEATURE:
<223> OTHER INFORMATION: VL2494-IGKV1-12*01 L5

<400> SEQUENCE: 138

```
Asp Ile Gln Met Thr Gln Ser Pro Ser Ser Val Ser Ala Ser Val Gly
1               5                   10                  15

Asp Arg Val Thr Ile Thr Cys Ile Thr Asn Thr Asp Ile Asp Asp Val
            20                  25                  30
```

Ile His Trp Tyr Gln Gln Lys Pro Gly Lys Ala Pro Lys Leu Leu Ile
            35                  40                  45

Tyr Glu Gly Asn Thr Leu Arg Pro Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Leu Gln Ser Asp Asn Met Leu Thr
                 85                  90                  95

Phe Gly Gln Gly Thr Lys Leu Glu Ile Lys
                100                 105

<210> SEQ ID NO 139
<211> LENGTH: 106
<212> TYPE: PRT
<213> ORGANISM: Artificial sequence
<220> FEATURE:
<223> OTHER INFORMATION: VL2494-IGKV1-5*01 L12

<400> SEQUENCE: 139

Asp Ile Gln Met Thr Gln Ser Pro Ser Thr Leu Ser Ala Ser Val Gly
 1               5                  10                  15

Asp Arg Val Thr Ile Thr Cys Ile Thr Asn Thr Asp Ile Asp Asp Val
                 20                  25                  30

Ile His Trp Tyr Gln Gln Lys Pro Gly Lys Ala Pro Lys Leu Leu Ile
            35                  40                  45

Tyr Glu Gly Asn Thr Leu Arg Pro Gly Val Pro Ser Arg Phe Ser Gly
 50                  55                  60

Ser Gly Ser Gly Thr Glu Phe Thr Leu Thr Ile Ser Ser Leu Gln Pro
 65                  70                  75                  80

Asp Asp Phe Ala Thr Tyr Tyr Cys Leu Gln Ser Asp Asn Met Leu Thr
                 85                  90                  95

Phe Gly Gln Gly Thr Lys Leu Glu Ile Lys
                100                 105

<210> SEQ ID NO 140
<211> LENGTH: 106
<212> TYPE: PRT
<213> ORGANISM: Artificial sequence
<220> FEATURE:
<223> OTHER INFORMATION: VL2494-IGKV1-9*01 L8

<400> SEQUENCE: 140

Asp Ile Gln Leu Thr Gln Ser Pro Ser Phe Leu Ser Ala Ser Val Gly
 1               5                  10                  15

Asp Arg Val Thr Ile Thr Cys Ile Thr Asn Thr Asp Ile Asp Asp Val
                 20                  25                  30

Ile His Trp Tyr Gln Gln Lys Pro Gly Lys Ala Pro Lys Leu Leu Ile
            35                  40                  45

Tyr Glu Gly Asn Thr Leu Arg Pro Gly Val Pro Ser Arg Phe Ser Gly
 50                  55                  60

Ser Gly Ser Gly Thr Glu Phe Thr Leu Thr Ile Ser Ser Leu Gln Pro
 65                  70                  75                  80

Glu Asp Phe Ala Thr Tyr Tyr Cys Leu Gln Ser Asp Asn Met Leu Thr
                 85                  90                  95

Phe Gly Gln Gly Thr Lys Leu Glu Ile Lys
                100                 105

<210> SEQ ID NO 141

```
<211> LENGTH: 106
<212> TYPE: PRT
<213> ORGANISM: Artificial sequence
<220> FEATURE:
<223> OTHER INFORMATION: VL2494-IGKV3-15*01 L2

<400> SEQUENCE: 141

Glu Ile Val Met Thr Gln Ser Pro Ala Thr Leu Ser Val Ser Pro Gly
1               5                   10                  15

Glu Arg Ala Thr Leu Ser Cys Ile Thr Asn Thr Asp Ile Asp Asp Val
            20                  25                  30

Ile His Trp Tyr Gln Gln Lys Pro Gly Gln Ala Pro Arg Leu Leu Ile
        35                  40                  45

Tyr Glu Gly Asn Thr Leu Arg Pro Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Leu Gln Ser Asp Asn Met Leu Thr
                85                  90                  95

Phe Gly Gln Gly Thr Lys Leu Glu Ile Lys
            100                 105

<210> SEQ ID NO 142
<211> LENGTH: 106
<212> TYPE: PRT
<213> ORGANISM: Artificial sequence
<220> FEATURE:
<223> OTHER INFORMATION: VL2494-IGKV1-39*01 O12b

<400> SEQUENCE: 142

Asp Ile Gln Met Thr Gln Ser Pro Ser Ser Leu Ser Ala Ser Val Gly
1               5                   10                  15

Asp Arg Val Thr Ile Thr Cys Ile Thr Asn Thr Asp Ile Asp Asp Val
            20                  25                  30

Ile His Trp Tyr Gln Gln Lys Pro Gly Lys Ala Pro Lys Leu Leu Ile
        35                  40                  45

Tyr Glu Gly Asn Thr Leu Arg Pro Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Ser Asp Asn Leu Leu Thr
                85                  90                  95

Phe Gly Gln Gly Thr Lys Leu Glu Ile Lys
            100                 105

<210> SEQ ID NO 143
<211> LENGTH: 117
<212> TYPE: PRT
<213> ORGANISM: Artificial sequence
<220> FEATURE:
<223> OTHER INFORMATION: VH2494-IGHV1-f*01

<400> SEQUENCE: 143

Glu Val Gln Leu Val Gln Ser Gly Ala Glu Val Lys Lys Pro Gly Ala
1               5                   10                  15

Thr Val Lys Ile Ser Cys Lys Val Ser Ala Phe Asn Ile Lys Asp Asp
            20                  25                  30

Tyr Met His Trp Val Gln Gln Ala Pro Gly Lys Gly Leu Glu Trp Met
        35                  40                  45
```

```
Gly Arg Ile Asp Pro Ala Ile Gly Asn Thr Glu Tyr Ala Glu Lys Phe
        50                  55                  60

Gln Gly Arg Val Thr Ile Thr Ala Asp Thr Ser Thr Asp Thr Ala Tyr
 65                  70                  75                  80

Met Glu Leu Ser Ser Leu Arg Ser Glu Asp Thr Ala Val Tyr Tyr Cys
                 85                  90                  95

Ala Thr Gly Asp Phe Tyr Ala Met Asp Tyr Trp Gly Gln Gly Thr Leu
                100                 105                 110

Val Thr Val Ser Ser
            115

<210> SEQ ID NO 144
<211> LENGTH: 117
<212> TYPE: PRT
<213> ORGANISM: Artificial sequence
<220> FEATURE:
<223> OTHER INFORMATION: VH2494-IGHV1-24*01

<400> SEQUENCE: 144

Gln Val Gln Leu Val Gln Ser Gly Ala Glu Val Lys Lys Pro Gly Ala
 1               5                  10                  15

Ser Val Lys Val Ser Cys Lys Val Ser Ala Phe Asn Ile Lys Asp Asp
                20                  25                  30

Tyr Met His Trp Val Arg Gln Ala Pro Gly Lys Gly Leu Glu Trp Met
             35                  40                  45

Gly Arg Ile Asp Pro Ala Ile Gly Asn Thr Glu Tyr Ala Pro Lys Phe
        50                  55                  60

Gln Asp Arg Val Thr Met Thr Glu Asp Thr Ser Thr Asp Thr Ala Tyr
 65                  70                  75                  80

Met Glu Leu Ser Ser Leu Arg Ser Glu Asp Thr Ala Val Tyr Tyr Cys
                 85                  90                  95

Ala Thr Gly Asp Phe Tyr Ala Met Asp Tyr Trp Gly Gln Gly Thr Leu
                100                 105                 110

Val Thr Val Ser Ser
            115

<210> SEQ ID NO 145
<211> LENGTH: 117
<212> TYPE: PRT
<213> ORGANISM: Artificial sequence
<220> FEATURE:
<223> OTHER INFORMATION: VH STLH201

<400> SEQUENCE: 145

Glu Val Gln Leu Val Gln Ser Gly Ala Glu Val Lys Lys Pro Gly Ala
 1               5                  10                  15

Thr Val Lys Ile Ser Cys Lys Val Ser Ala Phe Asn Ile Lys Asp Asp
                20                  25                  30

Tyr Met His Trp Val Gln Gln Ala Pro Gly Lys Gly Leu Glu Trp Met
             35                  40                  45

Gly Arg Ile Asp Pro Ala Ile Gly Asn Thr Glu Tyr Ala Glu Lys Phe
        50                  55                  60

Gln Gly Arg Val Thr Ile Thr Ala Asp Thr Ser Thr Asp Thr Ala Tyr
 65                  70                  75                  80

Met Glu Leu Ser Ser Leu Arg Ser Glu Asp Thr Ala Val Tyr Tyr Cys
                 85                  90                  95

Ala Thr Gly Asp Phe Tyr Ala Met Ala Tyr Trp Gly Gln Gly Thr Leu
                100                 105                 110
```

Val Thr Val Ser Ser
        115

<210> SEQ ID NO 146
<211> LENGTH: 8
<212> TYPE: PRT
<213> ORGANISM: Artificial sequence
<220> FEATURE:
<223> OTHER INFORMATION: HCDR3 of STLM226-STLM232

<400> SEQUENCE: 146

Gly Asp Phe Tyr Ala Met Ala Tyr
1               5

<210> SEQ ID NO 147
<211> LENGTH: 8
<212> TYPE: PRT
<213> ORGANISM: Artificial sequence
<220> FEATURE:
<223> OTHER INFORMATION: STLM266 VL

<400> SEQUENCE: 147

Leu Gln Ser Asp Asn Leu Leu Thr
1               5

<210> SEQ ID NO 148
<211> LENGTH: 109
<212> TYPE: PRT
<213> ORGANISM: Artificial
<220> FEATURE:
<223> OTHER INFORMATION: IGHV1-24*01 framework

<400> SEQUENCE: 148

Gln Val Gln Leu Val Gln Ser Gly Ala Glu Val Lys Lys Pro Gly Ala
1               5                   10                  15

Ser Val Lys Val Ser Cys Lys Val Ser Gly Tyr Thr Leu Thr Glu Leu
            20                  25                  30

Ser Met His Trp Val Arg Gln Ala Pro Gly Lys Gly Leu Glu Trp Met
        35                  40                  45

Gly Gly Phe Asp Pro Glu Asp Gly Glu Thr Ile Tyr Ala Gln Lys Phe
    50                  55                  60

Gln Gly Arg Val Thr Met Thr Glu Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Ala Thr Trp Gly Gln Gly Thr Leu Val Thr Val Ser Ser
            100                 105

<210> SEQ ID NO 149
<211> LENGTH: 109
<212> TYPE: PRT
<213> ORGANISM: Artificial
<220> FEATURE:
<223> OTHER INFORMATION: IGHV1-f*01 framework

<400> SEQUENCE: 149

Glu Val Gln Leu Val Gln Ser Gly Ala Glu Val Lys Lys Pro Gly Ala
1               5                   10                  15

Thr Val Lys Ile Ser Cys Lys Val Ser Gly Tyr Thr Phe Thr Asp Tyr
            20                  25                  30

Tyr Met His Trp Val Gln Gln Ala Pro Gly Lys Gly Leu Glu Trp Met
        35                  40                  45

```
Gly Leu Val Asp Pro Glu Asp Gly Glu Thr Ile Tyr Ala Glu Lys Phe
         50                  55                  60

Gln Gly Arg Val Thr Ile Thr Ala Asp Thr Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Thr Trp Gly Gln Gly Thr Leu Val Thr Val Ser Ser
                100                 105

<210> SEQ ID NO 150
<211> LENGTH: 106
<212> TYPE: PRT
<213> ORGANISM: Artificial
<220> FEATURE:
<223> OTHER INFORMATION: IGKV3-15*01 L2 framework

<400> SEQUENCE: 150

Glu Ile Val Met Thr Gln Ser Pro Ala Thr Leu Ser Val Ser Pro Gly
 1               5                  10                  15

Glu Arg Ala Thr Leu Ser Cys Arg Ala Ser Gln Ser Val Ser Ser Asn
                 20                  25                  30

Leu Ala Trp Tyr Gln Gln Lys Pro Gly Gln Ala Pro Arg Leu Leu Ile
             35                  40                  45

Tyr Gly Ala Ser Thr Arg Ala Thr Gly Ile Pro Ala Arg Phe Ser Gly
 50                  55                  60

Ser Gly Ser Gly Thr Glu Phe Thr Leu Thr Ile Ser Ser Leu Gln Ser
 65                  70                  75                  80

Glu Asp Phe Ala Val Tyr Tyr Cys Gln Gln Tyr Asn Trp Pro Pro Thr
                 85                  90                  95

Phe Gly Gln Gly Thr Lys Leu Glu Ile Lys
                100                 105

<210> SEQ ID NO 151
<211> LENGTH: 106
<212> TYPE: PRT
<213> ORGANISM: Artificial
<220> FEATURE:
<223> OTHER INFORMATION: IGKV1-9*01 L8 framework

<400> SEQUENCE: 151

Asp Ile Gln Leu Thr Gln Ser Pro Ser Phe Leu Ser Ala Ser Val Gly
 1               5                  10                  15

Asp Arg Val Thr Ile Thr Cys Arg Ala Ser Gln Gly Ile Ser Ser Tyr
                 20                  25                  30

Leu Ala Trp Tyr Gln Gln Lys Pro Gly Lys Ala Pro Lys Leu Leu Ile
             35                  40                  45

Tyr Ala Ala Ser Thr Leu Gln Ser Gly Val Pro Ser Arg Phe Ser Gly
 50                  55                  60

Ser Gly Ser Gly Thr Glu Phe Thr Leu Thr Ile Ser Ser Leu Gln Pro
 65                  70                  75                  80

Glu Asp Phe Ala Thr Tyr Tyr Cys Gln Gln Leu Asn Ser Tyr Pro Thr
                 85                  90                  95

Phe Gly Gln Gly Thr Lys Leu Glu Ile Lys
                100                 105

<210> SEQ ID NO 152
<211> LENGTH: 106
<212> TYPE: PRT
```

-continued

<213> ORGANISM: Artificial
<220> FEATURE:
<223> OTHER INFORMATION: IGKV1-5*01 L12

<400> SEQUENCE: 152

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Asp Ala Ser Ser Leu Glu Ser Gly Val Pro Ser Arg Phe Ser Gly
50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Asn Ser Tyr Ser Thr
                85                  90                  95

Phe Gly Gln Gly Thr Lys Leu Glu Ile Lys
            100                 105

<210> SEQ ID NO 153
<211> LENGTH: 106
<212> TYPE: PRT
<213> ORGANISM: Artificial
<220> FEATURE:
<223> OTHER INFORMATION: IGKV1-12*01 L5

<400> SEQUENCE: 153

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asn Ser Phe Pro Thr
                85                  90                  95

Phe Gly Gln Gly Thr Lys Leu Glu Ile Lys
            100                 105

<210> SEQ ID NO 154
<211> LENGTH: 106
<212> TYPE: PRT
<213> ORGANISM: Artificial
<220> FEATURE:
<223> OTHER INFORMATION: IGKV1-39*01 O12

<400> SEQUENCE: 154

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Thr
                85                  90                  95

Phe Gly Gln Gly Thr Lys Leu Glu Ile Lys
            100                 105

<210> SEQ ID NO 155
<211> LENGTH: 106
<212> TYPE: PRT
<213> ORGANISM: Artificial
<220> FEATURE:
<223> OTHER INFORMATION: IGKV1-27*01 A20

<400> SEQUENCE: 155

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Asn Tyr
            20                  25                  30

Leu Ala Trp Tyr Gln Gln Lys Pro Gly Lys Val Pro Lys Leu Leu Ile
        35                  40                  45

Tyr Ala Ala Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Lys Tyr Asn Ser Ala Pro Thr
                85                  90                  95

Phe Gly Gln Gly Thr Lys Leu Glu Ile Lys
            100                 105

<210> SEQ ID NO 156
<211> LENGTH: 106
<212> TYPE: PRT
<213> ORGANISM: Artificial
<220> FEATURE:
<223> OTHER INFORMATION: IGKV1-33*01 O18

<400> SEQUENCE: 156

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Tyr Asp Asn Leu Pro Thr
                85                  90                  95

Phe Gly Gln Gly Thr Lys Leu Glu Ile Lys
            100                 105

<210> SEQ ID NO 157
<211> LENGTH: 328
<212> TYPE: PRT
<213> ORGANISM: homo sapiens

<400> SEQUENCE: 157

```
Met Gly Phe Trp Ile Leu Ala Ile Leu Thr Ile Leu Met Tyr Ser Thr
1               5                   10                  15

Ala Ala Lys Phe Ser Lys Gln Ser Trp Gly Leu Glu Asn Glu Ala Leu
            20                  25                  30

Ile Val Arg Cys Pro Arg Gln Gly Lys Pro Ser Tyr Thr Val Asp Trp
        35                  40                  45

Tyr Tyr Ser Gln Thr Asn Lys Ser Ile Pro Thr Gln Glu Arg Asn Arg
50                  55                  60

Val Phe Ala Ser Gly Gln Leu Leu Lys Phe Leu Pro Ala Glu Val Ala
65                  70                  75                  80

Asp Ser Gly Ile Tyr Thr Cys Ile Val Arg Ser Pro Thr Phe Asn Arg
                85                  90                  95

Thr Gly Tyr Ala Asn Val Thr Ile Tyr Lys Lys Gln Ser Asp Cys Asn
                100                 105                 110

Val Pro Asp Tyr Leu Met Tyr Ser Thr Val Ser Gly Ser Glu Lys Asn
            115                 120                 125

Ser Lys Ile Tyr Cys Pro Thr Ile Asp Leu Tyr Asn Trp Thr Ala Pro
        130                 135                 140

Leu Glu Trp Phe Lys Asn Cys Gln Ala Leu Gln Gly Ser Arg Tyr Arg
145                 150                 155                 160

Ala His Lys Ser Phe Leu Val Ile Asp Asn Val Met Thr Glu Asp Ala
                165                 170                 175

Gly Asp Tyr Thr Cys Lys Phe Ile His Asn Glu Asn Gly Ala Asn Tyr
                180                 185                 190

Ser Val Thr Ala Thr Arg Ser Phe Thr Val Lys Asp Glu Gln Gly Phe
            195                 200                 205

Ser Leu Phe Pro Val Ile Gly Ala Pro Ala Gln Asn Glu Ile Lys Glu
        210                 215                 220

Val Glu Ile Gly Lys Asn Ala Asn Leu Thr Cys Ser Ala Cys Phe Gly
225                 230                 235                 240

Lys Gly Thr Gln Phe Leu Ala Ala Val Leu Trp Gln Leu Asn Gly Thr
                245                 250                 255

Lys Ile Thr Asp Phe Gly Glu Pro Arg Ile Gln Gln Glu Glu Gly Gln
                260                 265                 270

Asn Gln Ser Phe Ser Asn Gly Leu Ala Cys Leu Asp Met Val Leu Arg
            275                 280                 285

Ile Ala Asp Val Lys Glu Glu Asp Leu Leu Leu Gln Tyr Asp Cys Leu
        290                 295                 300

Ala Leu Asn Leu His Gly Leu Arg Arg His Thr Val Arg Leu Ser Arg
305                 310                 315                 320

Lys Asn Pro Ser Lys Glu Cys Phe
                325

<210> SEQ ID NO 158
<211> LENGTH: 109
<212> TYPE: PRT
<213> ORGANISM: Artificial
<220> FEATURE:
<223> OTHER INFORMATION: VH 3-23 framework

<400> SEQUENCE: 158

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30
```

```
Ala Met Ser Trp Val Arg Gln Ala Pro Gly Lys Gly Leu Glu Trp Val
            35                  40                  45

Ser Ala Ile Ser Gly Ser Gly Gly Ser Thr Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Trp Gly Gln Gly Thr Leu Val Thr Val Ser Ser
            100                 105

<210> SEQ ID NO 159
<211> LENGTH: 106
<212> TYPE: PRT
<213> ORGANISM: Artificial
<220> FEATURE:
<223> OTHER INFORMATION: Vk L6 framework (IGKV3-11 )

<400> SEQUENCE: 159

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
            35                  40                  45

Tyr Asp Ala Ser Asn Arg Ala Thr Gly Ile Pro Ala Arg Phe Ser Gly
        50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Thr
                85                  90                  95

Phe Gly Gln Gly Thr Lys Val Glu Ile Lys
            100                 105

<210> SEQ ID NO 160
<211> LENGTH: 5
<212> TYPE: PRT
<213> ORGANISM: Artificial
<220> FEATURE:
<223> OTHER INFORMATION: HCDR1 consensus
<220> FEATURE:
<221> NAME/KEY: Xaa1
<222> LOCATION: (1)..(1)
<223> OTHER INFORMATION: Xaa1 is S, F, D, I, G or V
<220> FEATURE:
<221> NAME/KEY: Xaa2
<222> LOCATION: (2)..(2)
<223> OTHER INFORMATION: Xaa2 is Y or D
<220> FEATURE:
<221> NAME/KEY: Xaa3
<222> LOCATION: (3)..(3)
<223> OTHER INFORMATION: Xaa3 is A, D or S
<220> FEATURE:
<221> NAME/KEY: Xaa4
<222> LOCATION: (5)..(5)
<223> OTHER INFORMATION: Xaa4 is S, F or I

<400> SEQUENCE: 160

Xaa Xaa Xaa Met Xaa
1               5

<210> SEQ ID NO 161
<211> LENGTH: 17
```

```
<212> TYPE: PRT
<213> ORGANISM: Artificial
<220> FEATURE:
<223> OTHER INFORMATION: HCDR2 consensus
<220> FEATURE:
<221> NAME/KEY: Xaa1
<222> LOCATION: (1)..(1)
<223> OTHER INFORMATION: Xaa1 is A, S, T, Y or D
<220> FEATURE:
<221> NAME/KEY: Xaa2
<222> LOCATION: (3)..(3)
<223> OTHER INFORMATION: Xaa2 is S, R, E, K, G or A
<220> FEATURE:
<221> NAME/KEY: Xaa3
<222> LOCATION: (5)..(5)
<223> OTHER INFORMATION: Xaa3 is S, E or N
<220> FEATURE:
<221> NAME/KEY: Xaa4
<222> LOCATION: (8)..(8)
<223> OTHER INFORMATION: Xaa4 is S, R, E, G, T, D or A
<220> FEATURE:
<221> NAME/KEY: Xaa5
<222> LOCATION: (10)..(10)
<223> OTHER INFORMATION: Xaa5 is Y, D, N, A or S

<400> SEQUENCE: 161

Xaa Ile Xaa Gly Xaa Gly Gly Xaa Thr Xaa Tyr Ala Asp Ser Val Lys
1               5                   10                  15

Gly

<210> SEQ ID NO 162
<211> LENGTH: 14
<212> TYPE: PRT
<213> ORGANISM: Artificial
<220> FEATURE:
<223> OTHER INFORMATION: HCDR3 consensus
<220> FEATURE:
<221> NAME/KEY: Xaa1
<222> LOCATION: (1)..(1)
<223> OTHER INFORMATION: Xaa1 is D, A, R, N, Q, P, E, I, H, S, T or Y
<220> FEATURE:
<221> NAME/KEY: Xaa2
<222> LOCATION: (2)..(2)
<223> OTHER INFORMATION: Xaa2 is P, A, H, Y, E, Q, L, S, N, T, V or I

<400> SEQUENCE: 162

Xaa Xaa Trp Ser Thr Glu Gly Ser Phe Phe Val Leu Asp Tyr
1               5                   10

<210> SEQ ID NO 163
<211> LENGTH: 11
<212> TYPE: PRT
<213> ORGANISM: Artificial
<220> FEATURE:
<223> OTHER INFORMATION: LCDR1 consensus
<220> FEATURE:
<221> NAME/KEY: Xaa1
<222> LOCATION: (9)..(9)
<223> OTHER INFORMATION: Xaa1 is A or D

<400> SEQUENCE: 163

Arg Ala Ser Gln Ser Val Asp Asp Xaa Leu Ala
1               5                   10

<210> SEQ ID NO 164
<211> LENGTH: 9
<212> TYPE: PRT
<213> ORGANISM: Artificial
<220> FEATURE:
<223> OTHER INFORMATION: LCDR3 consensus
<220> FEATURE:
<221> NAME/KEY: Xaa1
```

```
<222> LOCATION: (3)..(3)
<223> OTHER INFORMATION: Xaa1 is F or Y
<220> FEATURE:
<221> NAME/KEY: Xaa2
<222> LOCATION: (4)..(4)
<223> OTHER INFORMATION: Xaa2 is Y, I or N
<220> FEATURE:
<221> NAME/KEY: Xaa3
<222> LOCATION: (5)..(5)
<223> OTHER INFORMATION: Xaa3 is N, G, D or T
<220> FEATURE:
<221> NAME/KEY: Xaa4
<222> LOCATION: (6)..(6)
<223> OTHER INFORMATION: Xaa4 is W or A
<220> FEATURE:
<221> NAME/KEY: Xaa5
<222> LOCATION: (7)..(7)
<223> OTHER INFORMATION: Xaa5 is P or deleted
<220> FEATURE:
<221> NAME/KEY: Xaa6
<222> LOCATION: (8)..(8)
<223> OTHER INFORMATION: Xaa6 is L or I

<400> SEQUENCE: 164

Gln Gln Xaa Xaa Xaa Xaa Xaa Xaa Thr
1               5

<210> SEQ ID NO 165
<211> LENGTH: 14
<212> TYPE: PRT
<213> ORGANISM: Artificial
<220> FEATURE:
<223> OTHER INFORMATION: STLH255 HCDR3

<400> SEQUENCE: 165

Ala Pro Trp Ser Thr Glu Gly Ser Phe Phe Val Leu Asp Tyr
1               5                   10

<210> SEQ ID NO 166
<211> LENGTH: 14
<212> TYPE: PRT
<213> ORGANISM: Artificial
<220> FEATURE:
<223> OTHER INFORMATION: STLH256 HCDR3

<400> SEQUENCE: 166

Arg Pro Trp Ser Thr Glu Gly Ser Phe Phe Val Leu Asp Tyr
1               5                   10

<210> SEQ ID NO 167
<211> LENGTH: 14
<212> TYPE: PRT
<213> ORGANISM: Artificial
<220> FEATURE:
<223> OTHER INFORMATION: STLH257 HCDR3

<400> SEQUENCE: 167

Asn Pro Trp Ser Thr Glu Gly Ser Phe Phe Val Leu Asp Tyr
1               5                   10

<210> SEQ ID NO 168
<211> LENGTH: 14
<212> TYPE: PRT
<213> ORGANISM: Artificial
<220> FEATURE:
<223> OTHER INFORMATION: STLH258 HCDR3

<400> SEQUENCE: 168

Gln Pro Trp Ser Thr Glu Gly Ser Phe Phe Val Leu Asp Tyr
1               5                   10
```

<210> SEQ ID NO 169
<211> LENGTH: 14
<212> TYPE: PRT
<213> ORGANISM: Artificial
<220> FEATURE:
<223> OTHER INFORMATION: STLH259 HCDR3

<400> SEQUENCE: 169

Glu Pro Trp Ser Thr Glu Gly Ser Phe Phe Val Leu Asp Tyr
1               5                   10

<210> SEQ ID NO 170
<211> LENGTH: 14
<212> TYPE: PRT
<213> ORGANISM: Artificial
<220> FEATURE:
<223> OTHER INFORMATION: STLH260 HCDR3

<400> SEQUENCE: 170

Ile Pro Trp Ser Thr Glu Gly Ser Phe Phe Val Leu Asp Tyr
1               5                   10

<210> SEQ ID NO 171
<211> LENGTH: 14
<212> TYPE: PRT
<213> ORGANISM: Artificial
<220> FEATURE:
<223> OTHER INFORMATION: STLH261 HCDR3

<400> SEQUENCE: 171

His Pro Trp Ser Thr Glu Gly Ser Phe Phe Val Leu Asp Tyr
1               5                   10

<210> SEQ ID NO 172
<211> LENGTH: 14
<212> TYPE: PRT
<213> ORGANISM: Artificial
<220> FEATURE:
<223> OTHER INFORMATION: STLH262 HCDR3

<400> SEQUENCE: 172

Ser Pro Trp Ser Thr Glu Gly Ser Phe Phe Val Leu Asp Tyr
1               5                   10

<210> SEQ ID NO 173
<211> LENGTH: 14
<212> TYPE: PRT
<213> ORGANISM: Artificial
<220> FEATURE:
<223> OTHER INFORMATION: STLH263 HCDR3

<400> SEQUENCE: 173

Thr Pro Trp Ser Thr Glu Gly Ser Phe Phe Val Leu Asp Tyr
1               5                   10

<210> SEQ ID NO 174
<211> LENGTH: 14
<212> TYPE: PRT
<213> ORGANISM: Artificial
<220> FEATURE:
<223> OTHER INFORMATION: STLH264 HCDR3

<400> SEQUENCE: 174

Tyr Pro Trp Ser Thr Glu Gly Ser Phe Phe Val Leu Asp Tyr
1               5                   10

```
<210> SEQ ID NO 175
<211> LENGTH: 14
<212> TYPE: PRT
<213> ORGANISM: Artificial
<220> FEATURE:
<223> OTHER INFORMATION: STLH265 HCDR3

<400> SEQUENCE: 175

Asp Ala Trp Ser Thr Glu Gly Ser Phe Phe Val Leu Asp Tyr
1               5                   10

<210> SEQ ID NO 176
<211> LENGTH: 14
<212> TYPE: PRT
<213> ORGANISM: Artificial
<220> FEATURE:
<223> OTHER INFORMATION: STLH266 HCDR3

<400> SEQUENCE: 176

Asp His Trp Ser Thr Glu Gly Ser Phe Phe Val Leu Asp Tyr
1               5                   10

<210> SEQ ID NO 177
<211> LENGTH: 14
<212> TYPE: PRT
<213> ORGANISM: Artificial
<220> FEATURE:
<223> OTHER INFORMATION: STLH267 HCDR3

<400> SEQUENCE: 177

Asp Tyr Trp Ser Thr Glu Gly Ser Phe Phe Val Leu Asp Tyr
1               5                   10

<210> SEQ ID NO 178
<211> LENGTH: 14
<212> TYPE: PRT
<213> ORGANISM: Artificial
<220> FEATURE:
<223> OTHER INFORMATION: STLH268 HCDR3

<400> SEQUENCE: 178

Asp Glu Trp Ser Thr Glu Gly Ser Phe Phe Val Leu Asp Tyr
1               5                   10

<210> SEQ ID NO 179
<211> LENGTH: 14
<212> TYPE: PRT
<213> ORGANISM: Artificial
<220> FEATURE:
<223> OTHER INFORMATION: STLH269 HCDR3

<400> SEQUENCE: 179

Asp Gln Trp Ser Thr Glu Gly Ser Phe Phe Val Leu Asp Tyr
1               5                   10

<210> SEQ ID NO 180
<211> LENGTH: 14
<212> TYPE: PRT
<213> ORGANISM: Artificial
<220> FEATURE:
<223> OTHER INFORMATION: STLH270 HCDR3

<400> SEQUENCE: 180

Asp Leu Trp Ser Thr Glu Gly Ser Phe Phe Val Leu Asp Tyr
1               5                   10
```

```
<210> SEQ ID NO 181
<211> LENGTH: 14
<212> TYPE: PRT
<213> ORGANISM: Artificial
<220> FEATURE:
<223> OTHER INFORMATION: STLH271 HCDR3

<400> SEQUENCE: 181

Asp Ser Trp Ser Thr Glu Gly Ser Phe Phe Val Leu Asp Tyr
1               5                   10

<210> SEQ ID NO 182
<211> LENGTH: 14
<212> TYPE: PRT
<213> ORGANISM: Artificial
<220> FEATURE:
<223> OTHER INFORMATION: STLH272 HCDR3

<400> SEQUENCE: 182

Asp Asn Trp Ser Thr Glu Gly Ser Phe Phe Val Leu Asp Tyr
1               5                   10

<210> SEQ ID NO 183
<211> LENGTH: 14
<212> TYPE: PRT
<213> ORGANISM: Artificial
<220> FEATURE:
<223> OTHER INFORMATION: STLH273 HCDR3

<400> SEQUENCE: 183

Asp Thr Trp Ser Thr Glu Gly Ser Phe Phe Val Leu Asp Tyr
1               5                   10

<210> SEQ ID NO 184
<211> LENGTH: 14
<212> TYPE: PRT
<213> ORGANISM: Artificial
<220> FEATURE:
<223> OTHER INFORMATION: STLH274 HCDR3

<400> SEQUENCE: 184

Asp Val Trp Ser Thr Glu Gly Ser Phe Phe Val Leu Asp Tyr
1               5                   10

<210> SEQ ID NO 185
<211> LENGTH: 14
<212> TYPE: PRT
<213> ORGANISM: Artificial
<220> FEATURE:
<223> OTHER INFORMATION: STLH275 HCDR3

<400> SEQUENCE: 185

Asp Ile Trp Ser Thr Glu Gly Ser Phe Phe Val Leu Asp Tyr
1               5                   10

<210> SEQ ID NO 186
<211> LENGTH: 123
<212> TYPE: PRT
<213> ORGANISM: Artificial
<220> FEATURE:
<223> OTHER INFORMATION: ST2H52

<400> SEQUENCE: 186

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30
```

Ala Met Phe Trp Val Arg Gln Ala Pro Gly Lys Gly Leu Glu Trp Val
            35                  40                  45

Ser Ala Ile Glu Gly Glu Gly Gly Glu Thr Asn Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Arg Asp Pro Trp Ser Thr Glu Gly Ser Phe Phe Val Leu Asp Tyr
                100                 105                 110

Trp Gly Gln Gly Thr Leu Val Thr Val Ser Ser
            115                 120

<210> SEQ ID NO 187
<211> LENGTH: 123
<212> TYPE: PRT
<213> ORGANISM: Artificial
<220> FEATURE:
<223> OTHER INFORMATION: ST2H50

<400> SEQUENCE: 187

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Ile Tyr
             20                  25                  30

Asp Met Ile Trp Val Arg Gln Ala Pro Gly Lys Gly Leu Glu Trp Val
            35                  40                  45

Ser Thr Ile Lys Gly Glu Gly Gly Thr Tyr Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Arg Asp Pro Trp Ser Thr Glu Gly Ser Phe Phe Val Leu Asp Tyr
                100                 105                 110

Trp Gly Gln Gly Thr Leu Val Thr Val Ser Ser
            115                 120

<210> SEQ ID NO 188
<211> LENGTH: 123
<212> TYPE: PRT
<213> ORGANISM: Artificial
<220> FEATURE:
<223> OTHER INFORMATION: ST2H318

<400> SEQUENCE: 188

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Asp Asp
             20                  25                  30

Ala Met Ile Trp Val Arg Gln Ala Pro Gly Lys Gly Leu Glu Trp Val
            35                  40                  45

Ser Tyr Ile Gly Gly Asn Gly Gly Thr Thr Tyr Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys

```
                 85                  90                  95
Ala Arg Asp Pro Trp Ser Thr Glu Gly Ser Phe Phe Val Leu Asp Tyr
            100                 105                 110
Trp Gly Gln Gly Thr Leu Val Thr Val Ser Ser
        115                 120

<210> SEQ ID NO 189
<211> LENGTH: 123
<212> TYPE: PRT
<213> ORGANISM: Artificial
<220> FEATURE:
<223> OTHER INFORMATION: ST2H316

<400> SEQUENCE: 189

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Gly Tyr
            20                  25                  30

Ala Met Ile Trp Val Arg Gln Ala Pro Gly Lys Gly Leu Glu Trp Val
        35                  40                  45

Ser Tyr Ile Glu Gly Glu Gly Glu Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Pro Trp Ser Thr Glu Gly Ser Phe Phe Val Leu Asp Tyr
            100                 105                 110

Trp Gly Gln Gly Thr Leu Val Thr Val Ser Ser
        115                 120

<210> SEQ ID NO 190
<211> LENGTH: 123
<212> TYPE: PRT
<213> ORGANISM: Artificial
<220> FEATURE:
<223> OTHER INFORMATION: ST2H314

<400> SEQUENCE: 190

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Val Tyr
            20                  25                  30

Asp Met Ile Trp Val Arg Gln Ala Pro Gly Lys Gly Leu Glu Trp Val
        35                  40                  45

Ser Thr Ile Arg Gly Gly Gly Gly Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Pro Trp Ser Thr Glu Gly Ser Phe Phe Val Leu Asp Tyr
            100                 105                 110

Trp Gly Gln Gly Thr Leu Val Thr Val Ser Ser
        115                 120

<210> SEQ ID NO 191
<211> LENGTH: 123
```

<212> TYPE: PRT
<213> ORGANISM: Artificial
<220> FEATURE:
<223> OTHER INFORMATION: ST2H257

<400> SEQUENCE: 191

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ile Tyr
            20                  25                  30

Asp Met Ile Trp Val Arg Gln Ala Pro Gly Lys Gly Leu Glu Trp Val
        35                  40                  45

Ser Ser Ile Arg Gly Glu Gly Gly Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Pro Trp Ser Thr Glu Gly Ser Phe Val Leu Asp Tyr
            100                 105                 110

Trp Gly Gln Gly Thr Leu Val Thr Val Ser Ser
        115                 120

<210> SEQ ID NO 192
<211> LENGTH: 123
<212> TYPE: PRT
<213> ORGANISM: Artificial
<220> FEATURE:
<223> OTHER INFORMATION: ST2H232

<400> SEQUENCE: 192

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ile Tyr
            20                  25                  30

Asp Met Ile Trp Val Arg Gln Ala Pro Gly Lys Gly Leu Glu Trp Val
        35                  40                  45

Ser Thr Ile Arg Gly Glu Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Pro Trp Ser Thr Glu Gly Ser Phe Val Leu Asp Tyr
            100                 105                 110

Trp Gly Gln Gly Thr Leu Val Thr Val Ser Ser
        115                 120

<210> SEQ ID NO 193
<211> LENGTH: 123
<212> TYPE: PRT
<213> ORGANISM: Artificial
<220> FEATURE:
<223> OTHER INFORMATION: ST2H231

<400> SEQUENCE: 193

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ile Tyr

```
                    20                  25                  30
Asp Met Ile Trp Val Arg Gln Ala Pro Gly Lys Gly Leu Glu Trp Val
                35                  40                  45
Ser Thr Ile Arg Gly Glu Gly Gly Thr Ser Tyr Ala Asp Ser Val
            50                  55                  60
Lys Gly Arg Phe Thr Ile Ser Arg Asp Asn Ser Lys Asn Thr Leu Tyr
65                  70                  75                  80
Leu Gln Met Asn Ser Leu Arg Ala Glu Asp Thr Ala Val Tyr Tyr Cys
                85                  90                  95
Ala Arg Asp Pro Trp Ser Thr Glu Gly Ser Phe Phe Val Leu Asp Tyr
            100                 105                 110
Trp Gly Gln Gly Thr Leu Val Thr Val Ser Ser
            115                 120
```

<210> SEQ ID NO 194
<211> LENGTH: 123
<212> TYPE: PRT
<213> ORGANISM: Artificial
<220> FEATURE:
<223> OTHER INFORMATION: ST2H228

<400> SEQUENCE: 194

```
Glu Val Gln Leu Leu Glu Ser Gly Gly Gly Leu Val Gln Pro Gly Gly
1               5                   10                  15
Ser Leu Arg Leu Ser Cys Ala Ala Ser Gly Phe Thr Phe Ser Ser Tyr
                20                  25                  30
Asp Met Ile Trp Val Arg Gln Ala Pro Gly Lys Gly Leu Glu Trp Val
                35                  40                  45
Ser Thr Ile Arg Gly Glu Gly Gly Thr Thr Ala Tyr Ala Asp Ser Val
            50                  55                  60
Lys Gly Arg Phe Thr Ile Ser Arg Asp Asn Ser Lys Asn Thr Leu Tyr
65                  70                  75                  80
Leu Gln Met Asn Ser Leu Arg Ala Glu Asp Thr Ala Val Tyr Tyr Cys
                85                  90                  95
Ala Arg Asp Pro Trp Ser Thr Glu Gly Ser Phe Phe Val Leu Asp Tyr
            100                 105                 110
Trp Gly Gln Gly Thr Leu Val Thr Val Ser Ser
            115                 120
```

<210> SEQ ID NO 195
<211> LENGTH: 123
<212> TYPE: PRT
<213> ORGANISM: Artificial
<220> FEATURE:
<223> OTHER INFORMATION: ST2H202

<400> SEQUENCE: 195

```
Glu Val Gln Leu Leu Glu Ser Gly Gly Gly Leu Val Gln Pro Gly Gly
1               5                   10                  15
Ser Leu Arg Leu Ser Cys Ala Ala Ser Gly Phe Thr Phe Ser Phe Tyr
                20                  25                  30
Asp Met Ile Trp Val Arg Gln Ala Pro Gly Lys Gly Leu Glu Trp Val
                35                  40                  45
Ser Thr Ile Arg Gly Glu Gly Gly Asp Thr Asn Tyr Ala Asp Ser Val
            50                  55                  60
Lys Gly Arg Phe Thr Ile Ser Arg Asp Asn Ser Lys Asn Thr Leu Tyr
65                  70                  75                  80
```

```
Leu Gln Met Asn Ser Leu Arg Ala Glu Asp Thr Ala Val Tyr Tyr Cys
                85                  90                  95

Ala Arg Asp Pro Trp Ser Thr Glu Gly Ser Phe Phe Val Leu Asp Tyr
            100                 105                 110

Trp Gly Gln Gly Thr Leu Val Thr Val Ser Ser
        115                 120

<210> SEQ ID NO 196
<211> LENGTH: 123
<212> TYPE: PRT
<213> ORGANISM: Artificial
<220> FEATURE:
<223> OTHER INFORMATION: ST2H179

<400> SEQUENCE: 196

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met Phe Trp Val Arg Gln Ala Pro Gly Lys Gly Leu Glu Trp Val
        35                  40                  45

Ser Asp Ile Lys Gly Glu Gly Gly Arg Thr Ala Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Pro Trp Ser Thr Glu Gly Ser Phe Phe Val Leu Asp Tyr
            100                 105                 110

Trp Gly Gln Gly Thr Leu Val Thr Val Ser Ser
        115                 120

<210> SEQ ID NO 197
<211> LENGTH: 123
<212> TYPE: PRT
<213> ORGANISM: Artificial
<220> FEATURE:
<223> OTHER INFORMATION: ST2H173

<400> SEQUENCE: 197

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met Phe Trp Val Arg Gln Ala Pro Gly Lys Gly Leu Glu Trp Val
        35                  40                  45

Ser Asp Ile Lys Gly Glu Gly Gly Ala Thr Asn Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Pro Trp Ser Thr Glu Gly Ser Phe Phe Val Leu Asp Tyr
            100                 105                 110

Trp Gly Gln Gly Thr Leu Val Thr Val Ser Ser
        115                 120

<210> SEQ ID NO 198
```

```
<211> LENGTH: 123
<212> TYPE: PRT
<213> ORGANISM: Artificial
<220> FEATURE:
<223> OTHER INFORMATION: ST2H172

<400> SEQUENCE: 198

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met Phe Trp Val Arg Gln Ala Pro Gly Lys Gly Leu Glu Trp Val
        35                  40                  45

Ser Ala Ile Ala Gly Glu Gly Gly Arg Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Pro Trp Ser Thr Glu Gly Ser Phe Phe Val Leu Asp Tyr
            100                 105                 110

Trp Gly Gln Gly Thr Leu Val Thr Val Ser Ser
        115                 120

<210> SEQ ID NO 199
<211> LENGTH: 123
<212> TYPE: PRT
<213> ORGANISM: Artificial
<220> FEATURE:
<223> OTHER INFORMATION: ST2H163

<400> SEQUENCE: 199

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Val Tyr
            20                  25                  30

Asp Met Phe Trp Val Arg Gln Ala Pro Gly Lys Gly Leu Glu Trp Val
        35                  40                  45

Ser Asp Ile Lys Gly Glu Gly Gly Glu Thr Ser Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Pro Trp Ser Thr Glu Gly Ser Phe Phe Val Leu Asp Tyr
            100                 105                 110

Trp Gly Gln Gly Thr Leu Val Thr Val Ser Ser
        115                 120

<210> SEQ ID NO 200
<211> LENGTH: 123
<212> TYPE: PRT
<213> ORGANISM: Artificial
<220> FEATURE:
<223> OTHER INFORMATION: ST2H162

<400> SEQUENCE: 200

Glu Val Gln Leu Leu Glu Ser Gly Gly Gly Leu Val Gln Pro Gly Gly
1               5                   10                  15
```

Ser Leu Arg Leu Ser Cys Ala Ala Ser Gly Phe Thr Phe Ser Val Asp
            20                  25                  30

Ser Met Phe Trp Val Arg Gln Ala Pro Gly Lys Gly Leu Glu Trp Val
        35                  40                  45

Ser Ser Ile Glu Gly Asn Gly Gly Ala Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Pro Trp Ser Thr Glu Gly Ser Phe Phe Val Leu Asp Tyr
            100                 105                 110

Trp Gly Gln Gly Thr Leu Val Thr Val Ser Ser
            115                 120

<210> SEQ ID NO 201
<211> LENGTH: 123
<212> TYPE: PRT
<213> ORGANISM: Artificial
<220> FEATURE:
<223> OTHER INFORMATION: ST2H139

<400> SEQUENCE: 201

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Gly Tyr
            20                  25                  30

Asp Met Phe Trp Val Arg Gln Ala Pro Gly Lys Gly Leu Glu Trp Val
        35                  40                  45

Ser Asp Ile Gly Gly Glu Gly Gly Ser Thr Asn Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Pro Trp Ser Thr Glu Gly Ser Phe Phe Val Leu Asp Tyr
            100                 105                 110

Trp Gly Gln Gly Thr Leu Val Thr Val Ser Ser
            115                 120

<210> SEQ ID NO 202
<211> LENGTH: 123
<212> TYPE: PRT
<213> ORGANISM: Artificial
<220> FEATURE:
<223> OTHER INFORMATION: ST2H137

<400> SEQUENCE: 202

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Phe Tyr
            20                  25                  30

Asp Met Phe Trp Val Arg Gln Ala Pro Gly Lys Gly Leu Glu Trp Val
        35                  40                  45

Ser Asp Ile Arg Gly Glu Gly Gly Thr Ala Tyr Ala Asp Ser Val
    50                  55                  60

Lys Gly Arg Phe Thr Ile Ser Arg Asp Asn Ser Lys Asn Thr Leu Tyr
65                  70                  75                  80

```
Leu Gln Met Asn Ser Leu Arg Ala Glu Asp Thr Ala Val Tyr Tyr Cys
                85                  90                  95

Ala Arg Asp Pro Trp Ser Thr Glu Gly Ser Phe Phe Val Leu Asp Tyr
            100                 105                 110

Trp Gly Gln Gly Thr Leu Val Thr Val Ser Ser
        115                 120
```

<210> SEQ ID NO 203
<211> LENGTH: 123
<212> TYPE: PRT
<213> ORGANISM: Artificial
<220> FEATURE:
<223> OTHER INFORMATION: ST2H136

<400> SEQUENCE: 203

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ile Tyr
            20                  25                  30

Asp Met Phe Trp Val Arg Gln Ala Pro Gly Lys Gly Leu Glu Trp Val
        35                  40                  45

Ser Tyr Ile Arg Gly Glu Gly Gly Asp Thr Asn Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Pro Trp Ser Thr Glu Gly Ser Phe Phe Val Leu Asp Tyr
            100                 105                 110

Trp Gly Gln Gly Thr Leu Val Thr Val Ser Ser
        115                 120
```

<210> SEQ ID NO 204
<211> LENGTH: 123
<212> TYPE: PRT
<213> ORGANISM: Artificial
<220> FEATURE:
<223> OTHER INFORMATION: ST2H129

<400> SEQUENCE: 204

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ile Tyr
            20                  25                  30

Ser Met Phe Trp Val Arg Gln Ala Pro Gly Lys Gly Leu Glu Trp Val
        35                  40                  45

Ser Asp Ile Gly Gly Glu Gly Gly Thr Ser Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Pro Trp Ser Thr Glu Gly Ser Phe Phe Val Leu Asp Tyr
            100                 105                 110

Trp Gly Gln Gly Thr Leu Val Thr Val Ser Ser
        115                 120
```

-continued

```
<210> SEQ ID NO 205
<211> LENGTH: 123
<212> TYPE: PRT
<213> ORGANISM: Artificial
<220> FEATURE:
<223> OTHER INFORMATION: ST2H112

<400> SEQUENCE: 205

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Phe Tyr
            20                  25                  30

Asp Met Phe Trp Val Arg Gln Ala Pro Gly Lys Gly Leu Glu Trp Val
        35                  40                  45

Ser Ser Ile Arg Gly Glu Gly Gly Arg Thr Asp Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Pro Trp Ser Thr Glu Gly Ser Phe Phe Val Leu Asp Tyr
            100                 105                 110

Trp Gly Gln Gly Thr Leu Val Thr Val Ser Ser
        115                 120

<210> SEQ ID NO 206
<211> LENGTH: 107
<212> TYPE: PRT
<213> ORGANISM: Artificial
<220> FEATURE:
<223> OTHER INFORMATION: ST2L32

<400> SEQUENCE: 206

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Asp Asp Asp
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Tyr Ile Gly Ala Pro Ile
                85                  90                  95

Thr Phe Gly Gln Gly Thr Lys Val Glu Ile Lys
            100                 105

<210> SEQ ID NO 207
<211> LENGTH: 107
<212> TYPE: PRT
<213> ORGANISM: Artificial
<220> FEATURE:
<223> OTHER INFORMATION: ST2L35

<400> SEQUENCE: 207

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Asp Asp Asp
            20                  25                  30
```

Leu Ala Trp Tyr Gln Gln Lys Pro Gly Gln Ala Pro Arg Leu Leu Ile
            35                  40                  45

Tyr Asp Ala Ser Asn Arg Ala Thr Gly Ile Pro Ala Arg Phe Ser Gly
        50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Tyr Ile Asp Ala Pro Leu
                85                  90                  95

Thr Phe Gly Gln Gly Thr Lys Val Glu Ile Lys
            100                 105

<210> SEQ ID NO 208
<211> LENGTH: 106
<212> TYPE: PRT
<213> ORGANISM: Artificial
<220> FEATURE:
<223> OTHER INFORMATION: ST2L49

<400> SEQUENCE: 208

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Asp Asp Asp
            20                  25                  30

Leu Ala Trp Tyr Gln Gln Lys Pro Gly Gln Ala Pro Arg Leu Leu Ile
            35                  40                  45

Tyr Asp Ala Ser Asn Arg Ala Thr Gly Ile Pro Ala Arg Phe Ser Gly
        50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Tyr Asn Asp Ala Ile Thr
                85                  90                  95

Phe Gly Gln Gly Thr Lys Val Glu Ile Lys
            100                 105

<210> SEQ ID NO 209
<211> LENGTH: 107
<212> TYPE: PRT
<213> ORGANISM: Artificial
<220> FEATURE:
<223> OTHER INFORMATION: ST2L59

<400> SEQUENCE: 209

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Asp Asp Asp
            20                  25                  30

Leu Ala Trp Tyr Gln Gln Lys Pro Gly Gln Ala Pro Arg Leu Leu Ile
            35                  40                  45

Tyr Asp Ala Ser Asn Arg Ala Thr Gly Ile Pro Ala Arg Phe Ser Gly
        50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Tyr Ile Thr Ala Pro Leu
                85                  90                  95

Thr Phe Gly Gln Gly Thr Lys Val Glu Ile Lys
            100                 105

```
<210> SEQ ID NO 210
<211> LENGTH: 14
<212> TYPE: PRT
<213> ORGANISM: Artificial
<220> FEATURE:
<223> OTHER INFORMATION: ST2L epitope

<400> SEQUENCE: 210

Arg Cys Pro Arg Gln Gly Lys Pro Ser Tyr Thr Val Asp Trp
1               5                   10

<210> SEQ ID NO 211
<211> LENGTH: 369
<212> TYPE: DNA
<213> ORGANISM: Artificial
<220> FEATURE:
<223> OTHER INFORMATION: VH cDNA for STLM208

<400> SEQUENCE: 211
gaggtgcagc tgctggagag cggcggcggc ctggtgcagc ccggcggcag cctgcgcctg      60
agctgcgccg ccagcggctt caccttcagc atctacgaca tgatctgggt gcgccaggcc     120
cccggcaagg gcctggagtg ggtcagcagc atccgcggcg agggcggcgg cacctactac     180
gccgacagcg tgaagggccg cttcaccatc agccgcgaca cagcaagaa cacccctgtac     240 ctgcagatga acagcctgcg cgccgaggac accgccgtgt actactgcgc cgcgaccccc     300
tggagcaccg agggcagctt cttcgtgctg gactactggg gccagggcac cctggtgacc     360
gtgagcagc                                                             369

<210> SEQ ID NO 212
<211> LENGTH: 321
<212> TYPE: DNA
<213> ORGANISM: Artificial
<220> FEATURE:
<223> OTHER INFORMATION: VL cDNA for STLM208

<400> SEQUENCE: 212
gagatcgtgc tgacccagag ccccgccacc ctgagcctga gccccggcga gcgcgccacc      60
ctgagctgcc gcgccagcca gagcgtggac gacgacctgg cctggtacca gcagaagccc     120
ggccaggccc ccgcctgct gatctacgac gccagcaacc gcgccaccgg catccccgcc     180
cgcttcagcg gcagcggcag cggcaccgac ttcaccctga ccatcagcag cctggagccc     240
gaggacttcg ccgtgtacta ctgccagcag tacatcaccg ccccctgac cttcggccag     300 ggcaccaagg tggagatcaa g                                               321

<210> SEQ ID NO 213
<211> LENGTH: 351
<212> TYPE: DNA
<213> ORGANISM: Artificial
<220> FEATURE:
<223> OTHER INFORMATION: VH cDNA for c2244

<400> SEQUENCE: 213
gaggtgcagc ttcaggagtc aggacctggc ctggtgaaac cttctcagtc tctgtccctc      60
acctgcactg tcactggctt ctcaatcacc agtgattatg cctggaactg gatcggcag     120 tttccaggaa gcaagctaga gtggatgggc ttcataagct acagtggtga cactagcttc     180
aacccatctc tcaaaagtcg aatctctgtc actcgagaca catccaagaa ccagttcttc     240
ctgcagttga attctgtgac tactgaggac acagccacat attactgtgc aagttatgat     300
ggttactcat tgactactg ggccaaggc actactctca cagtctcctc a                351
```

<210> SEQ ID NO 214
<211> LENGTH: 333
<212> TYPE: DNA
<213> ORGANISM: Artificial
<220> FEATURE:
<223> OTHER INFORMATION: VL cDNA for c2244

<400> SEQUENCE: 214

```
gacattgtgc tgacccaatc tccagcttcc ttagctatat ctctgggca gagggccacc      60
atctcatgca gggccagcaa agtgtcagt acatctggct ctagttatat gttctggtac     120
caacagaaac caggacagcc acccaaactc ctcatctatc ttgcatccaa cctagaatct    180
ggggtccctg ccaggttcag tggcagtggg tctgggacag acttcaccct caacatacat    240
cctgtggagg aggaggatgc tgcagcctat tactgtcaac acagtaggga gattccgtac    300
acgttcggag gggggaccaa gctggaaata aaa                                 333
```

<210> SEQ ID NO 215
<211> LENGTH: 266
<212> TYPE: PRT
<213> ORGANISM: Mus musculus

<400> SEQUENCE: 215

```
Met Arg Pro Arg Met Lys Tyr Ser Asn Ser Lys Ile Ser Pro Ala Lys
1               5                   10                  15

Phe Ser Ser Thr Ala Gly Glu Ala Leu Val Pro Pro Cys Lys Ile Arg
            20                  25                  30

Arg Ser Gln Gln Lys Thr Lys Glu Phe Cys His Val Tyr Cys Met Arg
        35                  40                  45

Leu Arg Ser Gly Leu Thr Ile Arg Lys Glu Thr Ser Tyr Phe Arg Lys
    50                  55                  60

Glu Pro Thr Lys Arg Tyr Ser Leu Lys Ser Gly Thr Lys His Glu Glu
65                  70                  75                  80

Asn Phe Ser Ala Tyr Pro Arg Asp Ser Arg Lys Arg Ser Leu Leu Gly
                85                  90                  95

Ser Ile Gln Ala Phe Ala Ala Ser Val Asp Thr Leu Ser Ile Gln Gly
            100                 105                 110

Thr Ser Leu Leu Thr Gln Ser Pro Ala Ser Leu Ser Thr Tyr Asn Asp
        115                 120                 125

Gln Ser Val Ser Phe Val Leu Glu Asn Gly Cys Tyr Val Ile Asn Val
    130                 135                 140

Asp Asp Ser Gly Lys Asp Gln Glu Gln Asp Gln Val Leu Leu Arg Tyr
145                 150                 155                 160

Tyr Glu Ser Pro Cys Pro Ala Ser Gln Ser Gly Asp Gly Val Asp Gly
                165                 170                 175

Lys Lys Leu Met Val Asn Met Ser Pro Ile Lys Asp Thr Asp Ile Trp
            180                 185                 190

Leu His Ala Asn Asp Lys Asp Tyr Ser Val Glu Leu Gln Arg Gly Asp
        195                 200                 205

Val Ser Pro Pro Glu Gln Ala Phe Phe Val Leu His Lys Lys Ser Ser
    210                 215                 220

Asp Phe Val Ser Phe Glu Cys Lys Asn Leu Pro Gly Thr Tyr Ile Gly
225                 230                 235                 240
```

```
Val Lys Asp Asn Gln Leu Ala Leu Val Glu Glu Lys Asp Glu Ser Cys
            245                 250                 255

Asn Asn Ile Met Phe Lys Leu Ser Lys Ile
            260                 265
```

ST2L ANTIBODY ANTAGONISTS FOR THE TREATMENT OF ST2L-MEDIATED INFLAMMATORY PULMONARY CONDITIONS

CROSS REFERENCE TO RELATED APPLICATIONS

This application claims the benefit of U.S. Provisional Application No. 61/640,407, filed 30 Apr., 2012 and U.S. Provisional Application No. 61/640,238, filed 30 Apr., 2012, the entire contents of which are incorporated herein by reference.

BACKGROUND OF THE INVENTION

1. Field of the Invention

The present invention relates to ST2L antagonists, polynucleotides encoding the antagonists or fragments thereof, and methods of making and using the foregoing.

2. Description of Related Art

ST2L (IL-1RL1 or IL-33Rα) is a Toll/IL-1 receptor family member expressed on the cell surface of a wide variety of immune cells including T cell, NK/NKT cells, basophils, eosinophils, mast cells and the newly-described non-B/non-T innate lymphoid type 2 cells, nuocytes, and natural helper cells. ST2L expression is also inducible on dendritic cells (DCs), macrophages, and neutrophils. ST2L is able to down-regulate the responsiveness of Toll-like Receptors TLR2, TLR4, and TLR9, but also induce type 2 cytokine release via activation by its ligand IL-33 and association with accessory protein IL-1RAcP. IL-33 has been described as an 'alarmin', as its full-length form resides in the nuclei of epithelial and endothelial cells during homeostasis, but can be cleaved and released during necrosis.

ST2L signaling requires association of the accessory protein IL-1RAcP to preformed ST2L/IL-33 complex. The accessory protein IL-1RAcP is shared with the IL-1α/β signaling complex. Models of ST2L, IL-33, and IL-1RAcP interactions as well as interactions between IL-1R1 and IL-1RAcP have been proposed (Lingel et al., Cell 17:1398-1410, 2009; Wang et al., Nat Immunol 11:905-11, 2010). Recently, ST2L/IL-33/IL-1RAcP has been shown to form a signaling complex with c-Kit on mast cells, the receptor for stem cell factor (SCF). IL-33 induced cytokine production in primary mast cells in an SCF-dependent manner (Drube et al., Blood 115:3899-906, 2010).

Activation of ST2L leads to excessive type 2 cytokine responses (especially IL-5 and IL-13), mast cell and eosinophil activation, and airway hyper-reactivity, and has also been reported to amplify Th1 and Th17 responses through induction of IFNγ from NKT cells and IL-1β and IL-6 from mast cells. Dysregulation of the ST2L/IL-33 pathway has been implicated in a variety of immune-mediated diseases, including asthma, rheumatoid arthritis, inflammatory bowel disease, atopic dermatitis, allergic rhinitis, nasal polyposis, and systemic sclerosis (reviewed by Palmer and Gabay, Nat Rev Rheumatol 7:321-9, 2011 and Lloyd, Curr Opin Immunol 22:800-6, 2010; Shimizu et al., Hum Molec Gen 14:2919-27, 2005, Kamekura et al., Clin Exp Allergy 42:218-28, 2012; Manetti et al., Ann Rheum Dis 69:598-605, 2010).

Thus, there is a need for ST2L antagonists that are suitable for use in the treatment of ST2L mediated diseases and disorders.

BRIEF SUMMARY OF THE INVENTION

One aspect of the invention is an isolated human or human-adapted antibody antagonist or fragment thereof that specifically binds Domain I (SEQ ID NO: 9) of human ST2L.

In another aspect, the invention provides for human or human-adapted antibody antagonists specifically binding human ST2L having certain light chain and heavy chain variable region sequences, or certain heavy chain and light chain complementarity determining sequences.

In another aspect, the invention provides the invention provides for human or human-adapted antibody antagonists specifically biding human ST2L at defined epitope regions and/or having certain characteristics as described herein.

Another aspect of the invention is an isolated polynucleotide encoding the heavy chain variable regions (VH) or the light chain variable regions (VL) of the invention.

Another aspect of the invention is a vector comprising an isolated polynucleotide of the invention.

Another aspect of the invention is a host cell comprising a vector of the invention.

Another aspect of the invention is a method of producing an antibody of the invention comprising culturing a host cell of the invention and recovering the antibody from the cell.

Another aspect of the invention is a pharmaceutical composition comprising an isolated antibody of the invention and a pharmaceutically accepted carrier.

Another aspect of the invention is an method of treating or preventing a ST2L-mediated condition comprising administering a therapeutically effective amount of an isolated antibody of the invention to a patient in need thereof for a time sufficient to treat or prevent the ST2L-mediated condition.

Another aspect of the invention is an method of inhibiting mast cell response in a patient comprising administering a therapeutically effective amount of an isolated antibody of the invention to a patient in need thereof for a time sufficient to inhibit the mast cell response.

Another aspect of the invention is an method of inhibiting interaction of IL-33 and ST2L in a subject, comprising administering to the subject an antibody that specifically binds domain I of ST2L in an amount sufficient to inhibit the interaction of IL-33 and ST2L.

BRIEF DESCRIPTION OF THE DRAWINGS

FIG. 9 shows average percent (%) inhibition of anti-ST2L antibodies binding Domain I (D1) or Domain III (D3) of ST2L on GM-CSF, IL-5, IL-8, IL-10 and IL-13 release by human cord blood-derived mast cells upon IL-33 and SCF induction as indicated using either 50 μg/ml or 2 μg/ml of each antibody tested. Negative values indicate % activation.

FIG. 10 shows heavy chain variable regions (VH) and heavy chain CDR sequences of anti-ST2L antibodies derived from phage display libraries and after subsequent affinity-maturation campaigns.

FIG. 11 shows light chain variable regions (VL) and light chain CDR sequences of anti-ST2L antibodies derived from phage display libraries and after subsequent affinity-maturation campaigns.

FIG. 12 shows VH and VL regions and sequences of heavy chain CDRs of anti-ST2L antibody STLM208 VH ST2H257 HCDR3 variants.

FIG. 13 shows A) VH and B) VL sequences of anti-ST2L antibodies derived from phage display libraries and after subsequent affinity-maturation campaigns.

FIG. 14 shows delineation of C2494 VH and VL antigen binding sites transferred to human frameworks (transferred marked as HFA, "human framework adaptation"). Kabat CDRs are underlined and Chothia HVs indicated in dashed lines above the indicated transferred HFA regions. Numbering of VH and VL residues is according to Chothia. Residues highlighted in grey in VH were not transferred in some HFA variants. C2494 VH: SEQ ID NO: 48; C2494 VH: SEQ ID NO: 52.

FIG. 15 shows CDR sequences of human framework adapted (HFA) antibodies derived from C2494.

FIG. 19 shows kinetic and affinity constants for ST2L Domain I binding antibody for ST2L variants as indicated in the figure.

DETAILED DESCRIPTION OF THE INVENTION

Figure 1:
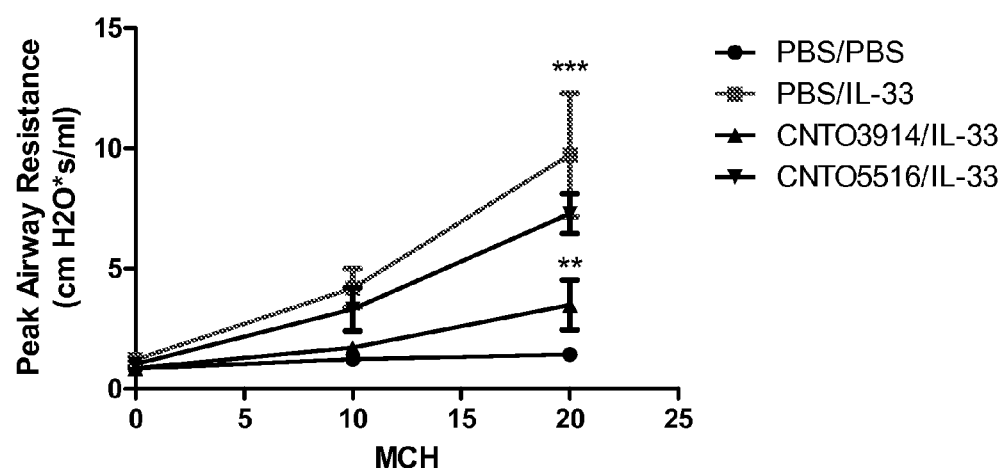
FIG. 1 shows inhibition of airway hyper-responsiveness by ST2L Domain I binding mAb CNTO3914 in a model of lung inflammation induced by intranasally administered IL-33 when compared to the isotype control CNTO5516. Peak airway resistance was measured upon methacholine (MCH) administration at increased doses (mg/ml). p<0.05 for CNTO3914/IL-33 vs. CNTO5516/IL-33; and *p<0.001 for CNTO3914/IL-33 vs. PBS with IL-33 treatment group.

All publications, including but not limited to patents and patent applications, cited in this specification are herein incorporated by reference as though fully set forth.

It is to be understood that the terminology used herein is for the purpose of describing particular embodiments only and is not intended to be limiting. Unless defined otherwise, all technical and scientific terms used herein have the same meaning as commonly understood by one of ordinary skill in the art to which the invention pertains.

Although any methods and materials similar or equivalent to those described herein can be used in the practice for testing of the present invention, exemplary materials and methods are described herein. In describing and claiming the present invention, the following terminology will be used.

The term "antagonist" as used herein means a molecule that partially or completely inhibits, by any mechanism, ST2L biological activity. Exemplary antagonists are antibodies, fusion proteins, peptides, peptidomimetics, nucleic acids, oligonucleotides and small molecules. Antagonists can be identified using assays for ST2L biological activity described below. ST2L antagonists may inhibit measured ST2L biological activity by 20%, 30%, 40%, 50%, 60%, 70%, 75%, 80%, 85%, 90%, 95%, 96%, 97%, 98%, 99% or 100%.

The term "ST2L" or "huST2L" or "human ST2L" refers to a human ST2L polypeptide having an amino acid sequence shown in GenBank Acc. No. NP 057316. SEQ ID NO: 1 shows the amino acid sequence of the full length human ST2L. "ST2L extracellular domain", "ST2L-ECD" or "huST2L-ECD" as used herein means a polypeptide having amino acids 19-328 of SEQ ID NO: 1. huST2L-ECD has three Ig-like C2-type domains spanning residues 19-122 (Domain I, SEQ ID NO: 9), residues 123-202 (Domain II, SEQ ID NO: 10), and residues 209-324 (Domain III, SEQ ID NO: 11) of SEQ ID NO: 1. "Domain I" or "ST2L Domain I" or "huST2L Domain I" or "D1" refers to the first immunoglobulin-like domain on human ST2L having the sequence shown in SEQ ID NO: 9. "Domain III" or "ST2L Domain III" refers to the third immunoglobulin-like domain on human ST2L having the sequence shown in SEQ ID NO: 11.

The term "IL-33" as used herein includes full length IL-33 (GenBank Acc. No. NP 254274 SEQ ID NO: 3), variants and active forms thereof. IL-33 variants include proteins having amino acid sequences shown in GenBank Acc. No. NP 001186569 and GenBank Acc. No. NP 001186570). IL-33 active forms include a "mature IL-33" having residues 112-270 of SEQ ID NO: 3. Additional active forms include IL-33 fragments having residues 11-270, 115-270, 95-270, 99-270, or 109-270 of SEQ ID NO: 3 (LeFrancais et al., Proc Natl Acad Sci (USA) 109:1673-8, 2012), or any form or combination of forms isolated from cells endogenously expressing IL-33. "IL-33 active form" is a fragment or a variant of IL-33 of SEQ ID NO: 3 that induces ST2L biological activity.

The term "antibodies" as used herein is meant in a broad sense and includes immunoglobulin molecules including polyclonal antibodies, monoclonal antibodies including murine, human, human-adapted, humanized and chimeric monoclonal antibodies, antibody fragments, bispecific or multispecific antibodies formed from at least two intact antibodies or antibody fragments, dimeric, tetrameric or multimeric antibodies, and single chain antibodies.

Immunoglobulins can be assigned to five major classes, namely IgA, IgD, IgE, IgG and IgM, depending on the heavy chain constant domain amino acid sequence. IgA and IgG are further sub-classified as the isotypes $IgA_1$, $IgA_2$, $IgG_1$, $IgG_2$, $IgG_3$ and $IgG_4$. Antibody light chains of any vertebrate species can be assigned to one of two clearly distinct types, namely kappa (κ) and lambda (λ), based on the amino acid sequences of their constant domains.

The term "antibody fragments" refers to a portion of an immunoglobulin molecule that retains the heavy chain and/or the light chain antigen binding site, such as a heavy chain complementarity determining regions (HCDR) 1, 2 and 3, a light chain complementarity determining regions (LCDR) 1, 2 and 3, a heavy chain variable region (VH), or a light chain variable region (VL). Antibody fragments include well known Fab, F(ab')2, Fd and Fv fragments as well as a domain antibodies (dAb) consisting one VH domain. VH and VL domains can be linked together via a synthetic linker to form various types of single chain antibody designs where the VH/VL domains pair intramolecularly, or intermolecularly in those cases when the VH and VL domains are expressed by separate single chain antibody constructs, to form a monovalent antigen binding site, such as single chain Fv (scFv) or diabody; described for example in Int. Pat. Publ. No. WO98/44001, Int. Pat. Publ. No. WO88/01649; Int. Pat. Publ. No. WO94/13804; Int. Pat. Publ. No. WO92/01047.

An antibody variable region consists of a "framework" region interrupted by three "antigen binding sites". The antigen binding sites are defined using various terms: (i) Complementarity Determining Regions (CDRs), three in the VH (HCDR1, HCDR2, HCDR3), and three in the VL (LCDR1, LCDR2, LCDR3), are based on sequence variability (Wu and Kabat, J Exp Med 132:211-50, 1970; Kabat et al., Sequences of Proteins of Immunological Interest, 5th Ed. Public Health Service, National Institutes of Health, Bethesda, Md., 1991). (ii) "Hypervariable regions", "HVR", or "HV", three in the VH (H1, H2, H3) and three in the VL (L1, L2, L3), refer to the regions of an antibody variable domains which are hypervariable in structure as defined by Chothia and Lesk (Chothia and Lesk, Mol Biol 196:901-17, 1987). Other terms include "IMGT-CDRs" (Lefranc et al., Dev Comparat Immunol 27:55-77, 2003) and "Specificity Determining Residue Usage" (SDRU) (Almagro, Mol Recognit 17:132-43, 2004). The International ImMunoGeneTics (IMGT) database (http://www_imgt_org) provides a standardized numbering and definition of antigen-binding sites. The correspondence between CDRs, HVs and IMGT delineations is described in Lefranc et al., Dev Comparat Immunol 27:55-77, 2003.

"Chothia residues" as used herein are the antibody VL and VH residues numbered according to Al-Lazikani (Al-Lazikani et al., J Mol Biol 273:927-48, 1997).

"Framework" or "framework sequences" are the remaining sequences of a variable region other than those defined to be antigen binding site. Because the antigen binding site can be defined by various terms as described above, the exact amino acid sequence of a framework depends on how the antigen-binding site was defined.

"Human antibody" or "fully human antibody" refers to antibodies containing variable region and constant region sequences derived from human immunoglobulin sequences. Human antibodies of the invention may include substitutions so that they may not be exact copies of expressed human immunoglobulin or germline gene sequences. However, antibodies in which antigen binding sites are derived from a non-human species are not included in the definition of "human antibody".

"Human-adapted" antibodies or "human framework adapted (HFA)" antibodies refers to antibodies adapted according to methods described in U.S. Pat. Publ. No. US2009/0118127 and also refers to antibodies in which antigen-binding site sequences derived from non-human species are grafted onto human frameworks.

"Humanized antibodies" refers to antibodies wherein the antigen binding sites are derived from non-human species and the variable region frameworks are derived from human immunoglobulin sequences. Humanized antibodies may include substitutions in the framework regions so that the framework may not be an exact copy of expressed human immunoglobulin or germline gene sequences.

The term "substantially identical" as used herein means that the two antibody variable region amino acid sequences being compared are identical or have "insubstantial differences". Insubstantial differences are substitutions of 1, 2, 3, 4, 5, 6, 7, 8, 9, 10, or 11 amino acids in an antibody or antibody variable region sequence that do not adversely affect antibody properties. Amino acid sequences substantially identical to the variable region sequences disclosed herein are within the scope of the application. In some embodiments, the sequence identity can be about 90%, 91%, 92%, 93%, 94%, 95%, 96%, 97%, 98%, 99% or higher. Percent identity can be determined for example by pairwise alignment using the default settings of the AlignX module of Vector NTI v.9.0.0 (Invitrogen, Carslbad, Calif.). The protein sequences of the present invention can be used as a query sequence to perform a search against public or patent databases to, for example, identify related sequences. Exemplary programs used to perform such searches are the XBLAST or BLASTP programs (http_//www_ncbi_nlm/nih_gov), or the GenomeQuest™ (GenomeQuest, Westborough, Mass.) suite using the default settings.

The term "epitope" as used herein means a portion of an antigen to which an antibody specifically binds. Epitopes usually consist of chemically active (such as polar, non-polar or hydrophobic) surface groupings of moieties such as amino acids or polysaccharide side chains and can have specific three-dimensional structural characteristics, as well as specific charge characteristics. An epitope can be composed of contiguous and/or discontiguous amino acids that form a conformational spatial unit. For a discontiguous epitope, amino acids from differing portions of the linear sequence of the antigen come in close proximity in 3-dimensional space through the folding of the protein molecule. An exemplary epitope is Domain I of huST2L shown in SEQ ID NO: 9.

The term "paratope" as used herein means a portion of an antibody to which an antigen specifically binds. A paratope can be linear in nature or can be discontinuous, formed by a spatial relationship between non-contiguous amino acids of an antibody rather than a linear series of amino acids. A "light chain paratope" and a "heavy chain paratope" or "light chain paratope amino acid residues" and "heavy chain paratope amino acid residues" refer to antibody light chain and heavy chain residues in contact with an antigen, respectively.

The term "specific binding" or "specifically binds" as used herein refers to antibody binding to a predetermined antigen with greater affinity than for other antigens or proteins. Typically, the antibody binds to a predetermined antigen with a dissociation constant ($K_D$) of $1 \times 10^{-7}$ M or less, for example $1 \times 10^{-8}$ M or less, $1 \times 10^{-9}$ M or less, $1 \times 10^{-10}$ M or less, $1 \times 10^{-11}$ M or less, or $1 \times 10^{-12}$ M or less, typically with a $K_D$ that is at least ten fold less than its $K_D$ for binding to a non-specific antigen (e.g., BSA, casein, or any other specified polypeptide). The dissociation constant can be measured using standard procedures. Antibodies that specifically bind to a predetermined antigen may, however, have cross-reactivity to other related antigens, for example to the same predetermined antigen from other species (homologs), such as human or monkey, for example *Macaca fascicularis* (cynomolgus).

"Bispecific" as used herein refers to an antibody that binds two distinct antigens or two distinct epitopes within an antigen.

"Monospecific" as used herein refers to an antibody that binds one antigen or one epitope.

The term "in combination with" as used herein means that the described agents can be administered to an animal together in a mixture, concurrently as single agents or sequentially as single agents in any order.

"Inflammatory condition" as used herein refers to acute or chronic localized or systemic responses to harmful stimuli, such as pathogens, damaged cells, physical injury or irritants, that are mediated in part by the activity of cytokines, chemokines, or inflammatory cells (e.g., neutrophils, monocytes, lymphocytes, macrophages) and is characterized in most instances by pain, redness, swelling, and impairment of tissue function.

The term "ST2L-mediated inflammatory condition" as used herein refers to an inflammatory condition resulting at least partially from inappropriate activation of ST2L signaling pathway. Exemplary ST2L-mediated inflammatory conditions are asthma and allergies.

The term "ST2L-mediated condition" as used herein encompasses all diseases and medical conditions in which ST2L plays a role, whether directly or indirectly, in the disease or medical condition, including the causation, development, progress, persistence or pathology of the disease or condition.

The term "ST2L biological activity" as used herein refers to any activity occurring as a result of ST2L ligand IL-33 binding to ST2L. An exemplary ST2L biological activity results in activation of NF-κB in response to IL-33. NF-κB activation can be assayed using a reporter-gene assay upon induction of ST2L with IL-33 (Fursov et al., Hybridoma 30: 153-62, 2011). Other exemplary ST2L biological activities result in proliferation of Th2 cells, or secretion of pro-inflammatory cytokines and chemokines, for example IL-5, GM-CSF, IL-8, IL-10, or IL-13. The release of cytokines and chemokines from cells, tissues or in circulation can be measured using well-known immunoassays, such as an ELISA immunoassay.

The term "vector" means a polynucleotide capable of being duplicated within a biological system or that can be moved between such systems. Vector polynucleotides typically contain elements, such as origins of replication, polyadenylation signal or selection markers, that function to facilitate the duplication or maintenance of these polynucleotides in a biological system. Examples of such biological systems may include a cell, virus, animal, plant, and reconstituted biological systems utilizing biological components capable of duplicating a vector. The polynucleotide comprising a vector may be DNA or RNA molecules or a hybrid of these.

The term "expression vector" means a vector that can be utilized in a biological system or in a reconstituted biological system to direct the translation of a polypeptide encoded by a polynucleotide sequence present in the expression vector.

The term "polynucleotide" means a molecule comprising a chain of nucleotides covalently linked by a sugar-phosphate backbone or other equivalent covalent chemistry. Double and single-stranded DNAs and RNAs are typical examples of polynucleotides.

The term "polypeptide" or "protein" means a molecule that comprises at least two amino acid residues linked by a peptide bond to form a polypeptide. Small polypeptides of less than 50 amino acids may be referred to as "peptides".

Conventional one and three-letter amino acid codes are used herein as follows:

| Amino acid | Three-letter code | One-letter code |
| --- | --- | --- |
| Alanine | ala | A |
| Arginine | arg | R |
| Asparagine | asn | N |
| Aspartate | asp | D |
| Cysteine | cys | C |
| Glutamate | glu | E |
| Glutamine | gln | Q |
| Glycine | gly | G |
| Histidine | his | H |
| Isoleucine | ile | I |
| Leucine | leu | L |
| Lysine | lys | K |
| Methionine | met | M |
| Phenylalanine | phe | F |
| Proline | pro | P |
| Serine | ser | S |
| Threonine | thr | T |
| Tryptophan | trp | W |
| Tyrosine | tyr | Y |
| Valine | val | V |

Compositions of Matter

The present invention provides antibodies specifically binding ST2L and inhibiting ST2L biological activity, and uses of such antibodies. The inventors have made a surprising finding that antibodies binding to Domain I of human ST2L (SEQ ID NO: 9) block IL-33/ST2L interaction and inhibit a spectrum of ST2L biological activities including IL-33-induced mast cell responses, whereas antibodies binding Domain III of human ST2L (SEQ ID NO: 11) do not block IL-33/ST2L interaction although they are inhibitory in a spectrum of ST2L biological activities. Domain III binding antibodies however have reduced or no inhibitory effect on, or in some cases stimulate IL-33-induced mast cell responses.

In some embodiments, the antibodies that block IL-33/ST2L interaction and inhibit a spectrum of ST2L biological activities including IL-33-induced mast cell responses bind an epitope within human ST2L Domain I, (RCPRQGKPSYTVDW; SEQ ID NO: 210), and optionally ST2L amino acid residues T93 and F94 (residue numbering according to SEQ ID NO: 1).

The term "mast cell response" or "mast cell activity" refers to the IL-33-induced release of cytokines such as GM-CSF, IL-8, IL-5, IL-13, and IL-10, and allergic mediators such as prostaglandin $D_2$ from mast cells.

The invention provides novel antigen-binding sites binding Domain I of human ST2L. The structure for carrying an antigen-binding site is typically an antibody VH or VL.

One embodiment of the invention is an isolated human or human-adapted antibody antagonist or fragment thereof that specifically binds Domain I (SEQ ID NO: 9) of human ST2L. An exemplary antibody binding Domain I of human ST2L (SEQ ID NO: 9) is an antibody STLM15 (C2244) comprising HCDR1, HCDR2 and HCDR3 sequences of SEQ ID NOs: 23, 27 and 31, respectively, and LCDR1, LCDR2 and LCDR3 sequences of SEQ ID NOs: 35, 39 and 43, respectively, or an antibody C2494 (STLM62) comprising HCDR1, HCDR2 and HCDR3 sequences of SEQ ID NOs: 24, 28 and 32, respectively, and LCDR1, LCDR2 and LCDR3 sequences of SEQ ID NOs: 36, 40 and 44, respectively (Table 3). Additional exemplary antibodies binding Domain I of human ST2L are antibodies shown in Table 16 and FIG. 13, for example antibodies STLM103, STLM107, STLM108, STLM123, STLM124, STLM208, STLM209, STLM210, STLM211, STLM212, and STLM213. Exemplary human antibody antagonists are shown in FIG. 12 and FIG. 13. Exemplary human-adapted antagonists are shown in Table 14.

In another embodiment, the isolated human or human-adapted antibody antagonist or fragment thereof that specifically binds Domain I (SEQ ID NO: 9) of human ST2L blocks IL-33/ST2L interaction.

Antibodies can be tested for their ability to block IL-33/ST2L interaction by standard ELISA. For example, plates are coated with extracellular domain of human ST2L (huST2L-ECD) and incubated with an antibody, after which binding of biotinylated IL-33 onto the plates is measured. Antibodies that "block IL-33/ST2L interaction" or "inhibit IL-33/ST2L interaction" are antibodies that in an ELISA assay using huST2L-ECD coated plates, reduce the signal derived from biotinylated IL-33 bound to the plate by at least 30%, 40%, 50%, 60%, 70%, 75%, 80%, 85%, 90%, 95%, 96%, 97%, 98%, 99% or 100% at 50 µg/ml antibody concentration when compared to binding of IL-33 in the absence of the antibody.

Antibodies can be tested for their inhibition of mast cell responses by assessing their inhibitory activity on for example GM-CSF, IL-5, IL-10 or IL-13 release by human cord blood-derived mast cells or primary human lung mast cells using standard methods and methods exemplified infra. Antibodies that "inhibit mast cell response" or "inhibit mast cell activity" are antibodies that reduce 1-3 ng/ml IL-33-induced GM-CSF, IL-5, IL-13 or IL-10 secretion by at least 40%, 45%, 50%, 55%, 60%, 65%, 70%, 75%, 80%, 85%, 90%, 95%, 96%, 97%, 98%, 99% or 100% at a concentration of 10 µg/ml when compared to mast cells not treated by the antibody. Typically mast cells may be derived from human cord blood or lung parenchyma and small airways $CD34^+$ progenitors by well known methods and as exemplified infra. Mast cell culture conditions may affect the measure of % inhibition for an antibody and therefore culture and test conditions may be kept standard using for example StemPro-34 media throughout the 6-10 week long differentiation procedure. At 4 days prior to the cytokine release assay mast cells are stimulated daily with 10 ng/ml IL-4, 10 ng/ml IL-6 and 100 ng/ml SCF. For the cytokine release assay, mast cells can be resuspended in fresh StemPro-34 media or RPMI containing 10% FCS without antibiotics, with 100 ng/ml SCF. Suitable plating densities for assays are 65,000 to 75,000 cells/0.16 mls/well. Exemplary antibodies of the invention inhibiting mast cell responses are antibodies STLM15, STLM62 and STLM208. Antibody CNTO3914 binds mouse ST2L Domain I without cross-reactivity to human ST2L and inhibits mast cell responses in mouse cells.

Those skilled in the art will appreciate that mast cell responses also include release of IL-1 and IL-32, and chemokines such as CCL1, CCL4, CCL5, CCL18 and CCL23 as well as allergic mediators such as cysteinyl leukotrienes, histamine, as well as a variety of mast cell proteases including tryptase, chymase, carboxypeptidase, and cathepsin G. Antibodies of the invention can be tested for their ability to inhibit these additional mast cell responses using standard methods. Antibodies of the invention binding Domain I of ST2L and blocking IL-33/ST2L interaction can be expected to inhibit these additional mast cell responses at least 40%, 50%, 60%, 70%, 75%, 80%, 85%, 90%, 95%, 96%, 97%, 98%, 99% or more when tested at a minimum concentration of 10 µg/ml under these conditions.

The antibodies of the invention bind human ST2L with a dissociation constant ($K_D$) between about $5×10^{-12}$ M to about $7×10^{-10}$ M, an on rate constant ($K_{on}$) to human ST2L between about $2×10^6$ $M^{-1}s^{-1}$ to about $1×10^8$ $M^{-1}s^{-1}$, or an off rate constant ($K_{off}$) to human ST2L between about $1×10^{-6}$ $S^{-1}$ to about $1×10^{-2}s^{-1}$. For example, the antibodies of the invention bind human ST2L with a $K_D$ of less than about $7×10^{-10}$ less than about $1×10^{-10}$ M, less than about $5×10^{-11}$ M, less than about $1×10^{-11}$ M or less than about $5×10^{-12}$ M.

The antibodies of the invention may cross-react with *Macaca fascicularis* (cyno) ST2L (SEQ ID NO: 2) and bind to cyno ST2L with a dissociation constant ($K_D$) between about $3×10^{-12}$ M to about $2×10^{-9}$ M, an on rate constant ($K_{on}$) to cyno ST2L between about $4×10^6 M^{-1}s^{-1}$ to about $1×10^8$ or an off rate constant ($K_{off}$) to cyno ST2L between about $7×10^{-5}s^{-1}$ to about $1×10^{-1}s^{-1}$. For example, the antibodies of the invention bind cyno ST2L with a $K_D$ of less than about $2×10^{-9}$ M, less than about $1×10^{-9}$ M, less than about $1×10^{-10}$ M, less than about $1×10^{-11}$ M or less than about $3×10^{-12}$ M.

The affinity of an antibody to ST2L can be determined experimentally using any suitable method. Such methods may utilize ProteOn XPR36, Biacore 3000 or KinExA instrumentation, ELISA or competitive binding assays known to those skilled in the art. The measured affinity of a particular antibody/ST2L interaction can vary if measured under different conditions (e.g., osmolarity, pH). Thus, measurements of affinity and other binding parameters (e.g., $K_D$, $K_{on}$, $K_{off}$) are preferably made with standardized conditions and a standardized buffer, such as the buffer described herein. Skilled in the art will appreciate that the internal error for affinity measurements for example using Biacore 3000 or ProteOn (measured as standard deviation, SD) can typically be within 5-33% for measurements within the typical limits of detection. Therefore the term "about" reflects the typical standard deviation in the assay. For example, the typical SD for a $K_D$ of $1×10^{-9}$ M is up to $+0.33×10^9$ M.

The antibodies binding human ST2L with a desired affinity and optionally cross-reacting with cyno ST2L can be selected from libraries of variants or fragments by panning with human and/or cyno ST2L and optionally by further antibody affinity maturation. Antibodies can be identified based on their inhibition of ST2L biological activity using any suitable method. Such methods may utilize reporter-gene assays or assays measuring cytokine production using well known methods and as described in the application.

One embodiment of the invention is an isolated antibody antagonist specifically binding human ST2L comprising:
  a heavy chain complementarity determining region (HCDR)
  1 (HCDR1) of SEQ ID NO: 160 ($X_1X_2X_3MX_4$); wherein
    $X_1$ is S, F, D, I, G or V;
    $X_2$ is Y or D;
    $X_3$ is A, D or S; and
    $X_4$ is S, F or I;
  a HCDR 2 (HCDR2) of SEQ ID NO: 161 ($X_5IX_6GX_7GGX_8TX_9YADSVKG$); wherein
    $X_5$ is A, S, T, Y or D;
    $X_6$ is S, R, E, K, G or A;
    $X_7$ is S, E or N;
    $X_8$ is S, R, E, G, T, D or A; and
    $X_9$ is Y, D, N, A or S; and a HCDR 3 (HCDR3) of SEQ ID NO: 162 ($X_{10}X_{11}$WSTEGSFFVLDY); wherein
$X_{10}$ is D, A, R, N, Q, P, E, I, H, S, T or Y; and
$X_{11}$ is P, A, H, Y, E, Q, L, S, N, T, V, or I.

Another embodiment of the invention is an isolated antibody antagonist specifically binding human ST2L comprising:
a light chain complementarity determining region (LCDR) 1 (LCDR1) of SEQ ID NO: 163 (RASQSVDD$X_{12}$LA); wherein
$X_{12}$ is A or D;
a LCDR 2 (LCDR2) of SEQ ID NO: 90 (DASNRAT); and
a LCDR 3 (LCDR3) of SEQ ID NO: 164 (QQX$_{13}$X$_{14}$X$_{15}$X$_{16}$X$_{17}$X$_{18}$T); wherein
$X_{13}$ is F or Y;
$X_{14}$ is Y, I or N;
$X_{15}$ is N, G, D or T;
$X_{16}$ is W or A;
$X_{17}$ is P or deleted; and
$X_{18}$ is L or I.

The antibodies of the invention comprising the HCDR1, HCDR2, HCDR3, LCDR1, LCDR2 and LCDR3 sequences of SEQ ID NOs: 160, 161, 162, 163, 90 and 164, respectively, can be made by well known mutagenesis methods using for example HCDR1, HCDR2, HCDR3, LCDR1, LCDR2 and LCDR3 sequences of SEQ ID NOs: 78, 81, 84, 87, 90 and 92, respectively as a template. The heavy chain CDRs and the light chain CDRs of SEQ ID NOs: 160, 161, 162, 163, 90 and 164, respectively, can be grafted to human frameworks, such as frameworks described infra. The antibodies can be assayed for binding to ST2L and for their ability to block IL-33/ST2L interaction and for other characteristics such as affinity to human ST2L and/or cyno ST2L, and inhibition of mast cell responses using methods described herein.

In one embodiment, an isolated antibody antagonist specifically binding human ST2L comprises:
the HCDR1 of SEQ ID NOs: 78 or 95-108;
the HCDR2 of SEQ ID NOs: 81, 109-118 or 120-129;
the HCDR3 of SEQ ID NOs: 84 or 165-185;
the LCDR1 of SEQ ID NOs: 87 or 130;
the LCDR2 or SEQ ID NO: 90; and
the LCDR3 of SEQ ID NOs: 92 or 131-134.

In another embodiment, an isolated antibody antagonist specifically binding human ST2L comprises HCDR1, HCDR2, HCDR3, LCDR1, LCDR2 and LCDR3 sequences as shown in FIG. 10, FIG. 11, and FIG. 12.

In another embodiment, an isolated antibody antagonist specifically binding human ST2L comprises:
the HCDR1 of SEQ ID NOs: 23 or 24;
the HCDR2 of SEQ ID NOs: 27 or 28;
the HCDR3 of SEQ ID NOs: 31 or 32;
the LCDR1 of SEQ ID NOs: 35 or 36;
the LCDR2 or SEQ ID NOs: 39 or 40; and
the LCDR3 of SEQ ID NOs: 43 or 44.

In another embodiment, an isolated antibody antagonist specifically binding human ST2L comprises HCDR1, HCDR2, HCDR3, LCDR1, LCDR2 and LCDR3 sequences:
SEQ ID NOs: 23, 27, 31, 35, 39 and 43, respectively;
SEQ ID NOs: 24, 28, 32, 36, 40 and 44, respectively; (HFA CDRs);
SEQ ID NOs: 24, 28, 146, 36, 40 and 147, respectively; or
SEQ ID NOs: 24, 28, 146, 36, 40 and 44, respectively.

Another embodiment of the invention is an isolated human or human-adapted antibody antagonist or fragment thereof specifically binding human ST2L (SEQ ID NO: 1) comprising a heavy chain variable region (VH) comprising a VH framework derived from human IGHV3-23 (SEQ ID NO: 158), IGHV1-24*01 (SEQ ID NO: 148) or IGHV1-f*01 (SEQ ID NO: 149) framework sequences, and a light chain variable region (VL) comprising a VL framework derived from a human IGKV3-11 (L6) (SEQ ID NO: 159), IGKV3-15*01 (L2) (SEQ ID NO: 150), IGKV1-9*01 (L8) (SEQ ID NO: 151), IGKV1-5*01 (L12) (SEQ ID NO: 152), IGKV1-12*01 (L5) (SEQ ID NO: 153), IGKV1-39*01 (O12) (SEQ ID NO: 154), IGKV1-27*01 (A20) (SEQ ID NO: 155) or IGKV1-33*01 (O18) (SEQ ID NO: 156) framework sequences.

In another embodiment, the isolated antibody specifically binding human Domain I of human ST2L comprises a VH comprising a VH framework derived from human VH 3-23 framework sequences (SEQ ID NO: 158); and a light chain variable region (VL) comprising a VL framework derived from a human Vκ L6 framework sequences (SEQ ID NO: 159). Human framework sequences are well known, and typically include human immunoglobulin germline variable region sequences joined to the joining (J) sequences. The human VH 3-23 framework amino acid sequence shown in SEQ ID NO: 158 includes human germline VH 3-23 sequence joined to IGHJ4 and the human Vk L6 framework amino acid sequence shown in SEQ ID NO: 159 includes human Vκ L6 germline sequence joined to IGKJ1 as described in Shi et al., J Mol Biol 397:385-96, 2010; Int. Pat. Publ. No. WO2009/085462; and U.S. Pat. Publ. No. US2010/0021477. Exemplary antibodies having a VH sequence derived from human VH 3-23 and a VL sequence derived from human Vκ L6 are those shown in FIG. 12 and FIG. 13.

Human or human-adapted antibodies comprising heavy or light chain variable regions "derived from" a particular framework or germline sequence refer to antibodies obtained from a system that uses human germline immunoglobulin genes, such as from transgenic mice or from phage display libraries as discussed infra. An antibody that is "derived from" a particular framework or germline sequence may contain amino acid differences as compared to the sequence it was derived from, due to, for example, naturally-occurring somatic mutations or intentional substitutions.

In another embodiment, the isolated human or human-adapted antibody antagonist or fragment thereof that specifically binds Domain I (SEQ ID NO: 9) of human ST2L competes for binding to human ST2L (SEQ ID NO: 1) with an isolated antibody comprising a heavy chain variable region (VH) of SEQ ID NO: 47 and a light chain variable region (VL) of SEQ ID NO: 51 (antibody C2244).

In another embodiment, the isolated antibody of the invention binds human ST2L at amino acid residues 35-48 of SEQ ID NO: 1 (RCPRQGKPSYTVDW; SEQ ID NO: 210). The antibody may further bind human ST2L at amino acid residues T93 and F94 of SEQ ID NO: 1.

Competition between specific binding to human ST2L with antibodies of the invention comprising certain HCDR1, HCDR2 and HCDR3, and LCDR1, LCDR2 and LCDR3 amino acid sequences or comprising certain VH and VL sequences can be assayed in vitro using well known methods. For example, binding of MSD Sulfo-Tag™ NHS-ester-labeled antibody to human ST2L in the presence of an unlabeled antibody can be assessed by ELISA, or Biacore analyses or flow cytometry may be used to demonstrate competition with the antibodies of the current invention. The ability of a test antibody to inhibit the binding of C2244 to human ST2L demonstrates that the test antibody can compete with these antibodies for binding to human ST2L. Such exemplary antibodies are C2494, STLM208 and STLM213 shown in Table 3 and FIG. 13.

Antibodies competing with C2244 for binding to Domain I of ST2L block IL-33/ST2L interaction and inhibit a spectrum of ST2L biological activities, including IL-33-induced mast cell responses. A non-neutralizing (i.e. non-inhibiting) epitope is also present on ST2L Domain I, as a second antibody competition group (represented by antibody C2240 which binds Domain I of ST2L, does not compete with C2244, and does not inhibit ST2L signaling).

Antibodies of the invention binding specific ST2L domains or epitopes can be made by immunizing mice expressing human immunoglobulin loci (Lonberg et al., Nature 368:856-9, 1994; Fishwild et al., Nature Biotechnology 14:845-51, 1996; Mendez et al., Nature Genetics 15:146-56, 1997, U.S. Pat. Nos. 5,770,429, 7,041,870, and 5,939,598) or Balb/c mice with the peptides encoding the epitopes, for example a peptide having an amino acid sequence of Domain I of human ST2L: KFSKQSWGLENEALIVRCPRQGKP-SYTVDWYYSQTNKSIPTQERNRVFASGQLLKFLPAAV ADSGIYTCIVRSPTFNRTGYAN-VTIYKKQSDCNVPDYLMYSTV (SEQ ID NO: 9), or a peptide having an amino acid sequence of RCPRQGKP-SYTVDW (SEQ ID NO: 210), and using the hybridoma method of Kohler et al., Nature 256:495-97, 1975. The resulting antibodies are tested for their binding to the epitope using standard methods. For example, when the structures of both individual components are known, in silico protein-protein docking can be carried out to identify compatible sites of interaction. Hydrogen-deuterium (H/D) exchange can be carried out with the antigen and antibody complex to map regions on the antigen that may be bound by the antibody. Segment and point mutagenesis of the antigen can be used to locate amino acids important for antibody binding. The identified mAbs can further be modified by incorporating altered framework support residues to preserve binding affinity by techniques such as those disclosed in Queen et al., Proc Natl Acad Sci (USA) 86:10029-32, 1989 and Hodgson et al., Bio/Technology 9:421, 1991.

The antibodies of the invention may be human or human-adapted. The antibodies of the invention may be of IgA, IgD, IgE, IgG or IgM type.

Antibodies whose antigen-binding site amino acid sequences are substantially identical to those shown in FIG. 10, FIG. 11, FIG. 12, FIG. 13, FIG. 15, Table 3, Table 9 and Table 12 are encompassed within the scope of the invention. Typically, this involves one or more amino acid substitutions with an amino acid having similar charge or hydrophobic or stereochemical characteristics, and are made to improve antibody properties, for example stability or affinity. For example, a conservative substitution may involve a substitution of a native amino acid residue with a nonnative residue such that there is little or no effect on the polarity or charge of the amino acid residue at that position. Furthermore, any native residue in the polypeptide may also be substituted with alanine, as has been previously described for alanine scanning mutagenesis (MacLennan et al., Acta Physiol Scand Suppl 643:55-67, 1998; Sasaki et al., Adv Biophys 35:1-24, 1998). Desired amino acid substitutions (whether conservative or non-conservative) can be determined by those skilled in the art at the time such substitutions are desired. For example, amino acid substitutions can be used to identify residues important for the function of the antibodies, such as residues affecting affinity, or residues that impart undesireable properties such as aggregation. Exemplary amino acid substitutions are shown in FIG. 12 and FIG. 13.

Substitutions in the framework regions, in contrast to antigen binding sites may also be made as long as they do not adversely affect the properties of the antibody. Framework substitutions can be made for example at the Vernier Zone residues (U.S. Pat. No. 6,649,055) to improve antibody affinity or stability. Substitutions can also be made at those framework positions in the antibody that differ in sequence when compared to the homologous human germline gene sequences to reduce possible immunogenicity. These modifications can be done for example to antibodies derived from de novo antibody libraries, such as pIX libraries.

Conservative amino acid substitutions also encompass non-naturally occurring amino acid residues which are typically incorporated by chemical peptide synthesis rather than by synthesis in biological systems. Amino acid substitutions can be done for example by PCR mutagenesis (U.S. Pat. No. 4,683,195). Libraries of variants can be generated using well known methods, for example using random (NNK) or non-random codons, for example DVK codons, which encode 11 amino acids (ACDEGKNRSYW), and screening the libraries or variants with desired properties.

Although the embodiments illustrated in the Examples comprise pairs of variable regions, pairs of full length antibody chains, or pairs of CDR1, CDR2 and CDR3 regions, one from a heavy chain and one from a light chain, a skilled artisan will recognize that alternative embodiments may comprise single heavy chain variable regions or single light chain variable regions, single full length antibody chains, or CDR1, CDR2 and CDR3 regions from one antibody chain, either heavy or light. The single variable region, full length antibody chain or CDR1, CDR2 and CDR3 region of one chain can be used to screen for corresponding domains in another chain, the two chains capable of forming an antibody that specifically binds ST2L. The screening may be accomplished by phage display screening methods using, e.g., a hierarchical dual combinatorial approach disclosed in PCT Publ. No. WO1992/01047. In this approach, an individual colony containing either a H or L chain clone is used to infect a complete library of clones encoding the other chain (L or H), and the resulting two-chain specific antigen-binding domain is selected in accordance with phage display techniques as described.

The invention provides for isolated VH and VL domains of the antibodies of the invention and antibodies comprising certain VH and VL domains. VH and VL variable regions for certain antibodies of the invention are shown in FIG. 13 and Table 12.

One embodiment of the invention is an isolated human or human-adapted antibody antagonist or fragment thereof that specifically binds Domain I (SEQ ID NO: 9) of human ST2L comprising the VH at least 90% identical to the VH of SEQ ID NO: 191.

Another embodiment of the invention is an isolated human or human-adapted antibody antagonist or fragment thereof that specifically binds Domain I (SEQ ID NO: 9) of human ST2L comprising the VL at least 94% identical to the VL of SEQ ID NO: 209.

In one embodiment, the invention provides for an antibody comprising the VH of SEQ ID NOs: 143, 144, 145, 186, 187, 188, 189, 190, 191, 192, 193, 194, 195, 196, 197, 198, 199, 200, 201, 202, 203, 204 or 205.

In another embodiment, the invention provides for an antibody comprising the VL of SEQ ID NOs: 135, 136, 137, 138, 139, 140, 141, 142, 206, 207, 208 or 209.

In another embodiment, the invention provides for an antibody comprising
the VH of SEQ ID NOs: 186, 187, 197, 198, 199, 200, 201, 202, 203, 204 or 205 and the VL of SEQ ID NO: 206; the VH of SEQ ID NOs: 195 or 196 and the VL of SEQ ID NO: 207;

the VH of SEQ ID NOs: 188, 189 or 190 and the VL of SEQ ID NO: 208; or the VH of SEQ ID NOs: 187, 191, 192, 193 or 194 and the VL of SEQ ID NO: 209.

Another embodiment of the invention an isolated human or human-adapted antibody antagonist or fragment thereof that specifically binds Domain I (SEQ ID NO: 9) of human ST2L comprising:

the HCDR1 of SEQ ID NO: 97;
the HCDR2 of SEQ ID NO: 114;
the HCDR3 of SEQ ID NO: 84;
the LCDR1 of SEQ ID NO: 130;
the LCDR2 of SEQ ID NO: 90;
the LCDR3 of SEQ ID NO: 134; or
the VH of SEQ ID NO: 191 and the VL of SEQ ID NO: 209.

Human mAbs lacking any non-human sequences can be prepared and optimized from phage display libraries by techniques referenced in, e.g., Knappik et al., J Mol Biol 296:57-86, 2000; and Krebs et al., J Immunol Meth 254:67-84 2001. In an exemplary method, the antibodies of the invention are isolated from libraries expressing antibody heavy and light chain variable regions as fusion proteins with bacteriophage pIX coat protein. The antibody libraries are screened for binding to human ST2L-ECD and the obtained positive clones are further characterized, the Fabs isolated from the clone lysates, and expressed as full length IgGs. Exemplary antibody libraries and screening methods are described in Shi et al., J Mol Biol 397:385-96, 2010; Int. Pat. Publ. No. WO2009/085462, and U.S. Ser. No. 12/546,850; U.S. Pat. Nos. 5,223,409, 5,969,108, and 5,885,793).

The resulting mAbs can further be modified in their framework regions to change certain framework residues to those present in a matching human germline.

Immune effector properties of the antibodies of the invention may be enhanced or silenced through Fc modifications by techniques known to those skilled in the art. For example, Fc effector functions such as C1q binding, complement dependent cytotoxicity (CDC), antibody-dependent cell-mediated cytotoxicity (ADCC), phagocytosis, down regulation of cell surface receptors (e.g., B cell receptor; BCR), etc. can be provided and/or controlled by modifying residues in the Fc responsible for these activities. Pharmacokinetic properties could also be enhanced by mutating residues in the Fc domain that extend antibody half-life (Strohl Curr Opin Biotechnol 20:685-91, 2009). Exemplary Fc modifications are IgG4 S228P/L234A/L235A, IgG2 M252Y/S254T/T256E (Dall'Acqua et al., J Biol Chem 281:23514-24, 2006; or IgG2 V234A/G237A/P238S, V234A/G237A/H268Q, H268A/V309L/A330S/P331 or V234A/G237A/P238S/H268A/V309L/A330S/P331S on IgG2 (Intl. Pat. Appl. No. WO2011/066501) (numbering according to the EU numbering).

Additionally, antibodies of the invention can be post-translationally modified by processes such as glycosylation, isomerization, deglycosylation or non-naturally occurring covalent modification such as the addition of polyethylene glycol moieties (pegylation) and lipidation. Such modifications may occur in vivo or in vitro. For example, the antibodies of the invention can be conjugated to polyethylene glycol (PEGylated) to improve their pharmacokinetic profiles. Conjugation can be carried out by techniques known to those skilled in the art. Conjugation of therapeutic antibodies with PEG has been shown to enhance pharmacodynamics while not interfering with function (Knigh et al., Platelets 15:409-18, 2004; Leong et al., Cytokine 16:106-19, 2001; Yang et al., Protein Eng 16:761-70, 2003).

Antibodies or fragments thereof of the invention modified to improve stability, selectivity, cross-reactivity, affinity, immunogenicity or other desirable biological or biophysical property are within the scope of the invention. Stability of an antibody is influenced by a number of factors, including (1) core packing of individual domains that affects their intrinsic stability, (2) protein/protein interface interactions that have impact upon the HC and LC pairing, (3) burial of polar and charged residues, (4) H-bonding network for polar and charged residues; and (5) surface charge and polar residue distribution among other intra- and inter-molecular forces (Worn et al., J Mol Biol 305:989-1010, 2001). Potential structure destabilizing residues may be identified based upon the crystal structure of the antibody or by molecular modeling in certain cases, and the effect of the residues on antibody stability can be tested by generating and evaluating variants harboring mutations in the identified residues. One of the ways to increase antibody stability is to raise the thermal transition midpoint (Tm) as measured by differential scanning calorimetry (DSC). In general, the protein Tm is correlated with its stability and inversely correlated with its susceptibility to unfolding and denaturation in solution and the degradation processes that depend on the tendency of the protein to unfold (Remmele et al., Biopharm 13:36-46, 2000). A number of studies have found correlation between the ranking of the physical stability of formulations measured as thermal stability by DSC and physical stability measured by other methods (Gupta et al., AAPS PharmSci 5E8, 2003; Zhang et al., J Pharm Sci 93:3076-89, 2004; Maa et al., Int J Pharm 140:155-68, 1996; Bedu-Addo et al., Pharm Res 21:1353-61, 2004; Remmele et al., Pharm Res 15:200-8, 1997). Formulation studies suggest that a Fab Tm has implication for long-term physical stability of a corresponding mAb. Differences in amino acids in either framework or within the CDRs could have significant effects on the thermal stability of the Fab domain (Yasui et al., FEBS Lett 353:143-6, 1994).

Antibodies of the invention specifically binding Domain I of human ST2L can be engineered into bispecific antibodies which are also encompassed within the scope of the invention. The VL and/or the VH regions of the antibodies of the invention can be engineered using published methods into single chain bispecific antibodies as structures such as TandAb® designs (Int. Pat. Publ. No. W01999/57150; U.S. Pat. Publ. No. US2011/0206672) or into bispecific scFVs as structures such as those disclosed in U.S. Pat. No. 5,869,620; Int. Pat. Publ. No. W01995/15388A, int. Pat. Publ. No. W01997/14719 or Int. Pat. Publ. No WO2011/036460.

The VL and/or the VH regions of the antibodies of the invention can be engineered into bispecific full length antibodies, where each antibody arm binds a distinct antigen or epitope. Such bispecific antibodies are typically made by modulating the CH3 interactions between the two antibody heavy chains to form bispecific antibodies using technologies such as those described in U.S. Pat. No. 7,695,936; Int. Pat. Publ. No. WO04/111233; U.S. Pat. Publ. No. US2010/0015133; U.S. Pat. Publ. No. US2007/0287170; Int. Pat. Publ. No. WO2008/119353; U.S. Pat. Publ. No. US2009/0182127; U.S. Pat. Publ. No. US2010/0286374; U.S. Pat. Publ. No. US2011/0123532; Int. Pat. Publ. No. WO2011/131746; Int. Pat. Publ. No. WO2011/143545; or U.S. Pat. Publ. No. US2012/0149876. Additional bispecific structures into which the VL and/or the VH regions of the antibodies of the invention can be incorporated are for example Dual Variable Domain Immunoglobulins (Int. Pat. Publ. No. WO2009/134776), or structures that include various dimerization domains to connect the two antibody arms with different specificity, such as leucine zipper or collagen dimerization domains (Int. Pat. Publ. No. WO2012/022811, U.S. Pat. No. 5,932,448; U.S. Pat. No. 6,833,441).

Another aspect of the invention is an isolated polynucleotide encoding any of the antibody heavy chain variable regions or the antibody light chain variable regions or fragments thereof of the invention or their complement. Certain exemplary polynucleotides are disclosed herein, however, other polynucleotides which, given the degeneracy of the genetic code or codon preferences in a given expression system, encode the antibody antagonists of the invention are also within the scope of the invention. Exemplary polynucleotides of the invention are those shown in SEQ ID NOs: 211, 212, 213 and 214.

Another embodiment of the invention is a vector comprising the polynucleotide of the invention. Such vectors may be plasmid vectors, viral vectors, vectors for baculovirus expression, transposon based vectors or any other vector suitable for introduction of the polynucleotides of the invention into a given organism or genetic background by any means.

Another embodiment of the invention is a host cell comprising the polynucleotide of the invention. Such host cells may be eukaryotic cells, bacterial cells, plant cells or archeal cells. Exemplary eukaryotic cells may be of mammalian, insect, avian or other animal origins. Mammalian eukaryotic cells include immortalized cell lines such as hybridomas or myeloma cell lines such as SP2/0 (American Type Culture Collection (ATCC), Manassas, Va., CRL-1581), NS0 (European Collection of Cell Cultures (ECACC), Salisbury, Wiltshire, UK, ECACC No. 85110503), FO (ATCC CRL-1646) and Ag653 (ATCC CRL-1580) murine cell lines. An exemplary human myeloma cell line is U266 (ATTC CRL-TIB-196). Other useful cell lines include those derived from Chinese Hamster Ovary (CHO) cells such as CHO-K1SV (Lonza Biologics, Walkersville, Md.), CHO-K1 (ATCC CRL-61) or DG44.

Another embodiment of the invention is a method of producing an antibody that specifically binds Domain I of ST2L, comprising culturing a host cell of the invention and recovering the antibody produced by the host cell. Methods of making antibodies and purifying them are well known in the art.

Another embodiment of the invention of a method of inhibiting interaction of ST2L with IL-33 in a subject comprising administering the subject an antibody specifically binding domain I of ST2L in an amount sufficient to inhibit interaction of ST2L and IL-33.

Methods of Treatment

ST2L antagonists of the invention, for example ST2L antibody antagonists blocking IL-33/ST2L interaction and binding Domain I of ST2L, antibodies that compete for binding to human ST2L (SEQ ID NO: 1) with an isolated antibody comprising a heavy chain variable region of SEQ ID NO: 47 and a light chain variable region of SEQ ID NO: 51, or antibodies binding human ST2L at amino acid residues 35-48 of SEQ ID NO: 1 (RCPRQGKPSYTVDW; SEQ ID NO: 210) may be utilized to modulate the immune system. Antibodies of the invention may be more efficient in antagonizing ST2L biological activity when compared to antibodies binding other domains and/or regions on ST2L as the antibodies of the invention are able to more efficiently reduce IL-33-induced mast cell responses. Any antibodies of the invention can be used in the methods of the invention. Exemplary antibodies that can be used in the methods of the invention are antibodies STLM62, STLM15, STLM103, STLM107, STLM108, STLM123, STLM124, STLM206, STLM207, STLM208, STLM209, STLM210, STLM211, STLM212, STLM213. Without wishing to be bound by any theory, it is suggested that antibody antagonists that bind Domain I and block IL-33/ST2L interaction may inhibit formation of the IL-1RAcP/IL-33/ST2L/cKit complex or downstream signaling on mast cells, whereas Domain III binding antibodies, while being able to inhibit recruitment of IL-1RAcP to the ST2L/IL-33 complex, may be unable to disrupt the formation of the larger IL-1RAcP/IL-33/ST2L/cKit complex specifically found on mast cells. Microarray analysis conducted supports the suggestion as it was demonstrated that anti-ST2L Domain I binding antibodies suppressed the majority of mast cell signaling pathways induced by IL-33, and that anti-ST2L Domain III binding antibodies were only able to inhibit a small subset of these signaling pathways. It is feasible that because IL-33 binds to ST2L prior to the association of the accessory protein IL-1RAcP, blockade of IL-33 binding to ST2L by Domain I-binding antibodies could prevent association of any other accessory protein, including cKit or as-yet unidentified co-receptors. Domain III-binding antibodies, which do not interfere with IL-33 binding to ST2L, could theoretically block IL-1RAcP association but not the association of other co-receptors, including as-yet unidentified co-receptors. Multiple models have been proposed for how IL-1RAcP interacts with the IL-1/IL-1R or ST2L/IL-33 complexes (Lingel et al., Structure 17: 1398-1410, 2009; and reviewed by Thomas et al., Nat Struct & Molec Biol 19: 455-457, 2012). These models indicate that IL-1RAcP could bind to one side of the complex, but which side has not been conclusively shown. Therefore it is feasible that the 'other side' or 'free side' of the complex is available for association with an alternate co-receptor, that would not be blocked by a Domain III antibody, and off-target effects such as increased recruitment of another co-receptor, resulting in increased signaling, is possible.

In the methods of the invention, any antibody antagonist specifically binding Domain I of human ST2L, antibody antagonist blocking IL-33/ST2L interaction and binding Domain I of human ST2L, antibodies that competes for binding to human ST2L (SEQ ID NO: 1) with an isolated antibody comprising a heavy chain variable region of SEQ ID NO: 47 and a light chain variable region of SEQ ID NO: 51, or antibodies binding human ST2L at amino acid residues 35-48 of SEQ ID NO: 1 (RCPRQGKPSYTVDW; SEQ ID NO: 210) may be used. Additional characteristics of such antibodies include ability of the antibody to block IL-33/ST2L interaction and to inhibit human mast cell responses.

Therefore, antibodies of the invention are suitable for treating a spectrum of ST2L-mediated conditions, ST2L-mediated inflammatory conditions and conditions where inhibition of mast cell responses is desired.

The methods of the invention may be used to treat an animal patient belonging to any classification. Examples of such animals include mammals such as humans, rodents, dogs, cats and farm animals. For example, the antibodies of the invention are useful in the prophylaxis and treatment of ST2L-mediated conditions, such as inflammatory diseases including asthma, airway hyper-reactivity, sarcoidosis, chronic obstructive pulmonary disease (COPD), idiopathic pulmonary fibrosis (IPF), cystic fibrosis, inflammatory bowel disease (IBD), rheumatoid arthritis, eosinophilic esophagitis, scleroderma, atopic dermatitis, allergic rhinitis, bullous pemphigoid, chronic urticaria, diabetic nephropathy, interstitial cystitis or Graft Versus Host Disease (GVHD). The antibodies of the invention are useful in the prophylaxis and treatment of immune diseases mediated at least in part by mast cells, such as asthma, eczema, itch, allergic rhinitis, allergic conjunctivitis, as well as autoimmune diseases such as rheumatoid arthritis, bullous pemphigoid and multiple sclerosis.

The antibodies of the invention and are also useful in the preparation of a medicament for such treatment, wherein the medicament is prepared for administration in dosages defined herein.

Mast cells play a central role in allergic inflammation and asthma through their release of a variety of mediators (reviewed by Amin, Respir Med 106:9-14, 2012). ST2L is highly expressed on mast cells and its activation leads to expression of many proinflammatory cytokines and other mediators. Inhibition of ST2L activity is proposed to interfere with mast cell mediated inflammatory cell recruitment and to modulate chronic inflammation.

Mast cells are rapid responders to stimulation, including allergen, cold air, pathogen; damage to the epithelium by these stimuli can result in release of IL-33 (reviewed by Zhao and Hu, Cell & Molec Immunol 7: 260-2, 2012). Mast cells release leukotrienes, histamine, prostaglandins, and cytokines to increase vascular permeability and bronchoconstriction, and recruit other immune cells such as neutrophils, eosinophils and T lymphocytes to the site (Henderson et al., JEM 184:1483-94, 1996; White et al., JACI 86:599-605, 1990). Additionally, they enhance immune responses by inducing adhesion molecule upregulation on endothelial cells to increase immune cell trafficking (Meng et al., J Cell Physiol 165:40-53, 1995). Mast cells play an important role in airway remodeling; in asthmatics, an increased number of mast cells is found within the airway smooth muscle (ASM) cell layer, and secrete mediators to promote ASM proliferation (reviewed by Okayama et al., Curr Opin Immunol 19:687-93, 2007).

Inflammatory pulmonary condition is an example of an inflammatory condition. Exemplary inflammatory pulmonary conditions include infection-induced pulmonary conditions including those associated with viral, bacterial, fungal, parasite or prion infections; allergen-induced pulmonary conditions; pollutant-induced pulmonary conditions such as asbestosis, silicosis, or berylliosis; gastric aspiration-induced pulmonary conditions, immune dysregulation, inflammatory conditions with genetic predisposition such as cystic fibrosis, and physical trauma-induced pulmonary conditions, such as ventilator injury. These inflammatory conditions also include asthma, emphysema, bronchitis, chronic obstructive pulmonary disease (COPD), sarcoidosis, histiocytosis, lymphangiomyomatosis, acute lung injury, acute respiratory distress syndrome, chronic lung disease, bronchopulmonary dysplasia, community-acquired pneumonia, nosocomial pneumonia, ventilator-associated pneumonia, sepsis, viral pneumonia, influenza infection, parainfluenza infection, rotavirus infection, human metapneumovirus infection, respiratory syncitial virus infection and *Aspergillus* or other fungal infections. Exemplary infection-associated inflammatory diseases may include viral or bacterial pneumonia, including severe pneumonia, cystic fibrosis, bronchitis, airway exacerbations and acute respiratory distress syndrome (ARDS). Such infection-associated conditions may involve multiple infections such as a primary viral infection and a secondary bacterial infection. Dysregulated ST2L signaling may play a role in the pathology of pulmonary diseases such as asthma and Chronic Obstructive Pulmonary Disease (COPD) (reviewed in Alcorn et al., Annu Rev Physiol 72:495-516, 2010). Commonly used animal models for asthma and airway inflammation include the ovalbumin challenge model, methacholine sensitization models and sensitization with *Aspergillus fumigatus* (Hessel et al., Eur J Pharmacol 293:401-12, 1995). Inhibition of cytokine and chemokine production from cultured human bronchial epithelial cells, bronchial fibroblasts or airway smooth muscle cells can also be used as in vitro models. The administration of antagonists of the present invention to any of these models can be used to evaluate the use of those antagonists to ameliorate symptoms and alter the course of asthma, airway inflammation, COPD and the like.

Asthma is an inflammatory disease of the lung that is characterized by airway hyperresponsiveness ("AHR"), bronchoconstriction, wheezing, eosinophilic or neutrophilic inflammation, mucus hypersecretion, subepithelial fibrosis, and elevated IgE levels. Patients with asthma experience "exacerbations", a worsening of symptoms, most commonly due to microbial infections of the respiratory tract (e.g. rhinovirus, influenza virus, *Haemophilus* influenza, etc.). Asthmatic attacks can be triggered by environmental factors (e.g. ascarids, insects, animals (e.g., cats, dogs, rabbits, mice, rats, hamsters, guinea pigs and birds), fungi, air pollutants (e.g., tobacco smoke), irritant gases, fumes, vapors, aerosols, chemicals, pollen, exercise, or cold air. Apart from asthma, several chronic inflammatory diseases affecting the lung are characterized by neutrophil infiltration to the airways, for example chronic obstructive pulmonary disease (COPD), bacterial pneumonia and cystic fibrosis (Linden et al., Eur Respir J 15:973-7, 2000; Rahman et al., Clin Immunol 115: 268-76, 2005), and diseases such as COPD, allergic rhinitis, and cystic fibrosis are characterized by airway hyperresponsiveness (Fahy and O'Byrne, Am J Respir Crit Care Med 163:822-3, 2001). Commonly used animal models for asthma and airway inflammation include the model of methacholine challenge after ovalbumin sensitization and challenge (Hessel et al., Eur J Pharmacol 293:401-12, 1995). Inhibition of cytokine and chemokine production from cultured human bronchial epithelial cells, bronchial fibroblasts or airway smooth muscle cells can also be used as in vitro models. The administration of antibody antagonists of the present invention to any of these models can be used to evaluate the use of those antagonists to ameliorate symptoms and alter the course of asthma, airway inflammation, COPD and the like.

IL-33 signaling through the ST2L receptor on TH2 cells, basophils, mast cells, and the newly described Innate Lymphoid Type 2 Cells results in IL-5 and IL-13 (type 2 cytokine) secretion (ILCs reviewed by Spits et al., Nature Reviews Immunology 13:145-149, 2013). Beneficial effects of therapeutics targeting IL-5 or IL-13 in asthma confirm the relevance of these pathways. IL-5 activates eosinophils, and treatment of a subgroup of severe asthmatics with sputum eosinophilia with a monoclonal antibody that neutralizes IL-5 resulted in fewer exacerbations (Nair et al. N Engl J Med. 2009; 360(10):985-93). IL-13 is reported to contribute to IgE synthesis, mucus secretion and fibrosis. Treatment of severe asthmatics with an anti-IL-13 monoclonal antibody resulted in an improvement in lung function, with a subgroup demonstrating a greater improvement (Corren et al., N. Engl. J. Med., 365:1088-1098, 2011). Other mediators of differential immunological pathways are also involved in asthma pathogenesis, and blocking these mediators, in addition to ST2L, may offer additional therapeutic benefit. Therapies that target multiple type 2 cytokines, or pathways upstream of type 2 cytokine production, could be beneficial in severe disease.

The VH and the VL domains of the ST2L antibodies of the invention may be incorporated into bispecific antibodies and molecules described herein, in which the bispecific antibody specifically binds Domain I of ST2L and a second antigen such as TSLP (thymic stromal lympohpoietin), IL-25, IL-17RB or TSLPR.

IL-25 and TSLP, like IL-33, trigger type 2 cytokine release via distinct signaling complexes: IL-25 (IL-17E) is a member of the IL-17 family and signals through IL-17RA/IL-17RB, and TSLP is a member of the IL-7 family and signals through the TSLPR/IL-7Rα heterodimers (reviewed by Koyasu et al., Immunol 132:475-481, 2011). Animals deficient in IL-33, ST2L, IL-25, IL-17RB, TSLP, or TSLPR demonstrate less severe airway inflammation in at least one of many different types of mouse models of asthma; however lack of protection from airway inflammation may be present in most of these animal models, raising the possibility that exposure of the epithelium to various allergens or pathogens could trigger release of IL-33, IL-25, and TSLP concomitantly. Hammad et al. reported that administration of house dust mite extract to mice resulted in the release of IL-25, TSLP and IL-33 (as well as IL-5 and IL-13 downstream of IL-33) into the airway (Hammad et al., Nat Med 15:210-216, 2009). This suggests that blocking ST2L and TSLP and/or IL-25 may have beneficial effects, particularly in severe airway disease.

In another embodiment of the invention the antibody antagonists specifically binding Domain I of human ST2L can be used to generate bispecific molecules that bind ST2L and TSLP, ST2L and IL-25, ST2L and TSLPR, ST2L and IL-17RA, or ST2L and IL-17RB.

In another embodiment of the invention, the antibody antagonists specifically binding Domain I of human ST2L is a bispecific antibody, wherein the antibody further binds TSLP, IL-25, TSLPR, IL-17RA or IL-17RB.

TSLP, IL-25, TSLPR, IL-17RA and IL-17RB binding antibodies can be generated using methods described herein, such as immunizing mice expressing human immunoglobulin loci (Lonberg et al., Nature 368:856-9, 1994; Fishwild et al., Nature Biotechnology 14:845-51, 1996; Mendez et al., Nature Genetics 15:146-56, 1997, U.S. Pat. Nos. 5,770,429, 7,041,870, and 5,939,598) or Balb/c mice with the corresponding proteins or extracellular domains of the proteins, or using phage display libraries as described herein. Alternatively, existing antibodies to TSLP, IL-25, TSLPR, IL-17RA and IL-17RB can be used to generate the bispecific molecules. Exemplary IL-25 antibodies that can be used are those described in for example Int. Pat. Publ. No. WO2011/123507.

Arthritis, including osteoarthritis, rheumatoid arthritis, arthritic joints as a result of injury, and the like, are common inflammatory conditions, which would benefit from the therapeutic use of anti-inflammatory proteins, such as the antagonists of the present invention. Activation of ST2L signaling may perpetuate inflammation and further tissue damage in the inflamed joint. Several animal models for rheumatoid arthritis are known. For example, in the collagen-induced arthritis (CIA) model, mice develop chronic inflammatory arthritis that closely resembles human rheumatoid arthritis. ST2L-deficient (ST2KO) mice developed attenuated disease in this model, and pathology in this model was dependent on ST2L expression by mast cells (Xu et al., PNAS 105:10913-8, 2008). In this model, there was reduced infiltration of mononuclear and polymorphonuclear cells and of synovial hyperplasia in the joints of ST2KO mice. The draining LNs of ST2KO mice cultured with collagen (CII) showed significantly decreased IL-17, IFNγ, and TNFα production. ST2L-deficient mice adoptively transferred with wild-type (WT) bone marrow-derived mast cells (BMMC), before CIA was induced, developed more severe CIA than those engrafted with ST2KO BMMCs. Therefore ST2L signaling by mast cells was critical to the development of arthritis in a mouse model that resembles human rheumatoid arthritis. Administration of the ST2L antibodies of the present invention, which inhibit mast cell responses, to the CIA model mice can be used to evaluate the use of these antagonists to ameliorate symptoms and alter the course of disease.

Exemplary gastrointestinal inflammatory conditions are inflammatory bowel disease (IBD), ulcerative colitis (UC) and Crohn's disease (CD), colitis induced by environmental insults (e.g., gastrointestinal inflammation (e.g., colitis) caused by or associated with (e.g., as a side effect) a therapeutic regimen, such as administration of chemotherapy, radiation therapy, and the like), infections colitis, ischemic colitis, collagenous or lymphocytic colitis, necrotizing enterocolitis, colitis in conditions such as chronic granulomatous disease or celiac disease, food allergies, gastritis, infectious gastritis or enterocolitis (e.g., *Helicobacter pylori*-infected chronic active gastritis) and other forms of gastrointestinal inflammation caused by an infectious agent. Several animal models for gastrointestinal inflammatory conditions exist. Some of the most widely used models are the 2,4,6-trinitrobenesulfonic acid/ethanol (TNBS)-induced colitis model or the oxazalone model, which induce chronic inflammation and ulceration in the colon (Neurath et al., Intern Rev Immunol 19:51-62, 2000). Another model uses dextran sulfate sodium (DSS), which induces an acute colitis manifested by bloody diarrhea, weight loss, shortening of the colon and mucosal ulceration with neutrophil infiltration. Another model involves the adoptive transfer of naïve CD45RB$^{high}$ CD4 T cells to RAG or SCID mice. In this model, donor naïve T cells attack the recipient gut causing chronic bowel inflammation and symptoms similar to human inflammatory bowel diseases (Read and Powrie, Curr Protoc Immunol Chapter 15 unit 15.13, 2001). The administration of antagonists of the present invention in any of these models can be used to evaluate the potential efficacy of those antagonists to ameliorate symptoms and alter the course of diseases associated with inflammation in the gut, such as inflammatory bowel disease.

Renal fibrosis can develop from either an acute insult such as graft ischemia/reperfusion (Freese et al., Nephrol Dial Transplant 16:2401-6, 2001) or chronic condition such as diabetes (Ritz et al., Nephrol Dial Transplant 11 Suppl 9:38-44, 1996). The pathogenesis is typically characterized by an initial inflammatory response followed by sustained fibrogenesis of the glomerular filtration apparatus and tubular interstitium (Liu, Kidney Int 69:213-7, 2006). Tubulointerstitial fibrosis has been shown to play a critical role in the pathogenesis of renal injury to end-stage renal failure and the proximal tubule cell has been revealed as a central mediator (Phillips and Steadman, Histol Histopathol 17:247-52, 2002; Phillips, Chang Gung Med J 30:2-6, 2007). Fibrogenesis in the tubulointerstitial compartment is mediated in part by activation of resident fibroblasts, which secrete pro-inflammatory cytokines that stimulate the proximal tubule epithelium to secrete local inflammatory and fibrogenic mediators. Additionally, chemotactic cytokines are secreted by fibroblasts and epithelial cells and provide a directional gradient guiding the infiltration of monocytes/macrophages and T-cells into the tubulointerstitium. The inflammatory infiltrate produces additional fibrogenic and inflammatory cytokines that further activate fibroblast and epithelial cytokine release while also stimulating the epithelium to undergo a phenotypic transition in which the cells deposit excess extracellular matrix components (Simonson, Kidney Int 71:846-54, 2007).

Other exemplary fibrotic conditions may include liver fibrosis (including but not limited to alcohol-induced cirrhosis, viral-induced cirrhosis, autoimmune-induced hepatitis); lung fibrosis (including but not limited to scleroderma, idiopathic pulmonary fibrosis); kidney fibrosis (including but not limited to scleroderma, diabetic nephritis, glomerular nephritis, lupus nephritis); dermal fibrosis (including but not limited to scleroderma, hypertrophic and keloid scarring, burns); myelofibrosis; neurofibromatosis; fibroma; intestinal fibrosis; and fibrotic adhesions resulting from surgical procedures.

The fibrosis can be organ specific fibrosis or systemic fibrosis. The organ specific fibrosis can be associated with lung fibrosis, liver fibrosis, kidney fibrosis, heart fibrosis, vascular fibrosis, skin fibrosis, eye fibrosis or bone marrow fibrosis. The lung fibrosis can be associated with idiopathic pulmonary fibrosis, drug induced pulmonary fibrosis, asthma, sarcoidosis or chronic obstructive pulmonary disease. The liver fibrosis can be associated with cirrhosis, schistomasomiasis or cholangitis. The cirrhosis can be selected from alcoholic cirrhosis, post-hepatitis C cirrhosis, primary biliary cirrhosis. The cholangitis can be sclerosing cholangitis. The kidney fibrosis can be associated with diabetic nephropathy or lupus glomeruloschelerosis. The heart fibrosis can be associated with myocardial infarction. The vascular fibrosis can be associated with postangioplasty arterial restenosis or atherosclerosis. The skin fibrosis can be associated with burn scarring, hypertrophic scarring, keloid, or nephrogenic fibrosing dermatopathy. The eye fibrosis can be associated with retroorbital fibrosis, postcataract surgery or proliferative vitreoretinopathy. The bone marrow fibrosis can be associated with idiopathic myelofibrosis or drug induced myelofibrosis. The systemic fibrosis can be systemic sclerosis or graft versus host disease.

Other inflammatory conditions and neuropathies, which may be prevented or treated by the methods of the invention are those caused by autoimmune diseases. These conditions and neuropathies include multiple sclerosis, systemic lupus erythematous, and neurodegenerative and central nervous system (CNS) disorders including Alzheimer's disease, Parkinson's disease, Huntington's disease, bipolar disorder and Amyotrophic Lateral Sclerosis (ALS), liver diseases including primary biliary cirrhosis, primary sclerosing cholangitis, non-alcoholic fatty liver disease/steatohepatitis, fibrosis, hepatitis C virus (HCV) and hepatitis B virus (HBV), diabetes and insulin resistance, cardiovascular disorders including atherosclerosis, cerebral hemorrhage, stroke and myocardial infarction, arthritis, rheumatoid arthritis, psoriatic arthritis and juvenile rheumatoid arthritis (JRA), osteoporosis, osteoarthritis, pancreatitis, fibrosis, encephalitis, psoriasis, Giant cell arteritis, ankylosing spondolytis, autoimmune hepatitis, human immunodeficiency virus (HIV), inflammatory skin conditions, transplant, cancer, allergies, endocrine diseases, wound repair, other autoimmune disorders, airway hyperresponsiveness and cell, virus, or prion-mediated infections or disorders.

One embodiment of the invention is method of treating or preventing a ST2L-mediated condition comprising administering a therapeutically effective amount of an isolated human or human-adapted antibody antagonist that specifically binds Domain I (SEQ ID NO: 9) of human ST2L, blocks IL-33/ST2L interaction, competes for binding to human ST2L (SEQ ID NO: 1) with an isolated antibody comprising a heavy chain variable region (VH) of SEQ ID NO: 47 and a light chain variable region (VL) of SEQ ID NO: 51 and/or binds human ST2L at amino acid residues 35-48 of SEQ ID NO: 1 (RCPRQGKPSYTVDW; SEQ ID NO: 210) to a patient in need thereof for a time sufficient to treat or prevent the ST2L-mediated condition.

Another embodiment of the invention is a method of inhibiting mast cell response in a patient comprising administering a therapeutically effective amount of an isolated human or human-adapted antibody antagonist that specifically binds Domain I (SEQ ID NO: 9) of human ST2L, blocks IL-33/ST2L interaction, competes for binding to human ST2L (SEQ ID NO: 1) with an isolated antibody comprising a heavy chain variable region (VH) of SEQ ID NO: 47 and a light chain variable region (VL) of SEQ ID NO: 51 and/or binds human ST2L at amino acid residues 35-48 of SEQ ID NO: 1 (RCPRQGKPSYTVDW; SEQ ID NO: 210) to a patient in need thereof for a time sufficient to inhibit the mast cell response.

Another embodiment of the invention is a method of inhibiting interaction of IL-33 and ST2L in a subject, comprising administering to the subject an isolated human or human-adapted antibody antagonist that specifically binds Domain I (SEQ ID NO: 9) of human ST2L, blocks IL-33/ST2L interaction, competes for binding to human ST2L (SEQ ID NO: 1) with an isolated antibody comprising a heavy chain variable region (VH) of SEQ ID NO: 47 and a light chain variable region (VL) of SEQ ID NO: 51 and/or binds human ST2L at amino acid residues 35-48 of SEQ ID NO: 1 (RCPRQGKPSYTVDW; SEQ ID NO: 210) in an amount sufficient to inhibit the interaction of IL-33 and ST2L.

In another embodiment, the ST2L-mediated condition is asthma, airway hyper-reactivity, sarcoidosis, chronic obstructive pulmonary disease (COPD), idiopathic pulmonary fibrosis (IPF), cystic fibrosis, inflammatory bowel disease, (IBD), eosinophilic esophagitis, scleroderma, atopic dermatitis, allergic rhinitis, bullous pemphigoid, chronic urticaria, diabetic nephropathy, rheumatoid arthritis, interstitial cystitis or Graft Versus Host Disease (GVHD).

In another embodiment, the ST2L-mediated condition is associated with inflammatory cell recruitment in lung, goblet cell hyperplasia, or increased mucous secretion.

In another embodiment, the ST2L-mediated condition is associated with mast cell response.

In another embodiment, the inhibiting mast cell response comprises inhibiting the level of GM-CSF, IL-5, IL-8, IL-10 or IL-13 released by human cord blood-derived mast cells by at least 50% with 50 µg/ml antibody.

In another embodiment, the antibody antagonist administered to a patient in need thereof is a bispecific antibody that specifically binds Domain I (SEQ ID NO: 9) of human ST2L, blocks IL-33/ST2L interaction, competes for binding to human ST2L (SEQ ID NO: 1) with an isolated antibody comprising a heavy chain variable region (VH) of SEQ ID NO: 47 and a light chain variable region (VL) of SEQ ID NO: 51 and/or binds human ST2L at amino acid residues 35-48 of SEQ ID NO: 1 (RCPRQGKPSYTVDW; SEQ ID NO: 210), and further binds TSLP, IL-25, TSLPR, IL-17RA or IL-17RB.

Administration/Pharmaceutical Compositions

The "therapeutically effective amount" of the anti-ST2L antibodies effective in the treatment of conditions where modulation of ST2L biological activity is desirable can be determined by standard research techniques. For example, the dosage of the anti-ST2L antibody that will be effective in the treatment of an inflammatory condition such as asthma or rheumatoid arthritis can be determined by administering the anti-ST2L antibody to relevant animal models, such as the models described herein.

In addition, in vitro assays can optionally be employed to help identify optimal dosage ranges. Selection of a particular effective dose can be determined (e.g., via clinical trials) by those skilled in the art based upon the consideration of several factors. Such factors include the disease to be treated or prevented, the symptoms involved, the patient's body mass, the patient's immune status and other factors known by the skilled artisan. The precise dose to be employed in the formulation will also depend on the route of administration, and the severity of disease, and should be decided according to the judgment of the practitioner and each patient's circumstances. Effective doses can be extrapolated from dose-response curves derived from in vitro or animal model test systems.

The mode of administration for therapeutic use of the antibody of the invention may be any suitable route that delivers the agent to the host. Pharmaceutical compositions of these antibodies are particularly useful for parenteral administration, e.g., intradermal, intramuscular, intraperitoneal, intravenous, subcutaneous, or intranasal.

The antibody of the invention may be prepared as pharmaceutical compositions containing an effective amount of the agent as an active ingredient in a pharmaceutically acceptable carrier. The term "carrier" refers to a diluent, adjuvant, excipient, or vehicle with which the active compound is administered. Such pharmaceutical vehicles can be liquids, such as water and oils, including those of petroleum, animal, vegetable or synthetic origin, such as peanut oil, soybean oil, mineral oil, sesame oil and the like. For example, 0.4% saline and 0.3% glycine can be used. These solutions are sterile and generally free of particulate matter. They may be sterilized by conventional, well-known sterilization techniques (e.g., filtration). The compositions may contain pharmaceutically acceptable auxiliary substances as required to approximate physiological conditions such as pH adjusting and buffering agents, stabilizing, thickening, lubricating and coloring agents, etc. The concentration of the antibody of the invention in such pharmaceutical formulation can vary widely, i.e., from less than about 0.5%, usually at or at least about 1% to as much as 15 or 20% by weight and will be selected primarily based on required dose, fluid volumes, viscosities, etc., according to the particular mode of administration selected.

Thus, a pharmaceutical composition of the invention for intramuscular injection could be prepared to contain 1 ml sterile buffered water, and between about 1 ng to about 100 mg, e.g. about 50 ng to about 30 mg or more preferably, about 5 mg to about 25 mg, of an anti-ST2L antibody of the invention. Similarly, a pharmaceutical composition of the invention for intravenous infusion could be made up to contain about 250 ml of sterile Ringer's solution, and about 1 mg to about 30 mg and preferably 5 mg to about 25 mg of an antagonist of the invention. Actual methods for preparing parenterally administrable compositions are well known and are described in more detail in, for example, "Remington's Pharmaceutical Science", 15th ed., Mack Publishing Company, Easton, Pa.

The antibodies of the invention can be lyophilized for storage and reconstituted in a suitable carrier prior to use. This technique has been shown to be effective with conventional immunoglobulins and protein preparations and art-known lyophilization and reconstitution techniques can be employed.

The present invention will now be described with reference to the following specific, non-limiting examples.

Materials and Methods (General)

Human and Cynomolgus (*Macaca fascicularis*, Cyno) Receptor-Ligand Binding Inhibition Assay (RLB Assay)

96-well plate was coated with 50 µl of 4 µg/ml human ST2L-ECD (amino acids 19-328 of SEQ ID NO: 1) or 2 µg/ml cyno ST2L-ECD (amino acids 19-321 of SEQ ID NO: 2) having C-terminal $His_6$ tag in bicarbonate buffer at 4° C. for 16 hrs. All subsequent steps were performed at room temperature. Plate was blocked with 200 µl blocking buffer, and was washed 3 times with 300 µl of wash buffer containing PBS+0.05% Tween. 30 µl of various dilutions of anti-ST2L mAbs were added to the wells and incubated for 1 hour. For human receptor-ligand binding assay 20 µl of biotinylated human IL-33 (residues 112-270 of SEQ ID NO: 3) was added at 100 ng/ml final concentration and incubated for 30 minutes. For cyno receptor-ligand binding assay 20 µl of biotinylated cyno IL-33 (residues 112-269 of SEQ ID NO: 4) was added at 200 ng/ml final concentration and incubated for 30 minutes. The plate was washed 3 times with 300 µl of wash buffer. 50 µl of 0.2 µg/ml Streptavidin-HRP (Jackson Immunoresearch) was added and incubated for 30 min. The plate was washed 3 times with 300 µl of wash buffer containing PBS+0.05% Tween. 50 µl of TMB substrate (EMD Biosciences) was added to each well. Reaction was stopped by the addition of 100 µl of 0.2N Sulfuric Acid. OD450 were measured using Envision plate reader (Perkin Elmer).

Generation of Chimeric ST2L Constructs

Various construct featuring human and mouse ST2L Domain I, II and III swaps were designed and generated using standard molecular biology techniques. The constructs are listed in Table 1. Amino acid numbering corresponds to human ST2L (hST2L) (SEQ ID NO: 1; NP 057316) and mouse ST2L (mST2L)(SEQ ID NO: 5; NP 001020773) proteins.

TABLE 1

| Construct | Origin of amino acid residues for each Domain in chimeric constructs | | |
|---|---|---|---|
| Name | Domain I | Domain II | Domain III |
| HHM-ST2L | hST2L aa. 19-122 | hST2L aa. 123-202 | mST2L aa. 209-324 |
| MHM-ST2L | mST2L aa. 28-128 | hST2L aa. 123-202 | mST2L aa. 209-324 |
| HMH-ST2L | hST2L aa. 19-122 | mST2L aa. 129-208 | hST2L aa. 203-321 |
| HH-ST2L | hST2L aa. 19-122 | hST2L aa. 123-205 | N/A | hST2L: human ST2L SEQ ID NO: 1
mST2L: mouse ST2L SEQ ID NO: 5

Domain Binding Determination Assay.

Antibody binding to ST2L domain I, II and III was determined using standard capture ELISA assay using electrochemiluminescent detection format (Meso-Scale Discovery (MSD) technology). 10 µg/mL of each antibody was coated onto each well of an MSD HighBind plate (5 µL/well) for 2 hr at room temperature. The plate was blocked with 150 µL of 5% MSD Blocking buffer for 2 hr at room temperature, and washed 3 times with HEPES wash buffer, followed by the addition of 25 µL of sulfo tag labeled huST2L-ECD or mouse ST2L-ECD (amino acids 28-326 of SEQ ID NO: 5) or HHM-ST2L (SEQ ID NO:6) or HMH-ST2L (SEQ ID NO: 8) chimeras or HH-ST2L (residues 19-205 of SEQ ID NO: 1) to the plate in increasing concentrations from 5 nM to 40 nM. The plate was covered with aluminum foil and incubated for 1 hr at room temperature with gentle shaking. The plate was then washed 3 times with HEPES wash buffer. MSD read buffer (150 µl) was added to each well, and the plate was then read using an MSD Sector Imager 6000.

Those antibodies bound by human ST2L-ECD, HHM-ST2L and HMH-ST2L, but not by mouse ST2L-ECD recognize Domain I of human ST2L-ECD. Antibodies bound by human ST2L-ECD and HMH-ST2L, but not HHM-ST2L and mouse ST2L-ECD, recognize Domain III of human ST2L-ECD. Antibodies bound by human and mouse ST2L-ECD but not HH-ST2L recognize Domain III of human and mouse ST2L-ECD.

Affinity Measurements of Anti-ST2L mAbs.

Anti-ST2L mAbs, huST2L-ECD and cynoST2L-ECD were expressed using standard methods. Goat anti-human IgG Fcγ fragment-specific Ab (cat #109-005-098) was obtained from Jackson ImmunoResearch laboratories (West Grove, Pa.). GLC sensor chips (Bio-Rad cat #176-5011), CM-5 sensor chips (GE Healthcare cat# BR100014) and reagents for preparation of the capture surface were obtained from Biacore (GE healthcare, Piscataway, N.J.) or from Bio-Rad Life Sciences (Bio-Rad, Hercules, Calif.).

The interactions of anti-ST2L antibodies with $His_6$-tagged human ST2L-ECD and $His_6$-tagged cyno ST2L-ECD were studied by ProteOn using a ProteOn XPR36 at 25° C. A biosensor surface was prepared by coupling goat anti-human IgG Fcγ fragment specific antibody (Ab) to the surface of a GLC sensor chip using the manufacturer instructions for amine-coupling chemistry. The coupling buffer was 10 mM sodium acetate, pH 4.5. The goat anti-human IgG Fcγ (about 4500 response units) was immobilized in the horizontal orientation. The anti-ST2L antibodies were provided purified, or in crude supernatants. In either case these antibodies were diluted in PRB (PBS pH 7.4, supplemented with, 3 mM EDTA, and 0.005% Tween 20) to a concentration of about 0.5 µg/mL. The antibodies were captured (60-130 RU) in the vertical orientation onto the anti-human Fcγ antibody-modified GLC chip. Capture of anti-ST2L mAbs was followed by injection of huST2L ECD in solution (0.024 to 15 nM in 5-fold dilutions) or cynoST2L ECD in solution (0.020-5 nM in 4-fold dilutions) in the horizontal orientation. The association was monitored for 4 minutes in all experiments (200 µL injected at 50 µL/min). The dissociation was monitored for 30 minutes. Regeneration of the sensor surface was obtained with three 15 sec pulses of 10 mM glycine pH 1.5. The data were fit using the ProteOn software and using a 1:1 binding model with mass transfer.

Biacore experiments were performed using a Biacore 2000 or a Biacore 3000 optical biosensor (Biacore AB). All experiments were run in BRB (PBS pH 7.4, supplemented with 3 mM EDTA and 0.005% Tween 20) with or without 0.1% BSA at 25° C.

A Biacore biosensor surface was prepared by coupling goat anti-human IgG Fcγ fragment specific Ab to the carboxymethylated dextran surface of a CM-5 chip using manufacturer instructions for amine-coupling chemistry. The coupling buffer was 10 mM sodium acetate, pH 4.5. An average of 6000 response units (RU) of Ab were immobilized in each of four flow cells. The anti-ST2L mAbs were captured (about 33 RU) onto the anti-human Fcγ antibody-modified sensor chip surface. Capture of anti-ST2L mAbs was followed by injection of huST2L ECD in solution (0.2 to 15 nM in 3-fold dilutions) or cynoST2L ECD in solution (0.2 to 15 nM or 0.020-5 nM, in 3-fold dilutions). The association was monitored for 4 minutes or 8 minutes (200 µL injected at 50 µl/min or 20 µL/min for C2521 and C2519). The dissociation was monitored for 10 minutes, or up to 2.5 hours. Regeneration of the sensor surface was obtained with injection of 50 mM NaOH and/or injection of 100 mM $H_3PO_4$.

Data were processed using the Scrubber software, version 1.1 g (Biologic Software). Double reference subtraction of the data was performed by subtracting the curves generated by buffer injection from the reference-subtracted curves for analyte injections to correct for buffer contribution to the signal and instrument noise (Myszka, Journal of Mol Recogn 12:279-84, 1999).

After data processing, the data generated for kinetic and affinity determination were analyzed using the Scrubber software or the BIAevaluation software, version 4.0.1 (Biacore, AB). The kinetic data were analyzed using a simple 1:1 binding model including a term for mass transfer.

Affinity Measurement of Anti-Mouse ST2L mAb (C1999/CNTO3914) to Murine ST2L ECD.

Anti-ST2L mAb (C1999/CNTO3914) and murine ST2L extracellular domain (muST2L-ECD) were expressed and purified using standard methods. Anti-murine IgG Fcγ fragment-specific Ab was obtained from Jackson ImmunoResearch laboratories (West Grove, Pa.). Sensor chips and reagents for preparation of the capture surface were obtained from Biacore (GE healthcare, Piscataway, N.J.). The experimental Biacore running buffer (BRB) contained PBS pH 7.4 with 0.005% Tween 20 and 0.1 mg/mL BSA and data were collected at 25° C.

The interaction of anti-ST2L antibody with muST2L-ECD was studied on a Biacore2000 at 25° C. A biosensor surface was prepared by coupling anti-mouse-Fc specific antibody to the surface of a CM4 sensor chip using the manufacturer instructions for amine-coupling chemistry. C1999/CNTO3914 and muST2L-ECD were diluted in BRB. C1999 was captured using the anti-mouse Fcγ antibody (about 85 RU). Capture was followed by injection muST2L ECD (residues 28-326 of SEQ ID NO: 5) in solution (starting at 15 nM, 5 concentrations, in a 3-fold serial dilution). The association was monitored for 8 minutes. The dissociation was monitored for up 6000 seconds. The regenerations were performed using a 1/100 dilution of phosphoric acid. The data were fit using a 1:1 binding model.

Human Basophil Cell Line Assay (Basophil Cytokine Release Assay)

KU812 cells (human basophil cell line; ATCC, CRL-2099) were plated in sterile 96-well U-bottom tissue culture plates at 25,000 or 50,000 cells per well in a total 40 µl of RPMI 1640 growth medium (Invitrogen) supplemented with 10% FBS and penicillin/streptomycin. Anti-human ST2L mAbs and controls were added at various concentrations (50 µl/well) and incubated at 37° C. After 1 hour of incubation, recombinant "mature" IL-33 (amino acids 111-270 of SEQ ID NO: 3) was added at a final concentration of 10 ng/ml in 10 µl of RPMI growth medium. The cells were then incubated at 37° C. for 18-24 hours to allow for IL-33-mediated induction of IL-5 and IL-6. Following incubation, the cells were harvested and the cell supernatant was collected for subsequent detection of IL-33-induced IL-5 and IL-6 using either ELISA (R&D systems) or bead-based multiplex analyses (Millipore).

Human Mast Cell Cytokine Release Assay and $PGD_2$ Release Assay

Mast cells were derived from $CD34^+$ human cord blood cells (Lonza). Frozen vials of >$1.0\times10^6$ $CD34^+$ cord blood cells were rapidly thawed and transferred to a 50 ml conical tube. Drops of warmed or room temp Stem-Pro 34 media+ supplements (25 mls total; Invitrogen) were slowly added to the cells. The cells were centrifuged at 1,000 rpm for 15 minutes and resuspended in media (10 mls of StemPro-34, with the following supplements: 30 ng/ml IL-3, 100 ng/ml IL-6, and 100 ng/ml SCF. Cells were plated in 2 wells of a 6-well plate, and cultured for 1 week. On day 4, cells were expanded 1:3 in supplemented Stem Pro-34 media. On day 7, non-adherent cells were removed and plated at $0.5\times10^6$/ml in StemPro-34 media containing 10 ng/ml IL-6 and 100 ng/ml SCF. Cells were expanded weekly to maintain cell density at $0.5\times10^6$/ml until mast cells were mature at 6-10 weeks (assessed by expression of FcεR1, cKit, and tryptase).

Mature mast cells were cultured at $0.5\times10$/ml in StemPro-34 and stimulated daily for 4 days in IL-4 (10 ng/ml; Peprotech), IL-6 (10 ng/ml; R&D Systems) and SCF (100 ng/ml; Invitrogen). Prior to assay, cells were harvested, centrifuged at 1,000 RPM for 10 min and resuspended in fresh StemPro- 34 media or RPMI containing 10% FCS without antibiotics, with 100 ng/ml human recombinant SCF. Cells were plated at a density of 65,000 to 75,000 cells/0.16 mls/well in a flat bottom, tissue culture-treated 96-well plate. The anti-ST2L mAbs were added to the plate for a final concentration of 50, 10, 2, 0.4, 0.08, 0.016, 0.0032 µg/ml for 30 minutes prior to the addition of IL-33. Recombinant human "mature" IL-33 (residues 111-270 of SEQ ID NO: 3) was also prepared at 10× (10 or 30 ng/ml) in media+100 ng/ml SCF. 20 µl of the 10× IL-33 was added to the wells, for a final concentration of 1 (FIGS. 6 and 7) or 3 ng/ml (FIG. 8), and the plates were incubated overnight at 37° C., 5% $CO_2$. Culture supernatant was harvested 18-24 hours after stimulation. The plates were centrifuged at 1,000 RPM for 10 minutes. The supernatant was removed and placed into a U bottom 96 well plate and stored at −20° C. prior to assaying. Human cytokine kits from Millipore were used to analyze cytokine levels using Luminex™ technology. Levels of PGD2 were measured using the Prostaglandin D2-MOX EIA kit from Cayman Chemical Company, according to manufacturer's instructions. In order to enhance the sensitivity of the ELISA, $PGD_2$ in the mast cell culture supernatants were converted into non-degradable $MOX-PGD_2$ (methoxylsamine-$PGD_2$) by treatment with methoxylsamine hydrochloride (MOX-HCl).

Mouse Receptor-Ligand Binding Inhibition Assay (Mouse RLB Assay)

A 96-well clear plate (VWR) was coated with 50 µl of 2 µg/ml goat anti-human IgG, Fcγ fragment-specific (Jackson Immunoresearch) antibody for approximately 16 hours at 4° C. The remaining steps were completed at room temperature. Wells were incubated with blocking buffer, washed and 50 µl of 2 µg/ml mouse ST2L-ECD fused to human Fc was added for 1 hour. The plate was washed and 1 µg/ml of biotinylated mIL-33 with or without anti-mST2L antibodies added. The plate was washed and detection done with streptavidin-HRP (Jackson Immune Research) and signal developed with TMB substrate (RDI Division of Fitzgerald Industries) following manufacturer's instructions.

Mouse and Human Reporter Gene Assays (Human or Mouse RGA Assay)

HEK293 cells were plated at 50,000 cells per well in white clear-bottom tissue culture-treated 96-well plates (NUNC) in DMEM, 10% FBS and incubated in humidified incubator at 37° C., 5% $CO_2$ for 24 hours. Cells were co-transfected with vectors encoding either human or mouse ST2L-ECD cDNA, NF-κB-Luciferase vector (Stratagene, Agilent Technologies, Santa Clara, Calif.) using Lipofectamine™ 2000 in Opti-MEM media (Invitrogen) using standard protocols. After 24 hour incubation at 37° C., 5% $CO_2$, the transfected ells were treated with mouse (R&D Systems, residues 109-266 of SEQ ID NO: 5) or human IL-33 (residues 112-270 or SEQ ID NO: 3) with or without anti-ST2L antibodies for 16 hours at 37° C., 5% $CO_2$. Luciferase activity was measured using Steady-Glo® reagent (Promega) according to the manufacturer's instructions.

Mouse T-Cell Proliferation Assay

Mouse Th2 cells (D10.G4.1, ATCC) were cultured in complete growth medium: RPMI 1640 medium with 2 mM L-glutamine adjusted to contain 1.5 g/L sodium bicarbonate, 4.5 g/L glucose, 10 mM HEPES, and 1.0 mM sodium pyruvate, and supplemented with: 0.05 mM 2-mercaptoethanol, 10 pg/ml IL-1α (R&D Systems), 10% fetal bovine serum, 10% rat T-STIM factor with Con A (rat IL-2 culture supplement available from Becton Dickinson). The cells were washed twice with assay media (RPMI, 10% FBS, no IL-1, no T-STIM), resuspended at $1.25 \times 10^5$ cells per ml and plated in 80 µl of medium in white clear bottom tissue culture treated 96-well plates (NUNC, Rochester, N.Y.). Various amounts of mouse IL-33 (residues 109-266 of SEQ ID NO: 5) were added to the cells for the final assay volume of 100 µl. When testing antibody neutralization, control antibodies (spiked in spent hybridoma medium) or hybridoma supernatants were added to the cells and incubated for 1 hour followed by addition of 20 pg/ml mIL-33. The plates were cultured for 24 hours in humidified incubator at 37 C, 5% $CO_2$. Quantitation of viable cells was achieved with CellTiter-Glo® reagents (Promega, Madison, Wis.); protocol performed according to the manufacturer's instructions.

Mouse Bone Marrow Derived Mast Cell Assay

Mouse mast cells were derived from bone marrow of Balb/c mice (6 weeks). Cells were plated at 300,000 cells/well in RPMI media (endotoxin free), 10% FBS, 10% WEHI cell line-conditioned medium, 10 ng/ml IL-3 (Peprotech), 0.1 mM essential amino acids, 1% Penicillin/Streptomycin (Invitrogen). Anti-ST2L mAbs (100, 10, 1, 0.1, or 0.01 µg/ml) were incubated with the cells for 1 hour prior to addition of recombinant mouse "mature" IL-33 (residues 109-266 of SEQ ID NO: 5 (10 ng/ml; R&D Systems). After approximately 24 h the supernatants were harvested and frozen until analysis using the Millipore Mouse 22-plex kit for Luminex™, according to manufacturer's instructions.

Cyno Endothelial Cell Assay

Cynomolgus Aortic Endothelial cells cultured in EGM®-2 Endothelial Cell Growth Medium-2 (Lonza) were plated in 96-well tissue culture plates at 10,000 or 20,000 cells per well. 50 µl of anti-ST2L antibodies were added to the cells starting at 100 µg/ml with subsequent 4- or 5-fold dilutions and incubated at 37° C. for 1 hour before the addition of recombinant cyno 'mature' IL-33 (SEQ ID NO: 4). Fifty microliters of 20 ng/ml cynomolgus IL-33 was then added to the cells and incubated at 37° C. for 24 hours. To evaluate IL-33-induced cytokine responses the supernatants were harvested and the cytokine levels were assessed by a Non-Human Primate IL-8 kit for Luminex™ (Millipore) according to manufacturer's instructions.

Mouse Peritoneal Lavage Assay

The peritoneums of 6 Balb/c mice was washed with a total of 3 ml PBS to collect peritoneal cells. The majority of these cells were found to be lymphocytes and macrophages, as determined by B220 and F4/80 expression (FACS analysis). Approximately 1% were $cKit^+$ ($CD117^+$) mast cells. Cells were centrifuged and the pellet was resuspended to $1 \times 10^6$ cells/ml in Alpha MEM media+10% FBS+100 U/ml Penicillin+100 µg/ml Streptomycin (Invitrogen). Cells were plated at 200 µl per well in a 96-well plate and rested 2 h at 37° C. Anti-ST2L mabs were added to the cells for 30 minutes prior to the addition of 10 ng/ml mouse "mature" IL-33 (R&D Systems; residues 109-266 of SEQ ID NO: 215). Supernatants were collected 24 h after IL-33 addition, stored at −20° C. until analysis, and analyzed using the Millipore Mouse 22-plex kit for Luminex™ according to manufacturer's instructions.

Example 1

Generation of Rat Anti-Mouse ST2L Antibodies

Rats were immunized intraperitoneally with mouse ST2-Fc (R&D Systems (Ser27-Ser342 of SEQ ID NO: 5) and assessed for specific IgG titers. Once sufficient titers were obtained, splenocytes were isolated and fused with FO cells. The resulting hybridomas were plated in 96 well plates or methylcellulose and cultured for 10 days. Antigen specific clones were identified by standard capture ELISA for binding to mST2-Fc and cross screened against the Fc protein alone. Murine ST2-specific hybridomas were further tested for the inhibition of IL-33 binding to ST2 in an ELISA and for the inhibition of IL-33-induced D10.G4.1 mouse Th2 cell proliferation. Hybridomas exhibiting neutralization in both receptor-ligand binding and cell-based proliferation assays were clonally selected by limiting dilution. Hybridoma V-regions were sequenced and cloned into mouse IgG1 background. ST2L-ECD domain specificity was addressed by standard immunosorbent assay with electrochemiluminescent detection using various human-mouse domain-swap constructs.

Antibody secreted by hybridoma C1999 was cloned into mouse IgG1 background and named CNTO3914. Sequences of CNTO3914 variable regions and CDRs are shown in Table 2. CNTO3914 does not cross-react with human ST2L and binds Domain I of mouse ST2L-ECD.

nocytes were isolated and fused with FO cells. The resulting hybridomas were plated in 96 well plates and cultured for 10 days. Antigen specific clones were identified by standard capture ELISA for binding to C-terminal $His_6$-tagged huST2L-ECD and cross-reactivity to $His_6$-tagged cyno ST2L-ECD. Human ST2L-specific hybridomas cross-reacting with cyno ST2L were further tested for the inhibition of IL-33 binding to huST2L in an ELISA assay and for the inhibition of NF-κB activation in reporter gene assay. Clones inhibiting in reporter gene assay or in both ELISA and reporter gene assay were selected for further studies.

Antibodies from hybridomas C2494, C2519A and C2521A were selected for further analyses. C2519A and C2521A bind human ST2L at Domain III, and C2494 binds human ST2L at Domain I. Antibody C2494 was cloned into human IgG2 background, and the full length antibody was named STLM62.

Anti-human ST2L mAbs were generated at Genovac Gmbh by proprietary DNA immunization technology using full length ST2L constructs and boosting with the cells transfected to express human ST2L-ECD. Hybridomas were screened for binding to human ST2L-ECD by flow cytometry. Clones that exhibited binding in this assay were confirmed to bind hST2L-ECD and further characterized for binding to cyno ST2L-ECD by standard capture ELISA. Select clones were characterized in receptor-ligand binding inhibition ELISA and reporter gene assay. Clones inhibiting

TABLE 2

| mAb Name | HCDR1 Sequence | SEQ ID NO: | HCDR2 Sequence | SEQ ID NO: | HCDR3 Sequence | SEQ ID NO: |
|---|---|---|---|---|---|---|
| C1999/CNTO3914 | HYGMA | 13 | SIITDGTSTYYRDSVKG | 14 | QSDDYFDY | 15 |

| mAb Name | LCDR1 Sequence | SEQ ID NO: | LCDR2 Sequence | SEQ ID NO: | LCDR3 Sequence | SEQ ID NO: |
|---|---|---|---|---|---|---|
| C1999/CNTO3914 | KSSQSLEYSDGDSYLE | 16 | GVSNRFS | 17 | FQATHDPFT | 18 |

| mAb Name | | SEQ ID NO: |
|---|---|---|
| | VH sequence | |
| C1999/CNTO3914 | EVQLVESGGGLLQPGRSLKLSCTASGFIFSHYGMAWVRQAPTKGLEWVSSIITDGTSTYYRDSVKGRFTISRDNAKNTQYLQMDSLRSEDTATYYCARQSDDYFDYWGQGVMVTVSS | 19 |
| | VL sequence | |
| | DVVLTQTPVSLSVTLGDQASISCKSSQSLEYSDGDSYLEWYLQKPGQSPQLLIYGVSNRFSGVPDRFIGSGSGTDFTLKISRVEPEDLGVYYCFQATHDPFTFGSGTKLEIK | 20 |

Example 2

Generation of Mouse Anti-Human ST2L Antibodies

Two different immunizations were performed for generation of mouse anti-human ST2 mAbs.

BALB/c were immunized intraperitoneally with soluble ST2-Fc (R&D Systems, SEQ ID NO: 157) and assessed for specific IgG titers. Once sufficient titers were obtained, splein reporter gene assay or in both ELISA and reporter gene assay were selected for further studies.

Antibody from Genovac hybridoma C2244 was selected for further analyses and cloned into human IgG2 background. The full length antibody was named STLM15. STLM15 binds human ST2L at Domain I.

Sequences of the VH, VL and CDR domains of the mouse anti-human antibodies are shown in Table 3.

TABLE 3

| mAb Name | HCDR1 Sequence | SEQ ID NO: | HCDR2 Sequence | SEQ ID NO: | HCDR3 Sequence | SEQ ID NO: |
|---|---|---|---|---|---|---|
| C2519A | DYNMN | 21 | NINPYYGSTTYNQKFKG | 25 | EGDTYLAWFAY | 29 |
| C2521A | TYWMN | 22 | QIFPASGSTYYNEMFKD | 26 | SENIYYINFQYYFAY | 30 |
| C2244/ STLM15 | SDYAWN | 23 | FISYSGDTSFNPSLKS | 27 | YDGYSFDY | 31 |
| C2494/ STLM62 | DDYMH | 24 | RIDPAIGNTEYAPKFQD | 28 | GDFYAMDY | 32 |

| mAb Name | LCDR1 Sequence | SEQ ID NO: | LCDR2 Sequence | SEQ ID NO: | LCDR3 Sequence | SEQ ID NO: |
|---|---|---|---|---|---|---|
| C2519A | RSSQSIVYSNGNTYLE | 33 | KVSNRFS | 37 | FQGSHVPPT | 41 |
| C2521A | RASQNIGTRMH | 34 | YASESIS | 38 | QQSNTWPFT | 42 |
| C2244/ STLM15 | RASKSVSTSGSSYMF | 35 | LASNLES | 39 | QHSREIPYT | 43 |
| C2494/ STLM62 | ITNTDIDDVIH | 36 | EGNTLRP | 40 | LQSDNMLT | 44 |

| mAb | | SEQ ID NO: |
|---|---|---|
| | VH sequence | |
| C2519A | EFQLQQSGPELVKPGASVKISCKASGYSFTDYNMNWVKQSHGKSLEWI GNINPYYGSTTYNQKFKGKATLTVDKSSNTAYMHLNSLTSEDSAVYYCA REGDTYLAWFAYWGQGTLVTVSA | 45 |
| C2521A | QIQLQQSGPELVRPGTSVKISCKASGYTFLTYWMNWVKQRPGQGLEWI GQIFPASGSTYYNEMFKDKATLTVDTSSSTAYMQLSSLTSEDTAVYFCAR SENIYYINFQYYFAYWGQGTTLTVSS | 46 |
| C2244/ STLM15 | EVQLQESGPGLVKPSQSLSLTCTVTGFSITSDYAWNWIRQFPGSKLEW MGFISYSGDTSFNPSLKSRISVTRDTSKNQFFLQLNSVTTEDTATYYCASY DGYSFDYWGQGTTLTVSS | 47 |
| C2494/ STLM62 | EVQLQQSVAELVRPGASVKLSCTASAFNIKDDYMHWVKQRPEQGLEW IGRIDPAIGNTEYAPKFQDKATMTADTSSNTAYLQLSSLTSEDTAVYYCA LGDFYAMDYWGQGTSVTVSS | 48 |
| | VL sequence | |
| C2519A | DVLMTQTPLSLPVSLGDQASISCRSSQSIVYSNGNTYLEWYLQKPGQSP KLLIYKVSNRFSGVPDRFSGSGSGTDFTLKISRVEAEDLGVYYCFQGSHVP PTFGGGTKLEIK | 49 |
| C2521A | ILLTQSPAILSVSPGERVSFSCRASQNIGTRMHWYQQRTNGSPRLLIKYA SESISGIPSRFSGSGSGTDFTLTISSVESEDIADYYCQQSNTWPFTFGSGTK LEIK | 50 |
| C2244/ STLM15 | DIVLTQSPASLAISLGQRATISCRASKSVSTSGSSYMFWYQQKPGQPPKL LIYLASNLESGVPARFSGSGSGTDFTLNIHPVEEEDAAAYYCQHSREIPYT FGGGTKLEIK | 51 |
| C2494/ STLM62 | ETTVTQSPASLSVATGEKVTIRCITNTDIDDVIHWYQQKPGEPPKLLISEG NTLRPGVPSRFSSSGYGTDFVFTIENTLSEDVADYYCLQSDNMLTFGAGT KLELK | 52 |

Example 3

Generation of Fully Human ST2L Antibodies

Human ST2L-binding Fabs were selected from de novo pIX phage display libraries as described in Shi et al., J Mol Biol 397:385-96, 2010; Int. Pat. Publ. No. WO2009/085462; U.S. Pat. Publ. No. US2010/0021477). Briefly, the libraries were generated by diversifying human scaffolds where germline VH genes IGHV1-69*01, IGHV3-23*01, and IGHV5-51*01 were recombined with the human IGHJ-4 minigene via the H3 loop, and human germline VLkappa genes O12 (IGKV1-39*01), L6 (IGKV3-11*01), A27 (IGKV3-20*01), and B3 (IGKV4-1*01) were recombined with the IGKJ-1 minigene to assemble complete VH and VL domains. The positions in the heavy and light chain variable regions around H1, H2, L1, L2 and L3 loops corresponding to positions identified to be frequently in contact with protein and peptide antigens were chosen for diversification. Sequence diversity at selected positions was limited to residues occurring at each position in the IGHV or IGLV germline gene families of the respective IGHV or IGLV genes. Diversity at the H3 loop was generated by utilizing short to mid-sized synthetic loops of lengths 7-14 amino acids. The amino acid distribution at H3 was designed to mimic the observed variation of amino acids in human antibodies. Library design is detailed in Shi et al., J Mol Biol 397:385-96, 2010. The scaffolds utilized to generate libraries were named according to their human VH and VL germline gene origin. The three heavy chain libraries were combined with the four germline light chains or germline light chain libraries to generate 24 unique VH:VL combinations for screening. All 24 VH:VL library combinations were utilized in phage panning experiments against huST2L-ECD-Fc.

The libraries were panned using a Fc fusion of the huST2L-ECD (residues 19-328 of SEQ ID NO: 1). Pannings were done in 2 different formats, antigen (Ag) in solution and Ag displayed. For Ag in solution the streptavidin-coated magnetic beads were blocked in PBS with 3% non-fat dry milk. The biotinylated (Bt) antigen huST2L-ECD human Fc fusion (Bt-huST2L-ECD-Fc) with a 10× higher concentration of human Fc protein as competitor was mixed with Fab-pIX phage libraries. The Fab-pIX phage bound to the Bt-huST2L-ECD-Fc was captured on the blocked streptavidin (SA)-coated magnetic beads. Phage selections were performed for three rounds where the huST2L-ECD-Fc concentrations varied from 100 nM, 10 nM, 10 nM from rounds 1 to 3, respectively. For Ag display the Bt-huST2L-ECD-Fc was coated on SA coated magnetic beads. Fab-pIX phage libraries plus 10× excess of human Fc protein was added simultaneously to the Bt-huST2L-ECD-Fc displayed SA-magnetic beads. Bt-Ag concentrations used were 100 nM, 10 nM, 10 nM for rounds 1 to 3, respectively. Screening was done for both panning formats by ELISA for Fab binding to huST2L-ECD-Fc protein. A total of 79 Fabs with binding to hST2L-Fc were isolated from these selections. Fab HuT2SU-39 was determined by a ranking ELISA to have the best binding activity overall.

An ELISA based IL-33 binding inhibition assay was performed on the 79 Fabs. A total of 32 Fabs showed inhibition of IL-33 binding to huST2L-ECD-Fc. 46 Fabs were chosen for affinity maturation from the pIX de novo campaign.

Example 4

Affinity-Maturation of Fully Human ST2L Antibodies

Select antibodies were affinity-matured using an "in-line" maturation process described in Shi et al., J Mol Biol 397: 385-96, 2010 and W009085462A1. In this technology, the VH regions of Fab clones obtained in the first selection are combined with libraries of the corresponding VL scaffold. All VH genes from the 46 Fabs identified in Example 3 were cloned into the appropriate VL maturation libraries as pools according to their original VL gene family. The used VL scaffold libraries and their diversification schemes are shown in Table 4. The human VL scaffolds are as follows: IGKV1-39*01 (012), IGKV3-11 (L6), IGKV3-20 (A27), IGKV4-1*01 (B3) and are described for example in U.S. Pat. Publ. No. US2012/0108795. For affinity maturation panning, the phage libraries were added to Bt-huST2-ECD-Fc first. After incubation the maturation library phage/Bt-hST2L-ECD-Fc complex was added to the SA-coated magnetic beads. The Bt-huST2-Fc concentrations varied respectively from R1 to R3 at 10 nM, 1 nM, and 0.1 nM. The final wash of round 3 was performed overnight at room temperature in the presence of 10 nM unlabelled huST2L-ECD-Fc to further drive affinity improvement.

TABLE 4

| Position | | VL library diversification scheme for different scaffolds | | | |
|---|---|---|---|---|---|
| Loop | (Kabat) | A27 | B3 | L6 | O12 |
| L1 | 30 | SRNTD | RNDGHSY | SRNAD | SRNAD |
|  | 30a | SNR | RNDGHWY | — |  |
|  | 30e |  | RNDGHSY | — |  |
|  | 31 | SNRADH | RNDGHWY | NSKD | SNKDG |
|  | 32 | YFHQSEK | YNWR | YWDFHSAN | YHNDWFSAV |
| L2 | 50 | ADGS | YWNK | ADKGYFTN | FYTNKADG |
| L3 | 91 | YSHA | SYWH | RYSGF | SAYHPD |
|  | 92 | YNDSHIFKG | SYGN | RHNSL | FIYHNDKGRE |
|  | 93 | SNTDGHR | STER | NDKR | STHNDRG |
|  | 94 | TYLVFAS | WYSH | WA | TYLVFSRGPI |
|  | 96 | WYFLIR | YRWH | WYFLIR | LWRFYIN |

A total of 161 sequence unique Fabs were obtained from the maturation pannings. Fabs showing highest binding to huST2L-ECD were converted to IgG for further characterization.

MAbs ST2M48, ST2M49, ST2M50 and ST2M51 were selected for further characterization, and their VH, VL and CDR sequences are shown in Table 5. Mabs ST2M48, ST2M49, ST2M50 and ST2M51 bind human ST2L at Domain III, and cross-react with mouse ST2L.

TABLE 5

| | | HCDR1 | | HCDR2 | | HCDR3 | |
|---|---|---|---|---|---|---|---|
| mAb ID | HC ID | Sequence | SEQ ID NO: | Sequence | SEQ ID NO: | Sequence | SEQ ID NO: |
| ST2M48 | STLH125 | TSYWIG | 53 | GIIYPGDSYTRYSPSFQG | 55 | LSGRFDY | 57 |
| ST2M49 | STLH149 | TSYWIG | 53 | GIIYPGDSYTRYSPSFQG | 55 | IGGMFDY | 58 |
| ST2M50 | STLH125 | TSYWIG | 53 | GIIYPGDSYTRYSPSFQG | 55 | LSGRFDY | 57 |
| ST2M51 | STLH130 | SSYAIS | 54 | GIIPIFGTANYAQKFQG | 56 | DTPQLDY | 59 |

TABLE 5-continued

| mAb ID | LC ID | LCDR1 Sequence | SEQ ID NO: | LCDR2 Sequence | SEQ ID NO: | LCDR3 Sequence | SEQ ID NO: |
|---|---|---|---|---|---|---|---|
| ST2M48 | STLL232 | RASQSVRDALA | 60 | FASNRAT | 64 | QQFNTWPIT | 67 |
| ST2M49 | STLL216 | RASQSVANALA | 61 | KASNRAT | 65 | QQYYGWPIT | 68 |
| ST2M50 | STLL228 | RASQSVSNALA | 62 | FASNRAT | 64 | QQFFNWPIT | 69 |
| ST2M51 | TC1L3 | RASQSISSYLN | 63 | YASSLQS | 66 | QQSYSTPLT | 70 |

| mAb Name | | SEQ ID NO: |
|---|---|---|
| | VH sequence | |
| ST2M48 | EVQLVQSGAEVKKPGESLKISCKGSGYSFTSYWIGWVRQMPGKGLEWM GIIYPGDSYTRYSPSFQGQVTISADKSISTAYLQWSSLKASDTAMYYCARLS GRFDYWGQGTLVTVSS | 71 |
| ST2M49 | EVQLVQSGAEVKKPGESLKISCKGSGYSFTSYWIGWVRQMPGKGLEWM GIIYPGDSYTRYSPSFQGQVTISADKSISTAYLQWSSLKASDTAMYYCARIG GMFDYWGQGTLVTVSS | 72 |
| ST2M50 | QVQLVQSGAEVKKPGSSVKVSCKASGGTFSSYAISWVRQAPGQGLEW MGGIIPIFGTANYAQKFQGRVTITADESTSTAYMELSSLRSEDTAVYYCAR YNFFFDYWGQGTLVTVSS | 71 |
| ST2M51 | QVQLVQSGAEVKKPGSSVKVSCKASGGTFSSYAISWVRQAPGQGLEW MGGIIPIFGTANYAQKFQGRVTITADESTSTAYMELSSLRSEDTAVYYCAR DTPQLDYWGQGTLVTVSS | 73 |
| | VL sequence | |
| ST2M48 | EIVLTQSPATLSLSPGERATLSCRASQSVRDALAWYQQKPGQAPRLLIYFA SNRATGIPARFSGSGSGTDFTLTISSLEPEDFAVYYCQQFNTWPITFGQGT KVEIK | 74 |
| ST2M49 | EIVLTQSPATLSLSPGERATLSCRASQSVANALAWYQQKPGQAPRLLIYKA SNRATGIPARFSGSGSGTDFTLTISSLEPEDFAVYYCQQYYGWPITFGQGT KVEIK | 75 |
| ST2M50 | EIVLTQSPATLSLSPGERATLSCRASQSVDDWLAWYQQKPGQAPRLLIYK ASNRATGIPARFSGSGSGTDFTLTISSLEPEDFAVYYCQQYNRAPWTFGQ GTKVEIK | 76 |
| ST2M51 | DIQMTQSPSSLSASVGDRVTITCRASQSISSYLNWYQQKPGKAPKLLIYYA SSLQSGVPSRFSGSGSGTDFTLTISSLQPEDFATYYCQQSYSTPLTFGQGTK VEIK | 77 |

Example 5

Characterization of Anti-ST2L Antibodies

Antibodies derived from various campaigns as described above were further characterized for their ability to block IL-33/ST2L interaction, for their inhibition of IL-33-induced signaling as measured by NF-κB reporter gene assay, ability of the antibodies to inhibit mast cell responses, for their affinity against human and cyno ST2L, and cross-reactivity with mouse ST2L. Epitope mapping was done using human/mouse ST2L domain swap chimeric constructs as described in Materials and Methods. Results of the experiments are shown in Tables 6, 7 and 8. In Tables 7 and 8, "+" indicates that the antibody blocks IL-33/ST2L interaction, and "−" indicates it does not block IL-33/ST2L interaction. Experiments with CNTO3914 were done using mouse cells and reagents due to lack of cross-reactivity to human. Human cells and human reagents were used in assays for all other antibodies.

Characterized antibodies were grouped to those that block IL-33/ST2L interaction (mAbs STLM15, STLM62 and CNTO3914) and those that do not block the IL-33/ST2L interaction (mAbs C2519, C2521, ST2M48, ST2M49, ST2M50 and ST2M51). The antibodies blocking IL-33/ST2L interaction bind to ST2L Domain I, whereas the non-blocking antibodies bind to ST2L Domain III. The antibodies tested inhibited ST2L downstream signaling as assessed by the NF-κB reporter gene assay and IL-33-induced cytokine release by the KU812 human basophil cell line, or in case of CNTO3914, assessed by mouse Th2 cell proliferation. Antibodies binding to ST2L Domain I inhibited at higher level human mast cell responses as assessed by cytokine and chemokine secretion when compared to anti-ST2L antibodies binding ST2L Domain III. CNTO3914, which binds mouse ST2L domain I and does not cross-react with human was also able to inhibit IL-33-induced mouse mast cell responses.

TABLE 6

| mAb | corresponding hybridoma | Affinity to human ST2L | | | Affinity to cyno ST2L | | |
|---|---|---|---|---|---|---|---|
| | | $k_{on}$ (M$^{-1}$s$^{-1}$) | $k_{off}$ (s$^{-1}$) | $K_D$ (pM) | $k_{on}$ (M$^{-1}$s$^{-1}$) | $k_{off}$ (s$^{-1}$) | KD (pM) |
| STLM15 | C2244 | 1.02E+06 | 4.25E−05 | 42 | 4.81E+06 | 5.30E−05 | 11 |
| STLM62 | C2494 | 4.26E+06 | 1.19E−04 | 28 | 4.51E+07 | 5.39E−04 | 12 |
| na | C2519 | 4.83E+05 | 8.70E−05 | 180 | 7.14E+04 | 3.20E−03 | 44800 |
| na | C2521 | 6.18E+05 | 4.90E−05 | 79 | 4.47E+05 | 1.66E−03 | 3710 |
| ST2M48 | na | 1.32E+06 | 7.33E−05 | 56 | 1.03E+07 | 2.65E−03 | 257 |
| ST2M49 | na | 1.59E+06 | 1.61E−04 | 101 | 4.66E+07 | 1.24E−02 | 266 |
| ST2M50 | na | 1.15E+06 | 5.10E−05 | 45 | 2.01E+07 | 2.49E−03 | 124 |
| ST2M51 | na | 1.29E+06 | 4.87E−05 | 38 | 4.42E+07 | 3.36E−03 | 76 |

TABLE 7

| mAb | corresponding hybridoma | RLB* | RGA# | Basophil cytokine release | Mast cell cytokine release | ST2L epitope |
|---|---|---|---|---|---|---|
| STLM15 | C2244 | + | + | + | + | hD1 |
| STLM62 | C2494 | + | + | + | + | hD1 |
| | C2519 | − | + | + | − | hD3 |
| | C2521 | − | + | + | − | hD3 |
| ST2M48 | NA | − | + | nt | − | h/mD3 |
| ST2M49 | NA | − | + | nt | − | h/mD3 |
| ST2M50 | NA | − | + | nt | − | h/mD3 |
| ST2M51 | NA | − | + | nt | − | h/mD3 |

*Receptor-Ligand binding inhibition
Reporter gene assay
hD1 = human ST2L D1 domain mD1 = mouse ST2L D1 domain hD3-human ST2L D3 domain h/mD3 = human and mouse ST2L D1 and D3 domains
nt = not tested

TABLE 8

| mAb | corresponding hybridoma | RLB* | RGA# | T-cell proliferation | Peritoniel cells lavage | Mast cell cytokine release** | ST2L epitope |
|---|---|---|---|---|---|---|---|
| CNTO3914 | C1999 | + | + | + | + | + | mD1 |

*Receptor-Ligand binding inhibition
Reporter gene assay
**Bone marrow derived

Example 7

ST2L Domain I Binding Antibody CNTO3914 Inhibits Intranasal IL-33-Induced Airway Hyper-Responsiveness (AHR), Airway Inflammation and Mouse Mast Cell Responses Four consecutive daily intranasal doses of 2 μg/mouse "mature" IL-33 (R&D Systems) (residues 109-266 of SEQ ID NO:215) were administered to female BALB/c mice. Anti-mouse ST2L antibody CNTO3914 was prophylactically dosed subcutaneously at 20 mg/kg (or 2 mg/kg or 0.2 mg/kg) 24 h prior to the first IL-33 intranasal administration. Control mice received isotype control CNTO5516 or PBS, 24 h prior to the first IL-33 intranasal administration. Airway hyper-responsiveness (AHR) to increasing doses of methacholine was measured using forced maneuvers with Flexivent system (Scireq, Montreal, Quebec, Canada). For measurement of airway hyper-responsiveness (AHR), mice were anesthetized with 100 mg/kg pentobarbital and 13 mg/kg phenytoin and tracheostomized before connecting to FlexiVent. The mice were nebulized with saline for baseline readings and then with two doses (10 and 20 mg/mL) of methacholine. For saline and each dose of methacholine, Resistance (R) values were collected for approximately 2 minutes using the "snapshot" perturbation. The peak resistance was calculated using only those values with a COD (coefficient of determination) above 0.9.

A separate group of mice was treated and analyzed for cellular response in the lungs. Twenty-four hours following the last mIL-33 isotype or PBS administration, mice were sacrificed by overdose of Sleepaway® I.P. Lungs of the mice were lavaged with 0.7 mls of cold PBS with 0.1% BSA. Resulting bronchioalveolar (BAL) fluids were centrifuged at 1200 rpm for 10 minutes and the cell-free supernatants were saved at −80° C. until analysis of cytokine/chemokines. The BAL samples were used for total counts using a hemacytometer. For differential BAl counts ~200 cells were counted from cytospin smears after staining with wright giemsa under light microscope.

The cell-free supernatants were collected and stored at −80° C. until used for Luminex protein analyses. The lung tissues were removed, and then perfused through the right ventricle using 5 mls of cold sterile PBS until adequate perfusion. The lung lobes were then placed in a Fast Prep® tube containing 1 ml of PBS+protease inhibitor and frozen and stored at −80° C. for cytokine/chemokine profiling. The cytokine/chemokine multiplex assay was performed following the manufacturer's protocol for the Murine Millipore 22-plex. Mouse mast cell protease-1 (mMCP-1) in the BAL fluid was analyzed by ELISA (Moredun Scientific).

Airway Hyper-Responsiveness

CNTO3914 significantly inhibited airway hyper-responsiveness in the model of lung inflammation induced by intranasally administered IL-33 (FIG. 1). CNTO3914 was dosed subcutaneously 24 hr prior to four daily consecutive intranasal administrations of 2 μg/mouse mIL-33. Peak Airway Resistance as determined by Flexivent was significantly decreased with a dose of CNTO3914 at 20 mg/kg. Each bar represents the mean±SEM of three (CNTO5516, an isotype control antibody) to six mice per group. The results have been repeated in two separate studies. Significance was determined using the Two-Way ANOVA with a Bonferroni post test, CNTO-3914/IL-33 p<0.05 vs. CNTO5516/IL-33; and *p<0.001, vs. PBS with IL-33 treatment group.

Airway Inflammation

Figure 2:
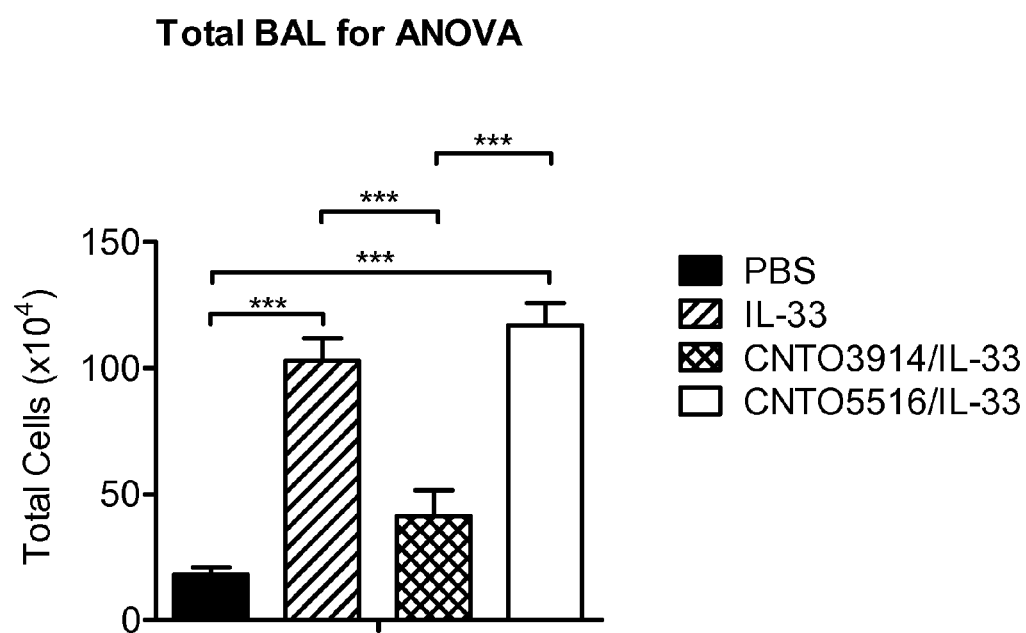
FIG. 2 shows inhibition of Bronchoalveolar Lavage (BAL) cell recruitment by ST2L Domain I binding mAb CNTO3914 in a model of lung inflammation induced by intranasally administered IL-33 when compared to the isotype control CNTO5516. ***p<0.001.

CNTO3914 significantly inhibited Bronchoalveolar Lavage (BAL) cell recruitment in the used model (FIG. 2). CNTO3914 was dosed subcutaneously 24 hr prior to four daily consecutive intranasal administrations of 2 mg/mouse mIL-33. BAL leukocytes were significantly increased with IL-33 administration and were significantly inhibited by CNTO3914 at 20 mg/kg. Each bar represents the mean±SEM of three (CNTO5516, an isotype control antibody) to six mice per group. The results have been repeated in two separate studies. Significance was determined using the Two-Way ANOVA with a Bonferroni post test, ***p<0.001.

Mast Cell Responses In Vivo

Figure 3:
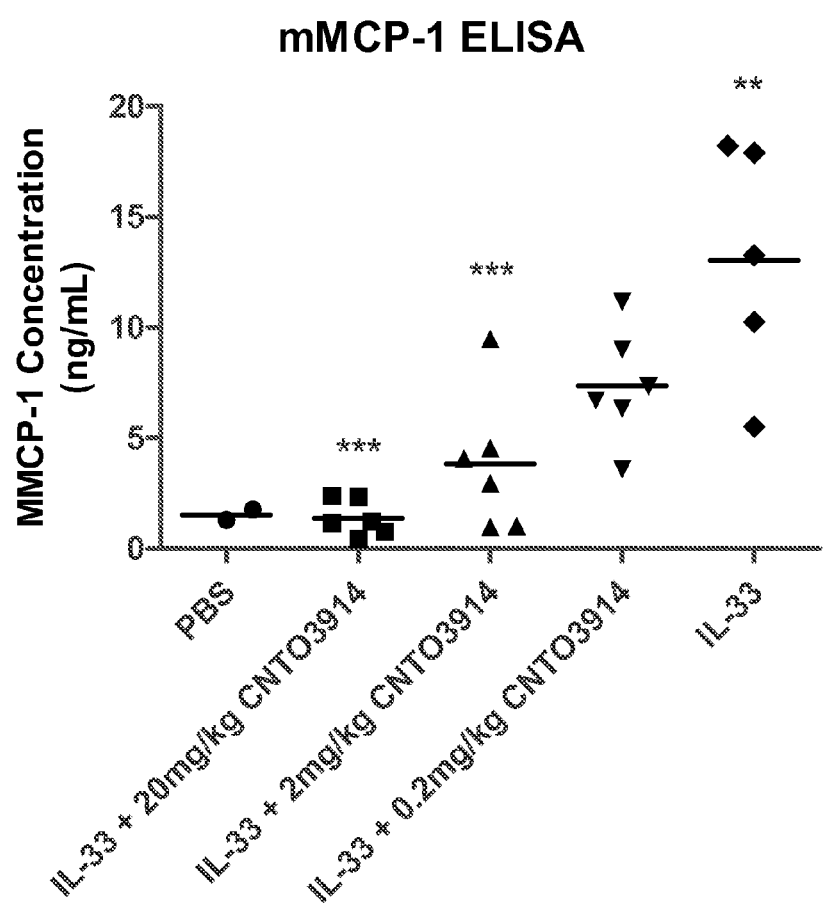
FIG. 3 shows dose-dependent inhibition of release of mouse Mast Cell Protease 1 (MMCP-1) by ST2L Domain I binding mAb CNTO3914 in cell free BAL fluid in a model of lung inflammation induced by intranasally administered IL-33. *p<0.01, ***p<0.001, vs. CNTO5516 (isotype control) with IL-33 treatment.

Mast cells store proteases including tryptases and chymases in their granules, which are released quickly upon mast cell activation. Mouse Mast Cell Protease 1 (mMCP-1) is a β chymase released by activated mast cells and known to be important for control of parasitic worm infections (Knight et al., J Exp Med 192:1849-56, 2000; Huntley et al., Parasite Immunol 12:85-95, 1990). Measurement of mMCP-1 can be used as a marker of mast cell activation, and has been shown to be induced in a mast cell-dependent model of airway inflammation: house dust mite (Yu and Chen, J Immunol 171:3808-15, 2003). MMCP-1 as determined by ELISA (Moredun Scientific) was significantly increased in BAL fluid from IL-33 administered mice, and was dose-dependently inhibited by CNTO3914 (FIG. 3). Significance was determined using the One-Way ANOVA with a Tukey post test, p<0.01, *p<0.001, vs. IL-33 treatment.

Example 8

Anti-ST2L Domain I Binding Antibodies Inhibit Mast Cell Responses In Vitro

Mast cell responses were assessed by release of chemokines and cytokines by mouse and human mast cells as well as prostaglandin $D_2$ in human mast cells.

Figure 4A:
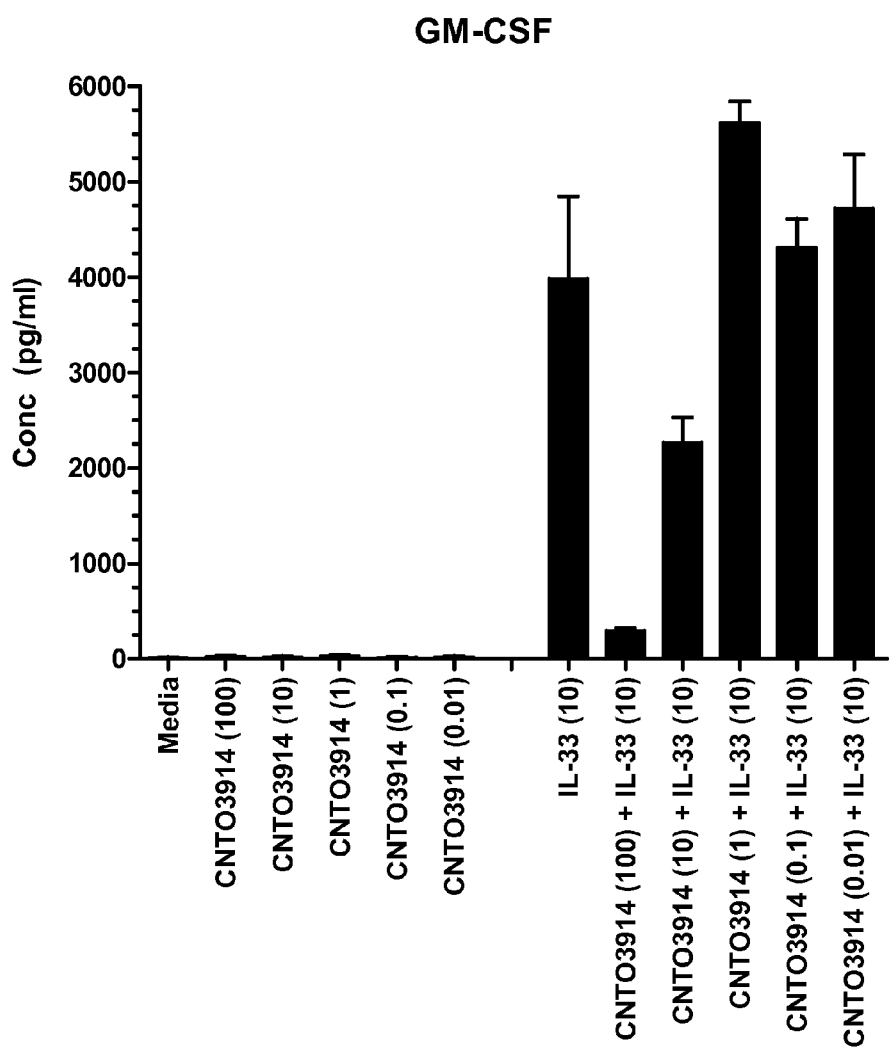
FIG. 4 shows inhibition of IL-33-induced GM-CSF (FIG. 4A), IL-5 (FIG. 4B), and TNFα (FIG. 4C) release by ST2L Domain I binding mAb CNTO3914 by mouse bone marrow-derived mast cells in vitro. The CNTO3914 concentrations used are shown as µg/ml and IL-33 concentrations as ng/ml in parenthesis.
Figure 4B:
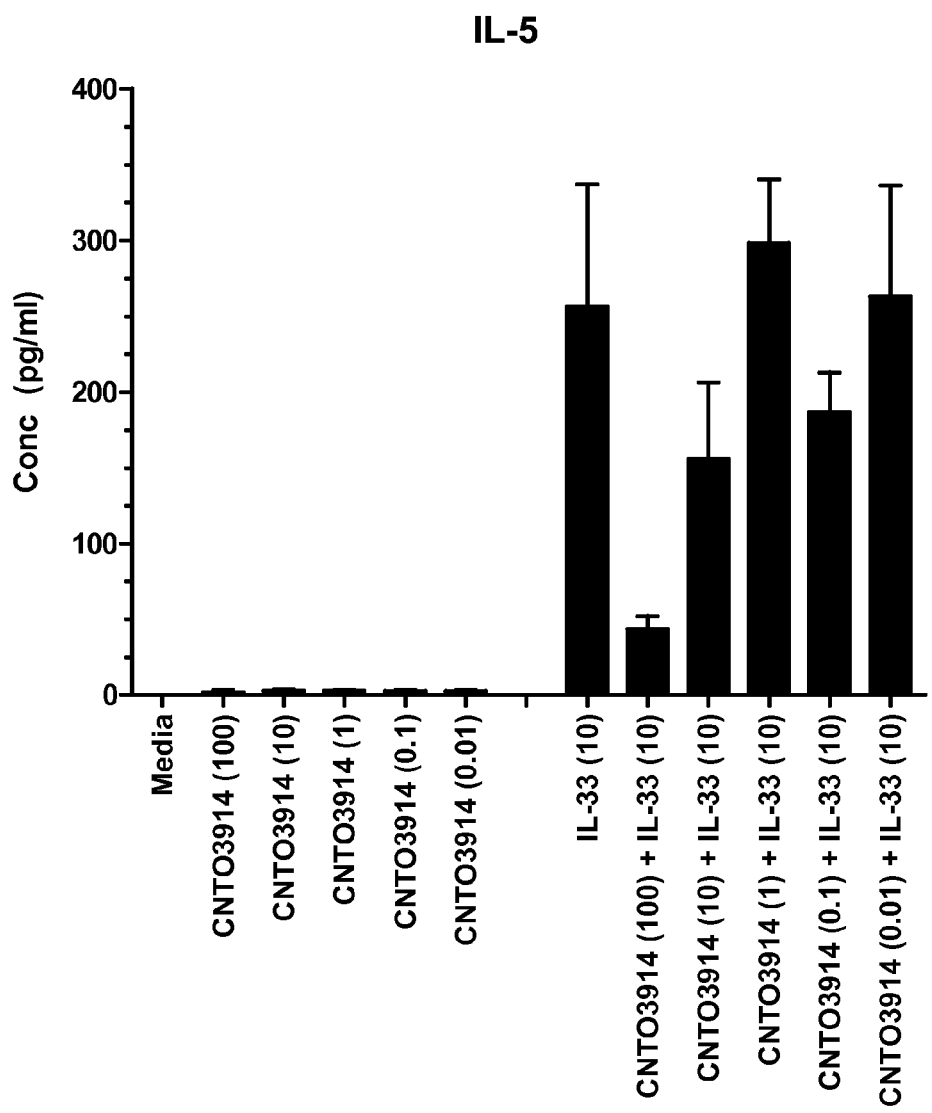
Figure 4C:
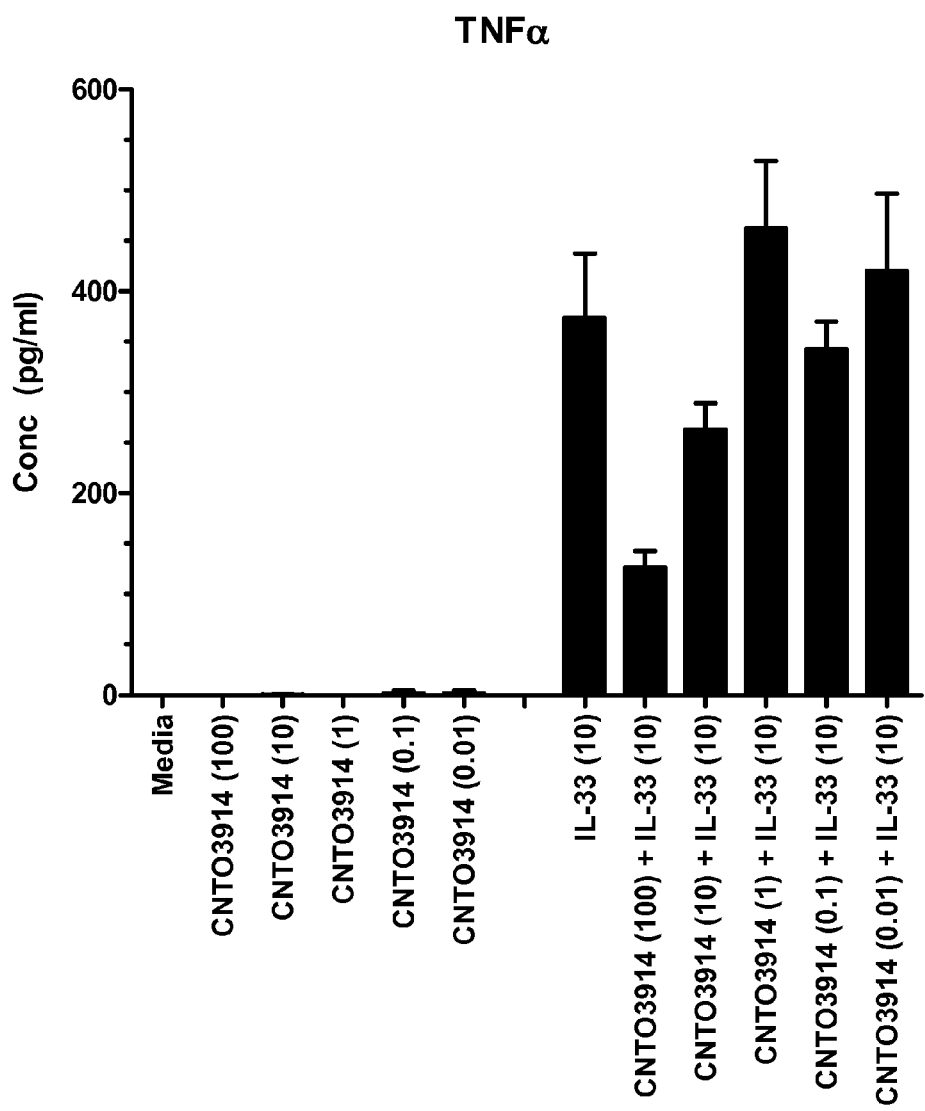

Anti-ST2L Domain I binding antibody CNTO3914 inhibited IL-33-induced cytokine release including GM-CSF (FIG. 4A), IL-5 (FIG. 4B), and TNFα (FIG. 4C) by mouse bone marrow-derived mast cells.

Figure 5:
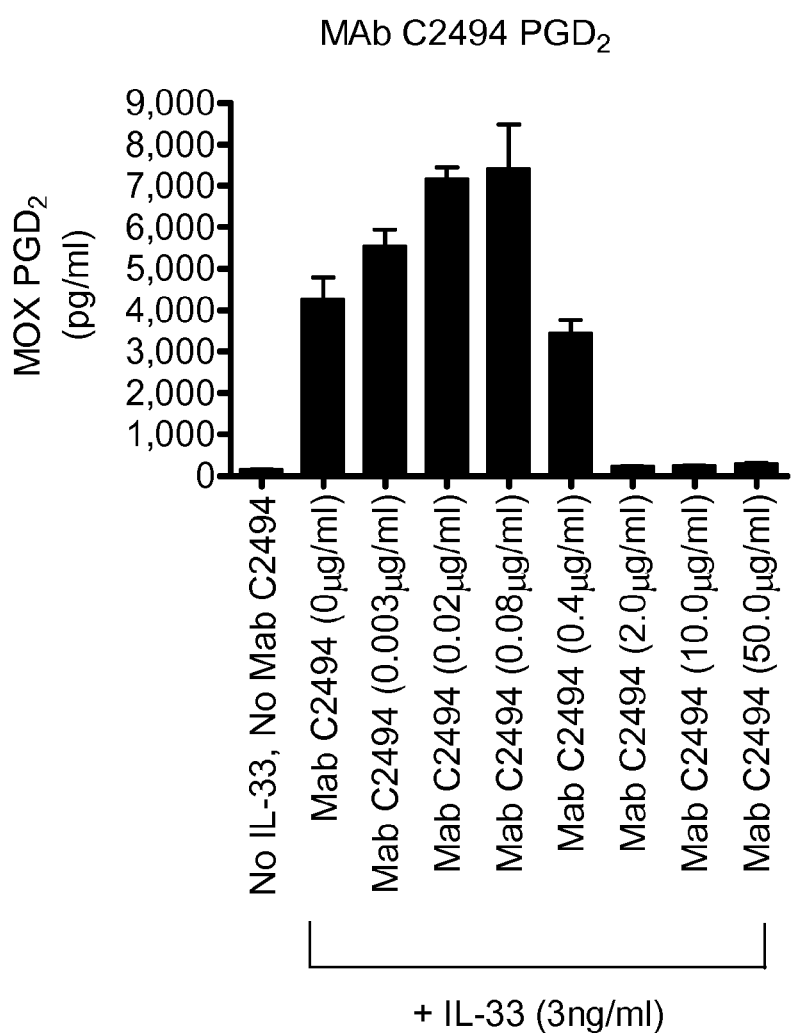
FIG. 5 shows inhibition of IL-33-induced prostaglandin D2 ($PGD_2$) release by human cord blood-derived mast cells by ST2L Domain I binding mAb C2494 (STLM62) at indicated IL-33 and C2494 concentrations. MOX-PDG$_2$: methoxylsamine-PGD$_2$.
Figure 6A:
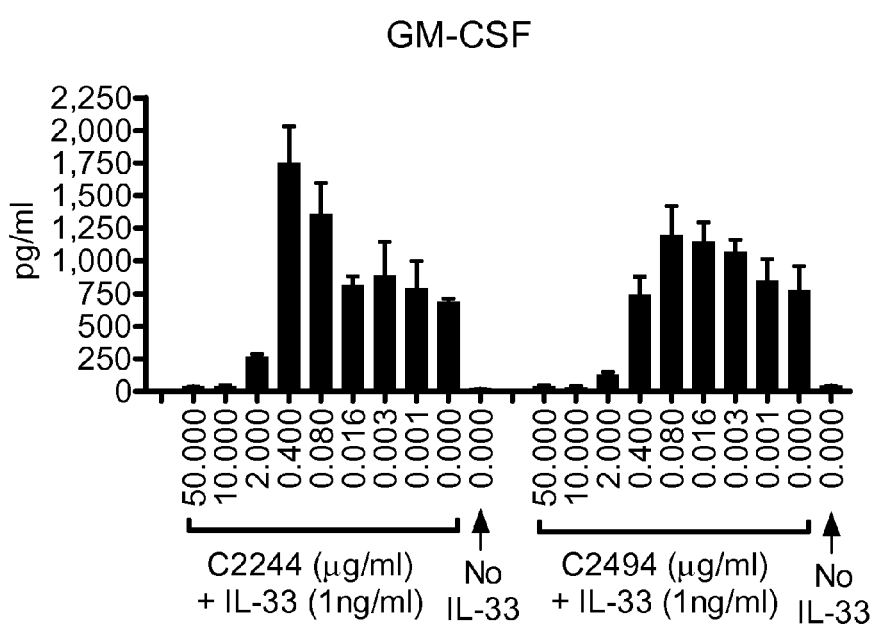
FIG. 6 shows inhibition of A) GM-CSF, B) IL-8, C) IL-5, D) IL-13 and E) IL-10 release by indicated concentrations (μg/ml) of ST2L Domain I binding mAbs C2244 and C2494 in human cord blood derived mast cells (hCBMCs) in the presence of 1 ng/ml IL-33 in StemPro-34 medium+100 ng/ml SCF (stem cell factor).
Figure 6B:
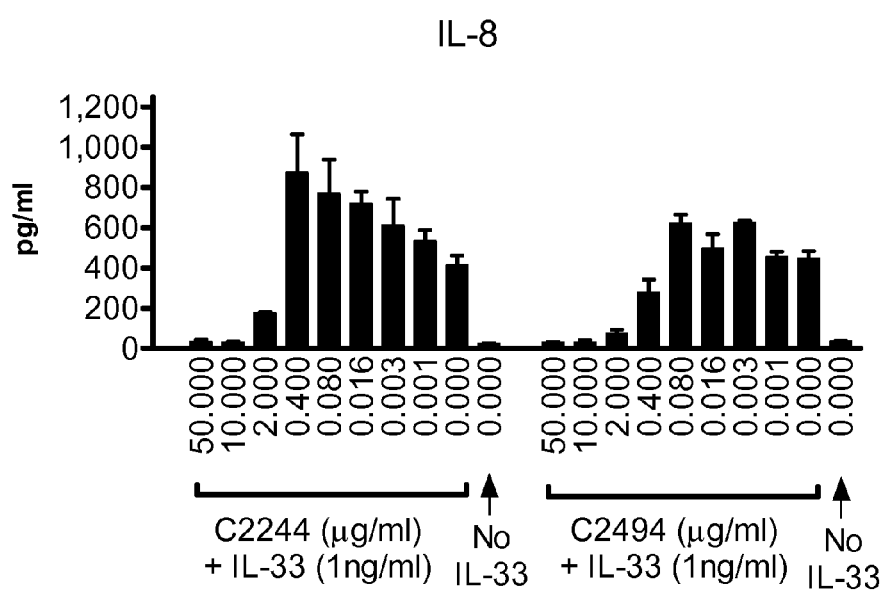
Figure 6C:
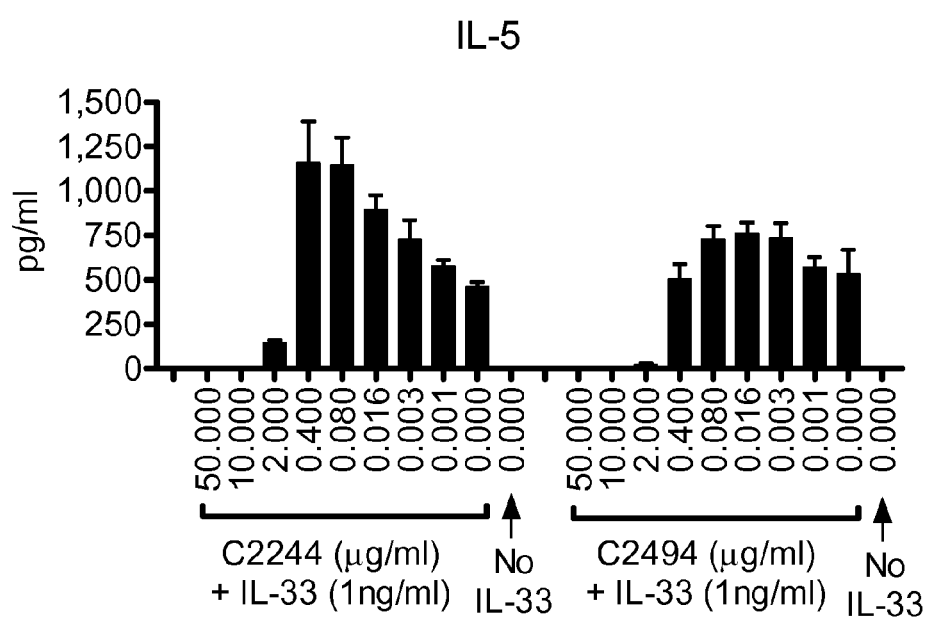
Figure 6D:
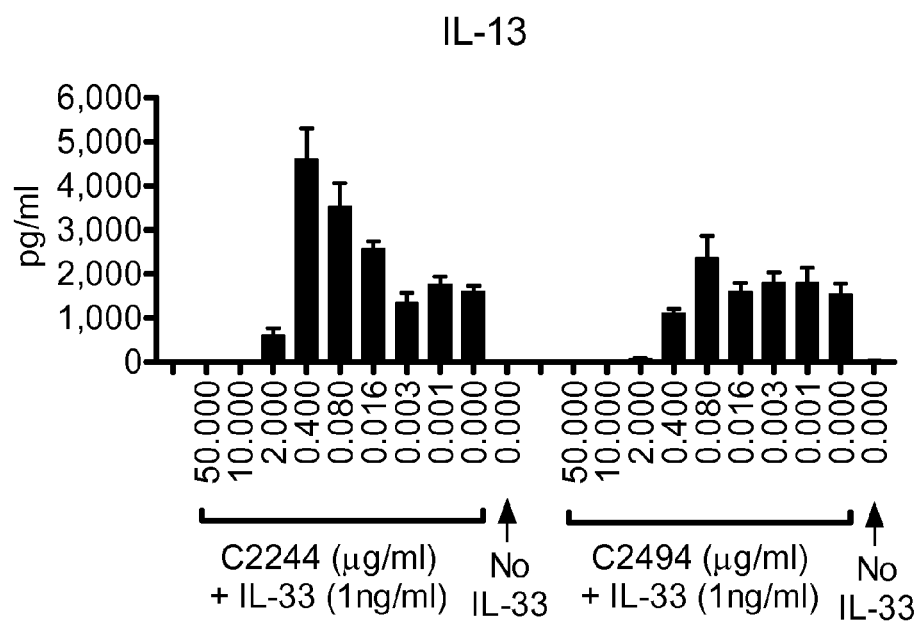
Figure 6E:
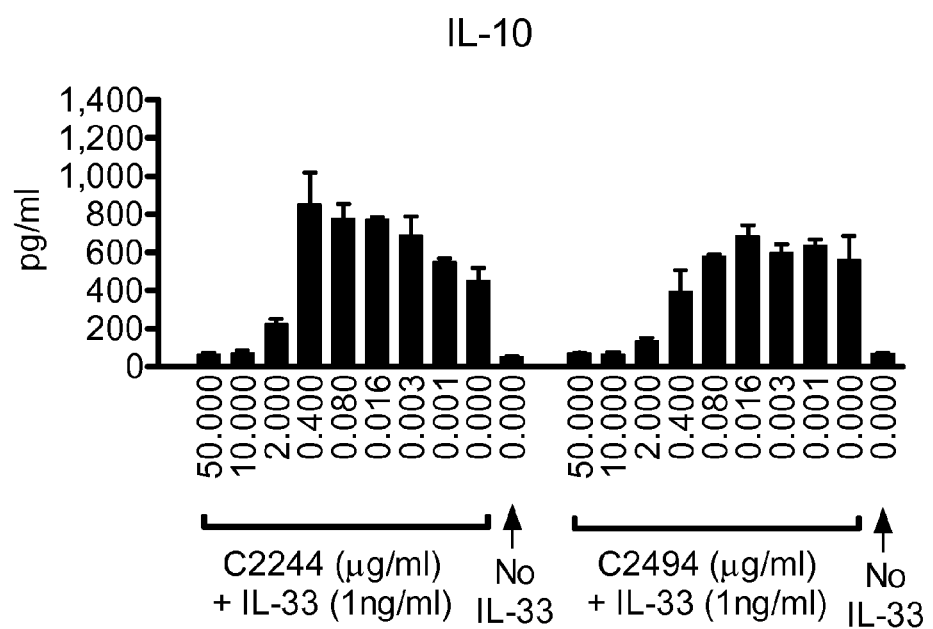
Figure 7A:
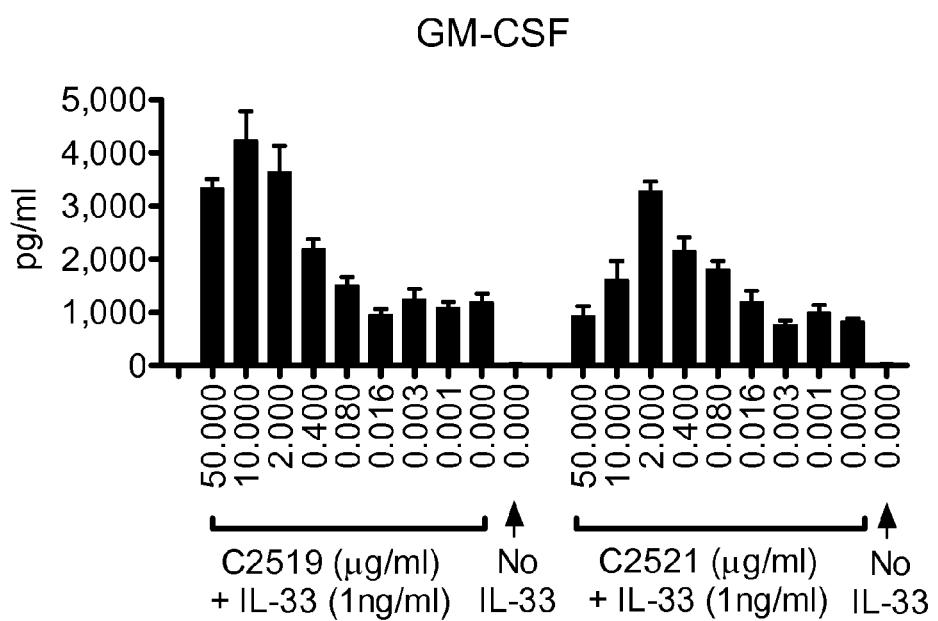
FIG. 7 shows effect on A) GM-CSF, B) IL-8, C) IL-5, D) IL-13 and E) IL-10 release by indicated concentrations (μg/ml) of ST2L Domain III binding mAbs C2519 or C2521 in human cord blood-derived mast cell in the presence of 1 ng/ml IL-33 in StemPro-34 medium+100 ng/ml SCF.
Figure 7B:
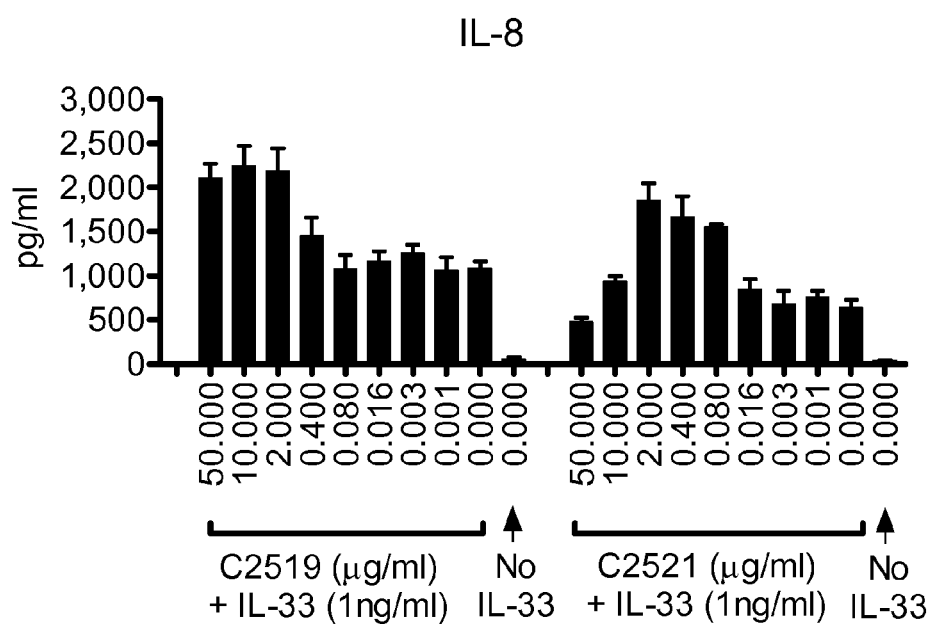
Figure 7C:
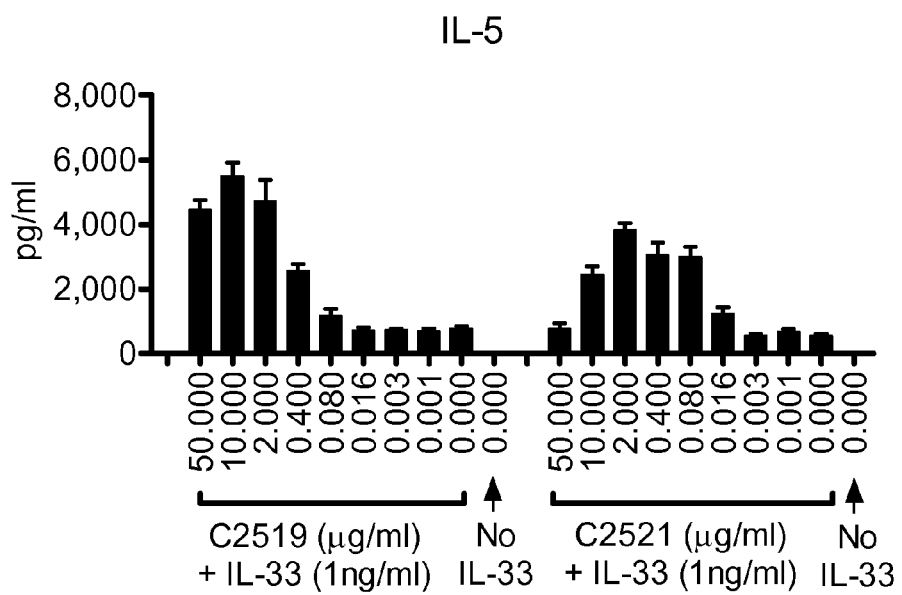
Figure 7D:
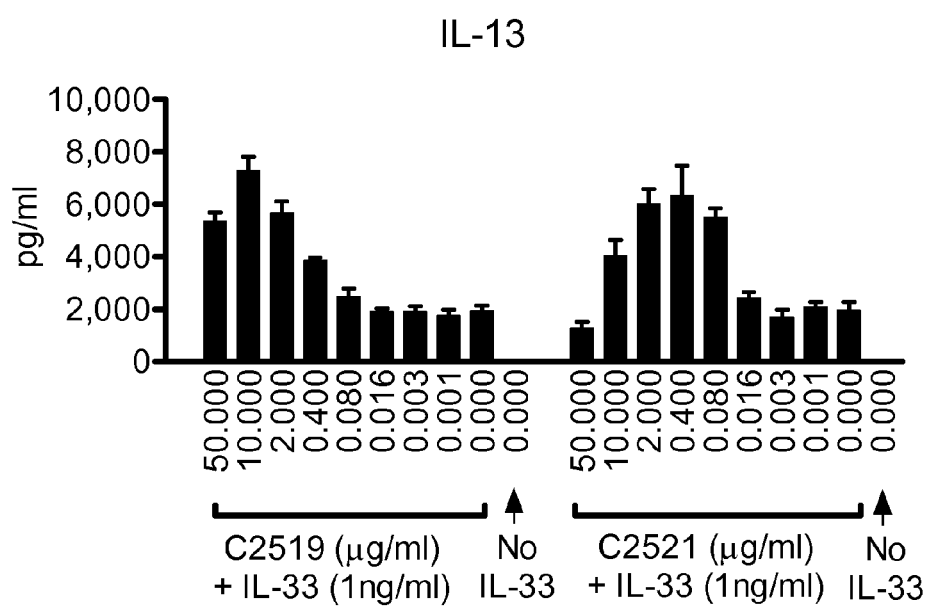
Figure 7E:
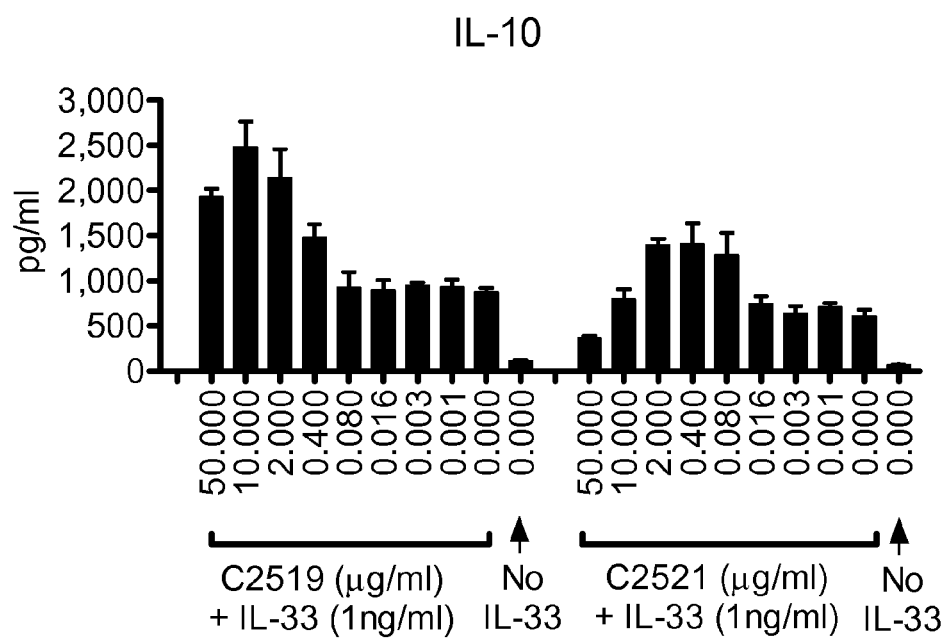
Figure 8A:
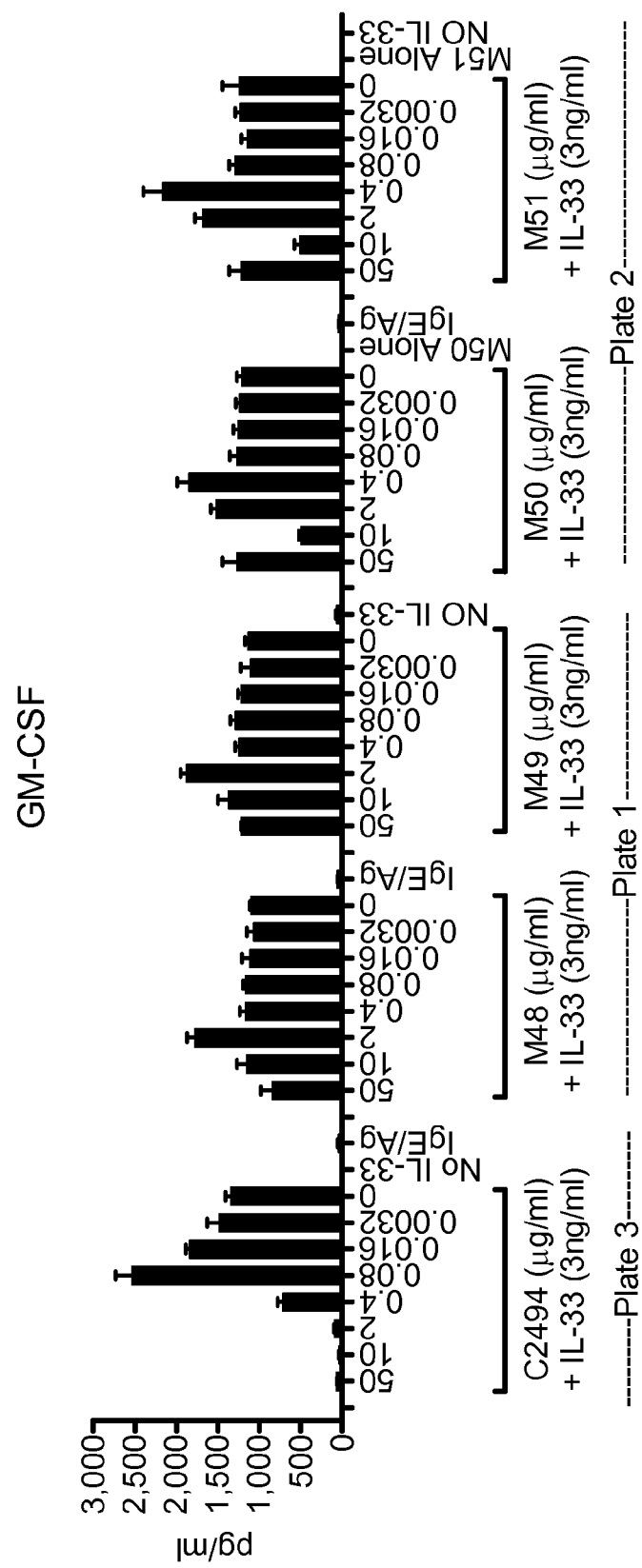
FIG. 8 shows effect on A) GM-CSF; B) IL-8; C) IL-5; D) IL-13 and E) IL-10 release by ST2L Domain I binding mAb C2494 and ST2L Domain III binding mAbs ST2M48 (M48), ST2M49 (M49), ST2M50 (M50), and ST2M51 (M51) in human cord blood-derived mast cells (hCBMCs) in the presence of 3 ng/ml IL-33 in RPMI/10% FCS medium+100 ng/ml SCF.
Figure 8B:
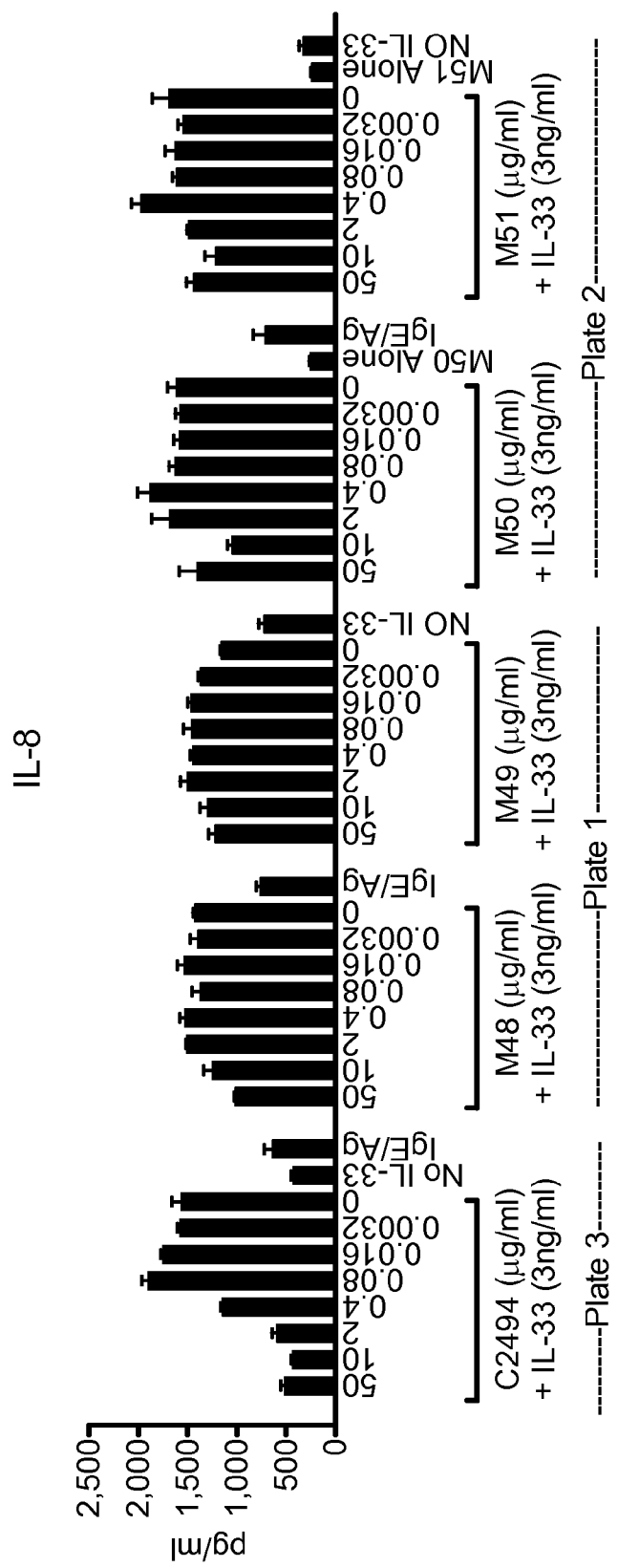
Figure 8C:
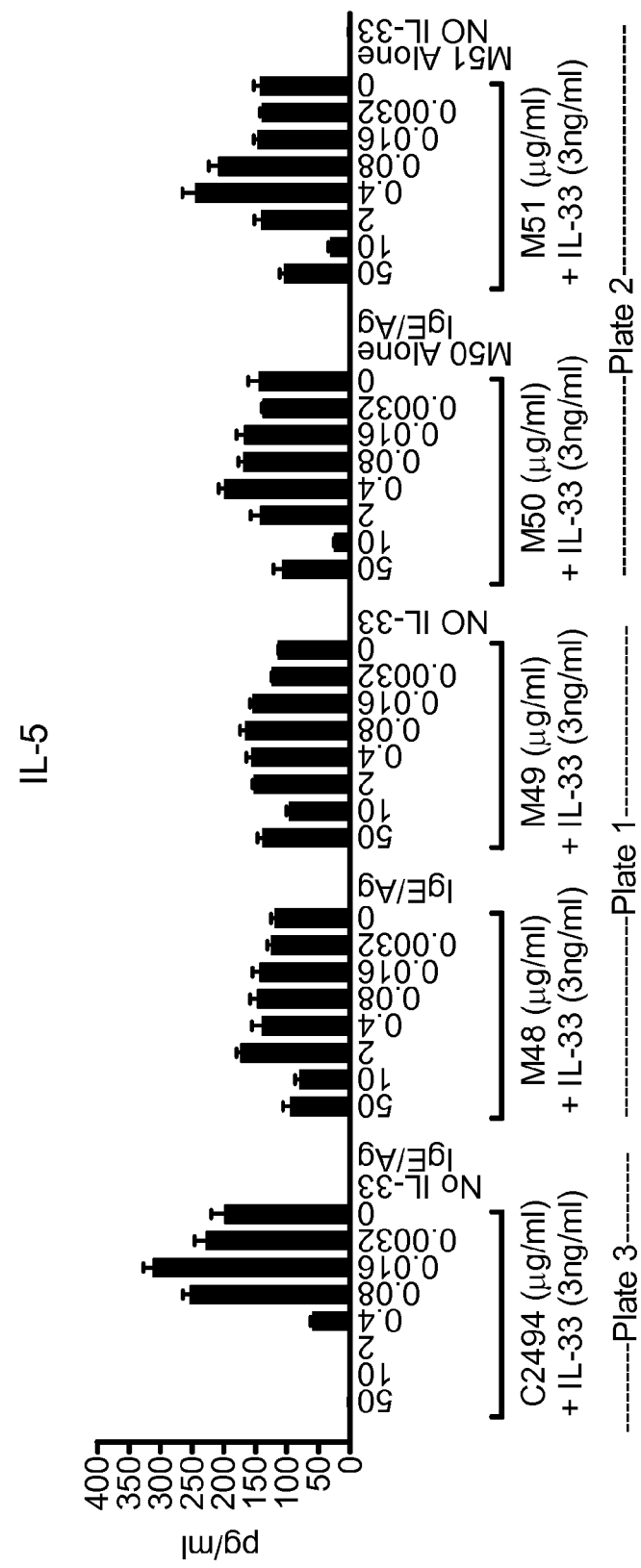
Figure 8D:
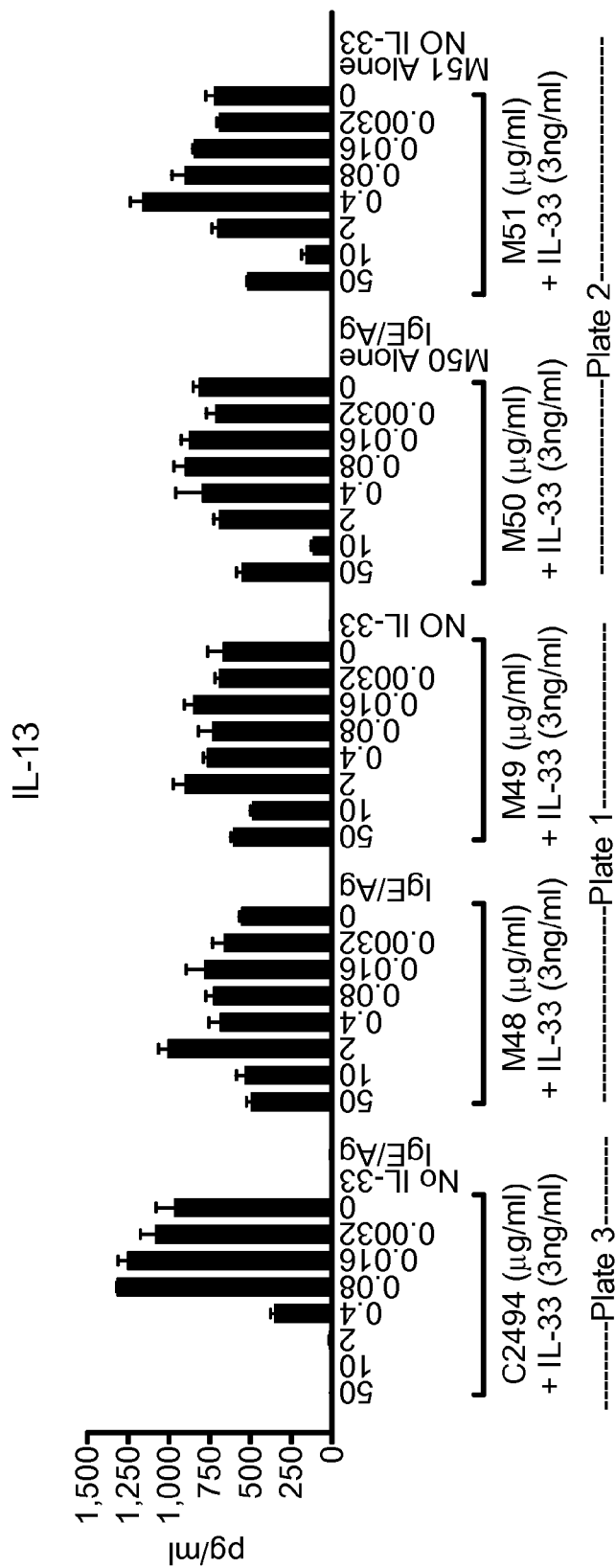
Figure 8E:
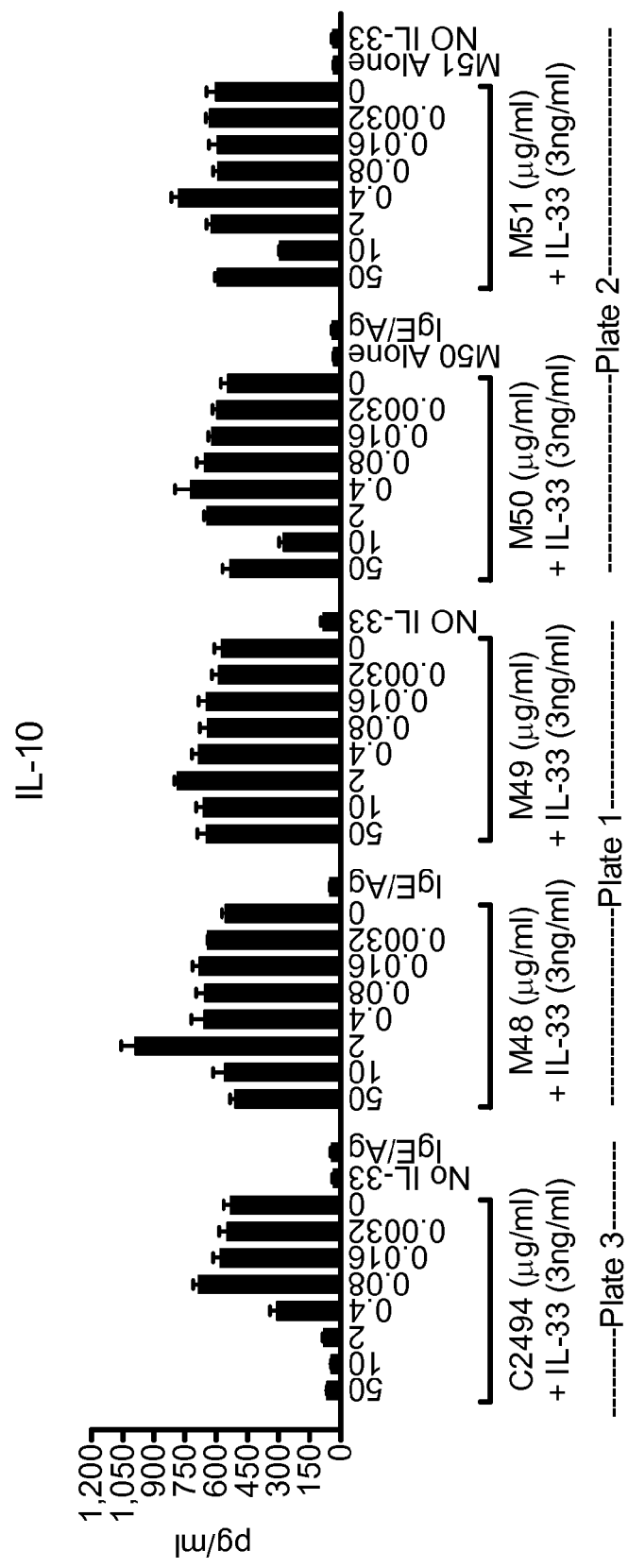

Anti-human ST2L Domain I binding mab C2494 (STLM62) inhibited IL-33-induced $PGD_2$ release by human cord blood-derived mast cells induced by 3 ng/ml IL-33 at antibody concentrations 2, 10 and 50 µg/ml (FIG. 5).

Anti-ST2L Domain I binding antibodies C2494 and C2244 inhibited IL-33-induced GM-CSF, IL-5, IL-8, IL-13 and IL-10 release by human cord blood-derived mast cells at antibody concentrations 50 µg/ml, 10 µg/ml and 2 µg/ml (FIGS. 6 and 8). The degree of inhibition was dependent on cytokine/chemokine measured, the antibody and antibody concentration tested, and media used. Calculated average percent (%) inhibition was between 50.6-100% in all assays conducted at antibody concentration 2 µg/ml, and between 62-100% at antibody concentration of 50 µg/ml (FIG. 9).

Anti-ST2L Domain III-binding antibodies C2521, C2519, ST2M48, ST2M49, ST2M50, and ST2M51 showed modest or no inhibition on, or stimulated IL-33-induced cytokine release by the mast cells (FIGS. 7 and 8) at antibody concentrations 50 µg/ml and 10 µg/ml. The degree of inhibition was dependent on cytokine/chemokine measured, the antibody tested, and media used. Calculated average percent (%) inhibition was between −594.4-31.9% in all assays conducted at antibody concentration 2 µg/ml, and between −481.5-36% at antibody concentration of 50 µg/ml (FIG. 9). In some assays, antibody ST2M50 inhibited GM-CSF, IL-5, IL-10 and IL-13 secretion at antibody concentration 10 µg/ml (FIG. 8).

Average % inhibition was calculated using the following formula: (1−(concentration of cytokine released in the presence of the mAb)/(concentration of the same cytokine released in response to IL-33 in the absence of mAb))×100. Cytokine concentrations are in pg/ml. In some cases, the % inhibition is a negative value, indicating that the cytokine release in the presence of mAb was actually higher than that released in the absence of mAb. Slight variations in the potency of the mAbs may occur depending on the IL-33 concentrations used to induce cytokine release in the mast cells. Similarly, there may be slight variations in the activity of the mAbs depending on the assay medium used (StemPro-34 vs. RPMI/10% FCS). All tested ST2L Domain I binding antibodies inhibited all measured cytokine and chemokine releases at least by 50% as measured by average % inhibition at a concentration of 2 µg/ml, 10 µg/ml or 50 µg/ml.

Example 9

ST2L Domain I Binding Antibodies Inhibit Intranasal IL-33-Induced Airway Remodeling C57BL/6 mice were dose intranasally with 1 µg/mouse "mature" IL-33 (or PBS) (residues 109-266 of SEQ ID NO: 215) on days D1, D3, D5, D7, and D9 and lungs were analyzed on Day 10 or Day 20. Anti-mouse ST2L antibody CNTO3914 or isotype control (CNTO5516) was dosed subcutaneously at 2 mg/kg 6 h prior to the first IL-33 intranasal administration. Control mice received isotype control CNTO5516 or PBS, 6 h prior to the first IL-33 intranasal administration. Inflated lungs were fixed in 10% buffered formalin for histology; stains used for analysis included H&E, Masson Trichrome and PAS.

IL-33 treatment induced moderate to marked bronchiolar epithelial hypertrophy and hyperplasia with goblet cell hyperplasia and peribronchiolar infiltrates mixed mainly with eosinophils. Bronchiolar epithelial hypertrophy and hyperplasia were not evident in the animals receiving CNTO3914. The Masson Trichome stains were to determine the amount of collagen present; this staining revealed goblet cell hypertrophy in IL-33 treated animals. In the animals treated with CNTO3914 infiltrates in the alveoli and peribonchiolar regions were absent.

Example 10

Generation of Fully Human ST2L-Antibodies

Additional human ST2L-binding Fabs were selected from de novo pIX phage display libraries essentially as described in Example 3 except that the libraries were panned using chimeric HHM-ST2L construct (SEQ ID NO: 6, Table 1) with the biotinylated antigen captured on streptavidin-coated magnetic beads. The phage library was blocked in PBS-T with 3% non-fat dry milk. Competitor protein, MHM-ST2L chimera (SEQ ID NO: 7, Table 1) was added to the blocking solution to drive the phage selection towards Fabs that would bind specifically to the human ST2L Domain I amino acid sequences. Phage selections were performed for three rounds followed by screening by ELISA for Fab binding to hST2L-Fc protein.

Nineteen Fabs with binding to hST2L-Fc were isolated from these selections and were further screened for binding to chimeric ST2L constructs (Table 1) as well as to the mouseST2L and humanST2L proteins to map the domain of specificity, and characterized for their ability to block IL-33/hST2L interaction. Fabs ST2F1, ST2F4 and ST2F6 blocked hIL-33/ST2L interaction and bound Domain I of ST2L and were moved forward into affinity maturation.

Fabs using ProteOn and demonstrated modest affinity improvements from 2 nM to 400 pM.

To further improve affinity of ST2F14, ST2F17, ST2F31 and ST2F41, the common heavy chain ST2H41 in ST2F14, ST2F17, ST2F31 and ST2F41 was randomized at HCDR1

TABLE 9

| Fab ID | VH ID | Framework | HCDR1 Sequence | SEQ ID NO: | HCDR2 Sequence | SEQ ID NO: | HCDR3 Sequence | SEQ ID NO: |
|---|---|---|---|---|---|---|---|---|
| ST2F6 | ST2H41 | VH3-23 | SYAMS | 78 | AISGSGGSTYYADSVKG | 81 | DPWSTEGSFFVLDY | 84 |
| ST2F4 | ST2H39 | VH3-23 | SYWMH | 79 | GISSGGGSTYYADSVKG | 82 | DGWGTVYFPFDY | 85 |
| ST2F1 | ST2H35 | VH5-51 | SYWIG | 80 | IIYPGDSDTRYSPSFQG | 83 | DTADFRRWDFDY | 86 |

| Fab ID | VL ID | Framework | LCDR1 Sequence | SEQ ID NO: | LCDR2 Sequence | SEQ ID NO: | LCDR3 Sequence | SEQ ID NO: |
|---|---|---|---|---|---|---|---|---|
| ST2F6 | ST2L24 | Vk-L6 | RASQSVDDALA | 87 | DASNRAT | 90 | QQFYNWPLT | 92 |
| ST2F4 | ST2L23 | Vk-L6 | RASQSVRDDLA | 88 | DASNRAT | 90 | QQYIHAPLT | 93 |
| ST2F1 | ST2L20 | Vk-B3 | KSSQSVLYSSNNKNYLA | 89 | WASTRES | 91 | QQSNTYPFT | 94 |

Example 11

Affinity-Maturation of Human ST2L Binding Fabs

ST2F1, ST2F4 and ST2F6 were affinity-matured using an "in-line" maturation process described in Shi et al., j Mol Biol 397:385-396, 2010 and Int. Pat. Publ. No. WO2009/085462 and Example 4. Affinity maturation libraries were made for ST2F1, ST2F4 and ST2F6 by diversifying corresponding light chain libraries, B3, L6 and L6, respectively, and combining the libraries with the Fab VH regions. The diversification scheme for light chain residues for the L6 and B3 affinity maturation libraries are shown in Table 10. Position numbering is according to Kabat. For affinity maturation panning, biotinylated huST2-ECD-Fc was captured on streptavidin (SA)-coated magnetic beads at concentrations of 10 nM for round 1, 1 nM for round 2, and 0.1 nM for round 3. The final wash of round 3 was performed overnight at room temperature in the presence of 10 nM unlabelled huST2L-ECD-Fc.

TABLE 10

|  |  | Scaffold | |
|---|---|---|---|
| Loop | Position | L6 | B3 |
| L1 | 30 | SRNAD | RNDGHSY |
|  | 30a | — | RNDGHWY |
|  | 30e | — | RNDGHSY |
|  | 31 | NSKD | RNDGHWY |
|  | 32 | YWDFHSAN | YNWR |
| L2 | 50 | ADKGYFTN | YWNK |
| L3 | 91 | RYSGF | SYWH |
|  | 92 | RHNSL | SYGN |
|  | 93 | NDKR | STER |
|  | 94 | WA | WYSH |
|  | 96 | WYFLIR | YRWH |

The ST2F6 light chain maturation library selections yielded improved binders (ST2F14, ST2F17, ST2F31 and ST2F41) (FIG. 10 and FIG. 11). These were examined as and HCDR2 Kabat positions 31, 32, 33, 35, 50, 52, 53, 56 and 58 using a diversification scheme shown in Table 11. The resulting heavy chain library was paired with the four affinity improved light chains ST2L32, ST2L35, ST2L49 and ST2L59, and this library was panned and screened as described for the light chain maturation libraries. Fabs with improved binding relative to ST2F14 were isolated and converted to IgG for further characterization. The resulting antibodies (STLM103, STLM107, STLM108, STLM123, STLM124, STLM206, STLM207, STLM208, STLM209, STLM210, STLM211, STLM212, STLM213, STLM214, STLM215, STLM216, STLM217, STLM218, STLM219, STLM220, STLM221, STLM222) (FIG. 10 and FIG. 11) have frameworks derived from VH3-23 or Vκ-L6. All antibodies bind ST2L Domain I and block IL-33/ST2L interaction.

TABLE 11

| Position | Amino Acids |
|---|---|
| 31 | SDNTAY |
| 32 | SDAY |
| 33 | SDAY |
| 35 | SN |
| 50 | SDNTAY |
| 52 | SANTKDEGR |
| 53 | SANEY |
| 56 | SANTKDEGR |
| 58 | SDNTAY |

Additional variants were designed and expressed for STLM208 VH ST2L257 to replace a DP motif at the beginning of HCDR3. The sequences of the variants are shown in FIG. 12.

Example 12

Human Framework Adaptation (HFA) of C2494

The framework adaptation process was done as essentially described in U.S. Pat. Publ. No. US2009/0118127 and Fransson et al., J Mol Biol 398:214-231, 2010. Briefly, the heavy and light chain sequences were compared with the human germline sequences (only the "01" alleles as of Oct. 1, 2007) using BLAST search against the IMGT database (Kaas, et al., Nucl. Acids. Res. 32, D208-D210, 2004; Lefranc et al., Nucl. Acid Res., 33, D593-D597, 2005). From this set of human germline genes, redundant genes (100% identical at amino acid level) and those with unpaired cysteine residues were removed. The remaining closest matching human germline genes in both the framework and CDR regions were chosen as the acceptor human frameworks. A total of 9 VL and 7 VH germline human frameworks were selected based upon overall sequence homology and CDR lengths as well as CDR similarity. FR-4 was selected based on sequence similarity of the IGHJ/IGJK germline genes, JK2 for the VL chains and JH1 for the VH chains (Kaas, et al., Nucl. Acid Res. 32, D208-D210, 2004; Lefranc M.-P et al., Nucl. Acid Res., 33, D593-D597, 2005) with C2494 sequence). Then, the CDRs of C2494 (underlined in FIG. 14) were transferred into the selected acceptor human frameworks to generate the HFA variants, except in the region corresponding to the CDR-H1 of $V_H$. For this region a combination of CDR and HV, or a shorter HCDR2 (referred to as Kabat-7, see U.S. Pat. Publ. No. US2009/0118127) were transferred from the non-human antibody into the human FRs because the HCDR2 residues highlighted in grey in FIG. 14 have not been found in contact in antigen-antibody complexes of known structures (Almagro, J Mol Recognit. 17, 132, 2004).

The mature protein sequence of C2494 (VL: SEQ ID NO:52; VH: SEQ ID NO: 48) is shown FIG. 14. In the figure, CDR residues (Kabat) are underlined, Chothia HV loops indicated below CDRs, and residues transferred into selected human frameworks indicated under HVs (HFA). HCDR2 residues highlighted in grey were not transferred in all variants.

A 3D homology model for the Fv fragment of C2494 was constructed using the antibody modeling module of MOE (CCG, Montreal). The model was utilized for evaluation of developability liabilities such as exposed methionine and tryptophan residues, potential N-glycosylation and deamidation motifs. In LCDR3, there is a potentially exposed Met (M94) residue, based upon the Fv structural model. To remove it, a variant (STLL280, O12b) with an M94L mutation was generated and characterized. For the heavy chain, the R residue in the CAR motif (Chothia residues 92-94, FIG. 14) just before HCDR3 may negatively impact a cluster of negatively charged residues (Chothia residues D31, D32, D96 and D101a, FIG. 14), which may be important for binding. A VH with substitution of arginine for leucine at Chothia residues 94 (CAR→CAL) was generated and characterized.

The mAbs combining designed heavy and light chains, together with the C2494 parents were expressed and assayed for binding to human ST2L. From the generated HFA mAbs, mAbs with VH chains having IGHV1-24*01 (SEQ ID NO: 148) and IGHV1-f*01 (SEQ ID NO: 149) heavy chain frameworks (STLH195 and STLH194) expressed antibodies well and bound ST2L when combined with various HFA light chains having IGKV3-15*01 (L2) (SEQ ID NO: 150), IGKV1-9*01 (L8) (SEQ ID NO: 151), IGKV1-5*01 (L12) (SEQ ID NO: 152), IGKV1-12*01 (L5) (SEQ ID NO: 153), IGKV1-39*01 (012) (SEQ ID NO: 154), IGKV1-27*01 (A20) (SEQ ID NO: 155) or IGKV1-33*01 (018) (SEQ ID NO: 156) frameworks (STLL280, STLL278, STLL277, STLL276, STLL275, STLL274, STLL273, STLL272).

Sequences of HFA VH and VL variants are shown in Table 12. Transferred residues are underlined, and additional substitutions described above highlighted in grey. Table 13 shows SEQ ID NOs: as well as unique pDR (plasmid) and CBIS ID for each HFA VH and VL. Heavy and light chain combination for generated mAbs selected for further characterization is shown in Table 14.

Table 15 shows the human frameworks (combined V and J regions) used to transfer C2494 CDRs.

TABLE 12

Framework adapted VL chains (coupled to JK2 sequence).
CDRs are underlined.

```
>VL2494 (parent) (SEQ ID NO: 52)
ETTVTQSPASLSVATGEKVTIRCITNTDIDDVIHWYQQKPGEPPKLLISEGNTLRP
GVPSRFSSSGYGTDFVFTIENTLSEDVADYYCLQSDNMLTFGAGTKLELK
>VL2494-IGKV1-33*01 O18 (SEQ ID NO: 135)
DIQMTQSPSSLSASVGDRVTITCITNTDIDDVIHWYQQKPGKAPKLLIYEGNTLRP
GVPSRFSGSGSGTDFTFTISSLQPEDIATYYCLQSDNMLTFGQGTKLEIK
>VL2494-IGKV1-27*01 A20 (SEQ ID NO: 136)
DIQMTQSPSSLSASVGDRVTITCITNTDIDDVIHWYQQKPGKVPKLLIYEGNTLRP
GVPSRFSGSGSGTDFTLTISSLQPEDVATYYCLQSDNMLTFGQGTKLEIK
>VL2494-IGKV1-39*01O12 (SEQ ID NO: 137)
DIQMTQSPSSLSASVGDRVTITCITNTDIDDVIHWYQQKPGKAPKLLIYEGNTLRP
GVPSRFSGSGSGTDFTLTISSLQPEDFATYYCLQSDNMLTFGQGTKLEIK
>VL2494-IGKV1-12*01 L5 (SEQ ID NO: 138)
DIQMTQSPSSVSASVGDRVTITCITNTDIDDVIHWYQQKPGKAPKLLIYEGNTLRP
GVPSRFSGSGSGTDFTLTISSLQPEDFATYYCLQSDNMLTFGQGTKLEIK
>VL2494-IGKV1-5*01 L12 (SEQ ID NO: 139)
DIQMTQSPSTLSASVGDRVTITCITNTDIDDVIHWYQQKPGKAPKLLIYEGNTLRP
GVPSRFSGSGSGTEFTLTISSLQPDDFATYYCLQSDNMLTFGQGTKLEIK
>VL2494-IGKV1-9*01 L8 (SEQ ID NO: 140)
DIQLTQSPSFLSASVGDRVTITCITNTDIDDVIHWYQQKPGKAPKLLIYEGNTLRP
GVPSRFSGSGSGTEFTLTISSLQPEDFATYYCLQSDNMLTFGQGTKLEIK
>VL2494-IGKV3-15*01 L2 (SEQ ID NO: 141)
EIVMTQSPATLSVSPGERATLSCITNTDIDDVIHWYQQKPGQAPRLLIYEGNTLRP
GVPSRFSGSGSGTEFTLTISSLQSEDFAVYYCLQSDNMLTFGQGTKLEIK
```

TABLE 12-continued

>VL2494-IGKV1-39*01 O12b (SEQ ID NO: 142)
DIQMTQSPSSLSASVGDRVTITC ITNTDIDDVIH WYQQKPGKAPKLLIY EGNTLRP
GVPSRFSGSGSGTDFTLTISSLQPEDFATYYC LQSDNLLT FGQGTKLEIK

Framework adapted VH chains coupled to JH1

>VH2494 (parent) (SEQ ID NO: 48)
EVQLQQSVAELVRPGASVKLSCTAS AFNIKDDYMH WVKQRPEQGLEWIG RIDPAIGNTE YAPKFQD
KATMTADTSSNTAYLQLSSLTSEDTAVYYCAL GDFYAMDY WGQGTSVTVSS >VH2494-IGHV1-f*01 (SEQ ID NO: 143)
EVQLVQSGAEVKKPGATVKISCKVS AFNIKDDYMH WVQQAPGKGLEWMG RIDPAIGNTE YAEKFQG
RVTITADTSTDTAYMELSSLRSEDTAVYYCAT GDFYAMDY WGQGTLVTVSS >VH2494-IGHV1-24*01 (SEQ ID NO: 144)
QVQLVQSGAEVKKPGATVKISCKVS AFNIKDDYMH WVQQAPGKGLEWMG RIDPAIGNTE YAPKFQD
RVTMTEDTSTDTAYMELSSLRSEDTAVYYCAT GDFYAMDY WGQGTLVTVSS

TABLE 13

| | HFA-variant | pDR# | CBIS ID | SEQ ID NO: |
|---|---|---|---|---|
| VH HFA chains | >VH2494-IGHV1-24*01 | 9870 | STLH195 | 144 |
| | >VH2494-IGHV1-f*01 | 9871 | STLH194 | 143 |
| VL HFA chains | >VL2494-IGKV1-39*01 O12b | 9865 | STLL280 | 142 |
| | >VL2494-IGKV3-15*01 L2 | 9873 | STLL278 | 141 |
| | >VL2494-IGKV1-9*01 L8 | 9874 | STLL277 | 140 |
| | >VL2494-IGKV1-5*01 L12 | 9875 | STLL276 | 139 |
| | >VL2494-IGKV1-12*01 L5 | 9876 | STLL275 | 138 |
| | >VL2494-IGKV1-39*01 O12 | 9877 | STLL274 | 137 |
| | >VL2494-IGKV1-27*01 A20 | 9878 | STLL273 | 136 |
| | >VL2494-IGKV1-33*01 O18 | 9879 | STLL272 | 135 |

TABLE 14

| | | VH chains | | |
|---|---|---|---|---|
| VL chains | pRD# | Parent* pDR4211 | >VH2494-IGHV1-24*01 pDR9870 | >VH2494-IGHV1-f*01 pDR9871 |
| Parent* | pDR4212 | STLM126 | STLM186 | STLM196 |
| >VL2494-IGKV1-39*01 O12b | pDR9865 | STLM127 | STLM187 | STLM197 |
| >VL2494-IGKV3-15*01 L2 | pDR9873 | STLM129 | STLM189 | STLM199 |
| >VL2494-IGKV1-9*01 L8 | pDR9874 | STLM130 | STLM190 | STLM200 |
| >VL2494-IGKV1-5*01 L12 | pDR9875 | STLM131 | STLM191 | STLM201 |
| >VL2494-IGKV1-12*01 L5 | pDR9876 | STLM132 | STLM192 | STLM202 |
| >VL2494-IGKV1-39*01 O12 | pDR9877 | STLM133 | STLM193 | STLM203 |
| >VL2494-IGKV1-27*01 A20 | pDR9878 | STLM134 | STLM194 | STLM204 |
| >VL2494-IGKV1-33*01 O18 | pDR9879 | STLM135 | STLM195 | STLM205 |

*Parent = C2494 VH and VL

TABLE 15

| Frameworks used for Human Framework Adaptation (HFA) | | | |
|---|---|---|---|
| Framework V region origin | Framework J region origin | Sequence | SEQ ID NO: |
| IGHV1-24*01 | JH1 | QVQLVQSGAEVKKPGASVKVSCKVSGYTLTELSMHWVRQAPGKGLEWMGGFDPE DGETIYAQKFQGRVTMTEDTSTDTAYMELSSLRSEDTAVYYCATWGQGTLVTVSS | 148 |

TABLE 15 -continued

Frameworks used for Human Framework Adaptation (HFA)

| Framework V region origin | Framework J region origin | Sequence | SEQ ID NO: |
|---|---|---|---|
| IGHV1-f*01 | JH1 | EVQLVQSGAEVKKPGATVKISCKVSGYTFTDYYMHWVQQAPGKGLEWMGLVDPED GETIYAEKFQGRVTITADTSTDTAYMELSSLRSEDTAVYYCATWGQGTLVTVSS | 149 |
| IGKV3-15*01 L2 | JK2 | EIVMTQSPATLSVSPGERATLSCRASQSVSSNLAWYQQKPGQAPRLLIYGASTRATGI PARFSGSGSGTEFTLTISSLQSEDFAVYYCQQYNNWPTFGQGTKLEIK | 150 |
| IGKV1-9*01 L8 | JK2 | DIQLTQSPSFLSASVGDRVTITCRASQGISSYLAWYQQKPGKAPKLLIYAASTLQSGV PSRFSGSGSGTEFTLTISSLQPEDFATYYCQQLNSYPTFGQGTKLEIK | 151 |
| IGKV1-5*01 L12 | JK2 | DIQMTQSPSTLSASVGDRVTITCRASQSISSWLAWYQQKPGKAPKLLIYDASSLESGV PSRFSGSGSGTEFTLTISSLQPDDFATYYCQQYNSYSTFGQGTKLEIK | 152 |
| IGKV1-12*01 L5 | JK2 | DIQMTQSPSSVSASVGDRVTITCRASQGISSWLAWYQQKPGKAPKLLIYAASSLQSG VPSRFSGSGSGTDFTLTISSLQPEDFATYYCQQANSFPTFGQGTKLEIK | 153 |
| IGKV1-39*01 O12 | JK2 | DIQMTQSPSSLSASVGDRVTITCRASQSISSYLNWYQQKPGKAPKLLIYAASSLQSGV PSRFSGSGSGTDFTLTISSLQPEDFATYYCQQSYSTPTFGQGTKLEIK | 154 |
| IGKV1-27*01 A20 | JK2 | DIQMTQSPSSLSASVGDRVTITCRASQGISNYLAWYQQKPGKVPKLLIYAASTLQSGV PSRFSGSGSGTDFTLTISSLQPEDVATYYCQKYNSAPTFGQGTKLEIK | 155 |
| IGKV1-33*01 O18 | JK2 | DIQMTQSPSSLSASVGDRVTITCQASQDISNYLNWYQQKPGKAPKLLIYDASNLETGV PSRFSGSGSGTDFTFTISSLQPEDIATYYCQQYDNLPTFGQGTKLEIK | 156 |

Example 13

Design of Alanine and Human Germline Mutants for Paratope Scanning

Site-directed mutagenesis was carried to assess the binding contributions of individual CDR residues as well as some residues having potential effect on other antibody characteristics. Based upon the molecular model of C2494 Fv above a subset of solvent-exposed CDR residues were predicted to be involved in binding antigen. These were mutated to alanine and/or corresponding 'human-like' residue, which is the corresponding residue in the closest matching germline gene. D101aA (Chothia residues), (D104A in SEQ ID NO: 48) substitution in C2494 VH decreased the $k_{off}$ about 4 fold, from $1.43\times10^{-4}$ to $3.2\times10^{-5}$.

As the D101aA substitution decreased of $k_{off}$ of C2494 Fab in binding to ST2L it was expected that the same mutation may also improve the off-rate in the C2494 HFA variants. Thus, D101aA (Chothia numbering) was incorporated in the VH of STLH194 (>VH2494-IGHV1-f*01, SEQ ID NO: 143) to generate a VH STLH201 (SEQ ID NO: 145). STLH201 was paired with 7 light chains STLL280, STLL277, STLL276, STLL275, STLL274, STLL273 and STLL272 (Table 13 and Table 14) to generate mAbs STLM226, STLM227, STLM228, STLM229, STLM230, STLM231 and STLM232 which were characterized further. mAbs STLM226, STLM227, STLM228, STLM229, STLM230, STLM231 and STLM232 therefore have identical LCDR1, LCDR2, LCDR3, HCDR1 and HCDR2 sequences when compared to the parent C2494 antibody and a different HCDR3 (SEQ ID NO: 146, GDFYAMAY). In addition, antibody STLM266 VL STLM280 had a unique LCDR3: LQSDNLLT (SEQ ID NO: 147)

STLH201 (SEQ ID NO: 145):

EVQLVQSGAEVKKPGATVKISCKVSAFNIKDDYMHWVQQAPGKGLEWMGRIDPAIGNTEYAEKFQG
RVTITADTSTDTAYMELSSLRSEDTAVYYCATGDFYAMAYWGQGTLVTVSS

HCDR3 incorporation D101aA (Chothia numbering) substitution:

SEQ ID NO: 146: GDFYAMAY antibody STLM266 VL STLM280 had a unique LCDR3: LQSDNLLT (SEQ ID NO: 147)

Example 14

Characterization of Anti-ST2L Antibodies

Antibodies obtained from phage display, hybridoma and human framework adaptation campaigns were characterized in various assays including binding to huST2L-ECD, cynoST2L-ECD, affinity measurements, binding to human/mouse chimeras to determine domain binding, receptor-ligand inhibition assay, reporter gene assays, and mast cell response assays.

Affinities of the antibodies derived from the phage display campaigns to human and cyno ST2L as well as their binding specificity to human ST2L is shown in Table 16. All antibodies in Table 16 bound Domain I of human ST2L.

experiments were performed at 25° C. using ProteOn's PBS-T-E buffer (PBS, 0.005% P20 and 3 mM EDTA) as running buffer. To perform the experiments a GLC sensor chip was prepared by covalent immobilization of goat anti-human Fc (5800 RUs) 122-146 response units (RU) of Mab were captured. Mab capture was followed by injection of ST2L-ECD from 0.024-15 nM (5-fold dilutions) for 4 min (200 µL at 50 µL/min). The dissociation was monitored for 30 minutes for all reaction. Regeneration was performed using two 15 sec pulses of 10 mM glycine pH1.5. The data was fitted to a 1:1 with baseline drift model.

Association rates for the samples are fast, the langmuir with mass transfer model was used for curve fitting and estimation of Affinity. All of the samples had faster off rates than the parental clone and control Mab. The difference in off rate was the primary contributor to the lower affinity of the HFA variants when compared to the parent antibody.

TABLE 16

| | human ST2L affinity | | | cyno ST2L affinity | | | ST2L-ECD |
|---|---|---|---|---|---|---|---|
| | $k_{on}$ (M$^{-1}$s$^{-1}$) | $k_{off}$ (s$^{-1}$) | KD (pM) | $k_{on}$ (M$^{-1}$s$^{-1}$) | $k_{off}$ (s$^{-1}$) | KD (pM) | domain binding |
| STLM103 | 3.97E+06 | 1.63E−04 | 41 | 6.42E+06 | 2.02E−04 | 31 | D1 |
| STLM107 | 2.90E+07 | 3.41E−04 | 12 | 1.00E+08 | 6.50E−04 | 7 | D1 |
| STLM108 | 2.29E+06 | 2.22E−04 | 97 | 2.05E+07 | 5.98E−04 | 29 | D1 |
| STLM123 | 1.37E+07 | 2.08E−04 | 15 | 1.00E+08 | 5.19E−04 | 5 | D1 |
| STLM124 | 1.65E+07 | 7.56E−04 | 46 | 8.71E+07 | 2.57E−03 | 30 | D1 |
| STLM206 | 6.39E+06 | 1.60E−04 | 25 | 9.40E+07 | 5.83E−04 | 6 | D1 |
| STLM207 | 8.33E+06 | 3.95E−04 | 48 | 1.00E+08 | 2.07E−03 | 21 | D1 |
| STLM208 | 5.97E+06 | 6.76E−05 | 11 | 1.39E+07 | 7.02E−05 | 5 | D1 |
| STLM209 | 6.59E+06 | 1.70E−04 | 26 | 3.39E+07 | 3.11E−04 | 9 | D1 |
| STLM210 | 1.21E+07 | 2.27E−04 | 19 | 5.70E+07 | 5.28E−04 | 9 | D1 |
| STLM211 | 1.70E+07 | 4.83E−04 | 29 | 1.00E+08 | 1.39E−03 | 14 | D1 |
| STLM212 | 1.24E+07 | 3.98E−04 | 32 | 1.43E+07 | 3.46E−04 | 24 | D1 |
| STLM213 | 7.54E+06 | 1.08E−04 | 14 | 1.64E+07 | 1.24E−04 | 8 | D1 |
| STLM214 | 9.16E+06 | 2.99E−04 | 33 | 7.20E+06 | 2.64E−04 | 37 | D1 |
| STLM215 | 6.91E+06 | 1.72E−04 | 25 | 3.54E+07 | 3.69E−04 | 10 | D1 |
| STLM216 | 9.63E+06 | 1.58E−04 | 16 | 7.89E+07 | 2.64E−04 | 3 | D1 |
| STLM217 | 7.27E+06 | 1.26E−04 | 17 | 3.81E+07 | 1.38E−04 | 4 | D1 |
| STLM218 | 9.89E+06 | 2.24E−04 | 23 | 1.45E+07 | 2.65E−04 | 18 | D1 |
| STLM219 | 7.54E+06 | 2.01E−04 | 27 | 1.07E+07 | 2.30E−04 | 22 | D1 |
| STLM220 | 5.80E+06 | 9.53E−05 | 16 | 1.60E+07 | 1.40E−04 | 9 | D1 |
| STLM221 | 2.73E+06 | 9.61E−05 | 35 | 6.04E+06 | 1.30E−04 | 22 | D1 |
| STLM222 | 8.22E+06 | 3.01E−04 | 37 | 1.18E+07 | 3.45E−04 | 29 | D1 |
| STLM226 | 2.16E+07 | 1.93E−03 | 90 | 1.00E+08 | 3.01E−02 | 301 | D1 |
| STLM227 | 2.66E+07 | 1.70E−03 | 64 | 1.00E+08 | 2.94E−02 | 294 | D1 |
| STLM228 | 2.01E+07 | 1.04E−03 | 52 | 1.00E+08 | 1.55E−02 | 155 | D1 |
| STLM229 | 1.29E+07 | 4.45E−04 | 35 | 1.00E+08 | 8.50E−03 | 85 | D1 |
| STLM230 | 1.11E+07 | 4.26E−04 | 38 | 5.06E+07 | 7.30E−03 | 144 | D1 |
| STLM231 | 1.97E+07 | 9.13E−04 | 46 | 8.27E+07 | 1.43E−02 | 172 | D1 |
| STLM232 | 1.78E+07 | 4.49E−04 | 25 | 1.00E+08 | 7.97E−03 | 80 | D1 |

Affinities of the anti-ST2L antibodies from the HFA campaign in relation to the parent (STLM62, C2494) are shown in Table 17. The affinities were analyzed by ProteOn. The

TABLE 17

| | human ST2L affinity | | | cyno ST2L affinity | | |
|---|---|---|---|---|---|---|
| Sample | $k_{on}$ (M-1s-1) | $k_{off}$ (s-1) | $K_D$ (pM) | $k_{on}$ (M-1s-1) | $k_{off}$ (s-1) | $K_D$ (pM) |
| STLM62* | 1.84E+07 | 1.59E−04 | 8.67 | 3.84E+07 | 4.57E−04 | 12.35 |
| STLM187 | 3.37E+07 | 1.59E−02 | 473.00 | 1.00E+08 | 1.10E−01 | 1100.00 |
| STLM190 | 1.00E+08 | 5.34E−02 | 534.00 | 1.00E+08 | 1.02E−01 | 1020.00 |
| STLM191 | 8.46E+07 | 2.47E−02 | 292.00 | 1.00E+08 | 6.66E−02 | 666.00 |
| STLM192 | 2.11E+07 | 8.85E−03 | 420.00 | 1.00E+08 | 9.99E−02 | 999.00 |
| STLM193 | 4.77E+07 | 1.27E−02 | 267.00 | 1.00E+08 | 9.32E−02 | 932.00 |
| STLM194 | 1.00E+08 | 7.03E−02 | 703.00 | 1.00E+08 | 1.90E−01 | 1900.00 |
| STLM195 | 2.49E+07 | 6.73E−03 | 271.00 | 1.00E+08 | 7.19E−02 | 719.00 |
| STLM197 | 1.83E+07 | 1.62E−03 | 88.50 | 2.97E+07 | 6.88E−03 | 232.00 |
| STLM199 | 2.17E+07 | 8.97E−04 | 41.40 | 7.78E+07 | 6.57E−03 | 84.50 |
| STLM200 | 2.35E+07 | 1.43E−03 | 60.80 | 8.23E+07 | 1.10E−02 | 134.00 |
| STLM201 | 1.76E+07 | 8.52E−04 | 48.40 | 3.55E+07 | 4.10E−03 | 116.00 |
| STLM202 | 2.24E+07 | 1.19E−03 | 52.90 | 7.75E+07 | 1.04E−02 | 134.00 |

TABLE 17-continued

| | human ST2L affinity | | | cyno ST2L affinity | | |
|---|---|---|---|---|---|---|
| Sample | $k_{on}$ (M−1s−1) | $k_{off}$(s−1) | $K_D$ (pM) | $k_{on}$ (M−1s−1) | $k_{off}$(s−1) | $K_D$ (pM) |
| STLM203 | 2.04E+07 | 9.67E−04 | 47.30 | 5.88E+07 | 6.56E−03 | 111.00 |
| STLM204 | 2.97E+07 | 2.41E−03 | 81.30 | 1.00E+08 | 2.05E−02 | 205.00 |
| STLM205 | 1.73E+07 | 6.95E−04 | 40.10 | 4.04E+07 | 4.04E−03 | 100.00 |

*STLM62 = C2494, parent antibody

TABLE 18

| Origin | mAb | RLB IC50, µg/ml | RGA IC50, µg/ml | Cyno endothelial assay | Basophil cytokine release |
|---|---|---|---|---|---|
| Phage display | STLM103 | 0.47 | 1.92 | NT | + |
| | STLM107 | 0.44 | 1.10 | NT | ++ |
| | STLM108 | 0.23 | 2.34 | ++ | ++ |
| | STLM116 | 0.29 | 6.71 | NT | + |
| | STLM123 | 0.28 | 1.25 | NT | ++ |
| | STLM124 | 0.35 | 0.87 | ++ | ++ |
| | STLM206 | 0.40 | 0.67 | ++ | ++ |
| | STLM207 | 0.36 | 2.30 | NT | ++ |
| | STLM208 | 0.47 | 0.61 | ++ | ++ |
| | STLM209 | 0.32 | 0.97 | ++ | ++ |
| | STLM210 | 0.30 | 2.10 | NT | ++ |
| | STLM211 | 0.28 | 2.52 | NT | ++ |
| | STLM212 | 0.33 | 4.32 | NT | + |
| | STLM213 | 0.34 | 0.49 | ++ | ++ |
| | STLM214 | 0.28 | 2.52 | NT | ++ |
| | STLM215 | 0.29 | 1.30 | NT | ++ |
| | STLM216 | 0.30 | 1.86 | NT | ++ |
| | STLM217 | 0.49 | 1.69 | NT | ++ |
| | STLM218 | 0.42 | 1.33 | NT | ++ |
| | STLM219 | 0.29 | 3.16 | NT | ++ |
| | STLM220 | 0.39 | 0.60 | NT | ++ |
| | STLM221 | 0.39 | 2.79 | NT | + |
| | STLM222 | 0.25 | 1.88 | NT | ++ |
| | STLM226 | 0.26 | 0.25 | ++ | ++ |
| | STLM227 | 0.17 | 0.23 | ++ | ++ |
| | STLM228 | 0.20 | 0.28 | ++ | ++ |
| HFA | STLM229 | 0.29 | 0.32 | ++ | ++ |
| | STLM230 | 0.28 | 0.15 | ++ | ++ |
| | STLM231 | 0.26 | 1.10 | + | + |
| | STLM232 | 0.31 | 0.15 | ++ | ++ |
| hybridoma C2494 | STLM62* | 0.70 | 0.11 | ++ | ++ |

++ strong inhibition
+ some inhibition
− no inhibition
NT Not tested
*Tested as a hybridoma
RLB = Receptor-Ligand binding inhibition
RGA = Reporter gene assay Select antibodies were tested for mast cell responses measuring inhibition of 3 ng/ml IL-33-induced IL-5, IL-13 and IL-8 release from human cord blood-derived mast cells as described using 100 µg/ml, 10 µg/ml, 1 µg/ml, 0.1 µg/ml or 0.01 µg/ml antibody in RPMI+10% FCS. In these assay conditions, all antibodies tested inhibited IL-33-induced IL-5, IL-13 and IL-8 cytokine release by about 40%-100% at an antibody concentration 100 µg/ml when compared to a control sample induced with IL-33.

Example 15

Anti-ST2L Antibody Inhibits Downstream Signaling Pathways in Human Basophils

Anti-ST2L antibodies were tested for their ability to inhibit p38 MAPK signaling in human basophils.

Whole blood was collected in heparinized tubes and brought to room temperature (RT) prior to initiation of the assay. 1 mL of blood was aliquotted into 50 mL conical tubes and either anti-ST2L antibody (STLB252) or isotype control (CNTO 8937) diluted in PBS was added for a final concentration of 2, 20, or 200 µg/mL. Tubes were swirled gently to mix and placed in incubator at 37° C.×30 minutes, swirling gently after 15 minutes. Blood was then stained with fluorochrome-labeled antibodies against cell surface antigens (CD123-FITC, CRTH2-PCP-CY5.5, and CD45-APC-C7) and tubes were incubated at 37° C. for 15 minutes. 1 mL of warmed culture media (RPMI-1640/10% FBS/1% pen-strep) was added to each tube before IL-33 diluted in warmed culture media was added for a final concentration of 10 ng/mL. Samples were incubated at 37° C.×10 minutes prior to the addition of 20 mLs of pre-warmed BD Phosflow Lyse/Fix buffer to each tube, in order to simultaneously lyse the red blood cells and fix the samples. Tubes were mixed well by inverting 10 times and incubated at 37° C.×10 minutes. Samples were washed with 20 mLs sterile RT PBS, resuspended in 2 mLs of 1×RT BD Perm/Wash Buffer, and incubated at RT×30 minutes. Samples were washed once with 2 mLs BD Perm/Wash buffer and then resuspended in 400 µL BD Perm/Wash buffer. PE-labelled antibody against intracellular p38-MAPK (vCell Signaling, Cat. 6908S) was added and samples were incubated 30 min at RT, protected from light. Samples were washed once with 5 mLs Perm/Wash buffer before being resuspended in 100 µL FACS buffer and transferred to a 96-well round-bottom plate. Samples were analyzed using a BD LSRII Flow Cytometer utilizing a high-throughput system (HTS) collecting as many events as possible for each sample. Data was analyzed using FloJo software. Basophils were identified as $CD45^+CRTH2^+CD123^+$ and the percent of p38 MAPK positive basophils was assessed for each condition. Pre-incubation of whole blood with anti-ST2L mAB (STLB252) resulted in a dose-dependent inhibition of IL-33 induced p38-MAPK phosphorylation, whereas no effect was seen with isotype control (CNTO 8937). The anti-human ST2L antibody specifically blocked basophil activation by recombinant human IL-33 in the context of whole blood. The results suggest that anti-ST2L antibodies inhibit signaling by endogenous IL-33 in vivo.

TABLE 19

| IL-33 (10 ng/ml) | STLB252 (µg/mL) | Isotype control (µg/mL) | % phosphorylated p38 MAPK |
|---|---|---|---|
| − | 0 | 0 | 2.2 |
| + | 0 | 0 | 80.6 |
| + | 2 | 0 | 44.4 |
| + | 20 | 0 | 15.7 |
| + | 200 | 0 | 1.2 |
| + | 0 | 2 | 76.7 |
| + | 0 | 20 | 79 |
| + | 0 | 200 | 77 |

Example 16

In Vivo Target Engagement by Anti-ST2L Antibody

Intranasal mIL-33 6 hour in vivo model of BAL cell recruitment A single dose of 1.2 µg/mouse mIL-33 (R&D systems #3626-ML/CF) or PBS was administered to male Balb/c mice (6-8 weeks old, Taconic). Rat anti-mouse ST2L antibody CNTO 3914 or at 2, 0.2, 0.06, or 0.02 mg/kg, 24 hrs prior to the first mIL-33 intranasal administration. Isotype control (ITC) mAb CNTO 5516 was dosed subcutaneously at 2 mg/kg. Six hours following the mIL-33 (or PBS) administration, mice were sacrificed and blood was collected for serum analysis. Bronchoalveolar lavages (BAL) were performed by injecting two volumes of 0.7 mL of PBS/0.1% BSA into the lungs and retrieving the effluent. The BALs were centrifuged (1200 rpm, 10 minutes) and the cell pellet was resuspended in 200 µl PBS for total and differential cell counts using a hemacytometer (on Wright's-Giemsa-stained cytospin preparations).

Measurement of CNTO 3914 in Mouse Serum

MSD SA-STD plates were blocked with 50 µL per well of assay buffer for 5 minutes. The plates were turned over to remove assay buffer and tapped on paper towels. 50 µl per well of 1.4 µg/mL biotinylated recombinant mouse ST2L/IL1R4/Fc chimera (R&D System) in assay buffer were added and incubated overnight in the refrigerator. 150 µL of assay buffer was added to each well of the pre-coated plates without removing the coating reagent and incubated for 30 minutes. The plates were washed three times with wash buffer on the plate washer. The plates were tapped lightly on paper towels to remove residual wash buffer. 50 µL per well of CNTO 3914 sample was added to each well of the plate. The plate was incubated for one hour with gentle vortexing at ambient temp. The plates were washed three times with wash buffer on the plate washer. 50 µL per well of titration of ruthenium-labeled mouse anti-mouse IgG1b (BD Biosciences) was added to each well of the plate. The plate was incubated for one hour with gentle vortexing at ambient temp. The plates were washed three times with wash buffer on the plate washer. 150 µL of read buffer were added to each well of the plate. The plates were immediately read on the MSD sector imager 6000 Reader for luminescence levels.

Whole Blood Assay

Blood was diluted 1:4 in DMEM media+1% Penicillin+streptomycin solution+/–10 ng/ml mouse IL-33 in Sarstedt filter tubes. The tubes were incubated at 37° C. overnight, then cytokine and chemokine levels were measured on the supernatants using the Millipore Milliplex Mouse Cytokine/Chemokine Kit according to manufacturer's instructions.

Results

Figure 16A:
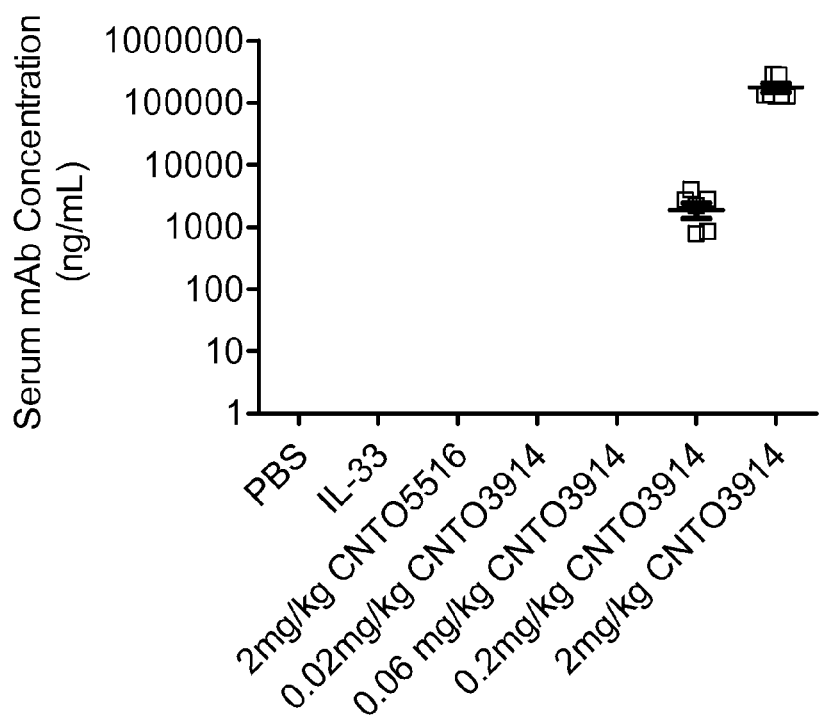
FIG. 16 A) Serum levels of anti-ST2L antibody CNTO3914 B) inhibition of bronchoalveolar Lavage (BAL) cell recruitment C) inhibition of IL-6 secretion by whole blood cells stimulated with IL-33; D) inhibition of MCP1 secretion by whole blood cells stimulated with IL-33 by CNTO3914 24 hours post-dosing in a 6 hour model of lung inflammation induced by intranasally administered IL-33. *p<0.05, *p<0.01, ***p<0.001; NQ=below the limit of detection; @=one data point is below the limit of detection.

Anti-ST2L antibody was detectable in the serum of mice 24 hours post-dosing with 0.2 or 2 mg/kg CNTO 3914 (FIG. 16A).

Figure 16B:
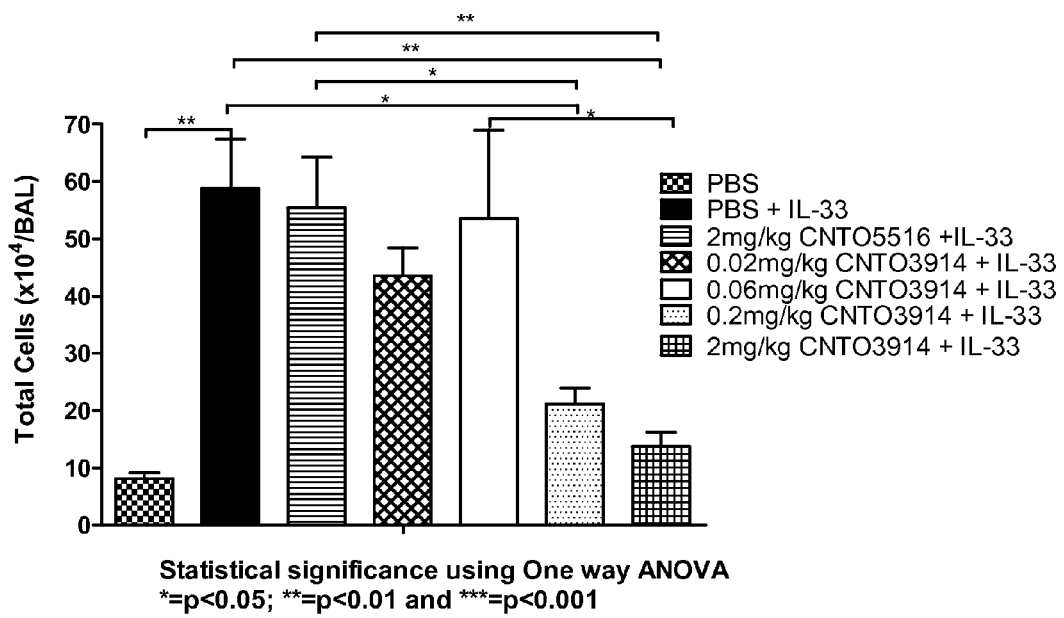
Figure 17A:
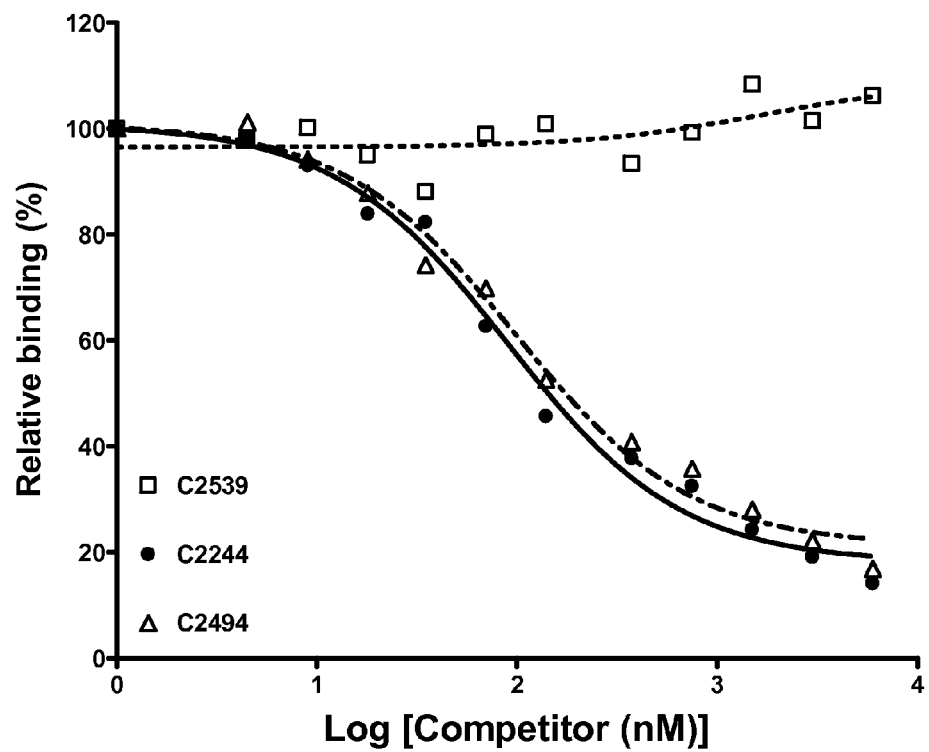
FIG. 17. Competition between various anti-ST2L antibodies. A) 30 nM labeled C2244 Fab was competed with indicated antibodies for binding to ST2L-ECD coated on microwells. C2244 competed with C2494 but not with C2539. B) 10 nM labeled C2494 was competed with indicated antibodies for binding to ST2L-ECD coated on microwells. C2494 competed with STLM208 and STLM213 but not with C2539.
Figure 17B:
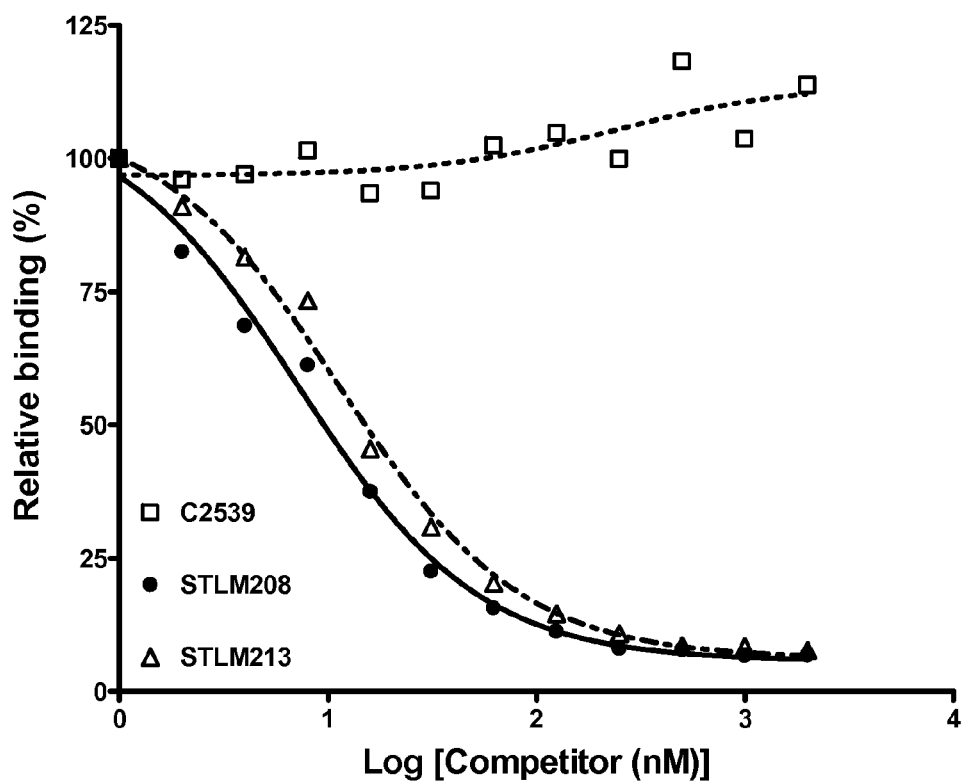

Intranasal administration of IL-33 induced cell recruitment to the airways at 6 h (FIG. 17B). Anti-ST2L mAb administration reduced BAL cell recruitment; 0.2 mg/kg was the minimum dose needed to see significant inhibition of BAL cell recruitment (FIG. 16B). Statistical significance was calculated using One-way ANOVA.

Figure 16C:
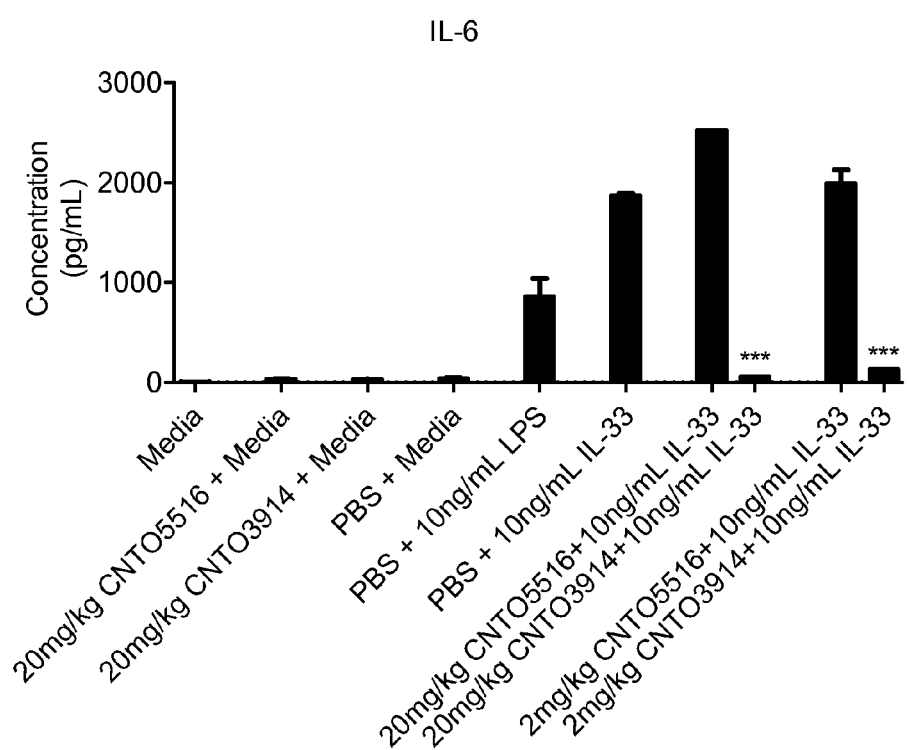
Figure 16D:
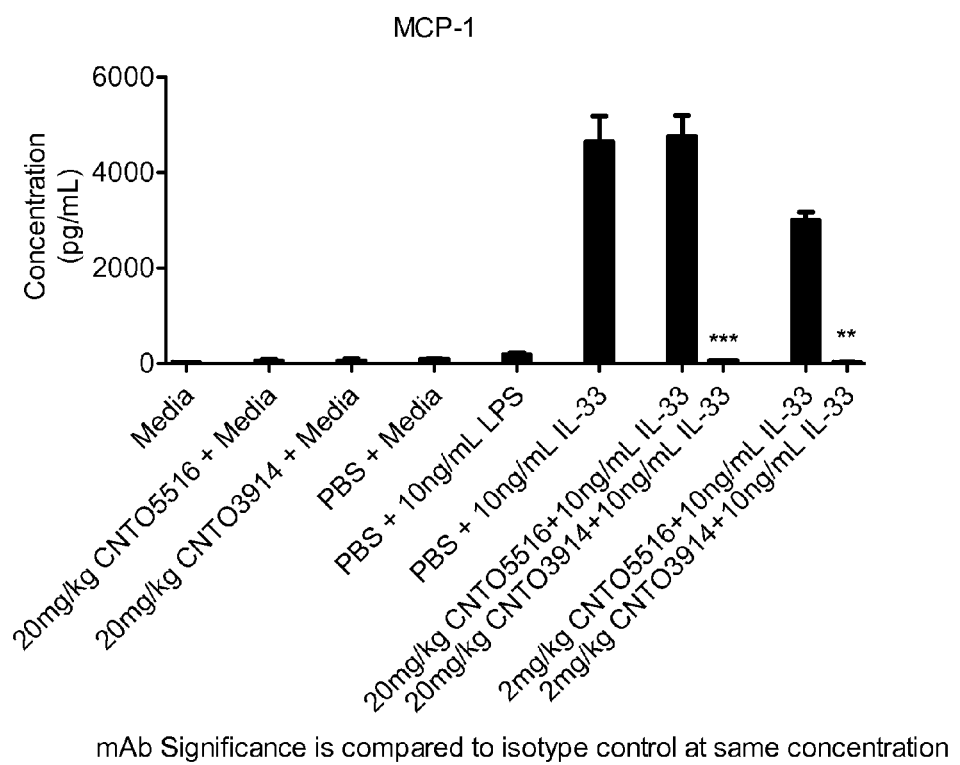

Whole blood stimulated with mouse IL-33 showed increased levels of cytokine and chemokines, including IL-6 (FIG. 16C) and MCP-1 (FIG. 17D), after 24 h. In mice dosed with 20 mg/kg or 2 mg/kg anti-ST2L mAb CNTO 3914, IL-6 and MCP-1 levels were reduced compared to CNTO5516 (isotypic control anti-mouse IgG1), implying target engagement. The minimum dose that correlated with inhibition in the whole blood assay, 2 mg/kg, also inhibited BAL cell recruitment (FIG. 16B).

Collectively this data confirms that the anti-ST2L mAb reaches site of action and the intended pharmacologic effect was accomplished (implies target engagement).

Example 17

Epitopes of Anti-ST2L Antibodies

Epitope mapping and competition studies were conducted to select anti-ST2L antibodies.

Competition Binding Assays

Competition binding assays were performed to evaluate different binding epitope groups for anti-ST2L mAbs. 5 µl (10 µg/ml) of ST2L-ECD protein was coated on MSD High-Bind plate (Meso Scale Discovery, Gaithersburg, Md.) per well for 2 hr at room temperature. One-hundred and fifty microliters of 5% MSD Blocker A buffer (Meso Scale Discovery, Gaithersburg, Md.) was added to each well and incubated for 2 hr at room temperature. Plates were washed three times with 0.1 M HEPES buffer, pH 7.4, followed by the addition of the mixture of the MSD fluorescence dye (sulfo tag, NHS ester) labeled individual anti-ST2L antibody with different competitors. Labeled antibody, 10 or 30 nM, was incubated with increasing concentrations of competitor antibodies, from 1 nM to 2 or 5 µM, and then added to the designated wells in a volume of 25 µL mixture. After 2-hour incubation with gentle shaking at room temperature, plates were washed 3 times with 0.1M HEPES buffer (pH 7.4). MSD Read Buffer T was diluted with distilled water (4-fold) and dispensed at a volume of 150 µL/well and analyzed with a SECTOR Imager 6000.

Following antibodies were used in competition assays: ST2L Domain I binding neutralizing antibodies STLM208, STLM213, C2244 (STLM15) and C2494 (STLM62), ST2L Domain III binding antibody C2539, and a non-neutralizing anti-ST2L antibody C2240 binding Domain I of human ST2L. FIGS. 17A and 18B shows the competition experiments. Based on the experiment, the epitope bins identified were: BinA: mAbs C2244, C2494, STLM208 or STLM213; BinB: mAb C2240, BinC: C2539. The antibodies blocking IL33/ST2L interaction and inhibiting mast cell responses were found in the same epitope bin and to cross-compete with each other. Summary of the competition data is shown in Table 20.

TABLE 20

| Competitor | Labeled Antibody | | | |
| --- | --- | --- | --- | --- |
|  | C2240 | C2539 | C2244 | C2494 |
| C2240 | + | − | − | − |
| C2539 | − | + | − | − |
| C2244 | − | − | + | + |
| C2494 | − | − | + | + |
| STLM208 | − | − | + | + |
| STLM213 | − | − | + | + |

Epitope Mapping: H/D Exchange Analysis

For H/D exchange, the procedure used to analyze the antibody perturbation are similar to the one described previously (Hamuro, Y., et al., Journal of Biomolecular Techniques, 14:171-182, 2003; Horn, J. R., et al., Biochemistry, 45: 8488-8498, 2006) with some modification. Recombinant ST2-ECD (expressed from HEK293E with C-terminal His-tag)

(residues 18-328 of SEQ ID NO: 157) was incubated in a deuterated water solution for pre-determined times resulting in deuterium incorporation at exchangeable hydrogen atoms. The deuterated ST2-ECD was captured on a column containing immobilized anti-ST2L C2244 Fab molecules and then washed with aqueous buffer. The back-exchanged ST2-ECD protein was eluted from the column and localization of deuterium containing fragments was determined by protease digestion and mass spec analysis.

Figure 18:
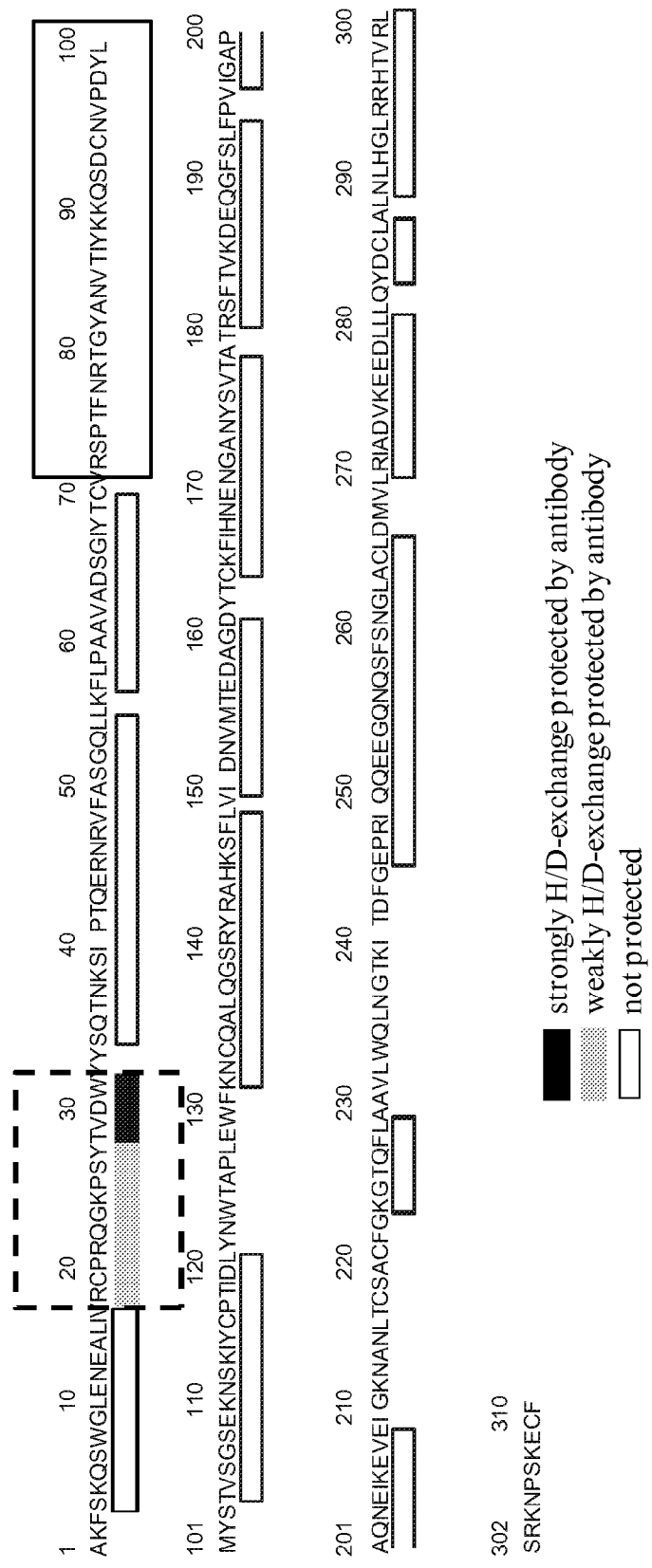
FIG. 18 shows a simplified H/D exchange map of the human ST2-ECD (SEQ ID NO: 119) complexed with C2244 Fab. The regions protected by the antibody were displayed in different gray scale as indicated. Segments encompassing residues 18-31 (boxed in dashed line) (corresponding to residues 35-48 of full length ST2L of SEQ ID NO: 1) were protected by the Fab. Region encompassing residues 71-100 (boxed in solid line) (corresponding to residues 88-117 of SEQ ID NO: 1) were heavily glycosylated and not covered by peptides.

FIG. 18 shows a simplified H/D exchange map of the human ST2-ECD (soluble ST2) complexed with C2244 Fab. Residues 18-31 of ST2-ECD of SEQ ID NO: 119 (amino acid residues RCPRQGKPSYTVDW; SEQ ID NO: 210) were protected by the Fab (corresponding to residues 35-48 of full length ST2L of SEQ ID NO: 1. The data indicates that C2244 binds to epitope RCPRQGKPSYTVDW; SEQ ID NO: 210), and that antibodies competing with C2244 (C2494, STLM208 or STLM213) are likely to bind the same or overlapping epitope.

Epitope Mapping by Mutagenesis

Several ST2L mutants were generated having substitutions to corresponding mouse residues at ST2L Domain I. The tested antibodies do not cross-react with mouse ST2L, therefore it is expected that ST2L variants with abolished and/or reduced binding are indicative of epitope residues at the substitution sites on ST2L. Variants were made into construct HH-ST2L having residues 19-205 of full length ST2L of SEQ ID NO: 1 using standard methods. Antibodies were tested for binding to the ST2L variants by ELISA or Proteon.

Surface Plasmon Resonance

Binding studies were performed using the ProteOn XPR36 Protein Interaction Array system (Bio-Rad) (Bravman T, et al. Anal Biochem 358:281-288, 2006). Anti-human/anti-mouse Fc mixture (Jackson ImmunoResearch, Cat#, 109-005-098/115-005-071) was immobilized on the GLC sensor chip by amine-coupling chemistry. Individual anti-ST2L mAb was then captured by flowing (1 µg/mL) antibody solution prepared in PBS containing 0.5% Nonidet P-40 and 0.5% Na-deoxycholate). The signal in the surfaces reached ~250 resonance units (RU, 1 RU=1 pg protein/mm$^2$) in the anti-Fc-coated surfaces, confirming that these antibodies specifically capture anti-ST2L mAbs. After 90° rotation of the fluid system, wild type of ST2L-D1D2 or variant proteins (0.5 mg/mL in PBS containing 0.5% Nonidet P-40 and 0.5% Na-deoxycholate) was injected in the parallel flow channels. All of these assays were performed at 25° C. The ST2L-D1D2-dependent signals on the surfaces were obtained by double referencing, subtracting the response observed on surfaces immobilizing the antibodies alone, and the signal observed injecting the vehicle alone (which allows correction for binding-independent responses). The resulting sensorgrams were fitted by the simplest 1:1 interaction model (ProteOn analysis software), to obtain the corresponding association and dissociation rate constants ($k_a$ and $k_d$).

FIG. 19 shows the ST2L variants that were made and affinity of ST2B206 and ST2B252 anti-ST2L antibodies to the variants. Variant 93NL94 (substitution 93TF94→93NL94) reduced binding affinity of both STLM208 and STLB252 by about 5-fold from about 10.8×10$^{-12}$ M to about 49.5×10$^{-12}$ M. Lack of significant reduction of binding affinity implies that the binding energy for the interaction between antibody and ST2L-D1D2 is a sum of epitope region (RCPRQGKPSYTVDW; SEQ ID NO: 210) identified by H/D exchange analysis and additional contribution from this 93NL94 site. Residue numbering is according to full length human ST2L of SEQ ID NO: 1.

Example 18

ST2L Domain I Binding Antibodies Inhibit Primary Human Lung Mast Cell Responses In Vitro Ability of the ST2L Domain I binding antibodies to inhibit lung mast cell responses were assessed by release of chemokines and cytokines in primary human lung mast cells.

Isolation of Primary Human Lung Mast Cells

Primary human lung mast cells were isolated from normal non-smoker tissue obtained from the International Institute for the Advancement of Medicine. Cells were dispersed from the lung parenchyma and small airways by mincing, washing, and digesting the parenchyma tissue overnight at 37° C. in collagenase and hyaluronidase enzymes. Cells were collected, washed, and subjected to an enrichment procedure using the CD117 MicroBead Kit (human) from MACS Miletnyi Biotec to positively select the mast cells from the population. Prior to experimentation, mast cells were cultured for 6 weeks in StemPro-34+200 ng/ml stem cell factor. Two weeks after isolation, cells were phenotypically characterized using flow cytometry to determine the percent mast cell purity. The cells used in subsequent assays were 89% double positive for CD117 (C-kit or stem cell factor receptor) and Fc£RI (the high affinity IgE receptor). Furthermore, they were 94.2% positive for ST2L; thereby confirming their mast cell phenotype.

Cytokine Release Assay from Primary Human Lung Mast Cells

Primary human lung mast cells that had been cultured in StemPro-34+200 ng/ml stem cell factor for approximately 6 weeks were collected, and washed by centrifugation in RPMI (10% heat-inactivated FCS). Cells were counted and plated in RPMI/10% FCS medium at a density of 65,000 cells in a 96 well plate. The Anti-ST2L Domain I binding Mabs were added to the primary lung mast cells, and allowed to bind for 30 minutes at 37° C. prior to stimulation with IL-33. Cells were stimulated for 24 hours with 3 ng/ml IL-33 in order to initiate accumulation of various mediators into the culture supernatant. Culture supernatant was harvested and stored frozen until assaying in a custom Milliplex 9-plex kit.

Figure 20A:
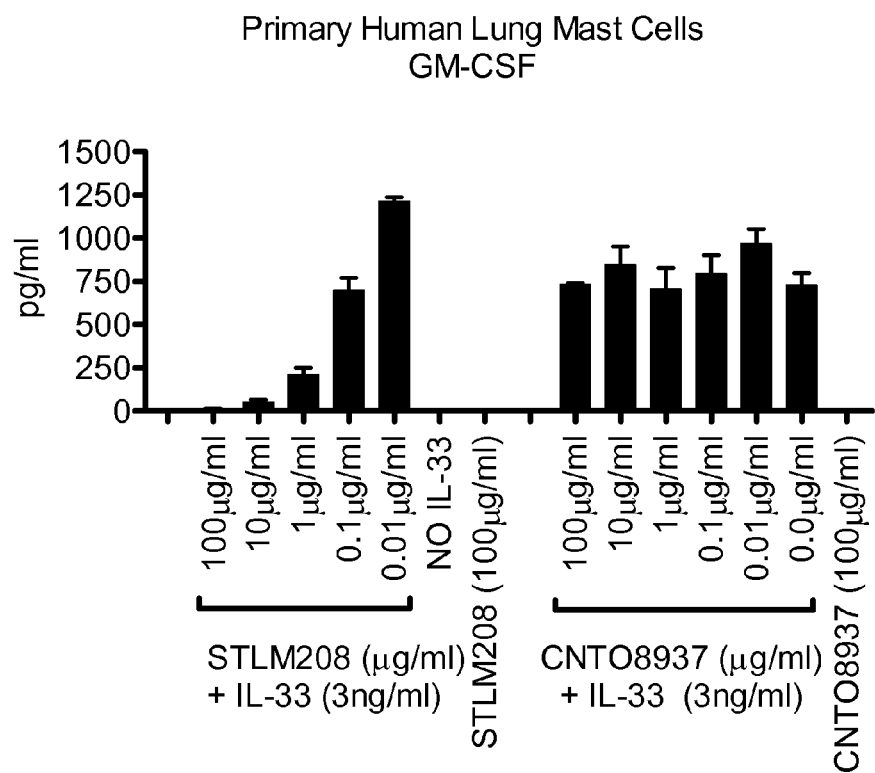
FIG. 20 shows inhibition of A) GM-CSF; B) IL-5; C) IL-8; D) IL-13 secretion from primary human lung mast cells by an anti-ST2L antibody STLM208.
Figure 20B:
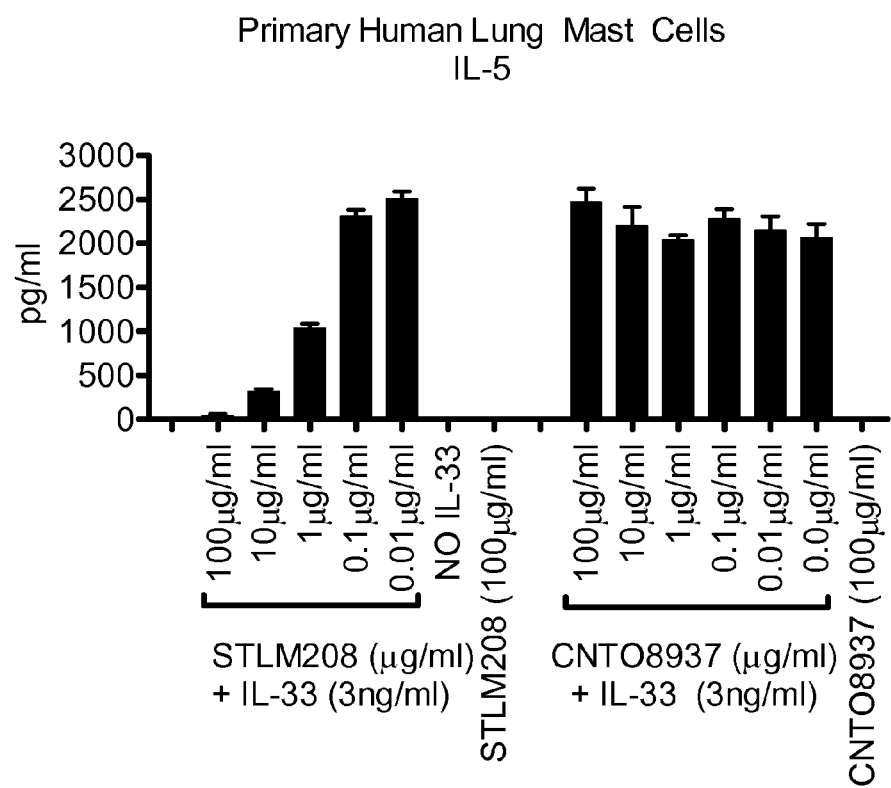
Figure 20C:
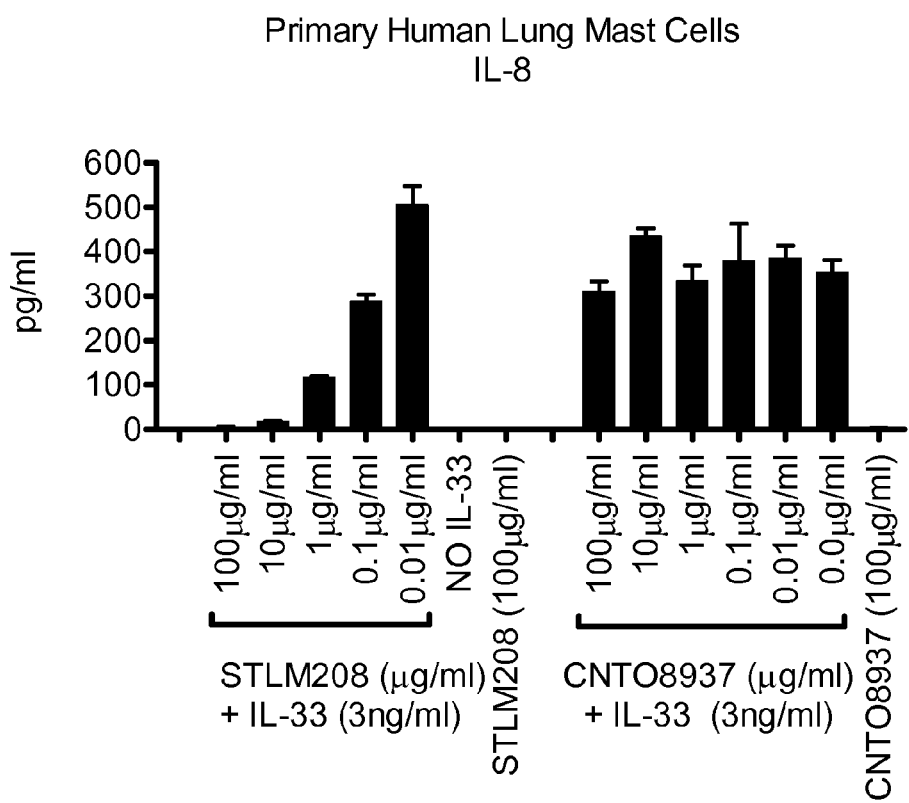
Figure 20D:
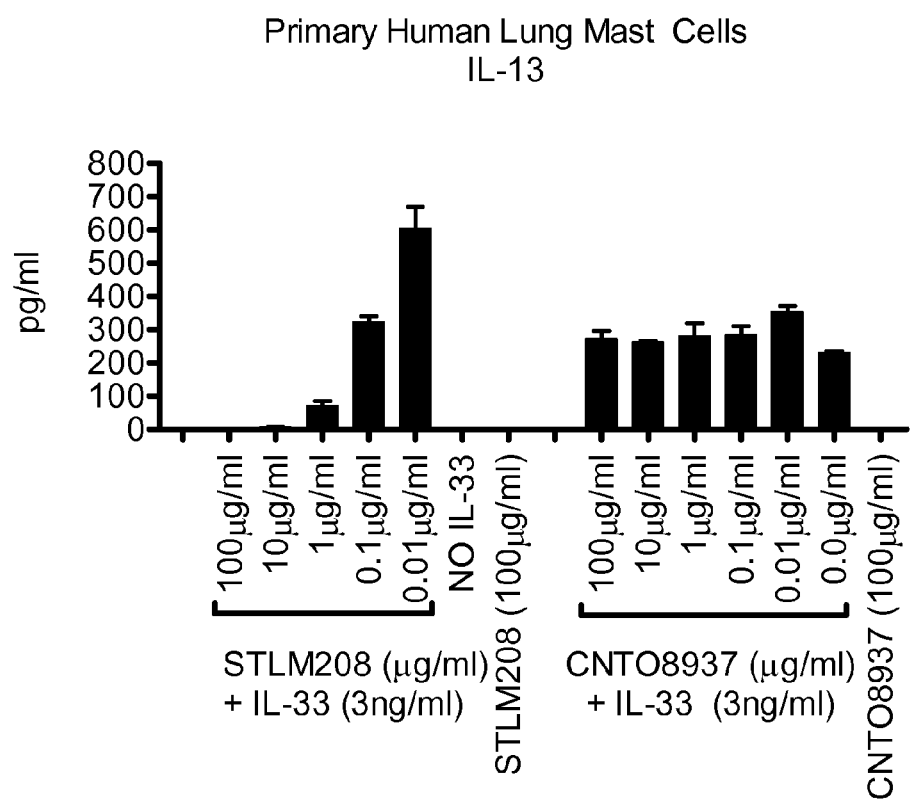

Anti-ST2L Domain I binding antibody, STLM208, inhibited IL-33-induced GM-CSF (FIG. 20A), IL-5 (FIG. 20B), IL-8 (FIG. 20C), and IL-13 (FIG. 20D) release in primary human lung mast cells at antibody concentrations 100 µg/ml, 10 µg/ml and 1 µg/ml. Similar results were obtained using the cord blood-derived mast cells (data not shown).

We claim:

1. A method of treating a ST2L-mediated inflammatory pulmonary condition, comprising administering a therapeutically effective amount of an isolated antibody antagonist or fragment thereof that specifically binds Domain I (SEQ ID NO: 9) of human ST2L to a patient in need thereof for a time sufficient to treat the ST2L-mediated inflammatory pulmonary condition, wherein the antibody antagonist comprises the heavy chain complementarity determining regions (HCDR1, HCDR2, HCDR3) and the light chain complementarity determining regions (LCDR1, LCDR2, LCDR3) of SEQ ID NOs: 97, 114, 84, 130, 90 and 134, respectively.

2. The method of claim 1, wherein the ST2L-mediated inflammatory pulmonary condition is asthma, airway hyper-reactivity, chronic obstructive pulmonary disease (COPD), idiopathic pulmonary fibrosis (IPF), cystic fibrosis or allergic rhinitis.

3. The method of claim 1 wherein the ST2L-mediated inflammatory pulmonary condition is associated with inflammatory cell recruitment in lung, goblet cell hyperplasia, or increased mucous secretion.

4. The method of claim 3, wherein the ST2L-mediated inflammatory pulmonary condition is associated with mast cell response.

5. The method of claim 1, wherein the antibody antagonist blocks IL-33/ST2L interaction.

6. The method of claim 1, wherein the antibody antagonist comprises a heavy chain variable region (VH) and a light chain variable region (VL), wherein the VH is derived from human IGHV3-23 (SEQ ID NO: 158) and the VL is derived from human IGKV3-11 (L6) (SEQ ID NO: 159) framework sequences.

7. The method of claim 6, wherein the antibody is of IgG1, IgG2, IgG3, or IgG4 isotype.

8. The method of claim 7, wherein the antibody comprises the VH of SEQ ID NO: 191 and the VL of SEQ ID NO: 209.

9. The method of claim 1, wherein the antibody antagonist is human or humanized.

10. A method of inhibiting IL-33-induced IL-13 release from primary human lung mast cells in a patient, comprising administering a therapeutically effective amount of an isolated antibody antagonist or fragment thereof that specifically binds Domain I (SEQ ID NO: 9) of human ST2L to a patient in need thereof for a time sufficient to inhibit the IL-33-induced IL-13 release from primary human lung mast cells, wherein the antibody comprises the heavy chain complementarity determining regions (HCDR1, HCDR2, HCDR3) and the light chain complementarity determining regions (LCDR1, LCDR2, LCDR3) of SEQ ID NOs: 97, 114, 84, 130, 90 and 134, respectively.

11. The method of claim 10, wherein the antibody antagonist blocks IL-33/ST2L interaction.

12. The method of claim 11, wherein the antibody antagonist comprises a heavy chain variable region (VH) and a light chain variable region (VL), wherein the VH is derived from human IGHV3-23 (SEQ ID NO: 158) and the VL is derived from human IGKV3-11 (L6) (SEQ ID NO: 159) framework sequences.

13. The method of claim 12, wherein the antibody is of IgG1, IgG2, IgG3, or IgG4 isotype.

14. The method of claim 13, wherein the antibody comprises the VH of SEQ ID NO: 191 and the VL of SEQ ID NO: 209.

15. The method of claim 10, wherein the antibody antagonist is human or humanized.

* * * * *